(12) United States Patent
Satoh et al.

(10) Patent No.: US 8,232,401 B2
(45) Date of Patent: Jul. 31, 2012

(54) 4-OXOQUINOLINE COMPOUND AND USE THEREOF AS HIV INTEGRASE INHIBITOR

(75) Inventors: Motohide Satoh, Takatsuki (JP); Hiroshi Kawakami, Takatsuki (JP); Yoshiharu Itoh, Takatsuki (JP); Hisashi Shinkai, Takatsuki (JP); Takahisa Motomura, Takatsuki (JP); Hisateru Aramaki, Takatsuki (JP); Yuji Matsuzaki, Takatsuki (JP); Wataru Watanabe, Takatsuki (JP); Shuichi Wamaki, Takatsuki (JP)

(73) Assignee: Japan Tobacco Inc., Tokyo (JP)

( * ) Notice: Subject to any disclaimer, the term of this patent is extended or adjusted under 35 U.S.C. 154(b) by 1790 days.

(21) Appl. No.: 11/446,128

(22) Filed: Jun. 5, 2006

(65) Prior Publication Data
US 2006/0217413 A1 Sep. 28, 2006

Related U.S. Application Data

(63) Continuation of application No. 10/492,833, filed as application No. PCT/JP03/14773 on Nov. 20, 2003, now Pat. No. 7,176,220.

(30) Foreign Application Priority Data

Nov. 20, 2002 (JP) ................................. 2002-336843
Mar. 11, 2003 (JP) ................................. 2003-065807
May 16, 2003 (JP) ................................. 2003-139616

(51) Int. Cl.
*C07D 215/38* (2006.01)
(52) U.S. Cl. ............................................. 546/156
(58) Field of Classification Search .................. 546/156; 514/312
See application file for complete search history.

(56) References Cited

U.S. PATENT DOCUMENTS

| | | | |
|---|---|---|---|
| 3,472,859 A * | 10/1969 | Lesher | ........................ 546/156 |
| 4,695,646 A | 9/1987 | Maurer et al. | |
| 5,182,401 A | 1/1993 | Grohe | |
| 5,217,972 A | 6/1993 | Grohe et al. | |
| 5,519,016 A | 5/1996 | Kimura et al. | |
| 5,686,482 A | 11/1997 | Ohmori et al. | |
| 5,688,791 A | 11/1997 | Kimura et al. | |
| 5,985,894 A | 11/1999 | Clemence et al. | |
| 5,989,451 A | 11/1999 | Lemieux et al. | |
| 6,034,086 A | 3/2000 | Kimura et al. | |
| 6,248,736 B1 | 6/2001 | Turner et al. | |
| 6,248,738 B1 | 6/2001 | Dickinson et al. | |
| 6,287,550 B1 * | 9/2001 | Trinh et al. | ................. 424/76.6 |
| 6,294,186 B1 * | 9/2001 | Beerse et al. | ................... 424/405 |
| 6,303,611 B1 * | 10/2001 | Zhang et al. | ............. 514/252.11 |
| 6,387,926 B1 | 5/2002 | Bhide et al. | |
| 6,559,145 B2 | 5/2003 | Ciske et al. | |
| 6,602,883 B1 | 8/2003 | Bhide et al. | |
| 6,730,682 B2 | 5/2004 | Schnute et al. | |
| 7,176,220 B2 * | 2/2007 | Satoh et al. | ........................ 514/312 |
| 7,531,554 B2 * | 5/2009 | Satoh et al. | ........................ 514/313 |
| 7,635,704 B2 * | 12/2009 | Satoh et al. | ........................ 514/312 |
| 7,825,252 B2 | 11/2010 | Dowdy et al. | |
| 2002/0019397 A1 | 2/2002 | Schnute et al. | |
| 2004/0180910 A1 | 9/2004 | Schnute et al. | |
| 2004/0198716 A1 | 10/2004 | Arad et al. | |
| 2004/0217708 A1 | 11/2004 | Matsumoto et al. | |
| 2009/0036684 A1 | 2/2009 | Matsuda et al. | |
| 2009/0099366 A1 | 4/2009 | Dowdy et al. | |
| 2009/0318702 A1 | 12/2009 | Matsuda et al. | |

FOREIGN PATENT DOCUMENTS

| | | |
|---|---|---|
| EP | 0 287 951 | 10/1988 |
| EP | 0 319 906 | 6/1989 |
| EP | 0 326 891 | 8/1989 |
| EP | 0 457 090 | 11/1991 |
| EP | 498721 B1 | 8/1992 |
| EP | 0905558 A1 | 3/1999 |
| EP | 1140851 B1 | 10/2001 |
| EP | 1375486 A1 | 1/2004 |
| JP | A-4826772 | 4/1973 |
| JP | A-4360872 | 12/1992 |
| JP | 6-116241 A | 4/1994 |

(Continued)

OTHER PUBLICATIONS

West, Solid State Chemistry and its APplication, Wiley, Ney York, 1988, pp. 358 & 365.*
Deprez, Molecular Pharmacology, vol. 65 (1), pp. 85-98, 2004.*
Abdul-Ahad, Europ. *J. Med. Chem.*, 17(4), pp. 301-306 (1982).
Baker, *J. Med. Chem.*, 15(3), pp. 235-237 (1972).
*Guidelines for the Use of Antiretroviral Agents in HIV-Infected Adults and Adolescent*, pp. i-iii and 1-111, (Aug. 13, 2001).
Hirao, I. et al., *Studies on the Synthesis of Quinoline Compounds, I.* Memoirs Kyushu Inst. Tech. (Eng.), 14:13-16 (1984).

(Continued)

*Primary Examiner* — D M Seaman
(74) *Attorney, Agent, or Firm* — Finnegan, Henderson, Farabow, Garrett & Dunner, LLP

(57) ABSTRACT

An anti-HIV agent containing, as an active ingredient, a 4-oxoquinoline compound represented by the following formula [I]

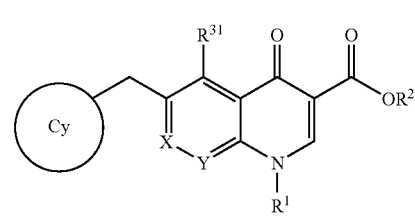

[I]

wherein each symbol is as defined in the specification, or a pharmaceutically acceptable salt thereof. The compound of the present invention has HIV integrase inhibitory action and is useful as an anti-HIV agent for the prophylaxis or therapy of AIDS. Moreover, by a combined use with other anti-HIV agents such as protease inhibitors, reverse transcriptase inhibitors and the like, the compound can become a more effective anti-HIV agent. Since the compound has high inhibitory activity specific for integrases, it can provide a safe pharmaceutical agent with a fewer side effects for human.

4 Claims, No Drawings

FOREIGN PATENT DOCUMENTS

| | | |
|---|---|---|
| JP | 6-199835 A | 7/1994 |
| JP | 6-271568 A | 9/1994 |
| JP | 8-183775 A | 7/1996 |
| JP | 10-316570 A | 12/1998 |
| JP | 11-084556 | 3/1999 |
| JP | 2002-293745 | 10/2002 |
| JP | A 2002-534416 | 10/2002 |
| JP | A 2002-534417 | 10/2002 |
| WO | WO 95/29891 A1 | 11/1995 |
| WO | WO-97/38999 | 10/1997 |
| WO | WO 98/34995 A1 | 8/1998 |
| WO | WO-98/45269 | 10/1998 |
| WO | WO 99/01434 | 1/1999 |
| WO | WO 99/52857 A1 | 10/1999 |
| WO | WO-00/01714 | 1/2000 |
| WO | WO-00/40561 | 7/2000 |
| WO | WO-00/40563 | 7/2000 |
| WO | WO 01/02385 A1 | 1/2001 |
| WO | WO-01/98275 A2 | 12/2001 |
| WO | WO 02/04422 A2 | 1/2002 |
| WO | WO-02/04444 | 1/2002 |
| WO | WO-02/36734 A2 | 5/2002 |
| WO | WO 02/48113 A1 | 6/2002 |
| WO | WO 02/055079 | 7/2002 |
| WO | WO 02/070486 A1 | 9/2002 |
| WO | WO 02/076939 A2 | 10/2002 |
| WO | WO 03/043992 A1 | 5/2003 |
| WO | WO 2007/102499 A1 | 9/2007 |
| WO | WO 2007/102512 A1 | 9/2007 |
| WO | WO 2009/036161 A1 | 3/2009 |
| WO | WO 2009/089263 A2 | 7/2009 |

OTHER PUBLICATIONS

Hirao, I. et al., *Antibacterial Activities of Oxodihydroquinoline Carboxylic Acid Derivatives*, Memoirs Department of Engineering, 14:21-32 (1990).

Stefenrich, Farmaro, Edizionie-Scientifica 42(1), pp. 3-16, 1987.

Vincent, K.A., et al., *Characterization of Human Immunodeficiency Virus Type I Integrase Expressed in Eschericia coli and Analysis of Variants with Amino-Terminal Mutations*, J. Virol. 67: 425-437 (1993).

Walton, *Antimicrobial Agents & Chemotherapy* 32(7) pp. 1086-1089, 1988.

Yoshimoto, *J. Med. Chem.*, 19(1), pp. 71-98 (1976).

Search Report from Austrian Patent Office dated Apr. 3, 2006.

Bouzard, D. et al., "Fluoronaphthyridines and Quinolones as Antibacterial Agents. 1. Synthesis and Structure-Activity Relationships of New 1-Substituted Derivatives," Journal of Medicinal Chemistry, American Chemical Society, Washington, US, vol. 32, No. 3, pp. 537-542 (Jan. 1, 1989).

Domagala, J.M. et al., "1-Substituted 7-[3-[(Ethylamino)methyl]-1-pyrrolidinyl]-6,8-difluoro-1,4-dihydro-4-oxo-3-quinolinecarboxylic Acids. New Quantitative Structure-Activity Relationships at $N_1$ for the Quinolone Antibacterials," Journal of Medicinal Chemistry, vol. 31, pp. 991-1001 (1988).

Extended European Search Report for European Patent Application No. 10011216.8, dated Feb. 15, 2011.

Dinescu, L. et al., "Design of Photonic Liquid Crystal Materials: Synthesis and Evaluation of New Chiral Thioindigo Dopants Designed to Photomodulate the Spontaneous Polarization of Ferroelectric Liquid Crystals," J. Mater. Chem., vol. 9, No. 8, pp. 1679-1686 (1999).

Gualtieri, F. et al., A Direct Metalation Approach to 2-Alkylthio-2,2-Diaryl Substituted Acetic Acids, SYNLETT, vol. 5, pp. 447-448 (1996).

Malamas, M.S. et al., "Design and synthesis of aryl diphenolic azoles as potent and selective estrogen receptor-β ligands," J. Med. Chem. 2004, vol. 47, No. 21, pp. 5021-5040.

Perry, R.J., "Synthesis of Polyimides via the Palladium-Catalyzed Carbonylation of Bis(o-iodo Esters) and Diamines," Macromolecules, vol. 28, pp. 3509-3515 (1995).

Šulcová, V., "Effect of Derivates of 3-Quinolinecarboxylic Acid on DNA Synthesis, Growth and Division in *Escherichia coli* 15 TAU," Folia Microbiologica, vol. 19, No. 4, pp. 281-291 (1974).

Zhurnal Organicheskoi Khimi 6,1, pp. 68-71 (1970).

International Search Report for Application No. PCT/JP2007/054311 dated Jun. 5, 2007.

International Search Report for Application No. PCT/JP2007/054348 dated Jun. 5, 2007.

Requirement for Restriction/Election mailed May 10, 2011, in U.S. Appl. No. 12/281,889, 8 pages.

Requirement for Restriction/Election mailed Jul. 21, 2011, in U.S. Appl. No. 12/281,889, 8 pages.

Non-Final Rejection mailed Jan. 4, 2012, in U.S. Appl. No. 12/281,889, 10 pages.

Requirement for Restriction/Election mailed May 10, 2011, in U.S. Appl. No. 12/281,921, 8 pages.

Requirement for Restriction/Election mailed Jul. 21, 2011, in U.S. Appl. No. 12/281,921, 8 pages.

\* cited by examiner

SEQUENCE LISTING

<160> NUMBER OF SEQ ID NOS: 4

<210> SEQ ID NO 1
<211> LENGTH: 32
<212> TYPE: DNA
<213> ORGANISM: Artificial Sequence
<220> FEATURE:
<223> OTHER INFORMATION: Donor plus strand for activity determination
      of HIV integrase.

<400> SEQUENCE: 1 accctttag tcagtgtgga aaatctctag ca                              32

<210> SEQ ID NO 2
<211> LENGTH: 31
<212> TYPE: DNA
<213> ORGANISM: Artificial Sequence
<220> FEATURE:
<223> OTHER INFORMATION: Donor minus strand for activity determination
      of HIV integrase.

<400> SEQUENCE: 2
actgctagag attttccaca ctgactaaaa g                              31

<210> SEQ ID NO 3
<211> LENGTH: 20
<212> TYPE: DNA
<213> ORGANISM: Artificial Sequence
<220> FEATURE:
<223> OTHER INFORMATION: Target plus strand for activity determination
      of HIV integrase.

<400> SEQUENCE: 3
tgaccaaggg ctaattcact                                           20

<210> SEQ ID NO 4
<211> LENGTH: 20
<212> TYPE: DNA
<213> ORGANISM: Artificial Sequence
<220> FEATURE:
<223> OTHER INFORMATION: Target minus strand for activity determination
      of HIV integrase.

<400> SEQUENCE: 4
agtgaattag cccttggtca                                           20

4-OXOQUINOLINE COMPOUND AND USE THEREOF AS HIV INTEGRASE INHIBITOR

This is a continuation of application Ser. No. 10/492,833, filed Oct. 15, 2004, now U.S. Pat. No. 7,176,220 which is a U.S. national stage application of PCT application PCT/JP2003/014773 filed on Nov. 20, 2003, and claims benefit of Japan Application Nos: JP2003-139616, filed May 16, 2003; JP2003-65807, filed Mar. 11, 2003; and JP 2002-336843, filed Nov. 20, 2002, the contents of which are incorporated herein by reference.

TECHNICAL FIELD

The present invention relates to a novel 4-oxoquinoline compound useful as an anti-HIV agent and a pharmaceutically acceptable salt thereof. The present invention also relates to a novel use of a certain 4-oxoquinoline compound and a pharmaceutically acceptable salt thereof as anti-HIV agents. More particularly, the present invention relates to an anti-HIV agent containing a 4-oxoquinoline compound that particularly shows an anti-HIV action based on an integrase inhibitory activity thereof, or a pharmaceutically acceptable salt thereof.

BACKGROUND ART

HIV (Human Immunodeficiency Virus (type 1)) belonging to retrovirus is a causative virus of AIDS (Acquired Immunodeficiency Syndrome).

HIV targets CD4 positive cell groups such as helper T cell, macrophage and dendritic cell and destroys these immunocompetent cells to cause immunodeficiency.

Accordingly, a pharmaceutical agent that eradicates HIV in the body or suppresses its growth is effective for the treatment or prophylaxis of AIDS.

HIV possesses a bimolecular RNA gene in a core protein, and which is covered with an envelope protein. The RNA codes for several enzymes (protease, reverse transcriptase, integrase) characteristic of the virus and the like, and has translated reverse transcriptase and integrase in the core, as well as protease inside and outside the core.

HIV attaches to and invades a host cell, causes uncoating, and releases a complex of RNA and integrase, and the like into the cytoplasm. From the RNA, DNA is transcribed by reverse transcriptase, and a full length double stranded DNA is produced. The DNA is imported into the nucleus of the host cell and integrated by integrase into the DNA of the host cell. The integrated DNA is converted to an mRNA by polymerase of the host cell, from which mRNA various proteins necessary for forming a virus are synthesized by HIV protease and the like, and a virus particle is finally formed, which then undergoes budding and its release.

These virus specific enzymes are considered to be essential for the growth of HIV. These enzymes are drawing attention as the target of the development of antiviral agents, and several anti-HIV agents have been already developed.

For example, zidovudine, didanosine, lamivudine and the like have been already on the market as reverse transcriptase inhibitors, and indinavir, nelfinavir and the like as protease inhibitors.

In addition, a multiple drug combination therapy concurrently using these pharmaceutical agents has been employed. For example, a combined use of two reverse transcriptase inhibitors (zidovudine and didanosine), and a combined use of three agents of reverse transcriptase inhibitors (zidovudine and lamivudine) and a protease inhibitor (nelfinavir) and the like have been clinically applied. Such multiple drug combination therapy is becoming a mainstream of AIDS therapy (see, e.g., Guidelines for the Use of Antiretroviral Agents in HIV-Infected Adults and Adlescent. Aug. 13, 2001).

However, some of these pharmaceutical agents are known to cause side effects such as liver function failure, central nervous disorders (e.g., vertigo), and the like. In addition, acquisition of resistance to a pharmaceutical agent causes a problem. Even worse, emergence of an HIV that shows multiple drug resistance in a multiple drug combination therapy has been known.

Under the circumstances, a further development of a novel pharmaceutical agent, particularly a development of an anti-HIV agent based on a new mechanism, has been desired, wherein a development of an anti-HIV agent having an integrase inhibitory activity is expected, because an integrase characteristic of retrovirus is an essential enzyme for the growth of HIV.

Nevertheless, an effective integrase inhibitor has not been found as yet.

Known compounds comparatively similar to the anti-HIV agent of the present invention are described in the following.

WO02/0704865 describes the following compounds [A], [B] and the like as anti-HIV agents having an integrase inhibitory activity (see WO02/0704865 p. 118, Example I-62, p. 203, Example I-152).

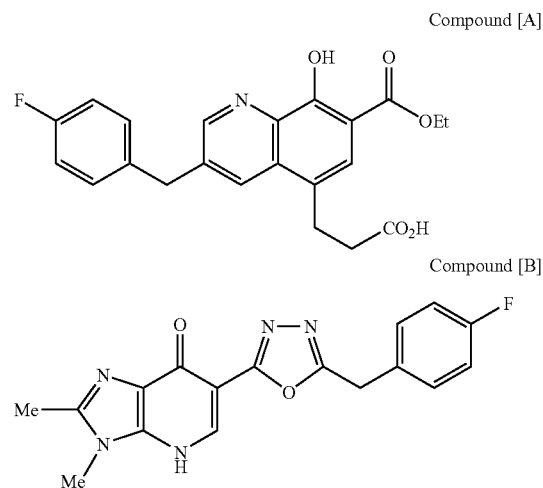

In addition, WO02/36734 describes the following compound [C] and the like as anti-HIV agents having an integrase inhibitory activity (see WO02/36734, p. 106, Ex. 3).

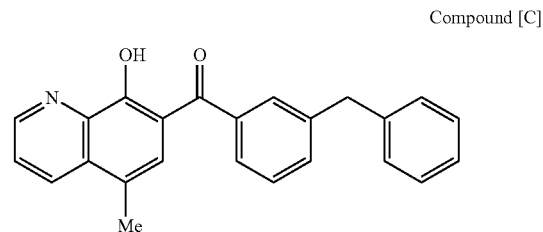

Moreover, WO02/55079 describes the following compound [D] and the like as anti-HIV agents having an integrase inhibitory activity (see WO02/055079, p. 79, Ex. 1).

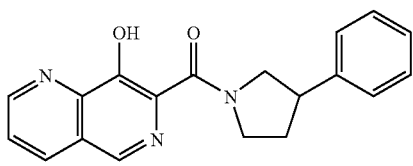
Compound [D]

However, these publications do not include the 4-oxo-quinoline compound disclosed in the present specification, or any description suggestive thereof.

The compounds comparatively similar to the compound of the present invention are described in the following.

U.S. Pat. No. 3,472,859 describes the following compound [E] and the like as antibacterial agents or antimicrobial agents (see U.S. Pat. No. 3,472,859, column 11, line 10).

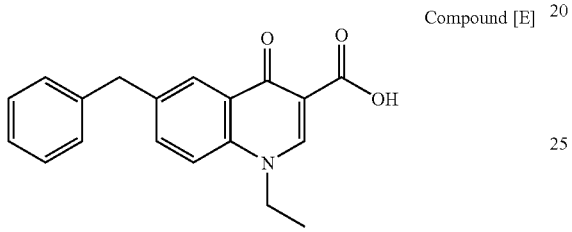
Compound [E]

In addition, JP-A-48-26772 describes the following compound [F] and the like as compounds having an antibacterial activity (see, e.g., JP-A-48-26772, p. 6, Example 9; KYUSHU KYORITSU UNIVERSITY, Memoirs Department of Engineering, No. 14, pp. 21-32, March 1990; Memoirs Kyushu Inst. Tech. (Eng.) No. 14, pp. 13-16, 1984).

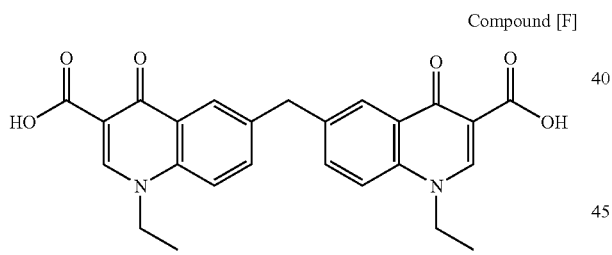
Compound [F]

As dehydrogenase inhibitors, moreover, the following compound [G] and the like have been pharmacologically evaluated (see Journal of Medicinal Chemistry, table 1, vol. 15, No. 3, pp. 235-237, 1972).

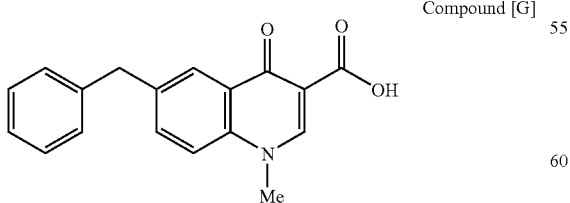
Compound [G]

In addition, JP-A-2002-534416 (patent family: WO0/40561, U.S. Pat. No. 6,248,739, EP1140850) describes the following compound [H] and the like as synthetic intermediates for compounds having an antiviral activity (see JP-A-2002-534416, p. 141, compound 60).

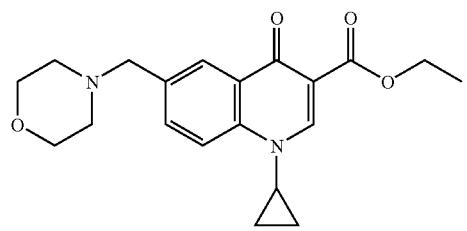
Compound [H]

JP-A-2002-534417 (patent family: WO00/40563, U.S. Pat. No. 6,248,736, EP1140851) also describes the following compound [J] and the like as synthetic intermediates for compounds having an antiviral activity (see JP-A-2002-534417, p. 34, compound 18).

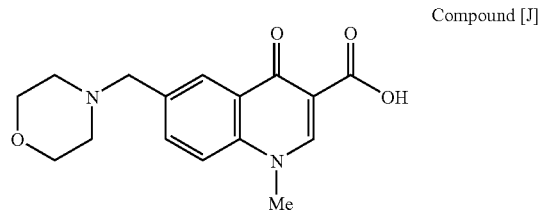
Compound [J]

Moreover, WO01/98275 (patent family: US20011103220) also describes the following compound [K] and the like as synthetic intermediates for compounds having an antiviral activity (see WO01/98275, p. 39, line 29).

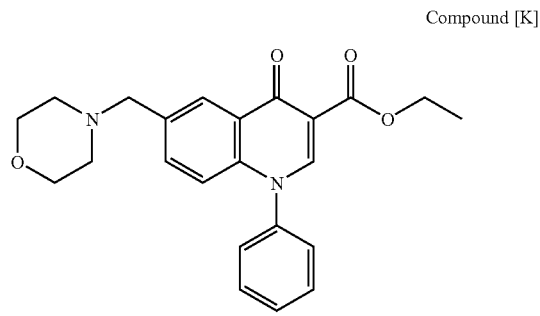
Compound [K]

Furthermore, JP-A-4-360872 (patent family: U.S. Pat. No. 5,985,894, EP498721B1) describes the following compound [L] and the like as compounds having an antagonistic action against anti-angiotensin II receptor (see JP-A-4-360872, p. 64, Table 1)).

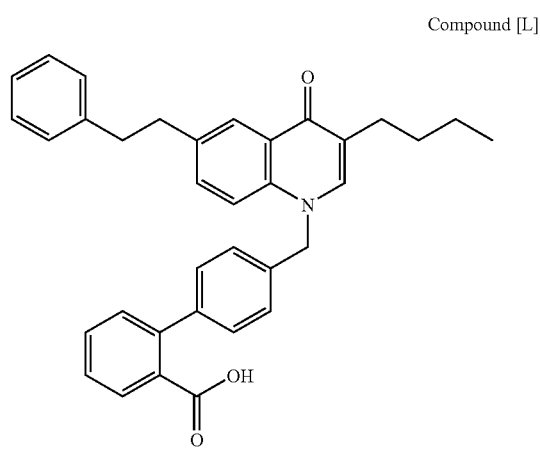
Compound [L]

DISCLOSURE OF THE INVENTION

From the findings based on the pharmacological researches and clinical results obtained so far, an anti-HIV agent is effective for the prophylaxis of the onset of AIDS and the treatment thereof, and particularly a compound having an integrase inhibitory action can provide an effective anti-HIV agent.

It is therefore an object of the present invention to provide a pharmaceutical agent having an anti-HIV action, particularly a pharmaceutical agent having an integrase inhibitory action.

The present inventors have conducted intensive studies in an attempt to find a compound having an anti-HIV action, particularly a compound having an integrase inhibitory action, and completed the present invention.

Accordingly, the present invention is shown in the following (1) to (41).

(1) An anti-HIV agent containing a 4-oxoquinoline compound represented by the following formula [I] or a pharmaceutically acceptable salt thereof as an active ingredient:

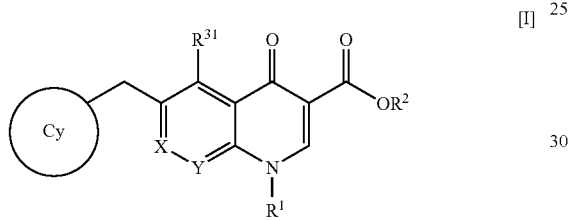

wherein ring Cy is a $C_{3-10}$ carbon ring group optionally substituted by 1 to 5 substituents selected from the following group A or a heterocyclic group optionally substituted by 1 to 5 substituents selected from the following group A wherein the heterocyclic group is a saturated or unsaturated ring containing, besides carbon atom(s), at least one heteroatom selected from a nitrogen atom, an oxygen atom and a sulfur atom, group A is a group consisting of cyano group, phenyl group, nitro group, halogen atom, $C_{1-4}$ alkyl group, halo $C_{1-4}$ alkyl group, halo $C_{1-4}$ alkyloxy group, —$OR^{a1}$, —$SR^{a1}$, —$NR^{a1}R^{a2}$, —$CONR^{a1}R^{a2}$, —$SO_2NR^{a1}R^{a2}$, —$COR^{a3}$, —$NR^{a1}COR^{a3}$, —$SO_2R^{a3}$, —$NR^{a1}SO_2R^{a3}$, —$COOR^{a1}$ and —$NR^{a2}COOR^{a3}$ wherein $R^{a1}$ and $R^{a2}$ are the same or different and each is hydrogen atom, $C_{1-4}$ alkyl group or benzyl group and $R^{a3}$ is $C_{1-4}$ alkyl group;

$R^1$ is a substituent selected from the following group B or a $C_{1-10}$ alkyl group optionally substituted by 1 to 3 substituents selected from halogen atom and the following group B wherein group B is a group consisting of $C_{3-10}$ carbon ring group optionally substituted by 1 to 5 substituents selected from the above-mentioned group A, heterocyclic group (as defined above) optionally substituted by 1 to 5 substituents selected from the above-mentioned group A, —$OR^{a4}$, —$SR^{a4}$, —$NR^{a4}R^{a5}$, —$CONR^{a4}R^{a5}$, —$SO_2NR^{a4}R^{a5}$, —$COR^{a6}$, —$NR^{a4}COR^{a6}$, —$SO_2R^{a6}$, —$NR^{a4}SO_2R^{a6}$, —$COOR^{a4}$ and —$NR^{a5}COOR^{a6}$ wherein $R^{a4}$ and $R^{a5}$ are the same or different and each is hydrogen atom, $C_{1-4}$ alkyl group, $C_{3-10}$ carbon ring group optionally substituted by 1 to 5 substituents selected from the above-mentioned group A or heterocyclic group (as defined above) optionally substituted by 1 to 5 substituents selected from the above-mentioned group A, and $R^{a6}$ is $C_{1-4}$ alkyl group, $C_{3-10}$ carbon ring group optionally substituted by 1 to 5 substituents selected from the above-mentioned group A or heterocyclic group (as defined above) optionally substituted by 1 to 5 substituents selected from the above-mentioned group A;

$R^2$ is a hydrogen atom or a $C_{1-4}$ alkyl group;

$R^{31}$ is a hydrogen atom, a cyano group, a hydroxy group, an amino group, a nitro group, a halogen atom, a $C_{1-4}$ alkyl group, a $C_{1-4}$ alkoxy group, a $C_{1-4}$ alkylsulfanyl group, a halo $C_{1-4}$ alkyl group or a halo $C_{1-4}$ alkyloxy group;

X is a C—$R^{32}$ or a nitrogen atom; and

Y is a C—$R^{33}$ or a nitrogen atom and wherein $R^{32}$ and $R^{33}$ are the same or different and each is hydrogen atom, cyano group, nitro group, halogen atom, $C_{3-10}$ carbon ring group optionally substituted by 1 to 5 substituents selected from the above-mentioned group A, heterocyclic group (as defined above) optionally substituted by 1 to 5 substituents selected from the above-mentioned group A or $C_{1-10}$ alkyl group optionally substituted by 1 to 3 substituents selected from halogen atom and the above-mentioned group B, —$OR^{a7}$, —$SR^{a7}$, —$NR^{a7}R^{a8}$, —$NR^{a7}COR^{a9}$, —$COOR^{a10}$ or —N=CH—$NR^{a10}R^{a11}$ wherein $R^{a7}$ and $R^{a8}$ are the same or different and each is hydrogen atom, group B or $C_{1-10}$ alkyl group optionally substituted by 1 to 3 substituents selected from halogen atom and the above-mentioned group B, $R^{a9}$ is $C_{1-4}$ alkyl group, and $R^{a10}$ and $R^{a11}$ are the same or different and each is hydrogen atom or $C_{1-4}$ alkyl group.

(2) The anti-HIV agent of the above-mentioned (1), wherein X is C—$R^{32}$ and Y is C—$R^{33}$.

(3) The anti-HIV agent of the above-mentioned (1), wherein ring Cy is

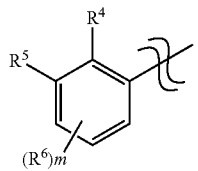

wherein $R^4$ and $R^6$ are the same or different and each is a substituent selected from the following group A wherein group A is a group consisting of cyano group, phenyl group, nitro group, halogen atom, $C_{1-4}$alkyl group, halo $C_{1-4}$ alkyl group, halo $C_{1-4}$ alkyloxy group, —$OR^{a1}$, —$SR^{a1}$, —$NR^{a1}R^{a2}$, —$CONR^{a1}R^{a2}$, —$SO_2NR^{a1}R^{a2}$, —$COR^{a3}$, —$NR^{a1}COR^{a3}$, —$SO_2R^{a3}$, —$NR^{a1}R^{a3}$, —$COOR^{a1}$ and —$NR^{a2}COOR^{a3}$ wherein $R^{a1}$ and $R^{a2}$ are the same or different and each is hydrogen atom, $C_{1-4}$ alkyl group or benzyl group and $R^{a3}$ is $C_{1-4}$ alkyl group;

$R^5$ is a substituent selected from hydrogen atom and group A, and $R^4$ and $R^5$ may form a fused ring together with a benzene ring they substitute; and m is 0 or an integer of 1 to 3, and when m is 2 or 3, then $R^6$ of each m may be the same or different.

(4) The anti-HIV agent of the above-mentioned (1), wherein $R^2$ is a hydrogen atom.

(5) A 4-oxoquinoline compound represented by the following formula [II] or a pharmaceutically acceptable salt thereof:

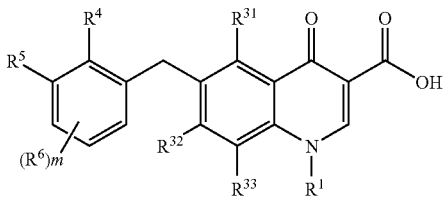

[II]

wherein
$R^4$ and $R^6$ are the same or different and each is a substituent selected from the following group A
wherein group A is a group consisting of cyano group, phenyl group, nitro group, halogen atom, $C_{1-4}$ alkyl group, halo $C_{1-4}$ alkyl group, halo $C_{1-4}$ alkyloxy group, —$OR^{a1}$, —$SR^{a1}$, —$NR^{a1}R^{a2}$, —$CONR^{a1}R^{a2}$, —$SO_2NR^{a1}R^{a2}$, —$COR^{a3}$, —$NR^{a1}COR^{a3}$, —$SO_2R^{a3}$, —$NR^{a1}SO_2R^{a3}$, —$COOR^{a1}$ and $NR^{a2}COOR^{a3}$
wherein $R^{a1}$ and $R^{a2}$ are the same or different and each is hydrogen atom, $C_{1-4}$ alkyl group or benzyl group and $R^{a3}$ is $C_{1-4}$ alkyl group;
$R^5$ is a substituent selected from hydrogen atom and the above-mentioned group A, and $R^4$ and $R^5$ may form a fused ring together with a benzene ring they substitute;
m is 0 or an integer of 1 to 3, and when m is 2 or 3, then $R^6$ of each m may be the same or different;
$R^1$ is a substituent selected from the following group B or a $C_{1-10}$ alkyl group optionally substituted by 1 to 3 substituents selected from halogen atom and the following group B
wherein group B is a group consisting of $C_{3-10}$ carbon ring group optionally substituted by 1 to 5 substituents selected from the above-mentioned group A, heterocyclic group (wherein the heterocyclic group is a saturated or unsaturated ring containing, besides carbon atom(s), at least one heteroatom selected from a nitrogen atom, an oxygen atom and a sulfur atom as defined above) optionally substituted by 1 to 5 substituents selected from the above-mentioned group A, —$OR^{a4}$, —$SR^{a4}$, —$NR^{a4}R^{a5}$, —$CONR^{a4}R^{a5}$, —$SO_2NR^{a4}R^{a5}$, —$COR^{a6}$, —$NR^{a4}COR^{a6}$, —$SO_2R^{a6}$, —$NR^{a4}SO_2R^{a6}$, —$COOR^{a4}$ and —$NR^{a5}COOR^{a6}$
wherein $R^{a4}$ and $R^{a5}$ are the same or different and each is hydrogen atom, $C_{1-4}$ alkyl group, $C_{3-10}$ carbon ring group optionally substituted by 1 to 5 substituents selected from the above-mentioned group A or heterocyclic group (as defined above) optionally substituted by 1 to 5 substituents selected from the above-mentioned group A, and $R^{a6}$ is $C_{1-4}$ alkyl group, $C_{3-10}$ carbon ring group optionally substituted by 1 to 5 substituents selected from the above-mentioned group A or heterocyclic group (as defined above) optionally substituted by 1 to 5 substituents selected from the above-mentioned group A;
$R^{31}$ is a hydrogen atom, a cyano group, a hydroxy group, an amino group, a nitro group, a halogen atom, a $C_{1-4}$ alkyl group, a $C_{1-4}$ alkoxy group, a $C_{1-4}$ alkylsulfanyl group, a halo $C_{1-4}$ alkyl group or a halo $C_{1-4}$ alkyloxy group; and
$R^{32}$ and $R^{33}$ are the same or different and each is a hydrogen atom, a cyano group, a nitro group, a halogen atom, a $C_{3-10}$ carbon ring group optionally substituted by 1 to 5 substituents selected from the above-mentioned group A, a heterocyclic group (as defined above) optionally substituted by 1 to 5 substituents selected from the above-mentioned group A, $C_{1-10}$ alkyl group optionally substituted by 1 to 3 substituents selected from halogen atom and the above-mentioned group B, $OR^{a7}$, —$SR^{a7}$, —$NR^{a7}R^{a8}$, —$NR^{a7}COR^{a9}$, —$COOR^{a10}$ or —N=CH—$NR^{a10}R^{a11}$
wherein $R^{a7}$ and $R^{a8}$ are the same or different and each is hydrogen atom, group B or $C_{1-10}$ alkyl group optionally substituted by 1 to 3 substituents selected from halogen atom and the above-mentioned group B, $R^{a9}$ is $C_{1-4}$ alkyl group, and $R^{a10}$ and $R^{a11}$ are the same or different and each is hydrogen atom or $C_{1-4}$ alkyl group.

(6) The 4-oxoquinoline compound of the above-mentioned (5), wherein $R^{31}$ is a hydrogen atom, a cyano group, a hydroxy group or a $C_{1-4}$ alkoxy group, or a pharmaceutically acceptable salt thereof.

(7) The 4-oxoquinoline compound of the above-mentioned (6), wherein $R^{31}$ is a hydrogen atom, or a pharmaceutically acceptable salt thereof.

(8) The 4-oxoquinoline compound of the above-mentioned (5), wherein
$R^{32}$ and $R^{33}$ are the same or different and each is a hydrogen atom, a cyano group, a halogen atom, a heterocyclic group optionally substituted by 1 to 5 substituents selected from the following group A
wherein the heterocyclic group is a saturated or unsaturated ring containing, besides carbon atom(s), at least one heteroatom selected from a nitrogen atom, an oxygen atom and a sulfur atom and group A is a group consisting of cyano group, phenyl group, nitro group, halogen atom, $C_{1-4}$ alkyl group, halo $C_{1-4}$ alkyl group, halo $C_{1-4}$ alkyloxy group, —$OR^{a1}$, —$SR^{a1}$, —$NR^{a1}R^{a2}$, —$CONR^{a1}R^{a2}$, —$SO_2NR^{a1}R^{a2}$, —$COR^{a3}$, —$NR^{a1}COR^{a3}$, —$SO_2R^{a3}$, —$NR^{a1}SO_2R^{a3}$, —$COOR^{a1}$ and —$NR^{a2}COOR^{a3}$
wherein $R^{a1}$ and $R^{a2}$ are the same or different and each is hydrogen atom $C_{1-4}$ alkyl group or benzyl group and $R^{a3}$ is $C_{1-4}$ alkyl group,
a $C_{1-10}$ alkyl group optionally substituted by 1 to 3 substituents selected from halogen atom and the following group B
wherein group B is a group consisting of $C_{3-10}$ carbon ring group optionally substituted by 1 to 5 substituents selected from the above-mentioned group A, heterocyclic group (as defined above) optionally substituted by 1 to 5 substituents selected from the above-mentioned group A, —$OR^{a4}$, —$SR^{a4}$, —$NR^{a4}R^{a5}$, —$CONR^{a4}R^{a5}$, —$SO_2NR^{a4}R^{a5}$, —$COR^{a6}$, —$NR^{a4}COR^{a6}$, —$SO_2R^{a6}$, —$NR^{a4}SO_2R^{a6}$, —$COOR^{a4}$ and —$NR^{a5}COOR^{a6}$
wherein $R^{a4}$ and $R^{a5}$ are the same or different and each is hydrogen atom, $C_{1-4}$ alkyl group, $C_{3-10}$ carbon ring group optionally substituted by 1 to 5 substituents selected from the above-mentioned group A or heterocyclic group (as defined above) optionally substituted by 1 to 5 substituents selected from the above-mentioned group A, and $R^{a6}$ is $C_{1-4}$ alkyl group, $C_{3-10}$ carbon ring group optionally substituted by 1 to 5 substituents selected from the above-mentioned group A or heterocyclic group (as defined above) optionally substituted by 1 to 5 substituents selected from the above-mentioned group A,
—$OR^{a7}$, —$SR^{a7}$, —$NR^{a7}R^{a8}$, —$NR^{a7}COR^{a9}$, —$COOR^{a10}$ or —N=CH—$NR^{a10}R^{a11}$
wherein $R^{a7}$ and $R^{a8}$ are the same or different and each is hydrogen atom, group B or $C_{1-10}$ alkyl group optionally substituted by 1 to 3 substituents selected from halogen atom and the above-mentioned group B, $R^{a9}$ is $C_{1-4}$ alkyl group, and $R^{a10}$ and $R^{a11}$ are the same or different and each is hydrogen atom or $C_{1-4}$ alkyl group, or a pharmaceutically acceptable salt thereof.

(9) The 4-oxoquinoline compound of the above-mentioned (5), wherein $R^{32}$ is a hydrogen atom, a cyano group, a halogen atom, a $C_{1-10}$ alkyl group optionally substituted by 1 to 3 substituents selected from halogen atom and the following group B wherein group B is a group consisting of $C_{3-10}$ carbon ring group optionally substituted by 1 to 5 substituents selected from the above-mentioned group A, heterocyclic group (wherein the heterocyclic group is a saturated or unsaturated ring containing, besides carbon atom(s), at least one heteroatom selected from a nitrogen atom, an oxygen atom and a sulfur atom) optionally substituted by 1 to 5 substituents selected from the above-mentioned group A, —$OR^{a4}$, —$SR^{a4}$, —$NR^{a4}R^{a5}$, —$CONR^{a4}R^{a5}$, —$SO_2NR^{a4}R^{a5}$, —$COR^{a6}$, —$NR^{a4}COR^{a6}$, —$SO_2R^{a6}$, —$NR^{a4}SO_2R^{a6}$, —$COOR^{a4}$ and —$NR^{a5}COOR^{a6}$ wherein $R^{a4}$ and $R^{a5}$ are the same or different and each is hydrogen atom, $C_{1-4}$ alkyl group, $C_{3-10}$ carbon ring group optionally substituted by 1 to 5 substituents selected from the above-mentioned group A or heterocyclic group (as defined above) optionally substituted by 1 to 5 substituents selected from the above-mentioned group A, and $R^{a6}$ is $C_{1-4}$ alkyl group, $C_{3-10}$ carbon ring group optionally substituted by 1 to 5 substituents selected from the above-mentioned group A or heterocyclic group (as defined above) optionally substituted by 1 to 5 substituents selected from the above-mentioned group A, —$OR^{a7}$, —$SR^{a7}$, —$NR^{a7}R^{a8}$, —$NR^{a7}COR^{a9}$ or —$COOR^{a10}$ wherein $R^{a7}$ and $R^{a8}$ are the same or different and each is hydrogen atom, group B or $C_{1-10}$ alkyl group optionally substituted by 1 to 3. substituents selected from halogen atom and the above-mentioned group B, $R^{a9}$ is $C_{1-4}$ alkyl group, and $R^{a10}$ is hydrogen atom or $C_{1-4}$ alkyl group, or a pharmaceutically acceptable salt thereof.

(10) The 4-oxoquinoline compound of the above-mentioned (9), wherein $R^{32}$ is a hydrogen atom, —$OR^{a7}$ or —$NR^{a7}R^{a8}$ wherein $R^{a7}$ and $R^{a8}$ are the same or different and each is hydrogen atom, group B or $C_{1-10}$ alkyl group optionally substituted by 1 to 3 substituents selected from halogen atom and the above-mentioned group B, or a pharmaceutically acceptable salt thereof.

(11) The 4-oxoquinoline compound of the above-mentioned (8), wherein $R^{33}$ is a hydrogen atom, a $C_{1-0}$ alkyl group optionally substituted by 1 to 3 substituents selected from halogen atom and the following group B wherein group B is a group consisting of $C_{3-10}$ carbon ring group optionally substituted by 1 to 5 substituents selected from the above-mentioned group A, heterocyclic group (wherein the heterocyclic group is a saturated or unsaturated ring containing, besides carbon atom(s), at least one heteroatom selected from a nitrogen atom, an oxygen atom and a sulfur atom) optionally substituted by 1 to 5 substituents selected from the above-mentioned group A, —$OR^{a4}$, —$SR^{a4}$, —$NR^{a4}R^{a5}$, —$CONR^{a4}R^{a5}$, —$SO_2NR^{a4}R^{a5}$, —$COR^{a6}$, —$NR^{a4}COR^{a6}$, —$SO_2R^{a6}$, —$NR^{a4}SO_2R^{a6}$, —$COOR^{a4}$ and —$NR^{a5}$—$COOR^{a6}$ wherein $R^{a4}$ and $R^{a5}$ are the same or different and each is hydrogen atom, $C_{1-4}$ alkyl group, $C_{3-10}$ carbon ring group optionally substituted by 1 to 5 substituents selected from the above-mentioned group A or heterocyclic group (as defined above) optionally substituted by 1 to 5 substituents selected from the above-mentioned group A, and $R^{a6}$ is $C_{1-4}$ alkyl group, $C_{3-10}$ carbon ring group optionally substituted by 1 to 5 substituents selected from the above-mentioned group A or heterocyclic group (as defined above) optionally substituted by 1 to 5 substituents selected from the above-mentioned group A, —$OR^{a7}$ or —$NR^{a7}R^{a8}$ wherein $R^{a7}$ and $R^{a8}$ are the same or different and each is hydrogen atom, group B or $C_{1-10}$ alkyl group, optionally substituted by 1 to 3 substituents selected from halogen atom and the above-mentioned group B, or a pharmaceutically acceptable salt thereof.

(12) The 4-oxoquinoline compound of the above-mentioned (11), wherein $R^{33}$ is a hydrogen atom, —$OR^{a7}$ or —$NR^{a7}R^{a8}$ wherein $R^{a7}$ and $R^{a8}$ are the same or different and each is hydrogen atom, group B or $C_{1-10}$ alkyl group, optionally substituted by 1 to 3 substituents selected from halogen atom and the above-mentioned group B, or a pharmaceutically acceptable salt thereof.

(13) The 4-oxoquinoline compound of any of the above-mentioned (8) to (12), wherein $R^{a7}$ and $R^{a8}$ are the same or different and each is a $C_{1-10}$ alkyl group optionally substituted by 1 to 3 substituents selected from halogen atom and the following group B wherein group B is a group consisting of $C_{3-10}$ carbon ring group optionally substituted by 1 to 5 substituents selected from the above-mentioned group A, heterocyclic group (wherein the heterocyclic group is a saturated or unsaturated ring containing, besides carbon atom(s), at least one heteroatom selected from a nitrogen atom, an oxygen atom and a sulfur atom) optionally substituted by 1 to 5 substituents selected from the above-mentioned group A, —$OR^{a4}$, —$SR^{a4}$, —$NR^{a4}R^{a5}$, —$CONR^{a4}R^{a5}$, —$SO_2NR^{a4}R^{a5}$, —$COR^{a6}$, —$NR^{a4}COR^{a6}$, —$SO_2R^{a6}$, —$NR^{a4}SO_2R^{a6}$, —$COOR^{a4}$ and —$NR^{a5}COOR^{a6}$ wherein $R^{a4}$ and $R^{a5}$ are the same or different and each is hydrogen atom, $C_{1-4}$ alkyl group, $C_{3-10}$ carbon ring group optionally substituted by 1 to 5 substituents selected from the above-mentioned group A or heterocyclic group (as defined above) optionally substituted by 1 to 5 substituents selected from the above-mentioned group A, and $R^{a6}$ is $C_{1-4}$ alkyl group, $C_{3-10}$ carbon ring group optionally substituted by 1 to 5 substituents selected from the above-mentioned group A or heterocyclic group (as defined above) optionally substituted by 1 to 5 substituents selected from the above-mentioned group A, or a pharmaceutically acceptable salt thereof.

(14) The 4-oxoquinoline compound of the above-mentioned (5), wherein $R^4$ and $R^5$ are the same or different and each is a substituent selected from cyano group, phenyl group, nitro group, halogen atom, $C_{1-4}$ alkyl group, halo $C_{1-4}$ alkyl group, halo $C_{1-4}$ alkyloxy group, —$OR^{a1}$, —$SR^{a1}$, —$NR^{a1}R^{a2}$, —$CONR^{a1}R^{a2}$, —$SO_2NR^{a1}R^{a2}$, —$NR^{a1}COR^{a3}$, —$SO_2R^{a3}$, —$NR^{a2}COOR^{a3}$ and —$COOR^{a1}$ wherein $R^{a1}$ and $R^{a2}$ are the same or different and each is hydrogen atom, $C_{1-4}$ alkyl group or benzyl group, and $R^{a3}$ is $C_{1-4}$ alkyl group, or a pharmaceutically acceptable salt thereof.

(15) The 4-oxoquinoline compound of the above-mentioned (14), wherein
$R^4$ is a phenyl group, a halogen atom, a $C_{1-4}$ alkyl group, a halo $C_{1-4}$ alkyloxy group, $-OR^{a1}$, $-NR^{a1}R^{a2}$, $-CONR^{a1}R^{a2}$, $-SO_2NR^{a1}R^{a2}$, $-NR^{a1}COR^{a3}$, $-SO_2R^{a3}$, $-NR^{a1}SO_2R^{a3}$ or $-COO^{a1}$
wherein $R^{a1}$ and $R^{a2}$ are the same or different and each is hydrogen atom, $C_{1-4}$ alkyl group or benzyl group, and $R^{a3}$ is $C_{1-4}$ alkyl group,
or a pharmaceutically acceptable salt thereof.
(16) The 4-oxoquinoline compound of the above-mentioned (15), wherein $R^4$ is a halogen atom,
or a pharmaceutically acceptable salt thereof.
(17) The 4-oxoquinoline compound of the above-mentioned (5), wherein
$R^5$ is a hydrogen atom, a cyano group, a phenyl group, a nitro group, a halogen atom, a $C_{1-4}$ alkyl group, a halo $C_{1-4}$ alkyl group, $-OR^{a1}$, $-SR^{a1}$, $-NR^{a1}R^{a2}$, $-CONR^{a1}R^{a2}$, $-SO_2NR^{a1}R^{a2}$ or $-NR^{a1}COR^{a3}$
wherein $R^{a1}$ and $R^{a2}$ are the same or different and each is hydrogen atom, $C_{1-4}$ alkyl group or benzyl group, and $R^{a3}$ is $C_{1-4}$ alkyl group,
or a pharmaceutically acceptable salt thereof.
(18) The 4-oxoquinoline compound of the above-mentioned (5), wherein $R^6$ is a halogen atom,
or a pharmaceutically acceptable salt thereof.
(19) The 4-oxoquinoline compound of the above-mentioned (5), wherein m is 0 or 1,
or a pharmaceutically acceptable salt thereof.
(20) The 4-oxoquinoline compound of the above-mentioned (5), wherein
$R^1$ is a $C_{3-10}$ carbon ring group optionally substituted by 1 to 5 substituents selected from the following group A
wherein group A is a group consisting of cyano group, phenyl group, nitro group, halogen atom, $C_{1-4}$ alkyl group, halo $C_{1-4}$ alkyl group, halo $C_{1-4}$ alkyloxy group, $-OR^{a1}$, $-SR^{a1}$, $-NR^{a1}R^{a2}$, $-CONR^{a1}R^{a2}$, $-SO_2NR^{a1}R^{a2}$, $-COR^{a3}$, $-NR^{a1}COR^{a3}$, $-SO_2R^{a3}$, $-NR^{a1}SO_2R^{a3}$, $-COOR^{a1}$ and $-NR^{a2}COR^{a3}$
wherein $R^{a1}$ and $R^{a2}$ are the same or different and each is hydrogen atom, $C_{1-4}$ alkyl group or benzyl group and $R^3$ is $C_{1-4}$ alkyl group,
a substituent selected from $-NR^{a4}R^{a5}$, $-NR^{a4}COR^{a6}$, $-NR^{a4}SO_2R^{a6}$ and $-NR^{a5}COOR^{a6}$
wherein $R^{a4}$ and $R^{a5}$ are the same or different and each is hydrogen atom, $C_{1-4}$ alkyl group, $C_{3-10}$ carbon ring group optionally substituted by 1 to 5 substituents selected from the above-mentioned group A or heterocyclic groups (wherein the heterocyclic group is a saturated or unsaturated ring containing, besides carbon atom(s), at least one heteroatom selected from a nitrogen atom, an oxygen atom and a sulfur atom) optionally substituted by 1 to 5 substituents selected from the above-mentioned group A, and $R^{a6}$ is $C_{1-4}$ alkyl group, $C_{3-10}$ carbon ring group optionally substituted by 1 to 5 substituents selected from the above-mentioned group A or heterocyclic group (as defined above) optionally substituted by 1 to 5 substituents selected from the above-mentioned group A, or
a $C_{1-10}$ alkyl group optionally substituted by 1 to 3 substituents selected from halogen atom and group B
wherein group B is a group consisting of $C_{3-10}$ carbon ring group optionally substituted by 1 to 5 substituents selected from the above-mentioned group A, heterocyclic group (as defined above) optionally substituted by 1 to 5 substituents selected from the above-mentioned group A, $-OR^{a4}$, $-SR^{a4}$, $-NR^{a4}R^{a5}$, $-CONR^{a4}R^{a5}$, $-SO_2NR^{a4}R^{a5}$, $-COR^{a6}$, $-NR^{a4}COR^{a6}$, $-SO_2R^{a6}$, $-NR^{a4}SO_2R^{a6}$, $-COOR^{a4}$ and $-NR^{a5}COOR^{a6}$ (wherein $R^{a4}$, $R^{a5}$, $R^{a6}$ and group A are as defined above),
or a pharmaceutically acceptable salt thereof.
(21) The 4-oxoquinoline compound of the above-mentioned (20), wherein
$R^1$ is a $C_{1-10}$ alkyl group optionally substituted by 1 to 3 substituents selected from halogen atom and group B
wherein group B is a group consisting of $C_{3-10}$ carbon ring group optionally substituted by 1 to 5 substituents selected from the above-mentioned group A, heterocyclic group (as defined above) optionally substituted by 1 to 5 substituents selected from the above-mentioned group A, $-OR^{a4}$, $-SR^{a4}$, $-NR^{a4}R^{a5}$, $-CONR^{a4}R^{a5}$, $-SO_2NR^{a4}R^{a5}$, $-COR^{a6}$, $-NR^{a4}COR^{a6}$, $-SO_2R^{a6}$, $-NR^{a4}SO_2R^{a6}$, $-COOR^{a4}$ and $-NR^{a5}COOR^{a6}$
wherein $R^{a4}$ and $R^{a5}$ are the same or different and each is hydrogen atom, $C_{1-4}$ alkyl group, $C_{3-10}$ carbon ring group optionally substituted by 1 to 5 substituents selected from the above-mentioned group A or heterocyclic group (as defined above) optionally substituted by 1 to 5 substituents selected from the above-mentioned group A, and $R^{a6}$ is $C_{1-4}$ alkyl group, $C_{3-10}$ carbon ring group optionally substituted by 1 to 5 substituents selected from the above-mentioned group A or heterocyclic group (as defined above) optionally substituted by 1 to 5 substituents selected from the above-mentioned group A,
or a pharmaceutically acceptable salt thereof.
(22) The 4-oxoquinoline compound of the above-mentioned 5, which is selected from the group consisting of the following compounds:
6-(2,3-Dichlorobenzyl)-1-(2-hydroxyethyl)-4-oxo-1,4-dihydroquinoline-3-carboxylic acid (Example 1-1),
6-(2,3-Dichlorobenzyl)-8-fluoro-1-(2-hydroxyethyl)-4-oxo-1,4-dihydroquinoline-3-carboxylic acid (Example 1-2),
6-(2,3-Dichlorobenzyl)-1-(2-methanesulfonylaminoethyl)-4-oxo-1,4-dihydroquinoline-3-carboxylic acid (Example 1-3),
6-(2,3-Dichlorobenzyl)-1-(2-imidazol-1-ylethyl)-4-oxo-1,4-dihydroquinoline-3-carboxylic acid (Example 1-4),
6-(2,3-Dichlorobenzyl)-1-dimethylcarbamoylmethyl-4-oxo-1,4-dihydroquinoline-3-carboxylic acid (Example -1-5),
6-(2,3-Dichlorobenzyl)-1-methylcarbamoylmethyl-4-oxo-1,4-dihydroquinoline-3-carboxylic acid (Example 1-6),
1-Carbamoylmethyl-6-(2,3-Dichlorobenzyl)-4-oxo-1,4-dihydroquinoline-3-carboxylic acid (Example 1-7),
6-(2,3-Dichlorobenzyl)-1-isopropyl-4-oxo-1,4-dihydroquinoline-3-carboxylic acid (Example 1-8),
6-(2,3-Dichlorobenzyl)-4-oxo-1-sulfamoylmethyl-1,4-dihydroquinoline-3-carboxylic acid (Example 1-9),
1-(2-Carboxyethyl)-6-(2,3-dichlorobenzyl)-4-oxo-1,4-dihydroquinoline-3-carboxylic acid (Example 1-10),
1-(2-Hydroxyethyl)-6-naphthalen-1-ylmethyl-4-oxo-1,4-dihydroquinoline-3-carboxylic acid (Example 1-11),
6-(2,3-Dichlorobenzyl)-1-(2-hydroxyethyl)-4-oxo-1,4-dihydroquinoline-3-carboxylic acid methyl ester (Example 1-12),
1-(2-Carbamoylethyl)-6-(2,3-dichlorobenzyl)-4-oxo-1,4-dihydroquinoline-3-carboxylic acid (Example 1-13),
6-(2,3-Dichlorobenzyl)-4-oxo-1-(2-oxopropyl)-1,4-dihydroquinoline-3-carboxylic acid (Example 1-14),
1-Benzyl-6-(2,3-dichlorobenzyl)-4-oxo-1,4-dihydroquinoline-3-carboxylic acid (Example 1-15),
6-(2,3-Dichlorobenzyl)-4-oxo-1-phenethyl-1,4-dihydroquinoline-3-carboxylic acid (Example 1-16), 6-(2,3-Dichlorobenzyl)-1-(3-phenylpropyl)-4-oxo-1,4-dihydroquinoline-3-carboxylic acid (Example 1-17),
6-(2,3-Dichlorobenzyl)-1-isobutyl-4-oxo-1,4-dihydroquinoline-3-carboxylic acid (Example 1-18),
6-(2,3-Dichlorobenzyl)-1-(4-phenylbutyl)-4-oxo-1,4-dihydroquinoline-3-carboxylic acid (Example 1-19),
1-Biphenyl-2-ylmethyl-6-(2,3-dichlorobenzyl)-4-oxo-1,4-dihydroquinoline-3-carboxylic acid (Example 1-20),
6-(2,3-Dichlorobenzyl)-1-(4-hydroxybutyl)-4-oxo-1,4-dihydroquinoline-3-carboxylic acid (Example 1-21),
1-Benzo[b]thiophen-2-ylmethyl-6-(2,3-dichlorobenzyl)-4-oxo-1,4-dihydroquinoline-3-carboxylic acid (Example 1-22),
6-(2,3-dichlorobenzyl)-1-(3,4-dichlorobenzyl)-4-oxo-1,4-dihydroquinoline-3-carboxylic acid (Example 1-23),
6-(2,3-Dichlorobenzyl)-1-(2-dimethylaminoethyl)-4-oxo-1,4-dihydroquinoline-3-carboxylic acid (Example 1-24),
6-(2,3-Dichlorobenzyl)-1-(3-hydroxypropyl)-4-oxo-1,4-dihydroquinoline-3-carboxylic acid (Example 1-25),
6-(2,3-Dichlorobenzyl)-1-(2-methoxyethyl)-4-oxo-1,4-dihydroquinoline-3-carboxylic acid (Example 1-26),
6-(2,3-Dichlorobenzyl)-1-(2,2,2-trifluoroethyl)-4-oxo-1,4-dihydroquinoline-3-carboxylic acid (Example 1-27),
1-Carboxymethyl-6-(2,3-dichlorobenzyl)-4-oxo-1,4-dihydroquinoline-3-carboxylic acid (Example 1-28),
6-(2,3-Dichlorobenzyl)-1-[2-(4-methylthiazol-5-yl)ethyl]-4-oxo-1,4-dihydroquinoline-3-carboxylic acid (Example 1-29),
6-(2,3-Dichlorobenzyl)-1-(2-hydroxypropyl)-4-oxo-1,4-dihydroquinoline-3-carboxylic acid (Example 1-30),
6-(2,3-Dichlorobenzyl)-1-(2-methylsulfanylethyl)-4-oxo-1,4-dihydroquinoline-3-carboxylic acid (Example 1-32),
6-(2-Chloro-6-fluorobenzyl)-1-(2-hydroxyethyl)-4-oxo-1,4-dihydroquinoline-3-carboxylic acid (Example 1-33),
6-(2,3-Dichlorobenzyl)-1-(5-hydroxypentyl)-4-oxo-1,4-dihydroquinoline-3-carboxylic acid (Example 1-34),
6-(2,3-dichlorobenzyl)-1-(2-morpholin-4-ylethyl)-4-oxo-1,4-dihydroquinoline-3-carboxylic acid (Example 1-35),
6-(2,3-Dichlorobenzyl)-1-methyl-4-oxo-1,4-dihydroquinoline-3-carboxylic acid (Example 1-36),
6-(2,3-Dichlorobenzyl)-1-ethyl-4-oxo-1,4-dihydroquinoline-3-carboxylic acid (Example 1-37),
6-(2,3-Dichlorobenzyl)-4-oxo-1-propyl-1,4-dihydroquinoline-3-carboxylic acid (Example 1-38),
1-Butyl-6-(2,3-Dichlorobenzyl)-4-oxo-1,4-dihydroquinoline-3-carboxylic acid (Example 1-39),
1-Cyclopentylmethyl-6-(2,3-dichlorobenzyl)-4-oxo-1,4-dihydroquinoline-3-carboxylic acid (Example 1-40),
6-(2,3-Dichlorobenzyl)-1-(2-methanesulfonylethyl)-4-oxo-1,4-dihydroquinoline-3-carboxylic acid (Example 1-41),
1-Cyclohexylmethyl-6-(2,3-dichlorobenzyl)-4-oxo-1,4-dihydroquinoline-3-carboxylic acid (Example 1-42),
6-(2,3-Dichlorobenzyl)-1-(2-hydroxy-2-phenylethyl)-4-oxo-1,4-dihydroquinoline-3-carboxylic acid (Example 1-43),
6-(2,3-Dichlorobenzyl)-1-(2-fluoroethyl)-4-oxo-1,4-dihydroquinoline-3-carboxylic acid (Example 1-44),
6-(2,3-Dichlorobenzyl)-4-oxo-1-(2-pyridin-2-ylethyl)-1,4-dihydroquinoline-3-carboxylic acid (Example 1-45),
1-(2-Aminoethyl)-6-(2,3-dichlorobenzyl)-4-oxo-1,4-dihydroquinoline-3-carboxylic acid (Example 1-46),
6-(2,3-Dichlorobenzyl)-1-(2-hydroxy-2-methylpropyl)-4-oxo-1,4-dihydroquinoline-3-carboxylic acid (Example 1-47),
1-(2-Acetylaminoethyl)-6-(2,3-dichlorobenzyl)-4-oxo-1,4-dihydroquinoline-3-carboxylic acid (Example 1-48),
6-(2,3-Dichlorobenzyl)-1-(2-ethoxycarbonylaminoethyl)-4-oxo-1,4-dihydroquinoline-3-carboxylic acid (Example 1-49),
6-(2,3-Difluorobenzyl)-1-(2-hydroxyethyl)-4-oxo-1,4-dihydroquinoline-3-carboxylic acid (Example 1-50),
6-(2-Chloro-4-fluorobenzyl)-1-(2-hydroxyethyl)-4-oxo-1,4-dihydroquinoline-3-carboxylic acid (Example 1-51),
6-(2-Chlorobenzyl)-4-oxo-1-phenethyl-1,4-dihydroquinoline-3-carboxylic acid (Example 1-65),
6-(2-Chloro-3-fluorobenzyl)-1-(2-hydroxyethyl)-4-oxo-1,4-dihydroquinoline-3-carboxylic acid (Example 1-66),
6-(2,3-Dichlorobenzyl)-1-methylsulfanylmethyl-4-oxo-1,4-dihydroquinoline-3-carboxylic acid (Example 1-68),
6-(2,3-Dichlorobenzyl)-1-methanesulfonylmethyl-4-oxo-1,4-dihydroquinoline-3-carboxylic acid (Example 1-69),
1-tert-Butylsulfamoylmethyl-6-(2,3-dichlorobenzyl)-4-oxo-1,4-dihydroquinoline-3-carboxylic acid (Example 1-70),
6-(2,3-Dichlorobenzyl)-1-methylsulfamoylmethyl-4-oxo-1,4-dihydroquinoline-3-carboxylic acid (Example 1-71),
6-(2,3-Dichlorobenzyl)-1-dimethylsulfamoylmethyl-4-oxo-1,4-dihydroquinoline-3-carboxylic acid (Example 1-72),
6-(2-Chloro-3,6-difluorobenzyl)-1-(2-hydroxyethyl)-4-oxo-1,4-dihydroquinoline-3-carboxylic acid (Example 1-73),
6-(2,3-Dichlorobenzyl)-1-(2,3-Dihydroxypropyl)-4-oxo-1,4-dihydroquinoline-3-carboxylic acid (Example 1-74),
6-(2-Chloro-6-fluorobenzyl)-1-sulfamoylmethyl-4-oxo-1,4-dihydroquinoline-3-carboxylic acid (Example 1-75),
6-(2-Chloro-6-fluorobenzyl)-1-methylsulfamoylmethyl-4-oxo-1,4-dihydroquinoline-3-carboxylic acid (Example 1-76),
6-(2-Chloro-6-fluorobenzyl)-1-dimethylsulfamoylmethyl-4-oxo-1,4-dihydroquinoline-3-carboxylic acid (Example 1-77),
6-(2-Chloro-3-methylbenzyl)-1-(2-hydroxyethyl)-4-oxo-1,4-dihydroquinoline-3-carboxylic acid (Example 1-79),
6-(2-Bromobenzyl)-1-(2-hydroxyethyl)-4-oxo-1,4-dihydroquinoline-3-carboxylic acid (Example 1-80),
6-(2-Chloro-3-methoxybenzyl)-1-(2-hydroxyethyl)-4-oxo-1,4-dihydroquinoline-3-carboxylic acid (Example 1-82),
1-(2-Hydroxyethyl)-6-(2-methanesulfonylbenzyl)-4-oxo-1,4-dihydroquinoline-3-carboxylic acid (Example 1-85),
6-Biphenyl-2-ylmethyl-1-(2-hydroxyethyl)-4-oxo-1,4-dihydroquinoline-3-carboxylic acid (Example 1-86),
6-(2-Chlorobenzyl)-1-(2-hydroxyethyl)-4-oxo-1,4-dihydroquinoline-3-carboxylic acid (Example 1-87),
6-(2-Chloro-5-methylsulfanylbenzyl)-1-(2-hydroxyethyl)-4-oxo-1,4-dihydroquinoline-3-carboxylic acid (Example 1-92)
1-(2-Hydroxyethyl)-4-oxo-6-(2-trifluoromethyloxybenzyl)-1,4-dihydroquinoline-3-carboxylic acid (Example 1-93),
6-(2-Chloro-5-methylbenzyl)-1-(2-hydroxyethyl)-4-oxo-1,4-dihydroquinoline-3-carboxylic acid (Example 1-97),
6-(3-Chloro-2-fluorobenzyl)-1-(2-hydroxyethyl)-4-oxo-1,4-dihydroquinoline-3-carboxylic acid (Example 1-99),
6-(3-Chloro-2,6-difluorobenzyl)-1-(2-hydroxyethyl)-4-oxo-1,4-dihydroquinoline-3-carboxylic acid (Example 1-100),
6-(2,3-Dichlorobenzyl)-1-(2-hydroxyethyl)-7-methoxy-4-oxo-1,4-dihydroquinoline-3-carboxylic acid (Example 1-101),
1-Cyclopropyl-6-(2,3-dichlorobenzyl)-4-oxo-1,4-dihydroquinoline-3-carboxylic acid (Example 1-102),
1-Amino-6-(2,3-dichlorobenzyl)-4-oxo-1,4-dihydroquinoline-3-carboxylic acid (Example 2-1),
6-(2,3-Dichlorobenzyl)-1-methoxycarbonylamino-4-oxo-1,4-dihydroquinoline-3-carboxylic acid (Example 2-2),
1-Acetylamino-6-(2,3-dichlorobenzyl)-4-oxo-1,4-dihydroquinoline-3-carboxylic acid (Example 2-3), 6-(2,3-Dichlorobenzyl)-1-methanesulfonylamino-4-oxo-1,4-dihydroquinoline-3-carboxylic acid (Example 2-4), 6-(2,3-Dichlorobenzyl)-1-(N-methanesulfonyl-N-methylamino)-4-oxo-1,4-dihydroquinoline-3-carboxylic acid (Example 2-5), 6-(2,3-Dichlorobenzyl)-1-dimethylamino-4-oxo-1,4-dihydroquinoline-3-carboxylic acid (Example 2-6), 6-(2,3-Dichlorobenzyl)-1-methylamino-4-oxo-1,4-dihydroquinoline-3-carboxylic acid (Example 2-7), 6-(2,3-Dichlorobenzyl)-1-ethylamino-4-oxo-1,4-dihydroquinoline-3-carboxylic acid (Example 2-8), 6-(2,3-Dichlorobenzyl)-1-(2-hydroxyethyl)-5-methoxy-4-oxo-1,4-dihydroquinoline-3-carboxylic acid (Example 3-1), 6-(3-Chloro-2-methylbenzyl)-1-(2-hydroxyethyl)-4-oxo-1,4-dihydroquinoline-3-carboxylic acid (Example 3-2), 6-(3-Chloro-2-methoxybenzyl)-1-(2-hydroxyethyl)-4-oxo-1,4-dihydroquinoline-3-carboxylic acid (Example 3-3), 6-(3-Chloro-2-fluorobenzyl)-1-(2-hydroxyethyl)-7-methoxy-4-oxo-1,4-dihydroquinoline-3-carboxylic acid (Example 3-4), 6-(2,3-Dichlorobenzyl)-5-hydroxy-1-(2-hydroxyethyl)-4-oxo-1,4-dihydroquinoline-3-carboxylic acid (Example 3-5), 6-(2,3-Dichlorobenzyl)-7-hydroxy-1-(2-hydroxyethyl)-4-oxo-1,4-dihydroquinoline-3-carboxylic acid (Example 3-6), 1-(2-Hydroxyethyl)-6-(2-methylaminobenzyl)-4-oxo-1,4-dihydroquinoline-3-carboxylic acid (Example 3-7), 6-(2-Dimethylaminobenzyl)-1-(2-hydroxyethyl)-4-oxo-1,4-dihydroquinoline-3-carboxylic acid (Example 3-8), 6-(2,3-Dichlorobenzyl)-4-oxo-1-phenyl-1,4-dihydroquinoline-3-carboxylic acid (Example 3-9), 6-(2,3-Dichlorobenzyl)-1-[2-hydroxy-1-(hydroxymethyl)ethyl]-4-oxo-1,4-dihydroquinoline-3-carboxylic acid (Example 3-10), 1-Cyclobutyl-6-(2,3-dichlorobenzyl)-4-oxo-1,4-dihydroquinoline-3-carboxylic acid (Example 3-12), 1-Cyclopentyl-6-(2,3-dichlorobenzyl)-4-oxo-1,4-dihydroquinoline-3-carboxylic acid (Example 3-13), 6-(2,3-Dichlorobenzyl)-1-(2-hydroxyethyl)-8-methoxy-4-oxo-1,4-dihydroquinoline-3-carboxylic acid (Example 3-14), 6-(2-Dimethylsulfamoylbenzyl)-1-(2-hydroxyethyl)-4-oxo-1,4-dihydroquinoline-3-carboxylic acid (Example 3-16), 6-(3-Chloro-2,4-difluorobenzyl)-1-(2-hydroxyethyl)-4-oxo-1,4-dihydroquinoline-3-carboxylic acid (Example 3-17), 6-(2-Carboxybenzyl)-1-(2-hydroxyethyl)-4-oxo-1,4-dihydroquinoline-3-carboxylic acid (Example 3-18), 1-(2-Hydroxyethyl)-6-(2-methylsulfamoylbenzyl)-4-oxo-1,4-dihydroquinoline-3-carboxylic acid (Example 3-19), 6-(2,3-Dichlorobenzyl)-7-ethoxy-1-(2-hydroxyethyl)-4-oxo-1,4-dihydroquinoline-3-carboxylic acid (Example 3-20), 7-Chloro-6-(2,3-dichlorobenzyl)-1-(2-hydroxyethyl)-4-oxo-1,4-dihydroquinoline-3-carboxylic acid (Example 3-21), 6-(2,3-Dichlorobenzyl)-1-(2-hydroxyethyl)-4-oxo-7-trifluoromethyl-1,4-dihydroquinoline-3-carboxylic acid (Example 3-22), (S)-6-(3-Chloro-2-fluorobenzyl)-1-(2-hydroxy-1-methylethyl)-4-oxo-1,4-dihydroquinoline-3-carboxylic acid (Example 3-23), (R)-6-(3-Chloro-2-fluorobenzyl)-1-(2-hydroxy-1-methylethyl)-4-oxo-1,4-dihydroquinoline-3-carboxylic acid (Example 3-24), 6-(3-Chloro-2-fluorobenzyl)-1-(2-hydroxyethyl)-4-oxo-8-trifluoromethyl-1,4-dihydroquinoline-3-carboxylic acid (Example 3-25), 6-(3-Chloro-2-fluorobenzyl)-1-[2-hydroxy-1-(hydroxymethyl)ethyl]-4-oxo-1,4-dihydroquinoline-3-carboxylic acid (Example 3-26), 7-Cyano-6-(2,3-dichlorobenzyl)-1-(2-hydroxyethyl)-4-oxo-1,4-dihydroquinoline-3-carboxylic acid (Example 3-27), 6-(2-Ethylmethylaminobenzyl)-1-(2-hydroxyethyl)-4-oxo-1,4-dihydroquinoline-3-carboxylic acid (Example 3-28), 6-[2-(N-Methyl-N-propylamino)benzyl]-1-(2-hydroxyethyl)-4-oxo-1,4-dihydroquinoline-3-carboxylic acid (Example 3-29), 6-[2-(N-Benzyl-N-methylamino)benzyl]-1-(2-hydroxyethyl)-4-oxo-1,4-dihydroquinoline-3-carboxylic acid (Example 3-30), 6-[2-(N-Methanesulfonyl-N-methylamino)benzyl]-1-(2-hydroxyethyl)-4-oxo-1,4-dihydroquinoline-3-carboxylic acid (Example 3-31), 6-[2-(N-Isopropyl-N-methylamino)benzyl]-1-(2-hydroxyethyl)-4-oxo-1,4-dihydroquinoline-3-carboxylic acid (Example 3-32), 1-tert-Butyl-6-(3-Chloro-2-fluorobenzyl)-4-oxo-1,4-dihydroquinoline-3-carboxylic acid (Example 3-33), 6-(3-Chloro-2-fluorobenzyl)-1-(2-hydroxyethyl)-8-methoxy-4-oxo-1,4-dihydroquinoline-3-carboxylic acid (Example 3-34), 8-Amino-6-(3-chloro-2-fluorobenzyl)-1-(2-hydroxyethyl)-4-oxo-1,4-dihydroquinoline-3-carboxylic acid (Example 3-35), 7-Carboxy-6-(2,3-dichlorobenzyl)-1-(2-hydroxyethyl)-4-oxo-1,4-dihydroquinoline-3-carboxylic acid (Example 3-36), 6-(3-Chloro-2,6-difluorobenzyl)-1-(2-hydroxyethyl)-8-methoxy-4-oxo-1,4-dihydroquinoline-3-carboxylic acid (Example 3-37), 6-(3-Chloro-2-fluorobenzyl)-8-dimethylamino-(2-hydroxyethyl)-4-oxo-1,4-dihydroquinoline-3-carboxylic acid (Example 3-38), 8-Acetylamino-6-(3-chloro-2-fluorobenzyl)-1-(2-hydroxyethyl)-4-oxo-1,4-dihydroquinoline-3-carboxylic acid (Example 3-39), 5-Cyano-6-(2,3-dichlorobenzyl)-1-(2-hydroxyethyl)-4-oxo-1,4-dihydroquinoline-3-carboxylic acid (Example 3-40), 6-[2-(N-Acetyl-N-methylamino)benzyl]-1-(2-hydroxyethyl)-4-oxo-1,4-dihydroquinoline-3-carboxylic acid (Example 3-41), 6-(2-Diethylaminobenzyl)-1-(2-hydroxyethyl)-4-oxo-1,4-dihydroquinoline-3-carboxylic acid (Example 3-42), 6-(3-Chloro-2-fluorobenzyl)-1-(1,1-dimethyl-2-hydroxyethyl)-4-oxo-1,4-dihydroquinoline-3-carboxylic acid (Example 3-43), 6-(3-Chloro-2-fluorobenzyl)-7-ethoxy-1-(2-hydroxyethyl)-4-oxo-1,4-dihydroquinoline-3-carboxylic acid (Example 3-44), 6-(3-Chloro-2-fluorobenzyl)-7,8-dimethoxy-1-(2-hydroxyethyl)-4-oxo-1,4-dihydroquinoline-3-carboxylic acid (Example 3-45), 6-(3-Chloro-2-fluorobenzyl)-8-ethoxy-1-(2-hydroxyethyl)-4-oxo-1,4-dihydroquinoline-3-carboxylic acid (Example 3-47), 6-(3-Chloro-2-fluorobenzyl)-1-(2-hydroxyethyl)-8-methylamino-4-oxo-1,4-dihydroquinoline-3-carboxylic acid (Example 3-48), 6-(3-Chloro-2-fluorobenzyl)-1-(2-hydroxyethyl)-4-oxo-7-propyloxy-1,4-dihydroquinoline-3-carboxylic acid (Example 3-49), 6-(3-Chloro-2-fluorobenzyl)-7-(dimethylaminomethyleneamino)-1-(2-hydroxyethyl)-4-oxo-1,4-dihydroquinoline-3-carboxylic acid (Example 3-50), 6-(3-Chloro-2-fluorobenzyl)-1-(2-hydroxyethyl)-7-methoxy-4-oxo-1,4-dihydroquinoline-3-carboxylic acid methyl ester (Example 3-51), 6-(3-Chloro-2-fluorobenzyl)-1-(2-hydroxyethyl)-4-oxo-8-phenoxy-1,4-dihydroquinoline-3-carboxylic acid (Example 3-52), 6-(3-Chloro-2-fluorobenzyl)-1-(2-hydroxyethyl)-7-isopropyloxy-4-oxo-1,4-dihydroquinoline-3-carboxylic acid (Example 3-53), 6-(3-Chloro-2-fluorobenzyl)-1-(2-hydroxyethyl)-4-oxo-8-propylamino-1,4-dihydroquinoline-3-carboxylic acid (Example 3-54), 6-(3-Chloro-2-fluorobenzyl)-8-ethylamino-1-(2-hydroxyethyl)-4-oxo-1,4-dihydroquinoline-3-carboxylic acid (Example 3-55), (S)-6-(3-Chloro-2-fluorobenzyl)-1-(2-hydroxy-1-methylethyl)-8-methoxy-4-oxo-1,4-dihydroquinoline-3-carboxylic acid (Example 3-56), (S)-6-(3-Chloro-2,6-difluorobenzyl)-1-(2-hydroxy-1-methylethyl)-8-methoxy-4-oxo-1,4-dihydroquinoline-3-carboxylic acid (Example-3-57), 6-(3-Chloro-2-fluorobenzyl)-1-(2-hydroxyethyl)-4-oxo-8-propyloxy-1,4-dihydroquinoline-3-carboxylic acid (Example 3-58), 6-(3-Chloro-2-fluorobenzyl)-1-(2-hydroxyethyl)-8-isopropyloxy-4-oxo-1,4-dihydroquinoline-3-carboxylic acid (Example 3-59), (S)-6-(3-Chloro-2-fluorobenzyl)-1-[1-(hydroxymethyl)propyl]-4-oxo-1,4-dihydroquinoline-3-carboxylic acid (Example 3-60), (S)-6-(3-Chloro-2-fluorobenzyl)-7-ethoxy-1-(2-hydroxy-1-methylethyl)-4-oxo-1,4-dihydroquinoline-3-carboxylic acid (Example 3-61), 6-(3-Chloro-2-fluorobenzyl)-7-dimethylamino-1-(2-hydroxyethyl)-4-oxo-1,4-dihydroquinoline-3-carboxylic acid (Example 3-62), 6-(3-Chloro-2-fluorobenzyl)-7-cyclohexylmethoxy-1-(2-hydroxyethyl)-4-oxo-1,4-dihydroquinoline-3-carboxylic acid (Example 3-63), 6-(3-Chloro-2-fluorobenzyl)-8-diethylamino-1-(2-hydroxyethyl)-4-oxo-1,4-dihydroquinoline-3-carboxylic acid (Example 3-64), 6-(3-Chloro-2-fluorobenzyl)-7-methylamino-1-(2-hydroxyethyl)-4-oxo-1,4-dihydroquinoline-3-carboxylic acid (Example 3-65), 6-(3-Chloro-2-fluorobenzyl)-1-(2-hydroxyethyl)-4-oxo-7-pyrrolidin-1-yl-1,4-dihydroquinoline-3-carboxylic acid (Example 3-66), (S)-6-(3-Chloro-2-fluorobenzyl)-8-ethoxy-1-(2-hydroxy-1-methylethyl)-4-oxo-1,4-dihydroquinoline-3-carboxylic acid (Example 3-67), (S)-6-(3-Chloro-2-fluorobenzyl)-7-ethoxy-1-[1-(hydroxymethyl)propyl]-4-oxo-1,4-dihydroquinoline-3-carboxylic acid (Example 3-68), 6-(3-Chloro-2-fluorobenzyl)-8-cyclohexylmethoxy-1-(2-hydroxyethyl)-4-oxo-1,4-dihydroquinoline-3-carboxylic acid (Example 3-69), (S)-6-(3-Chloro-2-fluorobenzyl)-1-(1-hydroxymethyl-2-methylpropyl)-4-oxo-1,4-dihydroquinoline-3-carboxylic acid (Example 3-70), (S)-6-(3-Chloro-2-fluorobenzyl)-1-(1-hydroxymethyl-3-methylbutyl)-4-oxo-1,4-dihydroquinoline-3-carboxylic acid (Example 3-71), (S)-6-(3-Chloro-2-fluorobenzyl)-1-[1-(hydroxymethyl)propyl]-7-isopropyloxy-4-oxo-1,4-dihydroquinoline-3-carboxylic acid (Example 3-72), (S)-6-(3-Chloro-2-fluorobenzyl)-1-[1-(hydroxymethyl)propyl]-7-methoxy-4-oxo-1,4-dihydroquinoline-3-carboxylic acid (Example 3-73), (S)-6-(3-Chloro-2-fluorobenzyl)-1-(2-hydroxy-1-methylethyl)-7-isopropyl-4-oxo-1,4-dihydroquinoline-3-carboxylic acid (Example 3-74), (S)-6-(3-Chloro-2-fluorobenzyl)-1-[2,2-dimethyl-1-(hydroxymethyl)propyl]-4-oxo-1,4-dihydroquinoline-3-carboxylic acid (Example -3-75), 6-(3-Chloro-2-fluorobenzyl)-1-(2-hydroxyethyl)-7-(2-hydroxyethyloxy)-4-oxo-1,4-dihydroquinoline-3-carboxylic acid (Example 3-76), 6-(3-Chloro-2-fluorobenzyl)-1-(2-hydroxyethyl)-1-7-(3-hydroxypropyloxy)-4-oxo-1,4-dihydroquinoline-3-carboxylic acid (Example 3-77), 6-(3-Chloro-2-fluorobenzyl)-1-(2-hydroxyethyl)-8-(2-hydroxyethylamino)-4-oxo-1,4-dihydroquinoline-3-carboxylic acid (Example 3-78), (S)-6-(3-Chloro-2-fluorobenzyl)-1-[1-(hydroxymethyl)propyl]-8-methoxy-4-oxo-1,4-dihydroquinoline-3-carboxylic acid (Example 3-79), (S)-6-(3-Chloro-2-fluorobenzyl)-8-dimethylamino-1-(2-hydroxy-1-methylethyl)-4-oxo-1,4-dihydroquinoline-3-carboxylic acid (Example 3-80), (S)-6-(3-Chloro-2-fluorobenzyl)-1-(2-hydroxy-1-phenylethyl)-4-oxo-1,4-dihydroquinoline-3-carboxylic acid (Example 3-81), (S)-6-(3-Chloro-2-fluorobenzyl)-1-[1-(hydroxymethyl)butyl]-4-oxo-1,4-dihydroquinoline-3-carboxylic acid (Example 3-82), 6-(3-Chloro-2-fluorobenzyl)-1-((1S,2S)-1-hydroxymethyl-2-methylbutyl)-4-oxo-1,4-dihydroquinoline-3-carboxylic acid (Example 3-83), (S)-6-(3-Chloro-2-fluorobenzyl)-1-(2-hydroxy-1-methylethyl)-7-methoxy-4-oxo-1,4-dihydroquinoline-3-carboxylic acid (Example 3-84), (S)-6-(3-Chloro-2-fluorobenzyl)-1-(1-benzyl-2-hydroxyethyl)-4-oxo-1,4-dihydroquinoline-3-carboxylic acid (Example 3-85), 6-(2-Chloro-5-methanesulfonylbenzyl)-1-(2-hydroxyethyl)-4-oxo-1,4-dihydroquinoline-3-carboxylic acid (Example 4-1), 6-(2-Ethylbenzyl)-1-(2-hydroxyethyl)-4-oxo-1,4-dihydroquinoline-3-carboxylic acid (Example 4-4), 6-(2-Chloro-5-methylbenzyl)-1-(2-hydroxyethyl)-4-oxo-1,4-dihydroquinoline-3-carboxylic acid (Example 4-5), 6-(2-Chloro-5-fluorobenzyl)-1-(2-hydroxyethyl)-4-oxo-1,4-dihydroquinoline-3-carboxylic acid (Example 4-6), 6-(5-Bromo-2-chlorobenzyl)-1-(2-hydroxyethyl)-4-oxo-1,4-dihydroquinoline-3-carboxylic acid (Example 4-7), 6-(2,3-Dichlorobenzyl)-7-fluoro-1-(2-hydroxyethyl)-4-oxo-1,4-dihydroquinoline-3-carboxylic acid (Example 4-9)

6-(2-Chloro-5-hydroxybenzyl)-1-(2-hydroxyethyl)-4-oxo-1,4-dihydroquinoline-3-carboxylic acid (Example 4-11), 6-(2,3-Dichlorobenzyl)-5-fluoro-1-(2-hydroxyethyl)-4-oxo-1,4-dihydroquinoline-3-carboxylic acid (Example 4-12), 6-(2-Ethoxybenzyl)-1-(2-hydroxyethyl)-4-oxo-1,4-dihydroquinoline-3-carboxylic acid (Example 4-13), 6-(2-Hydroxybenzyl)-1-(2-hydroxyethyl)-4-oxo-1,4-dihydroquinoline-3-carboxylic acid (Example 4-14), 6-(2,3-Dichlorobenzyl)-7-methyl-1-(2-hydroxyethyl)-4-oxo-1,4-dihydroquinoline-3-carboxylic acid (Example 4-15), (S)-6-(3-Chloro-2-fluorobenzyl)-1-(2-hydroxy-1-methylethyl)-8-isopropyloxy-4-oxo-1,4-dihydroquinoline-3-carboxylic acid (Example 4-16),
(S)-6-(3-Chloro-2-fluorobenzyl)-1-[1-(hydroxymethyl)propyl]-8-isopropyloxy-4-oxo-1,4-dihydroquinoline-3-carboxylic acid (Example 4-17),
(S)-6-(3-Chloro-2-fluorobenzyl)-1-(1-cyclohexyl-2-hydroxyethyl)-4-oxo-1,4-dihydroquinoline-3-carboxylic acid (Example 4-18),
(S)-6-(3-Chloro-2-fluorobenzyl)-1-(1-hydroxymethyl-2-methylpropyl)-7-isopropyloxy-4-oxo-1,4-dihydroquinoline-3-carboxylic acid (Example 4-19),
(S)-6-(3-Chloro-2-fluorobenzyl)-1-[2,2-dimethyl-1-(hydroxymethyl)propyl]-7-isopropyloxy-4-oxo-1, 4-dihydroquinoline-3-carboxylic acid (Example 4-20),
(S)-6-(3-Chloro-2-fluorobenzyl)-8-ethoxy-1-[1-(hydroxymethyl)propyl]-4-oxo-1,4-dihydroquinoline-3-carboxylic acid (Example 4-21),
(S)-6-(3-Chloro-2-fluorobenzyl)-1-[2-cyclohexyl-1-(hydroxymethyl)ethyl]-4-oxo-1,4-dihydroquinoline-3-carboxylic acid (Example 4-22),
(S)-6-(3-Chloro-2-fluorobenzyl)-1-(1-hydroxymethyl-3-methylbutyl)-7-isopropyloxy-4-oxo-1,4-dihydroquinoline-3-carboxylic acid (Example 4-23),
(S)-6-(3-Chloro-2-fluorobenzyl)-1-(1-hydroxymethyl-2-methylpropyl)-8-isopropyloxy-4-oxo-1,4-dihydroquinoline-3-carboxylic acid (Example 4-24),
(S)-6-(3-Chloro-2-fluorobenzyl)-1-(1-hydroxymethyl-3-methylbutyl)-8-isopropyloxy-4-oxo-1,4-dihydroquinoline-3-carboxylic acid (Example 4-25),
(S)-6-(3-Chloro-2-fluorobenzyl)-[2,2-dimethyl-1-(hydroxymethyl)propyl]-8-isopropyloxy-4-oxo-1,4-dihydroquinoline-3-carboxylic acid (Example 4-26),
6-(3-Chloro-2-fluorobenzyl)-1-((1S,2S)-1-hydroxymethyl-2-methylbutyl)-7-methoxy-4-oxo-1,4-dihydroquinoline-3-carboxylic acid (Example 4-27),
6-(3-Chloro-2-fluorobenzyl)-7-ethoxy-1-((1S,2S)-1-hydroxymethyl-2-methylbutyl)-4-oxo-1,4-dihydroquinoline-3-carboxylic acid (Example 4-28),
(S)-6-(3-Chloro-2-fluorobenzyl)-1-[1-(hydroxymethyl)propyl]-7-methylsulfanyl-4-oxo-1,4-dihydroquinoline-3-carboxylic acid (Example 4-29),
(S)-6-(3-Chloro-2-fluorobenzyl)-7-ethoxy-1-(1-hydroxymethyl-2-methylpropyl)-4-oxo-1,4-dihydroquinoline-3-carboxylic acid (Example 4-30),
(S)-6-(3-Chloro-2-fluorobenzyl)-7-ethoxy-1-[2,2-dimethyl-1-(hydroxymethyl)propyl]-4-oxo-1,4-dihydroquinoline-3-carboxylic acid (Example 4-31),
(S)-6-(3-Chloro-2-fluorobenzyl)-1-(1-hydroxymethyl-2-methylpropyl)-7-methoxy-4-oxo-1,4-dihydroquinoline-3-carboxylic acid (Example 4-32),
(S)-6-(3-Chloro-2-fluorobenzyl)-1-[2,2-dimethyl-1-(hydroxymethyl)propyl]-7-methoxy-4-oxo-1,4-dihydroquinoline-3-carboxylic acid (Example 4-33),
(S)-6-(3-Chloro-2-fluorobenzyl)-1-[2,2-dimethyl-1-(hydroxymethyl)propyl]-8-methoxy-4-oxo-1,4-dihydroquinoline-3-carboxylic acid (Example 4-34),
(S)-6-(3-Chloro-2-fluorobenzyl)-1-[1-(hydroxyethyl)butyl]-7-isopropyloxy-4-oxo-1,4-dihydroquinoline-3-carboxylic acid (Example 4-35),
(S)-6-(3-Chloro-2-fluorobenzyl)-7-ethoxy-1-[1-(hydroxymethyl)butyl]-4-oxo-1,4-dihydroquinoline-3-carboxylic acid (Example 4-36),
(S)-6-(3-Chloro-2-fluorobenzyl)-8-ethoxy-1-[2,2-dimethyl-1-(hydroxymethyl)propyl]-4-oxo-1,4-dihydroquinoline-3-carboxylic acid (Example 4-37),
(S)-6-(3-Chloro-2-fluorobenzyl)-1-[1-(hydroxymethyl)butyl]-7-methoxy-4-oxo-1,4-dihydroquinoline-3-carboxylic acid (Example 4-38),
6-(3-Chloro-2-fluorobenzyl)-1-((1S,2S)-1-hydroxymethyl-2-methylbutyl)-7-isopropyloxy-4-oxo-1,4-dihydroquinoline-3-carboxylic acid (Example 4-39),
(S)-6-(3-Chloro-2-fluorobenzyl)-1-(1-cyclohexyl-2-hydroxyethyl)-7-isopropyloxy-4-oxo-1,4-dihydroquinoline-3-carboxylic acid (Example 4-40),
(S)-6-(3-Chloro-2-fluorobenzyl)-1-(1-cyclohexyl-2-hydroxyethyl)-8-ethoxy-4-oxo-1,4-dihydroquinoline-3-carboxylic acid (Example 4-41),
(S)-6-(3-Chloro-2-fluorobenzyl)-1-(1-cyclohexyl-2-hydroxyethyl)-7-methoxy-4-oxo-1,4-dihydroquinoline-3-carboxylic acid (Example 4-42),
(S)-6-(3-Chloro-2-fluorobenzyl)-1-(1-cyclohexyl-2-hydroxyethyl)-7-ethoxy-4-oxo-1,4-dihydroquinoline-3-carboxylic acid (Example 4-43),
(S)-6-(3-Chloro-2-fluorobenzyl)-1-(1-cyclohexyl-2-hydroxyethyl)-8-methoxy-4-oxo-1,4-dihydroquinoline-3-carboxylic acid (Example 4-44),
(S)-6-(3-Chloro-2-fluorobenzyl)-8-ethoxy-1-(1-hydroxymethyl-2-methylpropyl)-4-oxo-1,4-dihydroquinoline-3-carboxylic acid (Example 4-45),
(S)-6-(3-Chloro-2-fluorobenzyl)-1-(1-hydroxymethyl-2-methylpropyl)-8-methoxy-4-oxo-1,4-dihydroquinoline-3-carboxylic acid (Example 4-46),
(S)-6-(3-Chloro-2-fluorobenzyl)-1-[1-(hydroxymethyl)butyl]-8-isopropyloxy-4-oxo-1,4-dihydroquinoline-3-carboxylic acid (Example 4-47),
(S)-6-(3-Chloro-2-fluorobenzyl)-8-ethoxy-1-[1-(hydroxymethyl)butyl]-4-oxo-1,4-dihydroquinoline-3-carboxylic acid (Example 4-48),
(S)-6-(3-Chloro-2-fluorobenzyl)-1-[1-(hydroxymethyl)butyl]-8-methoxy-4-oxo-1,4-dihydroquinoline-3-carboxylic acid (Example 4-49),
(S)-6-(3-Chloro-2-fluorobenzyl)-1-(1-cyclohexyl-2-hydroxyethyl)-8-isopropyloxy-4-oxo-1,4-dihydroquinoline-3-carboxylic acid (Example 4-50) and
(S)-6-(3-Chloro-2-fluorobenzyl)-1-[2,2-dimethyl-1-(hydroxymethyl)propyl]-4-oxo-1,4-dihydroquinoline-3-carboxylic acid (Example 4-52),
or a pharmaceutically acceptable salt thereof.

(23) A pharmaceutical composition comprising a 4-oxoquinoline compound of any of the above-mentioned (5) to (22), or a pharmaceutically acceptable salt thereof, and a pharmaceutically acceptable carrier.

(24) An integrase inhibitor comprising a 4-oxoquinoline compound of any of the above-mentioned (1) to (22), or a pharmaceutically acceptable salt thereof, as an active ingredient.

(25) An antiviral agent comprising a 4-oxoquinoline compound of any of the above-mentioned (5) to (22), or a pharmaceutically acceptable salt thereof, as an active ingredient.

(26) An anti-HIV agent comprising a 4-oxoquinoline compound of any of the above-mentioned (5) to (22), or a pharmaceutically acceptable salt thereof, as an active ingredient.

(27) An anti-HIV composition comprising a 4-oxoquinoline compound of any of the above-mentioned (1) to (22), or a pharmaceutically acceptable salt thereof, and other one or more kinds of anti-HIV active substance as an active ingredient.

(28) An anti-HIV agent comprising a 4-oxoquinoline compound of any of the above-mentioned (1) to (22), or a

(29) Use of a 4-oxoquinoline compound of any of the above-mentioned (5) to (22) or a pharmaceutically acceptable salt thereof, for the production of an anti-HIV agent.
(30) Use of a 4-oxoquinoline compound of any of the above-mentioned (5) to (22) or a pharmaceutically acceptable salt thereof, for the production of an integrase inhibitor.
(31) Use of a 4-oxoquinoline compound of any of the above-mentioned (5) to (22) or a pharmaceutically acceptable salt thereof, for the production of an antiviral agent.
(32) A method for the prophylaxis or treatment of an HIV infectious disease, which comprises administering an effective amount of a 4-oxoquinoline compound of any of the above-mentioned (5) to (22) or a pharmaceutically acceptable salt thereof to a mammal.
(33) The method for the prophylaxis or treatment of an HIV infectious disease according to the above-mentioned (32), which further comprises administering an effective amount of at least one different anti-HIV active substance to said mammal.
(34) A method for inhibiting integrase, which comprises administering an effective amount of a 4-oxoquinoline compound of any of the above-mentioned (5) to (22) or a pharmaceutically acceptable salt thereof to a mammal.
(35) A method for the prophylaxis or treatment of a virus infectious disease, which comprises administering an effective amount of a 4-oxoquinoline compound of any of the above-mentioned (5) to (22) or a pharmaceutically acceptable salt thereof to a mammal.
(36) An anti-HIV composition comprising a 4-oxoquinoline compound of any of the above-mentioned (5) to (22) or a pharmaceutically acceptable salt thereof, and a pharmaceutically acceptable carrier.
(37) A pharmaceutical composition for inhibiting integrase, which comprises a 4-oxoquinoline compound of any of the above-mentioned (5) to (22) or a pharmaceutically acceptable salt thereof, and a pharmaceutically acceptable carrier.
(38) An antiviral composition comprising a 4-oxoquinoline compound of any of the above-mentioned (5) to (22) or a pharmaceutically acceptable salt thereof, and a pharmaceutically acceptable carrier.
(39) A commercial package comprising the composition of the above-mentioned 36 and a written matter associated therewith, the written matter stating that the composition can or should be used for the prophylaxis or treatment of an HIV infectious disease.
(40) A commercial package comprising the composition of the above-mentioned (37) and a written matter associated therewith, the written matter stating that the composition can or should be used for inhibiting integrase.
(41) A commercial package comprising the composition of the above-mentioned (38) and a written matter associated therewith, the written matter stating that the composition can or should be used for the prophylaxis or treatment of a viral infectious disease.

The definitions of each substituent and each moiety used in the present specification are as follows.

The "halogen atom" means fluorine atom, chlorine atom, bromine atom or iodine atom, preferably fluorine atom, chlorine atom or bromine atom.

As $R^{32}$, $R^{33}$, $R^4$, $R^5$, $R^6$, $R^{6'}$, $R^{6''}$, $R^{6'''}$ and group A, fluorine atom and chlorine atom are particularly preferable, as $R^{32}$ and $R^5$, chlorine atom is more preferable, and as $R^{31}$, $R^{33}$, $R^4$, $R^{6'}$, $R^{6'''}$ and the halogen atom of the "$C_{1-10}$ alkyl group optionally substituted by 1 to 3 substituents selected from halogen atom and group B", fluorine atom is more preferable.

The "$C_{1-4}$ alkyl group" means a straight chain or branched chain alkyl group having 1 to 4 carbon atoms, which is specifically methyl group, ethyl group, propyl group, isopropyl group, butyl group, isobutyl group, sec-butyl group or tert-butyl group.

As $R^2$, $R^{31}$ and $R^{a6}$, methyl group and ethyl group are preferable, as $R^4$, $R^5$, $R^6$, $R^{6'}$, $R^{6''}$, $R^{6'''}$ and group A, methyl group, ethyl group and isopropyl group are preferable, methyl group is more preferable, as $R^{a1}$ and $R^{a2}$, methyl group, ethyl group, propyl group and isopropyl group are preferable, methyl group is more preferable, as $R^{a3}$, $R^{a9}$, $R^{a10}$, $R^{a11}$ and group A, methyl group is preferable, and as $R^{a4}$ and $R^{a5}$, methyl group, ethyl group and tert-butyl group are preferable.

The "halo $C_{1-4}$ alkyl group" is "$C_{1-4}$ alkyl group" defined above, which is substituted by 1 to 9, preferably 1 to 3, "halogen atom" defined above.

Specific examples thereof include 2-fluoroethyl group, 2-chloroethyl group, 2-bromomethyl group, 3-fluoropropyl group, 3-chloropropyl group, 4-fluorobutyl group, 4-chlorobutyl group, trifluoromethyl group, 2,2,2-trifluoroethyl group, 3,3,3-trifluoropropyl group, 4,4,4-trifluorobutyl group, pentafluoroethyl group, 2,2,2-trifluoro-1-trifluoromethyl-ethyl group and the like.

As $R^{31}$, $R^4$, $R^5$, $R^6$, $R^{6'}$, $R^{6''}$, $R^{6'''}$ and group A, trifluoromethyl group is preferable.

"The "$C_{1-4}$ alkoxy group" is an alkyloxy group wherein its alkyl moiety is "$C_{1-4}$ alkyl group" defined above, which is specifically exemplified by methoxy group, ethoxy group, propoxy group, isopropyloxy group, butoxy group, isobutyloxy group, tert-butyloxy group and the like.

It is preferably methoxy group for $R^{31}$.

The "$C_{1-4}$ alkylsulfanyl group" is an alkylsulfanyl group wherein its alkyl moiety is "$C_{1-4}$ alkyl group" defined above. Specific examples thereof include methylsulfanyl group, ethylsulfanyl group, propylsulfanyl group, isopropylsulfanyl group, butylsulfanyl group, isobutylsulfanyl group, tert-butylsulfanyl group and the like.

It is preferably methylsulfanyl group for $R^{31}$.

The "halo $C_{1-4}$ alkyloxy group" is a halo $C_{1-4}$ alkyloxy group wherein its haloalkyl moiety is "halo $C_{1-4}$ alkyl group" defined above.

Specific examples thereof include 2-fluoroethyloxy group, 2-chloroethyloxy group, 2-bromomethyloxy group, 3-fluoropropyloxy group, 3-chloropropyloxy group, 4-fluorobutyloxy group, 4-chlorobutyloxy group, trifluoromethyloxy group, 2,2,2-trifluoroethyloxy group, 3,3,3-trifluoropropyloxy group, 4,4,4-trifluorobutyloxy group, pentafluoroethyloxy group, 2,2,2-trifluoro-1-trifluoromethylethyloxy group and the like.

It is preferably trifluoromethyloxy group for $R^{31}$, $R^4$, $R^5$, $R^6$, $R^{6'}$, $R^{6''}$, $R^{6'''}$ and group A.

The "$C_{3-10}$ carbon ring group" is a saturated or unsaturated cyclic hydrocarbon group having 3 to 10 carbon atoms, which is specifically exemplified by aryl group, cycloalkyl group, cycloalkenyl group or a fused ring thereof.

Specific examples of the "aryl group" include phenyl group, naphthyl group, pentalenyl group, azulenyl group and the like, preferably phenyl group and naphthyl group, particularly preferably phenyl group.

Specific examples of the "cycloalkyl group" include cyclopropyl group, cyclobutyl group, cyclopentyl group, cyclohexyl group, cycloheptyl group, cyclooctyl group, adamantyl group, norbornanyl group and the like, preferably cyclopropyl group, cyclobutyl group, cyclopentyl group and cyclohexyl group.

The "cycloalkenyl group" contains at least one, preferably 1 or 2 double bonds, and is specifically exemplified by cyclopropenyl group, cyclobutenyl group, cyclopentenyl group, cyclopentadienyl group, cyclohexenyl group, cyclohexadienyl group (2,4-cyclohexadien-1-yl group, 2,5-cyclohexadien-1-yl group and the like), cycloheptenyl group and cyclooctenyl group and the like.

Specific examples of the fused ring of these "aryl group", "cycloalkyl group" and "cycloalkenyl group" include indenyl group, indanyl group, 1,4-dihydronaphthyl group, 1,2,3,4-tetrahydronaphthyl group (1,2,3,4-tetrahydro-2-naphthyl group, 5,6,7,8-tetrahydro-2-naphthyl group and the like), perhydronaphthyl group and the like. Preferably, it is a fused ring of phenyl group and a different ring, which is exemplified by indenyl group, indanyl group, 1,4-dihydronaphthyl group, 1,2,3,4-tetrahydronaphthyl group and the like, and indanyl group is particularly preferable.

The "$C_{3-10}$ carbon ring group optionally substituted by 1 to 5 substituents selected from group A" is a "$C_{3-10}$ carbon ring group" defined above, which is optionally substituted by 1 to 5, preferably 1 to 3, substituents selected from the following group A, and includes non-substituted "$C_{3-10}$ carbon ring group".

The "group A" is a group constituting of cyano group, phenyl group, nitro group, "halogen atom" defined above, "$C_{1-4}$ alkyl group" defined above, "halo $C_{1-4}$ alkyl group" defined above, "halo $C_{1-4}$ alkyloxy group" defined above, —$OR^{a1}$, —$SR^{a1}$, —$NR^{a1}R^{a2}$, —$CONR^{a1}R^{a2}$, —$SO_2NR^{a1}R^{a2}$, —$COR^{a3}$, —$NR^{a1}COR^{a3}$, —$SO_2R^{a3}$, —$NR^{a1}SO_2R^{a3}$, —$COOR^{a1}$ and —$NR^{a2}COOR^{a3}$, wherein $R^{a1}$ and $R^{a2}$ are the same or different and each is hydrogen atom, "$C_{1-4}$ alkyl group" defined above or benzyl group, and $R^{a3}$ is "$C_{1-4}$ alkyl group" defined above.

Specific examples of "—$OR^{a1}$" include hydroxy group, methoxy group, ethoxy group, propoxy group, isopropyloxy group, tert-butoxy group and the like, specific examples of "—$SR^{a1}$" include mercapto group, methylsulfanyl group, ethylsulfanyl group, propylsulfanyl group, isopropylsulfanyl group, tert-butylsulfanyl group and the like, specific examples of "—$NR^{a1}R^{a2}$" include amino group, methylamino group, ethylamino group, propylamino group, isopropylamino group, tert-butylamino group, dimethylamino group, diethylamino group, N-ethyl-N-methylamino group, N-methyl-N-propylamino group, N-isopropyl-N-methylamino group, N-benzyl-N-methylamino group and the like, specific examples of "—$CONR^{a1}R^{a2}$" include carbamoyl group, methylaminocarbonyl group, ethylaminocarbonyl group, propylaminocarbonyl group, isopropylaminocarbonyl group, tert-butylaminocarbonyl group, dimethylaminocarbonyl group, diethylaminocarbonyl group, N-methyl-N-ethylaminocarbonyl group and the like, specific examples of "—$SO_2NR^{a1}R^{a2}$" include sulfamoyl group, methylaminosulfonyl group, ethylaminosulfonyl group, propylaminosulfonyl group, isopropylaminosulfonyl group, tert-butylaminosulfonyl group, dimethylaminosulfonyl group, diethylaminosulfonyl group, N-methyl-N-ethylaminosulfonyl group and the like, specific examples of "—$COR^{a3}$" include acetyl group, propionyl group, butyryl group, isobutyryl group, pivaloyl group and the like, specific examples of "—$NR^{a1}COR^{a3}$" include acetylamino group, propionylamino group, butyrylamino group, isobutyrylamino group, pivaloylamino group, N-acetyl-N-methylamino group and the like, specific examples of "—$SO_2R^{a3}$" include methylsulfonyl group, ethylsulfonyl group, propylsulfonyl group, isopropylsulfonyl group, tert-butylsulfonyl group and the like, specific examples of "—$NR^{a1}SO_2R^{a3}$" include methylsulfonylamino group, ethylsulfonylamino group, propylsulfonylamino group, isopropylsulfonylamino group, tert-butylsulfonylamino group, N-methyl-N-(methylsulfonyl)amino group and the like, specific examples of "—$COOR^{a1}$" include carboxyl group, methoxycarbonyl group, ethoxycarbonyl group, propoxycarbonyl group, isopropyloxycarbonyl group, tert-butoxycarbonyl group and the like, and specific examples of "—$NR^{a2}COOR^{a3}$" include methoxycarbonylamino group, ethoxycarbonylamino group, propoxycarbonylamino group, isopropyloxycarbonylamino group, tert-butoxycarbonylamino group and the like.

As group A, cyano group, phenyl group, nitro group, fluorine atom, chlorine atom, bromine atom, methyl group, ethyl group, isopropyl group, trifluoromethyl group, trifluoromethyloxy group, hydroxy group, methoxy group, ethoxy group, propoxy group, methylsulfanyl group, amino group, methylamino group, ethylamino group, isopropylamino group, dimethylamino group, diethylamino group, N-ethyl-N-methylamino group, N-methyl-N-propylamino group, N-isopropyl-N-methylamino group, N-benzyl-N-methylamino group, carbamoyl group, methylaminocarbonyl group, dimethylaminocarbonyl group, sulfamoyl group, methylaminosulfonyl group, dimethylaminosulfonyl group, acetyl group, acetylamino group, N-acetyl-N-methylamino group, methylsulfonyl group, methylsulfonylamino group, N-methyl-N-(methylsulfonyl)amino group, carboxyl group, methoxycarbonyl group, carboxyamino group and methoxycarbonylamino group are preferable.

As group A, cyano group, phenyl group, nitro group, fluorine atom, chlorine atom, bromine atom, methyl group, trifluoromethyl group, trifluoromethyloxy group, hydroxy group, methoxy group, ethoxy group, methylsulfanyl group, amino group, methylamino group, dimethylamino group, diethylamino group, N-ethyl-N-methylamino group, N-methyl-N-propylamino group, N-isopropyl-N-methylamino group, N-benzyl-N-methylamino group, dimethylaminocarbonyl group, methylaminosulfonyl group, dimethylaminosulfonyl group, acetylamino group, N-acetyl-N-methylamino group, methylsulfonyl group, N-methyl-N-(methylsulfonyl)amino group and carboxyl group are particularly preferable, and fluorine atom and chlorine atom are more preferable.

The number of substituents is preferably 1 to 3, and when "$C_{3-10}$ carbon ring group" is phenyl group, ring Cy is preferably monosubstituted at the 2-position, monosubstituted at the 3-position, disubstituted at the 2,3-positions, disubstituted at the 2,4-positions, disubstituted at the 2,5-positions, disubstituted at the 2,6-positions, trisubstituted at the 2,3,4-positions, trisubstituted at the 2,3,5-positions, trisubstituted at the 2,3,6-positions, particularly preferably disubstituted at the 2,3-positions.

Specific examples of the "$C_{3-10}$ carbon ring group optionally substituted by 1 to 5 substituents selected from group A" include phenyl group, naphthyl group, 2-fluorophenyl group, 2-chlorophenyl group, 2-bromophenyl group, 3-fluorophenyl group, 3-chlorophenyl group, 3-bromophenyl group, 4-fluorophenyl group, 2-nitrophenyl group, 3-nitrophenyl group, 2-cyanophenyl group, 3-cyanophenyl group, 2-methylphenyl group, 3-methylphenyl group, 4-methylphenyl group, 2-ethylphenyl group, 3-ethylphenyl group, 2-isopropylphenyl group, 3-isopropylphenyl group, 2-trifluoromethylphenyl group, 3-trifluoromethylphenyl group, 2-hydroxyphenyl group, 3-hydroxyphenyl group, 4-hydroxyphenyl group, 2-methoxyphenyl group, 3-methoxyphenyl group, 2-ethoxyphenyl group, 3-ethoxyphenyl group, 2-propoxyphenyl group, 3-propoxyphenyl group, 2-(trifluoromethyl)phenyl group, 3-(trifluoromethyl)phenyl group, 2-(trifluoromethyloxy)phenyl group, 3-(trifluoromethyloxy)phenyl group, 2-methylsulfamoylphenyl group, 3-methylsulfamoylphenyl group, 2-aminophenyl group, 3-aminophenyl group, 2-(methylamino)phenyl group, 3-(methylamino)phenyl group, 2-(dimethylamino)phenyl group, 3-(dimethylamino)phenyl group, 2-(acetylamino)phenyl group, 3-(acetylamino)phenyl group, 2-biphenyl group, 3-biphenyl group, 2-(methylsulfonyl)phenyl group, 3-(methylsulfonyl)phenyl group, 2-sulfamoylphenyl group, 3-sulfamoylphenyl group, 2-(methylaminosulfonyl)phenyl group, 3-(methylaminosulfonyl)phenyl group, 2-(dimethylaminosulfonyl)phenyl group, 3-(dimethylaminosulfonyl)phenyl group, 2-(dimethylsulfonyl)phenyl group, 2-(methylsulfonylamino)phenyl group, 3-(methylsulfonylamino)phenyl group, 2-carbamoylphenyl group, 3-carbamoylphenyl group, 2-(methylcarbamoyl)phenyl group, 3-(methylcarbamoyl)phenyl group, 2-(dimethylcarbamoyl)phenyl group, 3-(dimethylcarbamoyl)phenyl group, 2,3-difluorophenyl group, 2,3-dichlorophenyl group, 2,3-dibromophenyl group, 2,4-difluorophenyl group, 2,4-dichlorophenyl group, 2,5-dichlorophenyl group, 2,6-dichlorophenyl group, 2-chloro-3-fluorophenyl group, 2-chloro-4-fluorophenyl group, 2-chloro-5-fluorophenyl group, 2-chloro-6-fluorophenyl group, 3-chloro-2-fluorophenyl group, 5-chloro-2-fluorophenyl group, 5-bromo-2-chlorophenyl group, 2-chloro-5-nitrophenyl group, 2-chloro-3-methylphenyl group, 2-chloro-5-methylphenyl group, 2-chloro-3-(trifluoromethyl)phenyl group, 2-chloro-5-(trifluoromethyl)phenyl group, 2-chloro-3-hydroxyphenyl group, 2-chloro-5-hydroxyphenyl group, 2-chloro-3-methoxyphenyl group, 2-chloro-5-methoxyphenyl group, 2-chloro-3-methylsulfamoylphenyl group, 2-chloro-5-methylsulfamoylphenyl group, 2-chloro-3-aminophenyl group, 2-chloro-5-aminophenyl group, 2-chloro-3-(methylamino)phenyl group, 2-chloro-5-(methylamino)phenyl group, 2-chloro-3-(dimethylamino)phenyl group, 2-chloro-5-(dimethylamino)phenyl group, 2-chloro-3-(acetylamino)phenyl group, 2-chloro-5-(acetylamino)phenyl group, 2-chloro-3-(methylsulfonyl)phenyl group, 2-chloro-5-(methylsulfonyl)phenyl group, 2-chloro-3-(methylsulfonylamino)phenyl group, 2-chloro-5-(methylsulfonylamino)phenyl group, 2,3,4-trifluorophenyl group, 2-chloro-3,4-difluorophenyl group, 2-chloro-3,5-difluorophenyl group, 2-chloro-3,6-difluorophenyl group, 2-chloro-4,5-difluorophenyl group, 2-chloro-4,6-difluorophenyl group, 3-chloro-2,4-difluorophenyl group, 3-chloro-2,5-difluorophenyl group, 3-chloro-2,6-difluorophenyl group, 2,3-dichloro-4-fluorophenyl group, 3-chloro-2-fluoro-5-trifluoromethylphenyl group, 2-chloro-3,5,6-trifluorophenyl group, 3-chloro-2,4,5-trifluorophenyl group, 3-chloro-2,4,6-trifluorophenyl group, 2,3-dichloro-4,5,6-trifluorophenyl group, 3,5-dichloro-3,4,6-trifluorophenyl group, 2,6-dichloro-3,4,5-trifluorophenyl group, perfluorophenyl group, cyclopropyl group, cyclobutyl group, cyclopentyl group, cyclohexyl group, 2-hydroxycyclopropyl group, 3-hydroxycyclobutyl group, 3-hydroxycyclopentyl group, 2-hydroxycyclohexyl group, 3-hydroxycyclohexyl group, 4-hydroxycyclohexyl group, 4-indanyl group and 1H-inden-4-yl group.

The ring Cy is preferably phenyl group, naphthyl group, 2-chlorophenyl group, 3-chlorophenyl group, 2-bromophenyl group, 3-bromophenyl group, 2-ethylphenyl group, 3-ethylphenyl group, 2-hydroxyphenyl group, 2-ethoxyphenyl group, 3-(trifluoromethyloxy)phenyl group, 3-(methylsulfonyl)phenyl group, 2,3-difluorophenyl group, 2,3-dichlorophenyl group, 2-chloro-3-fluorophenyl group, 2-chloro-4-fluorophenyl group, 2-chloro-5-fluorophenyl group, 2-chloro-6-fluorophenyl group, 3-chloro-2-fluorophenyl group, 5-bromo-2-chlorophenyl group, 2-chloro-5-methylphenyl group, 2-chloro-5-hydroxyphenyl group, 2-chloro-5-(methylsulfonyl)phenyl group, 2-chloro-3,6-difluorophenyl group, 3-chloro-2,4-difluorophenyl group, 3-chloro-2,6-difluorophenyl group, 2-chloro-3-methylphenyl group, 3-chloro-2-methylphenyl group, 2-chloro-3-methoxyphenyl group, 3-chloro-2-methoxyphenyl group, 3-nitrophenyl group, 3-cyanophenyl group, 4-methylphenyl group, 3-trifluoromethylphenyl group, 2-(trifluoromethyloxy)phenyl group, 3-hydroxyphenyl group, 3-ethoxyphenyl group, 3-aminophenyl group, 2-(methylamino)phenyl group, 2-(dimethylamino)phenyl group, 2-(diethylamino)phenyl group, 2-(N-ethyl-N-methylamino)phenyl group, 2-(N-isopropyl-N-methylamino)phenyl group, 2-(N-benzyl-N-methylamino)phenyl group, 2-(N-acetyl-N-methylamino)phenyl group, 2-(N-methyl-N-methylsulfonylamino)phenyl group, 3-(methylamino)phenyl group, 2-carboxyphenyl group, 3-(dimethylaminocarbonyl)phenyl group, 3-(acetylamino)phenyl group, 2-biphenyl group, 2-(methylsulfonyl)phenyl group, 2-chloro-5-methylsulfanylphenyl group, 2-chloro-5-methylphenyl group, 2-(methylaminosulfonyl)phenyl group, 2-(dimethylaminosulfonyl)phenyl group or 3-(dimethylaminosulfonyl)phenyl group, particularly preferably 2-chlorophenyl group, 2-bromophenyl group, 2-ethylphenyl group, 2-hydroxyphenyl group, 2-ethoxyphenyl group, 2,3-difluorophenyl group, 2,3-dichlorophenyl group, 2-chloro-3-fluorophenyl group, 3-chloro-2-fluorophenyl group, 2-chloro-4-fluorophenyl group, 2-chloro-5-fluorophenyl group, 2-chloro-6-fluorophenyl group, 5-bromo-2-chlorophenyl group, 2-chloro-5-hydroxyphenyl group, 2-chloro-5-(methylsulfonyl)phenyl group, 2-chloro-3,6-difluorophenyl group, 3-chloro-2,6-difluorophenyl group, 2-chloro-3-methylphenyl group, 2-chloro-3-methoxyphenyl group, 2-trifluoromethylphenyl group, 2-(methylsulfonyl)phenyl group, 2-chloro-5-methylsulfanylphenyl group, 2-chloro-5-methylphenyl group or 2-(dimethylaminosulfonyl)phenyl group, and more preferably 2,3-dichlorophenyl group, 2,3-difluorophenyl group, 2-chloro-3-fluorophenyl group or 3-chloro-2-fluorophenyl group.

$R^1$ and group B are preferably phenyl group, 3,4-dichlorophenyl group, 2-biphenyl group, cyclopropyl group, 2-hydroxycyclopropyl group, cyclobutyl group, 2-hydroxycyclobutyl group, 3-hydroxycyclobutyl group, cyclopentyl group, 2-hydroxycyclopentyl group, 3-hydroxycyclopentyl group, cyclohexyl group, 2-hydroxycyclohexyl group, 3-hydroxycyclohexyl group and 4-hydroxycyclohexyl group, particularly preferably phenyl group, 3,4-dichlorophenyl group, 2-biphenyl group, cyclopropyl group, cyclobutyl group, cyclopentyl group and cyclohexyl group.

As $R^{32}$, $R^{33}$, $R^1$ and group B, phenyl group and cyclohexyl group are preferable.

The "heterocyclic group" means a saturated or unsaturated (inclusive of partially unsaturated and completely unsaturated ones) monocyclic 5- or 6-membered heterocycle containing, besides carbon atom, at least one, preferably 1 to 4, heteroatoms selected from nitrogen atom, oxygen atom and sulfur atom, a fused ring of these heterocycles, or a fused ring of $C_{3-10}$ carbon ring and heterocycle, wherein the carbon ring is selected from benzene, cyclopentane and cyclohexane.

Examples of the "saturated monocyclic heterocyclic group" include pyrrolidinyl group, tetrahydrofuryl group, tetrahydrothienyl group, imidazolidinyl group, pyrazolidinyl group, 1,3-dioxolanyl group, 1,3-oxathiolanyl group, oxazolidinyl group, thiazolidinyl group, piperidinyl group, piperazinyl group, tetrahydropyranyl group, tetrahydrothiopyranyl group, dioxanyl group, morpholinyl group, thiomorpholinyl group, 2-oxopyrrolidinyl group, 2-oxopiperidinyl group, 4-oxopiperidinyl group, 2,6-dioxopiperidinyl group and the like. Preferably, it is pyrrolidinyl group, piperidinyl group or morpholinyl group.

Examples of the "unsaturated monocyclic heterocyclic group" include pyrrolyl group, furyl group, thienyl group, imidazolyl group, 1,2-dihydro-2-oxoimidazolyl group, pyrazolyl group, diazolyl group, oxazolyl group, isoxazolyl group, thiazolyl group, isothiazolyl group, 1,2,4-triazolyl group, 1,2,3-triazolyl group, tetrazolyl group, 1,3,4-oxadiazolyl group, 1,2,4-oxadiazolyl group, 1,3,4-thiadiazolyl group, 1,2,4-thiadiazolyl group, furazanyl group, pyridyl group, pyrimidinyl group, 3,4-dihydro-4-oxopyrimidinyl group, pyridazinyl group, pyrazinyl group, 1,3,5-triazinyl group, imidazolinyl group, pyrazolinyl group, oxazolinyl group (2-oxazolinyl group, 3-oxazolinyl group, 4-oxazolinyl group), isoxazolinyl group, thiazolinyl group, isothiazolinyl group, pyranyl group, 2-oxopyranyl group, 2-oxo-2,5-dihydrofuranyl group and 1,1-dioxo-1H-isothiazolyl group. Preferable examples include pyrrolyl group, furyl group, thienyl group, imidazolyl group, pyrazolyl group, oxazolyl group, isooxazolyl group, thiazolyl group, isothiazolyl group, pyridyl group, 2-oxo-2,5-dihydrofuranyl group and 1,1-dioxo-1H-isothiazolyl group.

As a "heterocyclic group, which is a fused ring", indolyl group (e.g., 4-indolyl group, 7-indolyl group and the like), isoindolyl group, 1,3-dihydro-1,3-dioxoisoindolyl group, benzofuranyl group (e.g., 4-benzofuranyl group, 7-benzofuranyl group and the like), indazolyl group, isobenzofuranyl group, benzothiophenyl group (e.g., 4-benzothiophenyl group, 7-benzothiophenyl group and the like), benzoxazolyl group (e.g., 4-benzoxazolyl group, 7-benzooxazolyl group and the like), benzimidazolyl group (e.g., 4-benzimidazolyl group, 7-benzimidazolyl group and the like), benzothiazolyl group (e.g., 4-benzothiazolyl group, 7-benzothiazolyl group and the like), indolizinyl group, quinolyl group, isoquinolyl group, 1,2-dihydro-2-oxoquinolyl group, quinazolinyl group, quinoxalinyl group, cinnolinyl group, phthalazinyl group, quinolizinyl group, puryl group, pteridinyl group, indolinyl group, isoindolinyl group, 5,6,7,8-tetrahydroquinolyl group, 1,2,3,4-tetrahydroquinolyl group, 2-oxo-1,2,3,4-tetrahydroquinolyl group, benzo[1,3]dioxolyl group, 3,4-methylenedioxypyridyl group, 4,5-ethylenedioxypyrimidinyl group, chromenyl group, chromanyl group, isochromanyl group and the like can be mentioned.

It is preferably a fused ring of monocyclic 5- or 6-membered heterocycle and benzene ring. Specific examples thereof include indolyl group, benzofuranyl group, benzothiophenyl group, benzimidazolyl group, benzoxazolyl group, benzothiazolyl group and benzo[1,3]dioxolyl group and the like.

The "heterocyclic group optionally substituted by 1 to 5 substituents selected from group A" is a "heterocyclic group" defined above, which is optionally substituted by 1 to 5, preferably 1 to 3, substituents selected from "group A" defined above and includes non-substituted "heterocyclic group".

The "heterocyclic group" is preferably a monocyclic heterocycle containing 1 or 2 heteroatoms, or a heterocycle which is a fused ring thereof with a benzene ring.

Specific examples of "heterocyclic group optionally substituted by 1 to 5 substituents selected from group A" include pyrrolidinyl group, piperidinyl group, morpholino group, pyrrolyl group, 2-pyrrolyl group, 3-pyrrolyl group, 2-furyl group, 3-furyl group, 2-thienyl group, 3-thienyl group, 4,5-dichlorothiophen-3-yl group, 2-oxo-2,5-dihydrofuran-3-yl group, 1,1-dioxo-1H-isothiazol-5-yl group, 4-methylthiazol-5-yl group, imidazolyl group, 2-imidazolyl group, 3-imidazolyl group, 4-imidazolyl group, pyrazolyl group, 2-oxazolyl group, 3-isoxazolyl group, 2-thiazolyl group, 3-isothiazolyl group, 3-fluoropyridin-2-yl group, 3-chloropyridin-2-yl group, 3-chloro-4-fluoropyridin-2-yl group, 3,5-dichloropyridin-2-yl group, 3-pyridyl group, 2-fluoropyridin-3-yl group, 2-chloropyridin-3-yl group, 2-chloro-4-fluoropyridin-3-yl group, 2-chloro-5-fluoropyridin-3-yl group, 2,5-dichloropyridin-3-yl group, 2-chloro-6-fluoropyridin-3-yl group, 2,6-dichloropyridin-3-yl group, 4-pyridyl group, 2-fluoropyridin-4-yl group, 2-chloropyridin-4-yl group, 2-chloro-3-fluoropyridin-4-yl group, 2,3-difluoropyridin-4-yl group, 2,3-dichloropyridin-4-yl group, 2,5-dichloropyridin-4-yl group, 2-chloro-6-fluoropyridin-4-yl group, 2,6-dichloropyridin-4-yl group, 2-chloro-3,6-difluoropyridin-4-yl group, 2-chloro-3,5-difluoropyridin-4-yl group, 2,3,6-trifluoropyridin-4-yl group, 2,3,5,6-tetrafluoropyridin-4-yl group, 2-indolyl group, 3-indolyl group, 4-indolyl group, 7-indolyl group, 2-benzofuranyl group, 4-benzofuranyl group, 7-benzofuranyl group, 2-benzothiophenyl group, 4-benzothiophenyl group, 7-benzothiophenyl group, 2-benzimidazolyl group, 4-benzimidazolyl group, 2-benzoxazolyl group, 4-benzoxazolyl group, 7-benzoxazolyl group, 2-benzothiazolyl group, 4-benzothiazolyl group, 7-benzothiazolyl group, 2-benzo[1,3]dioxolyl group, 4-benzo[1,3]dioxolyl group, 5-benzo[1,3]dioxolyl group and the like.

As ring Cy, 2-pyridyl group and 4-pyridyl group are preferable, as $R^1$ and group B, imidazolyl group, 2-pyridyl group, 2-benzothiophenyl group, morpholino group and 4-methylthiazol-5-yl group are preferable, and as $R^{32}$ and $R^{33}$, pyrrolidinyl group is preferable.

The "$C_{1-10}$ alkyl group optionally substituted by 1 to 3 substituents selected from halogen atom and group B" is a $C_{1-10}$ alkyl group optionally substituted by the substituent group selected from-the "halogen atom" defined above and the "group B" defined below, and may be a non-substituted alkyl group. The alkyl moiety is straight chain or branched chain alkyl group having 1 to 10 carbon atoms. Specific examples thereof include methyl group, ethyl group, propyl group, isopropyl group, butyl group, isobutyl group, sec-butyl group, tert-butyl group, pentyl group, isopentyl group, 1-methylbutyl group, 1-ethylpropyl group, 2-ethylpropyl group, 1,1-dimethylpropyl group, 1,2-dimethylpropyl group, tert-pentyl group, hexyl group, isohexyl group, 1-methylpentyl group, 1,1-dimethylbutyl group, 1,2-dimethylbutyl group, 1,3-dimethylbutyl group, 1-ethylbutyl group, 1-ethyl-1-methylpropyl group, 1-ethyl-2-methylpropyl group, 1,1,2-trimethylpropyl group, 1,2,2-trimethylpropyl group, 1-ethyl-1-methylpropyl group, heptyl group, isoheptyl group, 1-methylhexyl group, 1,1-dimethylpentyl group, 1,2-dimethylpentyl group, 1,3-dimethylpentyl group, 1,4-dimethylpentyl group, 1,1,2-trimethylbutyl group, 1,1,3-trimethylbutyl group, 1,2,2-trimethylbutyl group, 1,2,3-trimethylbutyl group, 1,3,3-trimethylbutyl group, 1-ethylpentyl group, 1-ethyl-2-methylbutyl group, 1-ethyl-3-methylbutyl group, 2-ethyl-1-methylbutyl group, 1-propylbutyl group, 1-ethyl-2,2-dimethylpropyl group, 1-isopropyl-2-methylpropyl group, 1-isopropyl-1-methylpropyl group, 1,1-diethylpropyl group, 1,1,2,2-tetramethylpropyl group, 1-isopropylbutyl group, 1-ethyl-1-methylbutyl group, octyl group, nonyl group, decanyl group and the like, with preference given to straight chain or branched chain alkyl group having 1 to 6 carbon atoms, particularly preferably branched chain alkyl group having 1 to 6 carbon atoms.

The "group B" is a group consisting of the "$C_{3-10}$ carbon ring group optionally substituted by 1 to 5 substituents selected from group A" defined above, the "heterocyclic group optionally substituted by 1 to 5 substituents selected from group A" defined above, $—OR^{a4}$, $—SR^{a4}$, $—NR^{a4}R^{a5}$, $—CONR^{a4}R^{a5}$, $—SO_2NR^{a4}R^{a5}$, $—COR^{a6}$, $—NR^{a4}COR^{a6}$, $—SO_2R^{a6}$, $—NR^{a4}SO_2R^{a6}$, $—COOR^{a4}$ and $—NR^{a5}COOR^{a6}$.

As used herein, $R^{a4}$ and $R^{a5}$ are the same or different and each is a hydrogen atom, a "$C_{1-4}$ alkyl group" defined above, a "$C_{3-10}$ carbon ring group optionally substituted by 1 to 5 substituents selected from group A" defined above or a "heterocyclic group optionally substituted by 1 to 5 substituents selected from group A" defined above, and $R^{a6}$ is a "$C_{1-4}$ alkyl group" defined above, a "$C_{3-10}$ carbon ring group optionally substituted by 1 to 5 substituents selected from group A" defined above or a "heterocyclic group optionally substituted by 1 to 5 substituents selected from group A" defined above.

Specific examples of $—OR^{a4}$, $—SR^{a4}$, $—NR^{a4}R^{a5}$, $—CONR^{a4}R^{a5}$, $—SO_2NR^{a4}R^{a5}$, $—COR^{a6}$, $—NR^{a4}COR^{a6}$, $—SO_2R^{a6}$, $—NR^{a4}SO_2R^{a6}$, $—COOR^{a4}$ and $—NR^{a5}COOR^{a6}$ include substituents recited in the definitions of "$—OR^{a1}$", "$—SR^{a1}$", "$—NR^{a1}R^{a2}$", "$—CONR^{a1}R^{a2}$", "$—SO_2NR^{a1}R^{a2}$", "$—COR^{a3}$", "$—NR^{a1}COR^{a3}$", "$—SO_2R^{a3}$", "$—NR^{a1}SO_2R^{a3}$", "$—COOR^{a1}$" and "$—NR^{a2}COOR^{a3}$" for "group A", respectively, and the like.

Specific examples of "$C_{-10}$ alkyl group optionally substituted by 1 to 3 substituents selected: from halogen atom and group B" include methyl group, ethyl group, propyl group, isopropyl group, butyl group, isobutyl group, sec-butyl group, tert-butyl group, pentyl group, isopentyl group, 1-methylbutyl group, 1-ethylpropyl group, 2-ethylpropyl group, 1,1-dimethylpropyl group, 1,2-dimethylpropyl group, tert-pentyl group, hexyl group, isohexyl group, 1-methylpentyl group, 1,1-dimethylbutyl group, 1,2-dimethylbutyl group, 1,3-dimethylbutyl group, 1-ethylbutyl group, 1-ethyl-1-methylpropyl group, 1-ethyl-2-methylpropyl group, 1,1,2-trimethylpropyl group, 1,2,2-trimethylpropyl group, 1-ethyl-1-methylpropyl group, heptyl group, isoheptyl group, 1-methylhexyl group, 1,1-dimethylpentyl group, 1,2-dimethylpentyl group, 1,3-dimethylpentyl group, 1,4-dimethylpentyl group, 1,1,2-trimethylbutyl group, 1,1,3-trimethylbutyl group, 1,2,2-trimethylbutyl group, 1,2,3-trimethylbutyl group, 1,3,3-trimethylbutyl group, 1-ethylpentyl group, 1-ethyl-2-methylbutyl group, 1-ethyl-3-methylbutyl group, 2-ethyl-1-methylbutyl group, 1-propylbutyl group, 1-ethyl-2,2-dimethylpropyl group, 1-isopropyl-2-methylpropyl group, 1-isopropyl-1-methylpropyl group, 1,1-diethylpropyl group, 1,1,2,2-tetramethylpropyl group, 1-isopropylbutyl group, 1-ethyl-1-methylbutyl group, fluoromethyl group, trifluoromethyl group, chloroethyl group, 2-fluoroethyl group, 2-chloroethyl group, 3-fluoropropyl group, 2-chloropropyl group, 2,2,2-trifluoroethyl group, 2-hydroxyethyl group, 2-hydroxypropyl group, 2-hydroxy-1-methylethyl group, 2-hydroxy-1,1-dimethylethyl group, 1-(hydroxymethyl)propyl group, 3-hydroxypropyl group, 2-hydroxybutyl group, 4-hydroxybutyl group, 2-hydroxypentyl group, 5-hydroxypentyl group, 2,3-dihydroxypropyl group, 2,3-dihydroxybutyl group, 2-hydroxy-1-(hydroxymethyl)ethyl group, 2-hydroxy-2-methylpropyl group, 1-(hydroxymethyl)butyl group, 1-(hydroxymethyl)-2-methylpropyl group, 1-(hydroxymethyl)-2,2-dimethylpropyl group, 1-(hydroxymethyl)-2-methylbutyl group, 2-hydroxy-1-phenylethyl group, 2-hydroxy-2-phenylethyl group, 1-(hydroxymethyl)-2-phenylethyl group, 3-methyl-1-(hydroxymethyl)butyl group, 2-ethyl-1-(hydroxymethyl)butyl group, 3-hydroxy-1-methylpropyl group, 1,1-dimethyl-3-hydroxypropyl group, 1,2-dimethyl-3-hydroxypropyl group, 1-isopropyl-3-hydroxypropyl group, 2,2-dimethyl-1-(2-hydroxyethyl)propyl group, 1-ethyl-3-hydroxypropyl group, 2-hydroxy-1-isopropylpropyl group, 1-ethyl-1-(hydroxymethyl)propyl group, 1,1-dimethyl-2-hydroxypropyl group, 1,2-dimethyl-2-hydroxypropyl group, 1-ethyl-2-hydroxypropyl group, 4-hydroxy-1-methylbutyl group, 2-ethyl-1-(hydroxymethyl)-2-methylbutyl group, 3,3-dimethyl-1-(hydroxymethyl)butyl group, 1-(hydroxymethyl)pentyl group, 4-methyl-1-(hydroxymethyl)pentyl group, methoxymethyl group, 2-methoxyethyl group, methylsulfanylmethyl group, 2-(methylsulfanyl)ethyl group, 2-aminoethyl group, 2-(dimethylamino)ethyl group, carboxymethyl group, 2-carboxyethyl group, 2-carboxypropyl group, 3-carboxypropyl group, carbamoylmethyl group, 2-carbamoylethyl group, methylaminocarbonylmethyl group, dimethylaminocarbonylmethyl group, 2-(phenylaminocarbonyl)ethyl group, 2-oxopropyl group, methylsulfonylmethyl group, 2-(methylsulfonyl)ethyl group, sulfamoylmethyl group, methylaminosulfonylmethyl group, dimethylaminosulfonylmethyl group, tert-butylaminosulfonylmethyl group, 2-(acetylamino)ethyl group, 2-(methylsulfonylamino)ethyl group, 2-(ethoxycarbonylamino)ethyl group, benzyl group, phenethyl group, 3-phenylpropyl group, 4-phenylbutyl group, 2-biphenylmethyl group, 3,4-dichlorobenzyl group, 2-hydroxy-2-phenylethyl group, cyclopentylmethyl group, cyclohexylmethyl group, 2-cyclohexylethyl group, 1-cyclohexyl-2-hydroxyethyl group, 1-cyclohexylmethyl-2-hydroxyethyl group, phenylaminocarbonylmethyl group, 2-pyridin-2-ylethyl group, 2-imidazol-1-ylethyl group, 2-benzothiophen-2-ylethyl group, 2-morpholinoethyl group, 2-(4-methylthiazolin-5-yl)ethyl group, 1-carboxyethyl group, 1-carbamoylethyl group, 1-carboxy-2-methylpropyl group, 1-carbamoyl-2-methylpropyl group, 2-hydroxy-1-(hydroxymethyl)propyl group, 1-(hydroxymethyl)-2-mercaptoethyl group, 1-(hydroxymethyl)-3-(methylsulfanyl)propyl group, 2-carboxy-1-(hydroxymethyl)ethyl group, 2-carbamoyl-1-(hydroxymethyl)ethyl group, 2-(indol-3-yl)-1-(hydroxymethyl)ethyl group, 2-(imidazol-4-yl)-1-(hydroxymethyl)ethyl group, 2-(4-hydroxyphenyl)-1-(hydroxymethyl)ethyl group, 3-carbamoyl-1-(hydroxymethyl)propyl group, 5-amino-1-(hydroxymethyl)pentyl group and the like.

$R^1$ is preferably methyl group, ethyl group, propyl group, isopropyl group, butyl group, isobutyl group, tert-butyl group, 2-fluoroethyl group, 2,2,2-trifluoroethyl group, 2-hydroxyethyl group, 2-hydroxypropyl group, 3-hydroxypropyl group, 4-hydroxybutyl group, 5-hydroxypentyl group, 2,3-dihydroxypropyl group, 2-hydroxy-1-methylethyl group, 2-hydroxy-1,1-dimethylethyl group, 2-hydroxy-1-(hydroxymethyl)ethyl group, 1-(hydroxymethyl)propyl group, 2-hydroxy-2-methylpropyl group, 1-(hydroxymethyl)butyl group, 1-(hydroxymethyl)-2-methylpropyl group, 1-(hydroxymethyl)-2,2-dimethylpropyl group, 1-(hydroxymethyl)-2-methylbutyl group, 1-(hydroxymethyl)-3-methylbutyl group, 2-hydroxy-1-phenylethyl group, 2-hydroxy-2-phenylethyl group, 1-(hydroxymethyl)-2-phenylethyl group, 2-methoxyethyl group, methylsulfanylmethyl group, 2-(methylsulfanyl)ethyl group, 2-aminoethyl group, 2-(dimethylamino)ethyl group, carboxymethyl group, 2-carboxyethyl group, 3-carboxypropyl group, carbamoylmethyl group, 2-carbamoylethyl group, methylaminocarbonylmethyl group, dimethylaminocarbonylmethyl group, 2-(phenylaminocarbonyl)ethyl group, 2-oxopropyl group, methylsulfonylmethyl group, 2-(methylsulfonyl)ethyl group, sulfamoylmethyl group, methylaminosulfonylmethyl group, dimethylaminosulfonylmethyl group, tert-butylaminosulfonylmethyl group, 2-(acetylamino)ethyl group, 2-(methylsulfonylamino)ethyl group, 2-(ethoxycarbonylamino)ethyl group, benzyl group, phenethyl group, 3-phenylpropyl group, 4-phenylbutyl group, 2-biphenylmethyl group, 3,4-dichlorobenzyl group, cyclopentylmethyl group, cyclohexylmethyl group, 1-cyclohexyl-2-hydroxyethyl group, 1-cyclohexylmethyl-2-hydroxyethyl group, 2-pyridin-2-ylethyl group, 2-imidazol-1-ylethyl group, 2-morpholinoethyl group, 2-(4-methylthiazolin-5-yl)ethyl group or benzothiophen-2-ylmethyl group, particularly preferably alkyl group branched at the 1-position and/or alkyl group substituted by hydroxy group. Specific examples thereof include 2-hydroxy-1-methylethyl group, 1-(hydroxymethyl)-2-methylpropyl group, 1-(hydroxymethyl)-2,2-dimethylpropyl group, 1-(hydroxymethyl)-2-methylbutyl group, 2-hydroxy-1-(hydroxymethyl)ethyl group and 2-phenyl-1-(hydroxymethyl) ethyl group. When these particularly preferable substituents are in optically active forms, S form is more preferable.

$R^{32}$ and $R^{33}$ are preferably methyl group, ethyl group and trifluoromethyl group, and $R^{a7}$ and $R^{a8}$ are preferably methyl group, ethyl group, propyl group, isopropyl group, 2-hydroxyethyl group, 3-hydroxypropyl group and cyclohexylmethyl group, more preferably methyl group, ethyl group and isopropyl group, and particularly preferably methyl group.

The ring Cy in the formula [I] is preferably a "$C_{3-10}$ carbon ring group optionally substituted by 1 to 5 substituents selected from group A" defined above, more preferably

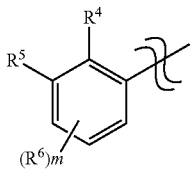

wherein $R^4$, $R^5$, $R^6$ and m are as defined above. A more preferable embodiment here is the same as the 4-oxoquinoline compound represented by the formula [II], wherein m is preferably 0 or 1, more preferably 0.

The group A for ring Cy is preferably cyano group, phenyl group, nitro group, "halogen atom" defined above, "$C_{1-4}$ alkyl group" defined above, "halo $C_{1-4}$ alkyl group" defined above, "halo $C_{1-4}$ alkyloxy group" defined above, "—$OR^{a1}$" defined above, "—$SR^{a1}$" defined above, "—$NR^{a1}R^{a2}$" defined above, "—$CONR^{a1}R^{a2}$" defined above, "—$SO_2NR^{a1}R^{a2}$" defined above, "—$NR^{a1}COR^{a3}$" defined above, "—$SO_2R^{a3}$" defined above or "—$NR^{a1}SO_2R^{a3}$" defined above, more preferably cyano group, phenyl group, nitro group, "halogen atom", "$C_{1-4}$ alkyl group", "halo $C_{1-4}$ alkyl group", "halo $C_{1-4}$ alkyloxy group", "—$OR^{a1}$", "—$SR^{a1}$", "—$NR^{a1}R^{a2}$", "—$SO_2R^{a3}$", "—$SO_2NR^{a1}R^{a2}$" or "—$NR^{a1}COR^{a3}$", and particularly preferably "halogen atom" defined above.

The ring Cy is more preferably

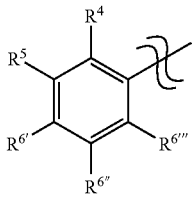

wherein $R^{6'}$, $R^{6''}$ and $R^{6'''}$ are substituents selected from hydrogen atom and "group A" defined above, and $R^4$ and $R^5$ are as defined above.

$R^4$ is preferably phenyl group, "halogen atom" defined above, "$C_{1-4}$ alkyl group" defined above, "halo $C_{1-4}$ alkyloxy group" defined above, "—$OR^{a1}$" defined above, "—$NR^{a1}R^{a2}$" defined above, "—$SO_2NR^{a1}R^{a2}$" defined above, "—$NR^{a1}COR^{a3}$" defined above, "—$SO_2R^{a3}$" defined above, "—$COOR^{a1}$" defined above or "—$NR^{a1}SO_2R^{a3}$" defined above,
more preferably "halogen atom", "$C_{1-4}$ alkyl group", "halo $C_{1-4}$ alkyloxy group", "—$OR^{a1}$" or "—$NR^{a1}R^{a2}$", and particularly preferably "halogen atom" defined above, $R^5$ is preferably hydrogen atom, cyano group, nitro group, "halogen atom" defined above, "$C_{1-4}$ alkyl group" defined above, "halo $C_{1-4}$ alkyl group" defined above, "—$OR^{a1}$", defined above, "—$SR^{a1}$" defined above, "—$NR^{a1}R^{a2}$" defined above, "—$CONR^{a1}R^{a2}$" defined above, "—$SO_2NR^{a1}R^{a2}$" defined above or "—$NR^{a1}COR^{a3}$" defined above,
more preferably hydrogen atom, "halogen atom" or "$C_{1-4}$ alkyl group", and particularly preferably "halogen atom".

$R^6$ is preferably "halogen atom", "$C_{1-4}$ alkyl group" defined above, "—$SO_2R^{a3}$" defined above, "—$OR^{a1}$" defined above or "—$SR^{a1}$" defined above, more preferably "halogen atom".

$R^{6'}$ and $R^{6'''}$ are preferably the same or different and each is hydrogen atom or "halogen atom" defined above, $R^{6''}$ is preferably hydrogen atom, "halogen atom" defined above, "$C_{1-4}$ alkyl group" defined above, "—$SO_2R^{a3}$" defined above, "—$OR^{a1}$" defined above or "—$SR^{a1}$" defined above, more preferably, hydrogen atom, "halogen atom", "$C_{1-4}$ alkyl group" defined above or "—$SR^{a1}$" defined above, and more preferably hydrogen atom.

$R^1$ is preferably "$C_{3-10}$ carbon ring group optionally substituted by 1 to 5 substituents selected from group A" defined above, "heterocyclic group optionally substituted by 1 to 5 substituents selected from group A" defined above, "—$OR^{a4}$" defined above (here, it is concretely preferably methoxy group), "—$NR^{a4}R^{a5}$" defined above (here, it is concretely preferably amino group, methylamino group, ethylamino group or dimethylamino group), "—$NR^{a4}COR^{a6}$" defined above (here, it is concretely preferably acetylamino group), "—$NR^{a4}SO_2R^{a6}$" defined above (here, it is concretely preferably, methylsulfonylamino group or N-methyl-N-(methylsulfonyl)amino group), "—$NR^{a5}COOR^{a6}$" defined above (here, it is concretely preferably methoxycarbonylamino group) or "$C_{1-10}$ alkyl group optionally substituted by 1 to 3 substituents selected from halogen atom and group B" defined above, more preferably, "$C_{3-10}$ carbon ring group optionally substituted by 1 to 5 substituents selected from group A" defined above or "$C_{1-10}$ alkyl group optionally substituted by 1 to 3 substituents selected from halogen atom and group B", more preferably "$C_{1-10}$ alkyl group optionally substituted by 1 to 3 substituents selected from halogen atom and group B" defined above.

$R^2$ is preferably hydrogen atom.

$R^{31}$ is preferably hydrogen atom, cyano group, "halogen atom" defined above, hydroxy group or "$C_{1-4}$ alkoxy group" defined above, more preferably hydrogen atom, cyano group, "halogen atom" defined above or "$C_{1-4}$ alkoxy group" defined above, more preferably hydrogen atom, cyano group or "$C_{1-4}$ alkoxy group" defined above, particularly preferably hydrogen atom.

$R^{32}$ is preferably hydrogen atom, cyano group, "halogen atom" defined above, "heterocyclic group optionally substituted by 1 to 5 substituents selected from group A" defined above, "$C_{1-10}$ alkyl group optionally substituted by 1 to 3 substituents selected from halogen atom and group B" defined above, "—$OR^{a7}$" defined above, "—$SR^{a7}$" defined above, "—NR$^{a7}$R$^{a8}$" defined above, "—COOR$^{a10}$" defined above or "—N=CH—NR$^{a10}$R$^{a11}$" defined above, more preferably hydrogen atom, "—OR$^{a7}$" defined above, "—SR$^{a7}$" defined above or "—NR$^{a7}$R$^{a8}$" defined above, more preferably hydrogen atom or "—OR$^{a7}$" defined above, particularly preferably "—OR$^{a7}$".

R$^{33}$ is preferably hydrogen atom, "C$_{1-10}$ alkyl group optionally substituted by 1 to 3 substituents selected from halogen atom and group B" defined above, "—OR$^{a7}$" defined above or "—NR$^{a7}$R$^{a8}$" defined above, more preferably hydrogen atom, "—OR$^{a7}$" defined above or "—NR$^{a7}$R$^{a8}$" defined above, more preferably hydrogen atom or "—OR$^{a7}$" defined above, particularly preferably hydrogen atom.

It is preferable that one of R$^{32}$ and R$^{33}$ be hydrogen atom, and the other be "—OR$^{a7}$" defined above.

It is preferable that R$^{31}$ be hydrogen atom and R$^{32}$ or R$^{33}$ be other than hydrogen atom.

The "pharmaceutically acceptable salt thereof" may be any as long as it forms a non-toxic salt with a compound of the above-mentioned formula [I] or [II]. For example, it can be obtained by reaction with an inorganic acid such as hydrochloric acid, sulfuric acid, phosphoric acid, hydrobromic acid and the like; an organic acid such as oxalic acid, malonic acid, citric acid, fumaric acid, lactic acid, malic acid, succinic acid, tartaric acid, acetic acid, trifluoroacetic acid, gluconic acid, ascorbic acid, methylsulfonic acid, benzylsulfonic acid and the like; an inorganic base such as sodium hydroxide, potassium hydroxide, calcium hydroxide, magnesium hydroxide, ammonium hydroxide and the like; an organic base such as methylamine, diethylamine, triethylamine, triethanolamine, ethylenediamine, tris(hydroxymethyl)methylamine, guanidine, choline, cinchonine and the like; or an amino acid such as lysin, arginine, alanine and the like. The present invention encompasses water-containing products, hydrates and solvates of each compound.

In addition, the compounds represented by the above-mentioned formulas [I] and [II] have various isomers. For example, E form and Z form are present as geometric isomers, and when an asymmetric carbon atom exists, enantiomer and diastereomer are present as stereoisomers based thereon, and tautomer can be present. Accordingly, the present invention encompasses all these isomers and mixtures thereof. The compound of the present invention is preferably isolated and purified from various isomers, byproducts, metabolites or prodrugs, where one having a purity of 90% or above is preferable and one having a purity of 95% or above is more preferable.

The present invention also encompasses prodrugs and metabolites of each compound.

By the "prodrug" is meant a derivative of the compound of the present invention, which has a chemically or metabolically decomposable group and which, after administration to a body, restores to the original compound to show its inherent efficacy, including a complex and a salt free of covalent bond.

The prodrug is utilized for, for example, improving absorption by oral administration or targeting of a target site.

As the site to be modified, highly reactive functional groups in the compound of the present invention, such as hydroxyl group, carboxyl group, amino group, thiol group and the like, are mentioned.

Examples of the hydroxyl-modifying group include acetyl group, propionyl group, isobutyryl group, pivaloyl group, benzoyl group, 4-methylbenzoyl group, dimethylcarbamoyl group, sulfo group and the like. Examples of the carboxyl-modifying group include ethyl group, pivaloyloxymethyl group, 1-(acetyloxy)ethyl group, 1-(ethoxycarbonyloxy) ethyl group, 1-(cyclohexyloxycarbonyloxy)ethyl group, carboxylmethyl group, (5-methyl-2-oxo-1,3-dioxol-4-yl)methyl group, phenyl group, o-tolyl group and the like. Examples of the amino-modifying group include hexylcarbamoyl group, 3-methylthio-1-(acetylamino)propylcarbonyl group, 1-sulfo-1-(3-ethoxy-4-hydroxyphenyl)methyl group, (5-methyl-2-oxo-1,3-dioxol-4-yl)methyl group and the like.

The compound of the present invention can be administered to a mammal (human, mouse, rat, hamster, rabbit, cat, dog, bovine, sheep, swine and the like) as an anti-HIV agent, an integrase inhibitor, an antiviral agent and the like.

When the compound of the present invention is used as a pharmaceutical preparation, it is admixed with pharmaceutically acceptable carriers, excipients, diluents, extending agents, disintegrants, stabilizers, preservatives, buffers, emulsifiers, flavoring agents, coloring agents, sweetening agents, thickeners, correctives, dissolution aids, and other additives, that are generally known per se, such as water, vegetable oil, alcohol (e.g., ethanol or benzyl alcohol etc.), polyethylene glycol, glycerol triacetate, gelatin, carbohydrate (e.g., lactose, starch etc.), magnesium stearate, talc, lanolin, petrolatum and the like, formed into tablet, pill, powder, granule, suppository, injection, eye drop, liquid, capsule, troche, aerosol, elixir, suspension, emulsion, syrup and the like by a conventional method, and administered systemically or topically, and orally or parenterally.

While the dose varies depending on age, body weight, symptom, treatment effect, administration method and the like, it is generally 0.01 mg to 1 g per administration for an adult, which is given once to several times a day orally or in a dosage form of an injection such as intravenous injection and the like.

An anti-HIV agent is generally required to sustain its effect for a long time, so that can be effective not only for temporal suppression of viral growth but also for prohibition of viral re-growth. This means that a long term administration is necessary and that a high single dose may be frequently inevitable to sustain effect for a longer period through the night. Such long term and high dose administration increases the risk of causing side effects.

In view of this, one of the preferable modes of the 4-oxo-quinoline compound of the present invention is such compound permitting high absorption by oral administration, and such compound capable of maintaining blood concentration of the administered compound for an extended period of time.

By the "prophylaxis of AIDS" is meant, for example, administration of a pharmaceutical agent to an individual who tested HIV positive but has not yet developed the disease state of AIDS, administration of a pharmaceutical agent to an individual who shows an improved disease state of AIDS after treatment but who carries HIV still to be eradicated and whose relapse of AIDS is worried, and administration of a pharmaceutical agent before the infection of HIV out of a fear of possible infection.

Examples of the "other anti-HIV agents" and "other anti-HIV active substance" to be used for a multiple drug combination therapy include an anti-HIV antibody, an HIV vaccine, immunostimulants such as interferon and the like, an HIV ribozyme, an HIV antisense drug, a reverse transcriptase inhibitor, a protease inhibitor, an inhibitor of bond between a bond receptor (CD4, CXCR4, CCR5 and the like) of a host cell recognized by virus and the virus, and the like.

Specific examples of the HIV reverse transcriptase inhibitor include Retrovir(R) (zidovudine), Epivir(R) (lamivudine), Zerit(R) (sanilvudine), Videx(R) (didanosine), Hivid(R) (zalcitabine), Ziagen(R) (abacavir sulfate), Viramune(R) (nevirapine), Stocrin(R) (efavirenz), Rescriptor(R) (delavirdine mesylate), Combivir(R) (zidovudine+lamivudine), Trizivir (R) (abacavir sulfate+lamivudine+zidovudine), Coactinon (R) (emivirine), Phosphonovir(R), Coviracil(R), alovudine (3'-fluoro-3'-deoxythymidine), Thiovir (thiophosphonoformic acid), Capravirin (5-[(3,5-dichlorophenyl)thio]-4-isopropyl-1-(4-pyridylmethyl)imidazole-2-methanol carbamic acid), Tenofovir disoproxil fumarate ((R)-[[2-(6-amino-9H-purin-9-yl)-1-methylethoxy]methyl]phosphonic acid bis (isopropoxycarbonyloxymethyl)ester fumarate), DPC-083 ((4S)-6-chloro-4-[(1E)-cyclopropylethenyl]-3,4-dihydro-4-trifluoromethyl-2(1H)-quinazolinone), DPC-961 ((4S)-6-chloro-4-(cyclopropylethynyl)-3,4-dihydro-4-(trifluoromethyl)-2(1H)-quinazolinone), DAPD ((−)-β-D-2,6-diaminopurine dioxolane), Immunocal, MSK-055, MSA-254, MSH-143, NV-01, TMC-120, DPC-817, GS-7340, TMC-125, SPD-754, D-A4FC, capravirine, UC-781, emtricitabine, alovudine, Phosphazid, UC-781, BCH-10618, DPC-083, Etravirine, BCH-13520, MIV-210, Abacavir sulfate/lamivudine, GS-7340, GW-5634, GW-695634 and the like, wherein (R) means a registered trademark (hereinafter the same) and the names of other pharmaceutical agents are general names.

Specific examples of the HIV protease inhibitor include Crixivan(R) (indinavir sulfate ethanolate), saquinavir, Invirase(R) (saquinavir mesylate), Norvir(R) (ritonavir), Viracept (R) (nelfinavir mesylate), lopinavir, Prozei(R) (amprenavir), Kaletra(R) (ritonavir+lopinavir), mozenavir dimesylate ([4R-(4α,5α,6β)]-1-3-bis[(3-aminophenyl)methyl]-hexahydro-5,6-dihydroxy-4,7-bis(phenylmethyl)-2H-1,3-diazepin-2-one dimethanesulfonate), tipranavir (3'-[(1R)-1-[(6R)-5,6-dihydro-4-hydroxy-2-oxo-6-phenylethyl-6-propyl-2H-pyran-3-yl]propyl]-5-(trifluoromethyl)-2-pyridinesulfonamide), lasinavir (N-[5(S)-(tert-butoxycarbonylamino)-4(S)-hydroxy-6-phenyl-2(R)-(2,3,4-trimethoxybenzyl)hexanoyl]-L-valine 2-methoxyethylenamide), KNI-272 ((R)-N-tert-butyl-3-[(2S,3S)-2-hydroxy-3-N-[(R)-2-N-(isoquinolin-5-yloxy-acetyl)amino-3-methylthiopropanoyl]amino-4-phenylbutanoyl]-5,5-dimethyl-1,3-thiazolidine-4-carboxamide), GW-433908, TMC-126, DPC-681, buckminsterfullerene, MK-944A (MK944 (N-(2(R)-hydroxy-1(S)-indanyl)-2(R)-phenylmethyl-4(S)-hydroxy-5-[4-(2-benzo[b]furanylmethyl)-2(S)-(tert-butylcarbamoyl)piperazin-1-yl]pentanamide)+indinavir sulfate), JE-2147 ([2(S)-oxo-4-phenylmethyl-3(S)-[(2-methyl-3-oxy) phenylcarbonylamino]-1-oxabutyl]-4-[(2-methylphenyl) methylamino]carbonyl-4(R)-5,5-dimethyl-1,3-thiazole), BMS-232632 ((3S,8S,9S,12S)-3,12-bis(1,1-dimethylethyl)-8-hydroxy-4,11-dioxo-9-(phenylmethyl)-6-[[4-(2-pyridinyl) phenyl]methyl]-2,5,6,10,13-pentaazatetradecanedicarboxylic acid dimethyl ester), DMP-850 ((4R,5S,6S,7R)-1-(3-amino-1H-indazol-5-ylmethyl)-4,7-dibenzyl-3-butyl-5,6-dihydroxyperhydro-1,3-diazepin-2-one), DMP-851, RO-0334649, Nar-DG-35, R-944, VX-385, TMC-114, Tipranavir, Fosamprenavir sodium, Fosamprenavir-calcium, Darunavir, GW-0385, R-944, RO-033-4649, AG-1859 and the like.

The HIV integrase inhibitor is exemplified by S-1360, L-870810 and the like, the DNA polymerase inhibitor or DNA synthesis inhibitor is exemplified by Foscavir(R), ACH-126443 (L-2',3'-didehydro-dideoxy-5-fluorocytidine), entecavir ((1S,3S,4S)-9-[4-hydroxy-3-(hydroxymethyl)-2-methylenecyclopentyl]guanine), calanolide A ([10R-(10α,11β, 12α)]-11,12-dihydro-12-hydroxy-6,6,10,11-tetramethyl-4-propyl-2H,6H,10H-benzo[1,2-b:3,4-b':5,6-b"]tripyran-2-one), calanolide B, NSC-674447 (1,1'-azobisformamide), Iscador (viscum alubm extract), Rubutecan and the like, the HIV antisense drug is exemplified by HGTV-43, GEM-92 and the like, the anti-HIV antibody or other antibody is exemplified by NM-01, PRO-367, KD-247, Cytolin(R), TNX-355 (CD4 antibody), AGT-1, PRO-140 (CCR$^5$ antibody), Anti-CTLA-4 MAb and the like, the HIV vaccine or other vaccine is exemplified by ALVAC(R), AIDSVAX(R), Remune(R), HIV gp41 vaccine, HIV gp120 vaccine, HIV gp140 vaccine, HIV gp160 vaccine, HIV p17 vaccine, HIV p24 vaccine, HIV p55 vaccine, AlphaVax Vector System, canarypox gp160 vaccine, AntiTat, MVA-F6 Nef vaccine, HIV rev vaccine, C4-V3 peptide, p2249f, VIR-201, HGP-30W, TBC-3B, PARTICLE-3B and the like, Antiferon (interferon-α vaccine) and the like, the interferon or interferon agonist is exemplified by Sumiferon(R), MultiFeron(R), interferon-τ, Reticulose, Human leukocyte interferon alpha and the like, the CCR$^5$ antagonist is exemplified by SCH-351125 and the like, the pharmaceutical agent acting on HIV p24 is exemplified by GPG-NH2 (glycyl-prolyl-glycinamide) and the like, the HIV fusion inhibitor is exemplified by FP-21399 (1,4-bis[3-[(2,4-dichlorophenyl)carbonylamino]-2-oxo-5,8-disodium sulfonyl] naphthyl-2,5-dimethoxyphenyl-1,4-dihydrazone), T-1249, Synthetic Polymeric Construction No 3, pentafuside, FP-21399, PRO-542, Enfuvirtide and the like, the IL-2 agonist or antagonist is exemplified by interleukin-2, Imunace (R), Proleukin(R), Multikine(R), Ontak(R) and the like, the TNF-α antagonist is exemplified by Thalomid(R) (thalidomide), Remicade(R) (infliximab), curdlan sulfate and the like,the α-glucosidase inhibitor is exemplified by Bucast(R) and the like, the purine nucleoside phosphorylase inhibitor is exemplified by peldesine (2-amino-4-oxo-3H,5H-7-[(3-pyridyl)methyl]pyrrolo[3,2-d]pyrimidine) and the like, the apoptosis agonist or inhibitor is exemplified by Arkin Z(R), Panavir(R), Coenzyme Q10 (2-deca(3-methyl-2-butenylene)-5,6-dimethoxy-3-methyl-p-benzoquinone) and the like, the cholinesterase inhibitor is exemplified by Cognex(R) and the like, and the immunomodulator is exemplified by Imunox(R), Prokine(R), Met-enkephalin (6-de-L-arginine-7-de-L-arginine-8-de-L-valinamide-adrenorphin), WF-10 (10-fold dilute tetrachlorodecaoxide solution), Perthon, PRO-542, SCH-D, UK-427857, AMD-070, AK-602 and the like.

In addition, Neurotropin(R), Lidakol(R), Ancer 20(R), Ampligen(R), Anticort(R), Inactivin(R) and the like, PRO-2000, Rev M10 gene, HIV specific cytotoxic T cell (CTL immunotherapy, ACTG protocol 080 therapy, CD4-ζ gene therapy), SCA binding protein, RBC-CD4 complex, Motexafin gadolinium, GEM-92, CNI-1493, (±)-FTC, Ushercell, D2S, BufferGel(R), VivaGel(R), Glyminox vaginal gel, sodium lauryl sulfate, 2F5, 2F5/2G12, VRX-496, Ad5gag2, BG-777, IGIV-C, BILR-255 and the like are exemplified.

As the "other anti-HIV agents" and "other anti-HIV active substance" to be used for a multiple drug combination therapy with the compound of the present invention, preferred are a reverse transcriptase inhibitor and a protease inhibitor. Two or three, or even a greater number of pharmaceutical agents can be used in combination, wherein a combination of pharmaceutical agents having different action mechanisms is one of the preferable embodiments. In addition, selection of pharmaceutical agents free of side effect duplication is preferable.

Specific combination of pharmaceutical agents include a combination of a group consisting of Efavirenz, Tenofovir, Emtricitabine, Indinavir, Nelfinavir, Atanazavir, Ritonavir+ Indinavir, Ritonavir+Lopinavir, Ritonavir+Saquinavir, Didanosine+Lamivudine, Zidovudine+Didanosine, Stavudine+Didanosine, Zidovudine+Lamivudine, Stavudine+ Lamivudine, and Emtriva with the 4-oxoquinoline compound [I] of the present invention (Guidelines for the Use of Antiretroviral Agents in HIV-Infected Adults and Adolescents. Aug. 13, 2001). Particularly preferably, two drug therapy by the combination with Efavirenz, Indinavir, Nelfinavir, Tenofovir, Emtricitabine, Zidovudine and Lamivudine, and three drug therapy by the combination with Zidovudine+Lamivudine, Tenofovir+Lamivudine, Tenofovir+Zidovudine, Tenofovir+Efavirenz, Tenofovir+Nelfinavir, Tenofovir+Indinavir, Tenofovir+Emtricitabine, Emtricitabine+Lamivudine, Emtricitabine+Zidovudine, Emtricitabine+Efavirenz, Emtricitabine+Nelfinavir, Emtricitabine+Indinavir, Nelfinavir+Lamivudine, Nelfinavir+Zidovudine, Nelfinavir+Efavirenz, Nelfinavir+Indinavir, Efavirenz+Lamivudine, Efavirenz+Zidovudine, and Efavirenz+Indinavir can be mentioned.

Some examples of the production methods of the compounds used for embodiment of the present invention are shown in the following. However, the production method of the compounds of the present invention is not limited to these examples.

Even in the absence of description in the production method, efficient production can be afforded, where necessary, by introducing a protecting group into a functional group followed by deprotection in a subsequent step, by using a compound with a functional group as a precursor in each step and converting the group to a desired functional group in a suitable step, by exchanging the order of respective production methods and steps, or by other method.

The workup in each step can be applied by a typical method, wherein isolation and purification is performed by selecting or combining conventional methods as necessary, such as crystallization, recrystallization, distillation, partitioning, silica gel chromatography, preparative HPLC and the like.

Production Method 1-1

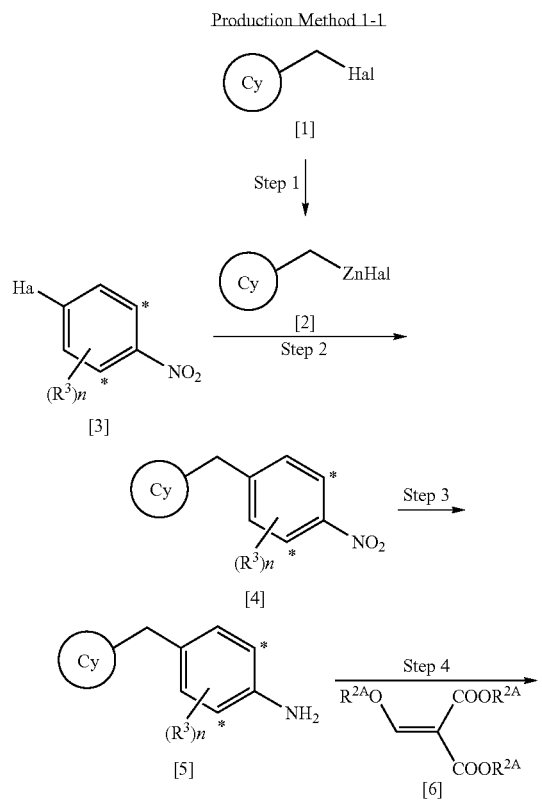

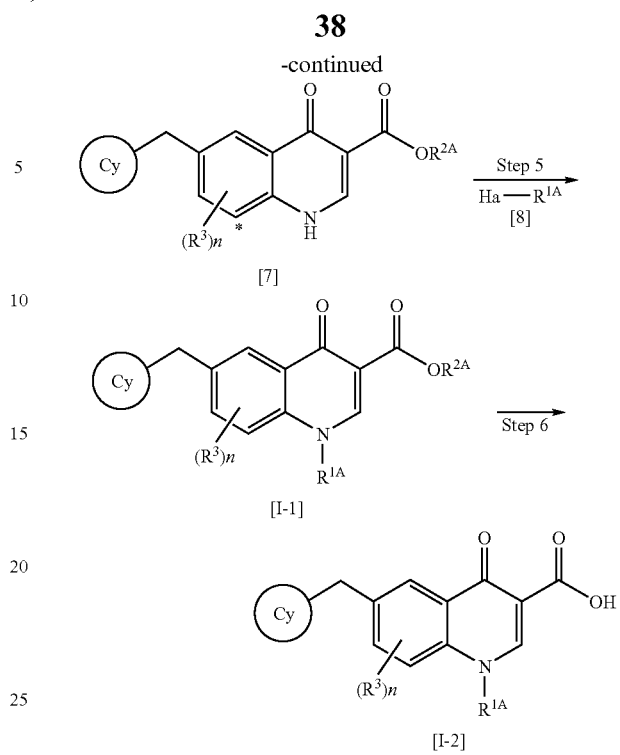

wherein Hal is a halogen atom such as chlorine atom, bromine atom and the like; $Hal^1$ is a halogen atom such as bromine atom, iodine atom and the like; $R^{1A}$ is "$C_{1-10}$ alkyl group optionally substituted by 1 to 3 substituents selected from halogen atom and group B" defined above; $R^{2A}$ is "$C_{1-4}$ alkyl group" defined above, which is preferably methyl group or ethyl group; in compound [6], each $R^{2A}$ may be different but preferably the same; $(R^3)_n$ is a substituent of any of $R^{31}$, $R^{32}$ and $R^{33}$, which may be the same or different; n is an integer of 1 to 3; where the substituent $R^3$ does not simultaneously substitute at both of the * positions, and other symbols are as defined above.

Step 1

Under an argon or nitrogen stream, zinc powder and 1,2-dibromoethane are reacted in a solvent with heating, and trimethylsilyl chloride is added to allow reaction. Then, to the reaction solution is added a solution of compound [1] to allow reaction to give compound [2].

As preferable solvents, ether solvents such as 1,4-dioxane, diethyl ether, 1,2-dimethoxyethane, tetrahydrofuran (THF) and the like; hydrocarbon solvents such as benzene, toluene, hexane, xylene and the like; and the like can be mentioned.

Step 2

The compound [2] is reacted with compound [3] in a solvent in the presence of a catalyst and, where necessary, a ligand such as triphenylphosphine, tri(2-furyl)phosphine and the like, and under an argon or nitrogen stream with cooling or with heating to give compound [4].

As the catalyst, palladium catalysts such as bis(dibenzylideneacetone)palladium, tris(dibenzylideneacetone)dipalladium, dichlorobis(triphenylphosphine)palladium, dichlorobis(benzonitrile)palladium, dichloroethylenediamine palladium, palladium acetate, tetrakis(triphenylphosphine)palladium and the like, nickel catalyst and the like can be mentioned.

As preferable solvents, ether solvents such as 1,4-dioxane, diethyl ether, 1,2-dimethoxyethane, tetrahydrofuran (THF) and the like; hydrocarbon solvents such as benzene, toluene, hexane, xylene and the like and the like can be mentioned.

Step 3

The compound [4] is reduced by a conventional method such as reduction with zinc or iron under neutral or alkaline conditions; iron and acid; tin or tin(II) chloride and conc. hydrochloric acid; alkali sulfide; alkaline hydrosulfite and the like, catalytic reduction under a hydrogen atmosphere, and the like to give compound [5].

For example, to compound [4] are added acetic acid and zinc powder with cooling, and the mixture is reacted at room temperature to give compound [5]. Alternatively, palladium-carbon is added to a solution of compound [4] in a mixed solvent of THF and methanol and the mixture is reacted under a hydrogen atmosphere at room temperature to give compound [5].

Step 4

The compound [5] is reacted with compound [6] in a solvent with heating.

As preferable solvents, alcohol solvents such as methanol, ethanol, n-propanol, isopropanol and the like; hydrocarbon, solvents such as benzene, toluene, hexane, xylene and the like; halogenated solvents such as dichloromethane, chloroform, carbon tetrachloride, 1,2-dichloroethane and the like; ether solvents such as 1,4-dioxane, diethyl ether, 1,2-dimethoxyethane, tetrahydrofuran and the like and a mixed solvents thereof can be mentioned.

Then, after removal of the solvent, the residue is reacted in a solvent such as diphenyl ether or a mixture of diphenyl ether and diphenyl, such as Dowtherm A (trademark, Fluka) and the like, with heating to give compound [7].

Step 5

The compound [7] is reacted with compound [8] in a solvent in the presence of a base to give compound [I-1].

As the base, potassium carbonate, sodium carbonate, lithium hydride, sodium hydride, potassium hydride and the like can be mentioned, with preference given to potassium carbonate.

As the solvents, hydrocarbon solvents such as benzene, toluene, hexane, xylene and the like; ether solvents such as 1,4-dioxane, diethyl ether, 1,2-dimethoxyethane, tetrahydrofuran and the like; polar solvents such as dimethylformamide, dimethyl sulfoxide, acetonitrile and the like and a mixed solvent thereof can be mentioned.

Step 6

The compound [I-1] is subjected to hydrolysis in a solvent at room temperature or with heating under basic conditions with sodium hydroxide, potassium hydroxide, lithium hydroxide and the like, or under acidic conditions with hydrochloric acid, sulfuric acid and the like to give compound [I-2].

As the solvents, alcohol solvents such as methanol, ethanol, n-propanol, isopropanol and the like; hydrocarbon solvents such as benzene, toluene, hexane, xylene and the like; halogenated solvents such as dichloromethane, carbon tetrachloride, 1,2-dichloroethane and the like; ether solvents such as 1,4-dioxane, diethyl ether, 1,2-dimethoxyethane, tetrahydrofuran and the like; polar solvents such as dimethylformamide, dimethyl sulfoxide, acetonitrile and the like; water and a mixed solvent thereof can be mentioned.

By a reaction in the same manner as in Production Method 1-1 using compound [20] represented by

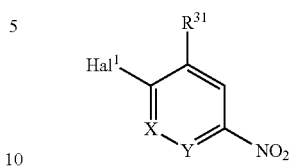

instead of compound [3], compound [I] can be obtained.

Production Method 1-2 Example of production method using compound [9] in which a hydroxyl-protecting group has been introduced

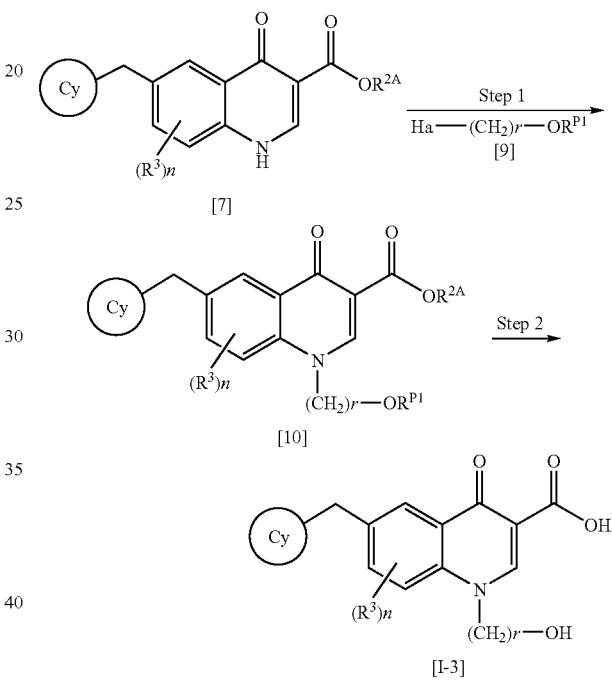

wherein r is an integer of 1 to 6, $R^{P1}$ is a hydroxyl-protecting group, and other symbols are as defined above.

Step 1

The compound [7] obtained in the same manner as in Production Method 1-1 and compound [9] are reacted in the same manner as in Production Method 1-1, Step 5 to give compound [10].

Step 2

The compound [10] is deprotected by a conventional method to give compound [I-3].

As the hydroxyl-protecting group, acetyl group, methyloxycarbonyl group, methoxymethyl group, methoxyethoxymethyl group, trimethylsilyl group, tert-butyldimethylsilyl group, tert-butyldiphenylsilyl group and the like can be mentioned.

For example, when $R^{P1}$ is acetyl group or methyloxycarbonyl group, a reaction with heating in the presence of a base such as sodium hydroxide, potassium hydroxide and the like achieves deprotection. A treatment comprising addition of conc. hydrochloric acid and heating, heating in conc. ammonia and the like may be applied.

For example, when $R^{P1}$ is tert-butyldimethylsilyl group, deprotection can be achieved by a treatment with tetrabutylammonium fluoride in THF at room temperature, a treatment in the presence of sodium hydroxide in THF with heating, a treatment with acetic acid-water-THF at room temperature or with heating, and the like. In this step, the deprotection of $R^{P1}$ and hydrolysis of $R^{2A}$ can be performed in two stages.

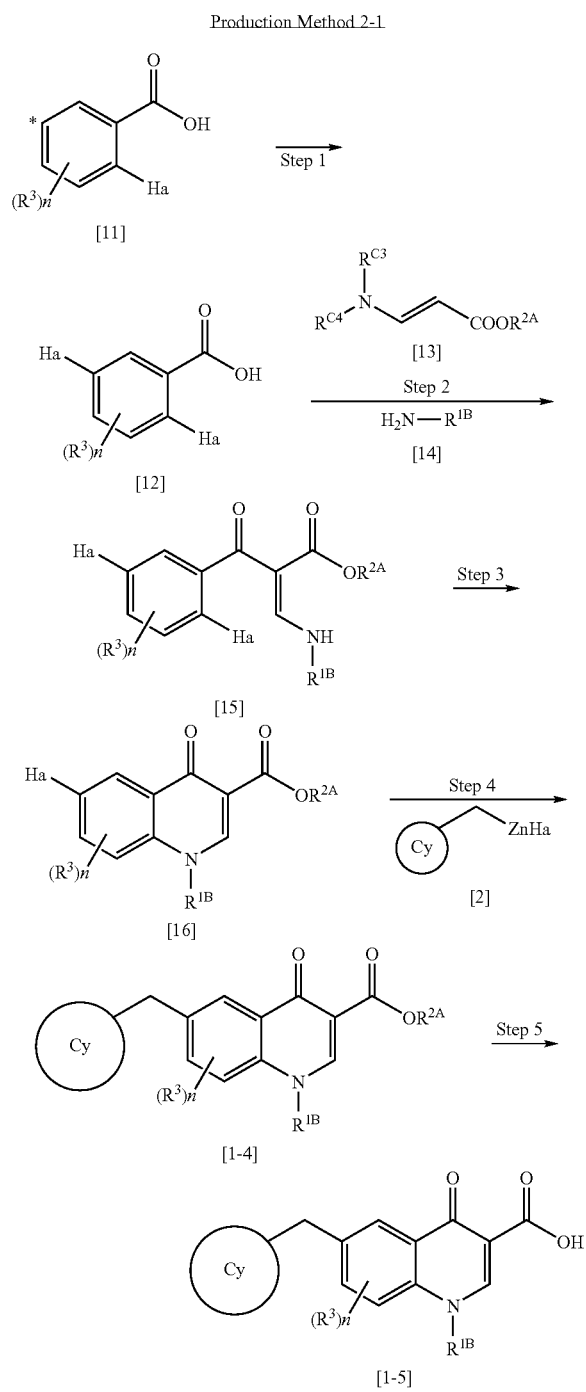

wherein $Hal^2$ is a halogen atom and preferably a fluorine atom or a chlorine atom, $R^{C3}$ and $R^{C4}$ are the same or different and each is a lower alkyl group such as methyl group, ethyl group and the like, $R^{1B}$ is a "$C_{1-10}$ alkyl group optionally substituted by 1 to 3 substituents selected from halogen atom and group B" defined above, a "$C_{3-10}$ carbon ring group optionally substituted by 1 to 5 substituents selected from group A" defined above, a "heterocyclic group optionally substituted by 1 to 5 substituents selected from group A" defined above or "—$OR^{a4}$" defined above, and other symbols are as defined above, wherein the substituent $R^3$ is not substituted at the * position.

Step 1

Here, $Hal^1$ is preferably bromine or iodine, and compound [12] can be obtained by conventional halogenation.

For example, compound [11] is reacted with a halogenating agent such as N-bromosuccinimide, N-iodosuccinimide and the like in a solvent such as trifluoromethanesulfonic acid, acetic acid, conc. sulfuric acid, DMF and the like at room temperature or with heating to give compound [12].

Step 2

An acid halide is obtained by a conventional method by, for example, reacting compound [12] with heating with a halogenating agent such as oxalyl chloride, thionyl chloride and the like, in a solvent such as hydrocarbon solvents (e.g., toluene, xylene etc.); halogenated solvent (e.g., dichloromethane, carbon tetrachloride, 1,2-dichloroethane etc.); ethyl acetate and the like.

Here, for example, when thionyl chloride is used as a halogenating agent, a catalytic amount of DMF may be added.

Then, compound [13] is added to allow reaction in a solvent in the presence of a base such as triethylamine, diisopropylethylamine, potassium carbonate, pyridine and the like at room temperature or with heating, after which the resulting compound is reacted with compound [14] at room temperature or with heating to give compound [15].

As the solvent, hydrocarbon solvents such as benzene, toluene, hexane, xylene and the like; halogenated solvents such as dichloromethane, carbon tetrachloride, 1,2-dichloroethane and the like; ether solvents such as 1,4-dioxane, diethyl ether, 1,2-dimethoxyethane, tetrahydrofuran and the like; polar solvents such as acetonitrile and the like, ethyl acetate and a mixed solvent thereof can be mentioned.

Step 3

The compound [15] is reacted in the presence of a base such as sodium carbonate, potassium carbonate, sodium hydroxide, potassium hydroxide, lithium hydroxide, potassium tert-butoxide, sodium hydride, potassium hydride and the like, in a solvent to give compound [16].

As one of the preferable production methods, compound [15] may be reacted in the presence of 1,8-diazacyclo[5.4.0]-7-undecene in a solvent at room temperature or with heating to give compound [16].

As the solvent, hydrocarbon solvents such as benzene, toluene, hexane, xylene and the like; halogenated solvents such as dichloromethane, carbon tetrachloride, 1,2-dichloroethane and the like; ether solvents such as 1,4-dioxane, diethyl ether, 1,2-dimethoxyethane, tetrahydrofuran and the like; polar solvents such as dimethylformamide, dimethyl sulfoxide, acetonitrile and the like and a mixed solvent thereof can be mentioned.

Step 4

The compound [16] is reacted with compound [2] in the same manner as in Production Method 1-1, Step 2 to give compound [I-4].

Step 5

The compound [I-4] is subjected to hydrolysis in the same manner as in Production Method 1-1, Step 6 to give compound [I-5].

Production Method 2-2 Example of Production Method Comprising Introduction and Removal of Hydroxyl-Protecting Group

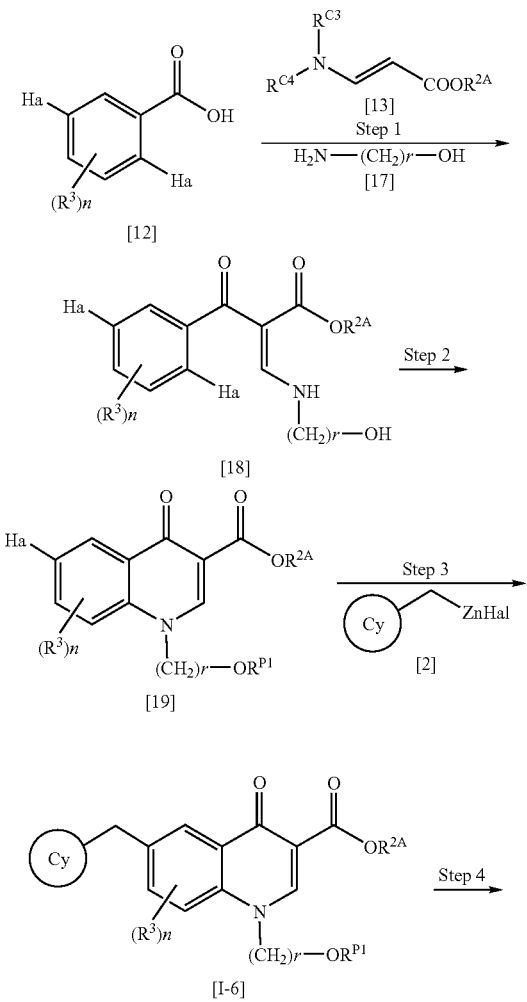

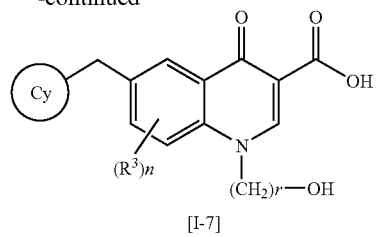

wherein each symbol is as defined above.

Step 1

The compound [12] obtained in the same manner as in Production Method 2-1, Step 1 is reacted with compound [13] and compound [17] in the same manner as in Production Method 2-1, Step 2 to give compound [18].

Step 2

A protecting group is introduced into hydroxyl group of compound [18] by a conventional method and then the compound is cyclized in the same manner as in Production Method 2-1, Step 3 to give compound [19].

Alternatively, compound [18] is cyclized in the same manner as in Production Method 2-1, Step 3 and then a protecting group is introduced into hydroxyl group by a conventional method to give compound [19].

For example, when $R^{P1}$ is a tert-butyldimethylsilyl group, compound [18] may be reacted with imidazole and tert-butyldimethylsilyl chloride in a solvent such as DMF and toluene at room temperature.

When $R^{P1}$ is a methoxycarbonyl group, compound [18] may be reacted with pyridine and methyl chlorocarbonate in a solvent such as chloroform with cooling or at room temperature.

A similar production method can be use(d for $NH_2$—$R^{1A}$, wherein $R^{1A}$ is a $C_{1-10}$ alkyl group optionally substituted by at least one hydroxyl group instead of compound [17].

Step 3

The compound [19] is reacted with compound [2] in the same manner as in Production Method 1-1, Step 2 to give compound [I-6].

Step 4

The compound [I-6] is subjected to hydrolysis by a conventional method in the same manner as in Production Method 1-2, Step 2 to give compound [I-7]. In this step, the deprotection of $R^{P1}$ and hydrolysis of $R^{2A}$ can be performed in two stages.

Production Method 3

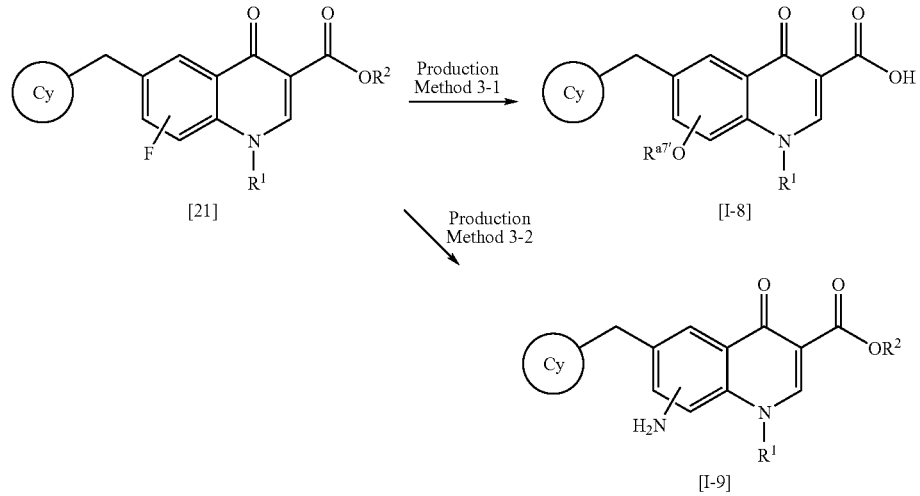

wherein $R^{a7'}$ is a $C_{1-10}$ alkyl group optionally substituted by 1 to 3 substituents selected from halogen atom and group B, and other symbols are as defined above.

The fluorine atom on 4-oxoquinoline can be converted to —$OR^{a7}$, —$SR^{a7}$ or —$NR^{a7}R^{a8}$ by a reaction with nucleophilic agent by a conventional method. They can be further converted to —$NR^{a7}COR^{a9}$ or —N=CH—$NR^{a10}R^{a11}$ by a conventional method.

This production method is suitable for introducing a substituent into the 7-position on 4-oxoquinoline.

Production Method 3-1

An alkoxy group is introduced into compound [21] by a conventional method to give compound [I-8].

For example, compound [I-8] can be obtained by reaction with metal alkoxide with heating in an alcohol solvent such as methanol, ethanol, propanol, butanol and the like, and then hydrolysis.

A solvent and a metal alkoxide need to be determined corresponding to a desired alkoxy group. In the case of a methoxy group, sodium methoxide or potassium methoxide is reacted in methanol, and in the case of an ethoxy group, sodium ethoxide or potassium ethoxide is reacted in ethanol.

Production Method 3-2

The compound [21] is subjected to amination by a conventional method to give compound [I-9].

For example, compound [I-9] can be obtained by a reaction with an amine in an inactive organic solvent such as THF, dioxane, chloroform, dichloromethane, methanol, ethanol, pyridine and the like with heating.

In addition, compound [I-9] can be also obtained by a reaction with an amine with microwave irradiation in DMF.

Production Method 4

Examples of the production methods of intermediate compound [12] are shown below.

In the case of esterification, for example, compound [23] can be obtained by a reaction with an alkylating agent such as methyl iodide and the like in a solvent such as DMF, THF, toluene and the like in the presence of a base such as sodium carbonate, potassium carbonate, sodium hydride, potassium hydride and the like.

The compound [23] is reduced by a conventional method in the same manner as in Production Method 1-1, Step 3 to give compound [24].

Step 3

The compound [24] is subjected to halogenation by a conventional method in the same manner as in Production Method 2-1, Step 1 to give compound [25].

Step 4

The compound [25] is subjected to diazotization with sodium nitrite and hydrochloric acid or sulfuric acid in water or an inactive organic solvent such as THF, dioxane, ethyl acetate, chloroform, dichloromethane, methanol, ethanol, pyridine and the like with cooling or at room temperature, and then subjected to halogenation with cuprous halide such as copper chloride and the like and conc. hydrochloric acid with cooling or with heating to give compound [26]. Here, $Hal^2$ is preferably a chlorine atom.

Step 5

The hydroxyl group of compound [26] is deprotected by a conventional method to give compound [27].

For example, when $R^{P1}$ is a methyl group, compound [27] can be obtained by reaction with boron tribromide in dichloromethane with cooling.

Step 6

The compound [27] is reacted with compound [8] in the presence of a base in a solvent to give compound [28].

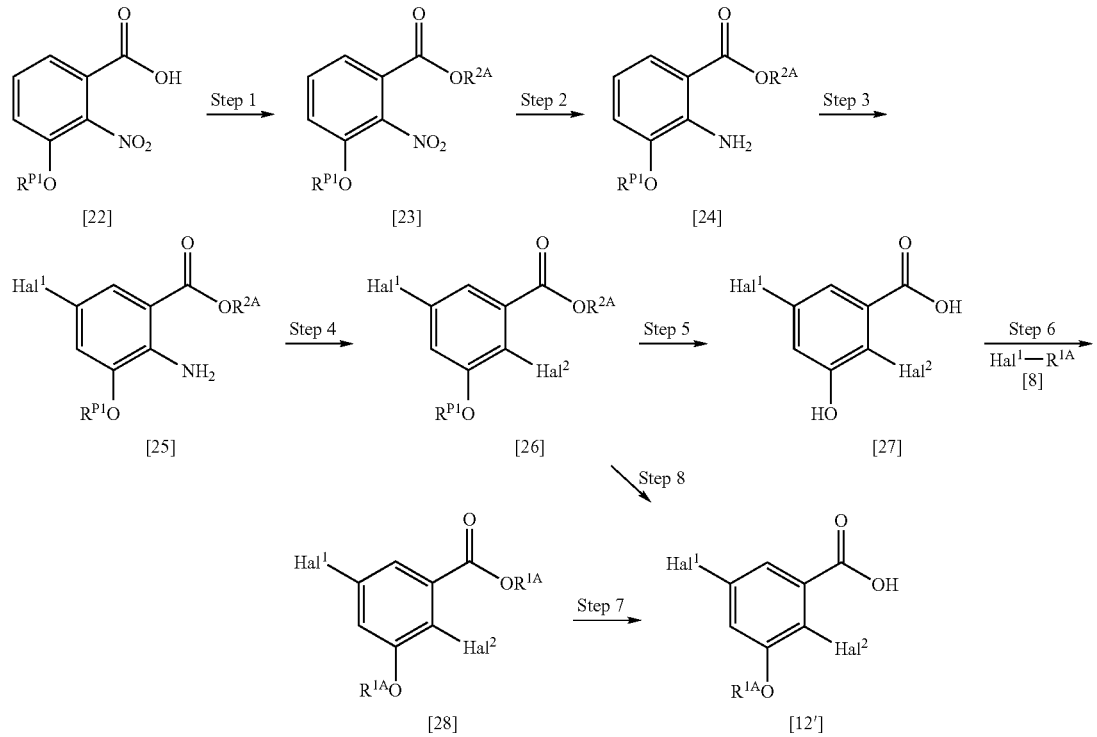

wherein each symbol is as defined above.

Step 1

A protecting group is introduced into carboxylic acid of compound [22] by a conventional method to give compound [23].

As compound [8], for example, an, alkylating agent such as ethyl iodide and the like can be mentioned.

As the base, potassium carbonate, sodium carbonate, lithium hydride, sodium hydride, potassium hydride and the like can be mentioned, with preference given to potassium carbonate.

As the solvent, alcohol solvents such as methanol, ethanol, n-propanol, isopropanol and the like; hydrocarbon solvents such as benzene, toluene, hexane, xylene and the like; halogenated solvents such as dichloromethane, chloroform, carbon tetrachloride, 1,2-dichloroethane and the like; ether solvents such as 1,4-dioxane, diethyl ether, 1,2-dimethoxyethane, tetrahydrofuran and the like; polar solvents such as dimethylformamide, dimethyl sulfoxide, acetonitrile and the like; water and a mixed solvent thereof can be mentioned.

Step 7

The compound [28] is subjected to hydrolysis by a conventional method in the same manner as in Production Method 1-1, Step 6 to give compound [12].

Step 8

When $R^{P1}$ in compound [26] is a desired substituent, compound [12'] can be obtained in the same manner as in Step 7.

Production Method 5

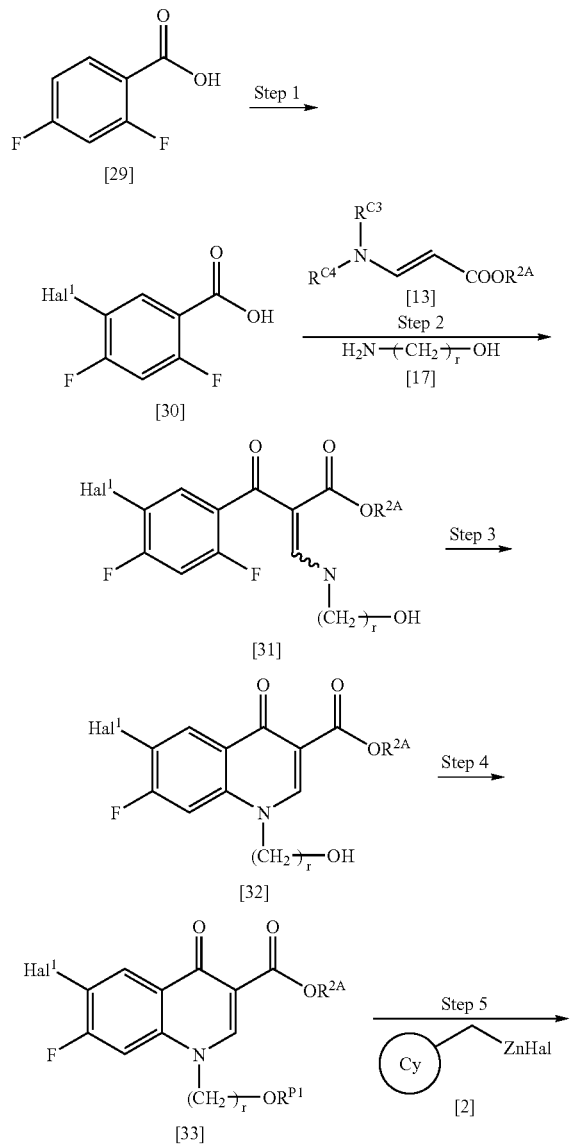

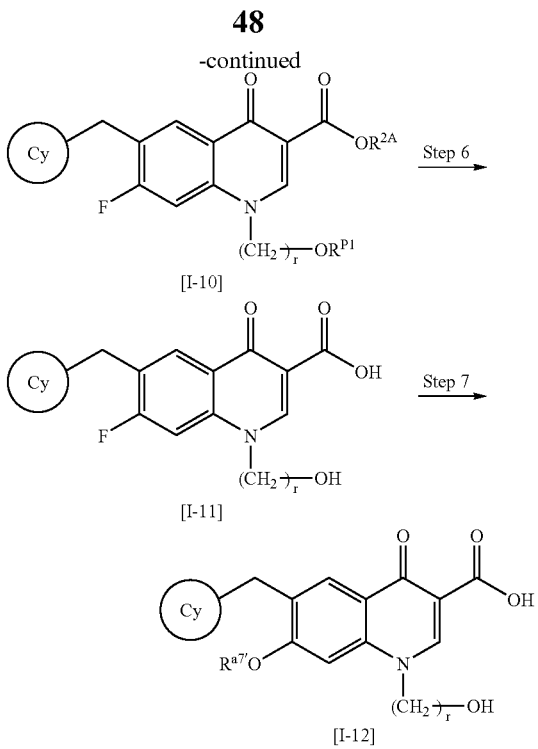

wherein each symbol is as defined above.

Step 1

The compound [29] is subjected to halogenation by a conventional method in the same manner as in Production Method 2-1, Step. 1 to give compound [30].

Step 2

The compound [30] is reacted with compound [13] and compound [17] in the same manner as in Production Method 2-1, Step 2 to give compound [31].

Step 3

The compound [31] is reacted in the same manner as in Production Method 2-1, Step 3 to give compound [32].

Step 4

The compound [32] is reacted in the same manner as in Production Method 2-2, Step 2 to give compound [33].

Step 5

The compound [33] is reacted with compound [2] in the similar as in Production Method 1-1, Step 2 to give compound [I-10].

Step 6

The compound [I-10] is subjected to hydrolysis in the same manner as in Production Method 1-2, Step 2 to give compound [I-11].

Step 7

The compound [I-12] can be obtained by introducing an alkoxy group into compound [I-11] by a conventional method in a similar manner as in Production Method 3-1.

The 4-oxoquinoline compound represented by the formula [I] of the present invention, a pharmaceutically acceptable salt thereof and a production method are explained in detail by referring to Examples, which are not to be construed as limitative.

REFERENCE EXAMPLE 1

Preparation of a solution of 2,3-dichlorobenzylzinc chloride in THF

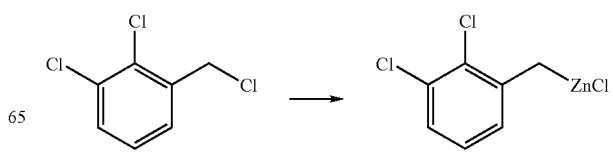

Under an argon stream, to a suspension of zinc powder (55.1 g, 843 mmol) in tetrahydrofuran (THF; 56 ml) was added 1,2-dibromoethane (2.9 ml, 33.8 mmol) and the mixture was heated under reflux for 5 min. Then, trimethylsilyl chloride (8.6 ml, 67.5 mmol) was added at 0° C. and the mixture was stirred at 0° C. for 5 min, after which a solution of 2,3-dichlorobenzyl chloride (82.4 g, 421.7 mmol) in THF (330 ml) was added dropwise with ice-cooling. After Completion of the dropwise addition, the mixture was warmed to room temperature and stirred for 1 hr to give a solution of 2,3-dichlorobenzylzinc chloride in THF.

EXAMPLE 1-1

Synthesis of 6-(2,3-dichlorobenzyl)-1,4-dihydro-1-(2-hydroxyethyl)-4-oxo-3-quinolinecarboxylic acid Step 1 Synthesis of 1,2-dichloro-3-(4-nitrobenzyl)benzene

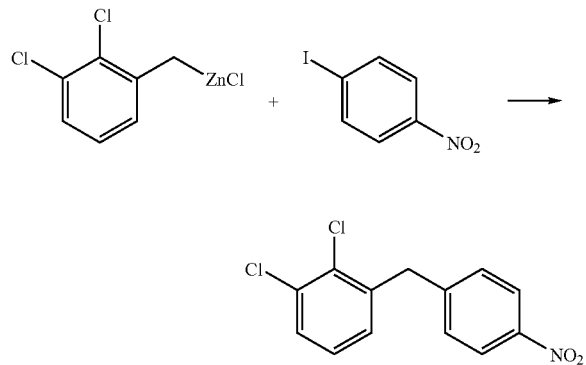

Under an argon stream, bis(dibenzylideneacetone)palladium (0) (3.2 g, 5.6 mmol) and tri(2-furyl)phosphine (2.6 g, 11.2 mmol) were dissolved in THF (310 ml). To this solution was added dropwise a solution of 2,3-dichlorobenzylzinc chloride (421.7 mmol) in THF obtained in Reference Example 1 with ice-cooling through a cannula, and then a solution of 4-iodonitrobenzene (70.0 g, 281 mmol) in THF (700 ml) was added dropwise. After stirring at room temperature for 2 hrs, saturated aqueous ammonium chloride solution was added to the reaction solution and the mixture was filtered through Celite. The filtrate was concentrated under reduced pressure. Water was added to the residue and the mixture was extracted with ethyl acetate. The organic layer was washed with water and saturated brine, and dried over sodium sulfate. After filtration, the filtrate was concentrated under reduced pressure and the solid precipitated during the concentration was collected by filtration. The filtrate was again concentrated under reduced pressure and the solid precipitated during the concentration was collected by filtration. The solids obtained by filtration were combined, washed with n-hexane and vacuum-dried to give an object product (60.2 g, yield 76%) as a pale-brown solid.

$^1$H NMR(CDCl$_3$, 400 MHz) (δ) ppm: 4.24(2H,s), 7.09(1H, d,J=7.7 Hz), 7.18(1H,dd,J=7.8 Hz,7.9 Hz), 7.32(2H,d,J=8.9 Hz), 7.40(1H,d,J=8.0 Hz), 8.15(2H,d,J=8.7 Hz)

MS(ESI): M−280

Step 2 Synthesis of 4-(2,3-dichlorobenzyl)phenylamine

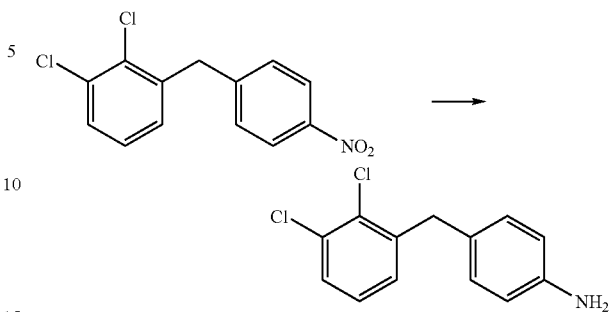

1,2-Dichloro-3-(4-nitrobenzyl)benzene (25.0 g, 88.6 mmol) obtained in Step 1 was dissolved in acetic acid (400 ml) and zinc powder (70 g, 1.1 mol) was added by portions at 0° C. The mixture was stirred at room temperature for 1 hr. The reaction mixture was filtered through Celite and washed with ethanol. The filtrate was concentrated under reduced pressure and the solid precipitated during concentration was collected by filtration. The solid obtained by the filtration was washed with diethyl ether, and dissolved in ethyl acetate (500 ml) and water (500 ml). A 4N aqueous sodium hydroxide solution was added to neutralize the aqueous layer. The organic layer was separated, and the aqueous layer was further extracted with ethyl acetate. The organic layers were combined, washed with water and saturated brine, and dried over sodium sulfate. After the filtration, the filtrate was concentrated under reduced pressure and the solid precipitated during the concentration was collected by filtration. The solid obtained by filtration was washed with n-hexane and vacuum-dried to give an object product (18.1 g, yield 81%) as a pale-brown solid.

$^1$H NMR (CDCl$_3$, 400 MHz) (δ) ppm: 3.52(2H,brs), 4.01 (2H,s), 6.63(2H,d,J=8.2 Hz), 6.97(2H,d,J=8.1 Hz), 7.02(1H, d,J=7.6 Hz), 7.09(1H,dd,J=7.8 Hz,7.8 Hz), 7.31(1H,d,J=7.8 Hz)

MS(ESI): M+252

Step 3 Synthesis of ethyl 6-(2,3-dichlorobenzyl)-1,4-dihydro-4-oxo-3-quinolinecarboxylate

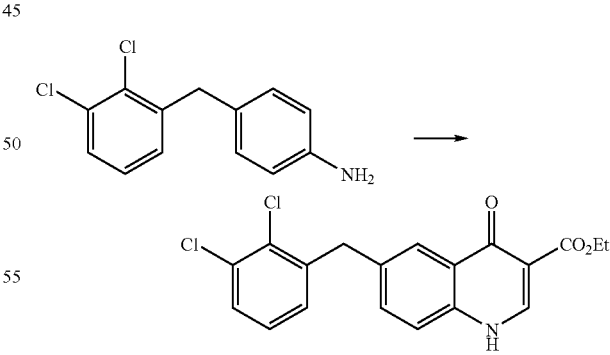

4-(2,3-Dichlorobenzyl)phenylamine (10.0 g, 39.7 mmol) obtained in Step 2 was dissolved in toluene (100 ml) and diethyl ethoxymethylenemalonate (8.8 ml, 43.7 mmol) was added. The mixture was heated under reflux for 3 hrs. The reaction solution was concentrated under reduced pressure, and diphenyl ether (100 ml) was added to dissolve the residue. The mixture was stirred with heating at 250° C. for 3 hrs. After allowing the mixture to cool, n-hexane was added to the reaction solution and the precipitate was collected by filtration, washed with chloroform and vacuum-dried to give an object product (10.1 g, yield 68%) as a pale-yellow solid.

$^1$H NMR(DMSO-$d_6$ 400 MHz) (δ) ppm: 1.27(3H,t,J=7.1 Hz), 4.20(2H,q,J=7.1 Hz), 4.27(2H,s), 7.34-7.41(2H,m), 7.55-7.57(3H,m), 7.90(1H,s), 8.49(1H,d,J=6.6 Hz), 12.26(1H,brs)

MS(ESI): M+376

Step 4 Synthesis of ethyl 1-(2-acetoxyethyl)-6-(2,3-dichlorobenzyl)-1,4-dihydro-4-oxo-3-quinolinecarboxylate

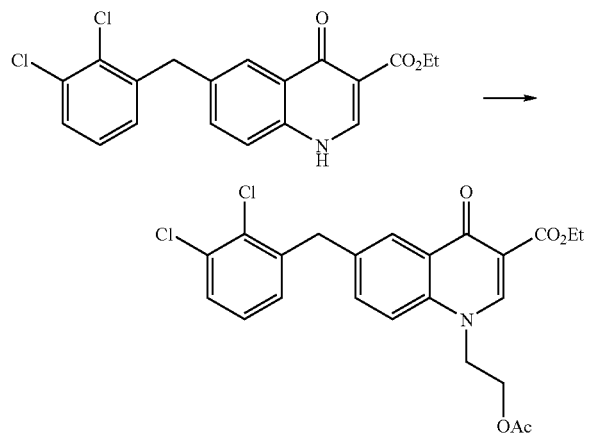

Ethyl 6-(2,3-dichlorobenzyl)-1,4-dihydro-4-oxo-3-quinolinecarboxylate obtained in Step 3 (400 mg, 1.1 mmol) was suspended in dimethylformamide (DMF; 8 ml) and 2-bromoethyl acetate (152 μl, 1.4 mmol) and potassium carbonate (440 mg, 3.2 mmol) were added. The mixture was stirred with heating at 80° C. During the stirring, 2-bromoethyl acetate (152 μl, 1.4 mmol) was added twice and the mixture was stirred with heating at 80° C. for the total of 1.5 hrs. After allowing the mixture to cool, saturated aqueous ammonium chloride was added to the reaction solution, and the precipitate was collected by filtration, washed with water and vacuum-dried to give an object product (468 mg, yield 95%) as a white solid.

$^1$H NMR(DMSO-$d_6$ 400 MHz) (δ) ppm: 1.25(3H,t,J=9.3 Hz), 1.88(3H,s), 4.20(2H,q,J=9.3 Hz), 4.27(2H,s), 4.33-4.41 (2H,m), 4.59-4.62(2H,m), 7.32-7.41(3H,m), 7.54(1H,dd, J=2.9 Hz,10.2 Hz), 7.64(1H,dd,J=2.4 Hz,11.2 Hz), 7.81(1H, d,J=11.7 Hz), 7.88(1H,d,J=2.4 Hz), 8.57(1H,s)

Step 5 Synthesis of 6-(2,3-dichlorobenzyl)-1,4-dihydro-1-(2-hydroxyethyl)-4-oxo-3-quinolinecarboxylic acid

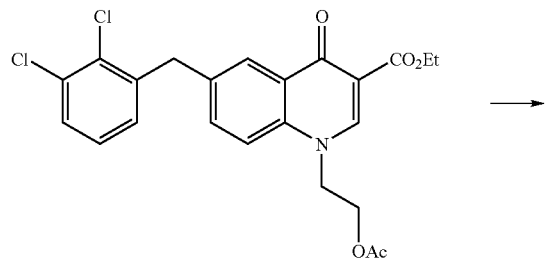

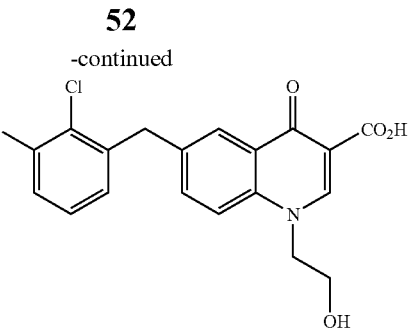

Ethyl 1-(2-acetoxyethyl)-6-(2,3-dichlorobenzyl)-1,4-dihydro-4-oxo-3-quinolinecarboxylate obtained in Step 4 (6.0 g, 13.0 mmol) was suspended in ethanol (480 ml) and 4N aqueous sodium hydroxide solution (84 ml, 21 mmol) was added. The mixture was heated under reflux for 30 min. After allowing the mixture to cool, the reaction solution was partly concentrated under reduced pressure. Hydrochloric acid was added and the precipitate was collected by filtration, washed with water and ethanol and vacuum-dried to give an object product (4.5 g, yield 85%) as a white solid.

$^1$H NMR (DMSO-$d_6$ 400 MHz) (δ) ppm: 3.75(2H, t, J=4.7 Hz), 4.36(2H, s), 4.60(2H, t, J=4.8 Hz), 4.98(1H, brs), 7.37-7.39(1H, m), 7.45(1H, dd, J=1.4, 7.6 Hz), 7.57(1H, dd, J=1.5, 8.0 Hz), 7.81(1H, dd, J=2.1, 8.9 Hz), 8.02(1H, d, J=8.8 Hz), 8.15(1H, d, J=1.8 Hz), 8.86(1H, s), 15.18(1H, brs)

MS (ESI): M+392 m.p.: 247-249° C.

EXAMPLE 1-2

Synthesis of 6-(2,3-dichlorobenzyl)-1,4-dihydro-8-fluoro-1-(2-hydroxyethyl)-4-oxo-3-quinolinecarboxylic acid Step 1 Synthesis of 2,3-difluoro-5-iodobenzoic acid

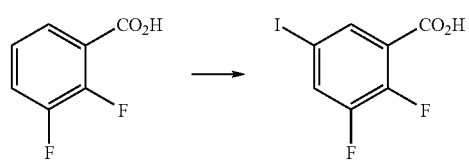

2,3-Difluorobenzoic acid (5.0 g, 31.6 mmol) was dissolved in trifluoromethanesulfonic acid (25 ml), and N-iodosuccinimide (8.55 g, 38.0 mmol) was added by portions at 0° C. under an argon stream. The mixture was stirred at room temperature for 3 hrs., and the reaction solution was poured into sodium sulfite in ice water. The mixture was stirred and the precipitate was collected by filtration, washed with water and vacuum-dried to give an object product (7.5 g, yield 84%) as a pale-pink solid.

$^1$H NMR(CDCl$_3$ 300 MHz) (δ) ppm: 7.74(1H,m), 8.11 (1H,m)

MS(ESI): M−283

Step 2 Synthesis of ethyl 2-(2,3-difluoro-5-iodobenzoyl)-3-(2-hydroxyethylamino)acrylate

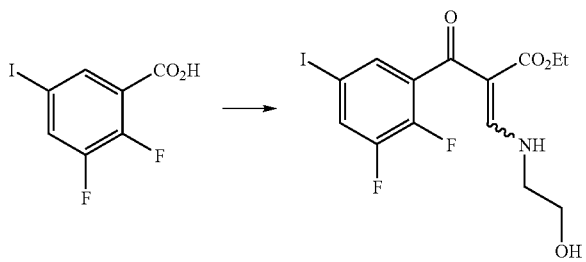

2,3-Difluoro-5-iodobenzoic acid (3.0 g, 10.6 mmol) obtained in Step 1 was dissolved in toluene, and thionyl chloride (3.0 ml, 41.1 mmol) and DMF (catalytic amount) were added. The mixture was heated under reflux for 3 hrs. The reaction solution was concentrated under reduced pressure and THF (15 ml) was added to dissolve the residue. The resulting solution was added dropwise to a solution of ethyl 3-dimethylaminoacrylate (1.66 g, 11.6 mmol) and triethylamine (1.77 ml, 12.7 mmol) in THF (10 ml) and the mixture was stirred with heating at 50° C. for 2.5 hrs. After allowing the mixture to cool, the reaction mixture was filtered and washed with THF (10 ml). Aminoethanol (0.77 ml, 12.7 mmol) was added to the filtrate and the mixture was stirred with heating at 40° C. for 1 hr. After allowing the mixture to cool, water was added to the reaction solution and the mixture was extracted with ethyl acetate. The organic layer was washed with water and saturated brine, and dried over sodium sulfate. After filtration, the filtrate was concentrated under reduced pressure, and the obtained residue was purified by silica gel chromatography (ethyl acetate:hexane=2:1) to give an object product (3.8 g, yield 85%). of a mixture of E form and Z form as a yellow solid.

1H NMR(CDCl$_3$ 400 MHz) (δ) ppm: 0.91-1.09(3H,m), 1.80-1.89(1H,m), 3.52-3.63(2H,m), 3.83-3.91(2H,m), 3.98-4.09(2H,m), 7.36-7.52(2H,m), 8.15(1H,d,J=14.4 Hz), 9.6(0.22H,brs), 11.0(0.78H,brs)

MS(ESI): M+426

Step 3 Synthesis of ethyl 2-(2,3-difluoro-5-iodobenzoyl)-3-[2-(tert-butyldimethylsilyloxy)ethylamino]acrylate

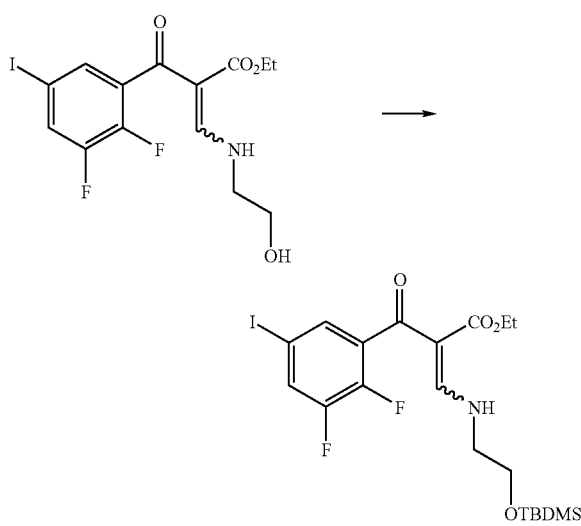

Ethyl 2-(2,3-difluoro-5-iodobenzoyl)-3-(2-hydroxyethylamino)acrylate (2.0 g, 4.7 mmol) obtained in Step 2 was dissolved in DMF (10 ml), imidazole (705 mg, 10.4 mmol) and tert-butyldimethylsilyl chloride (1.49 g, 9.9 mmol) were added, and stirred at room temperature for 4 hrs. Water was added to the reaction solution and the mixture was extracted with ethyl acetate. The organic layer was washed with water and saturated brine, and dried over sodium sulfate. After filtration, the filtrate was concentrated under reduced pressure, and the obtained residue was purified by silica gel chromatography (ethyl acetate:hexane=1:4) to give an object product (2.3 g, yield 91%) as a white solid.

$^1$H NMR(CDCl$_3$ 300 MHz) (δ) ppm: 0.07(6H,s), 0.90(9H,s), 1.07(3H,t,J=7.1 Hz), 3.45-3.55(2H,m), 3.70-3.80(2H,m), 4.04(2H,q,J=7.1 Hz), 7.30-7.50(2H,m), 8.14(1H,d,J=14.1 Hz), 10.80-1.10(1H,m)

MS(ESI): M+540

Step 4 Synthesis of ethyl 1,4-dihydro-8-fluoro-6-iodo-1-[2-(tert-butyldimethylsilyloxy)ethyl]-4-oxo-3-quinolinecarboxylate

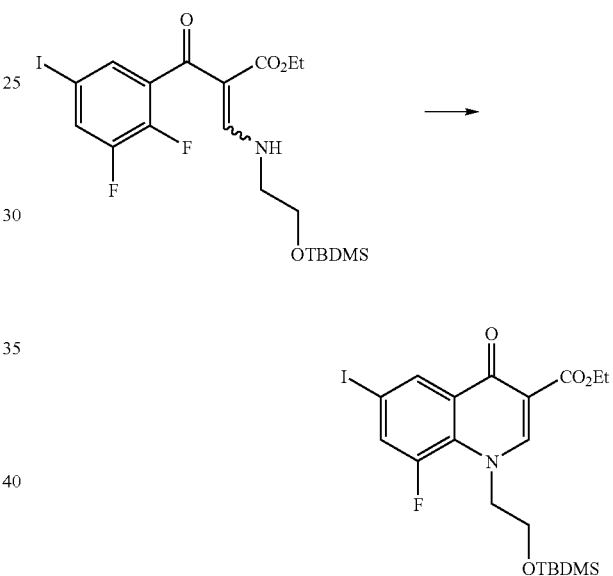

Ethyl 2-(2,3-difluoro-5-iodobenzoyl)-3-[2-(tert-butyldimethylsilyloxy)ethylamino]acrylate (2.3 g, 4.3 mmol) obtained in Step 3 was dissolved in THF (25 ml) and sodium hydride (256 mg, 6.4 mmol) was added with ice-cooling. The mixture was stirred at 0° C. for 1 hr. 1N Hydrochloric acid (6.4 ml, 6.4 mmol) was added to neutralize the reaction solution. Water was further added and the mixture was extracted with ethyl acetate. The organic layer was washed with water and saturated brine, and dried over sodium sulfite. After filtration, the filtrate was concentrated under reduced pressure, and the obtained residue was purified by silica gel chromatography (ethyl acetate:hexane=1:2 to ethyl acetate:hexane=2:1) to give an object product (2.0 g, yield 92%) as a white solid.

$^1$H NMR(CDCl$_3$ 300 MHz) (δ) ppm: −0.12(6H,s), 0.79(9H,s), 1.38(3H,t,J=7.1 Hz), 3.90-4.00(2H,m), 4.37(2H,q,J=7.1 Hz), 4.40-4.50(2H,m), 7.69(1H,dd,J=2.0 Hz,13.7 Hz), 8.40(1H,s), 8.69(1H,d,J=2.0 Hz)

MS(ESI): M+520

Step 5 Synthesis of ethyl 6-(2,3-dichlorobenzyl)-1,4-dihydro-8-fluoro-1-[2-(tert-butyldimethylsilyloxy)ethyl]-4-oxo-3-quinolinecarboxylate

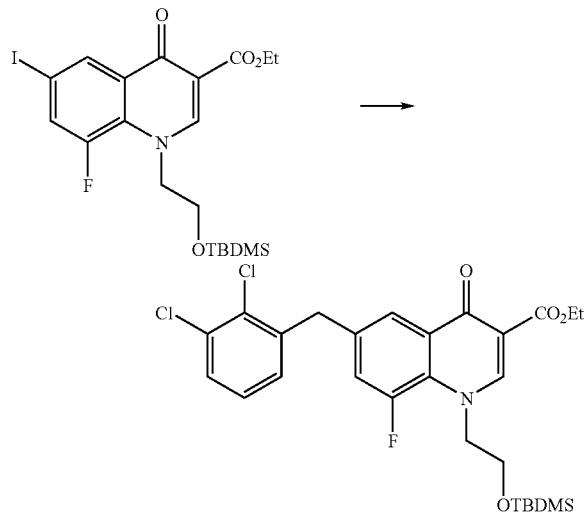

Under an argon stream, 1M solution (2.9 ml, 2.9 mmol) of 2,3-dichlorobenzylzinc chloride in THF obtained in the same manner as in Reference Example 1 was added to THF (20 ml), and then bis(dibenzylideneacetone)palladium(0) (22 mg, 0.039 mmol), tri(2-furyl)phosphine (18 mg, 0.077 mmol) and ethyl 1,4-dihydro-8-fluoro-6-iodo-1-[2-(tert-butyldimethylsilyloxy)ethyl]-4-oxo-3-quinolinecarboxylate (1.0 g, 1.9 mmol) obtained in Step 4 were added. The mixture was stirred at room temperature for 17 hrs, and then a solution (1.0 ml, 1.0 mmol) of 2,3-dichlorobenzylzinc chloride in THF was added. The mixture was heated under reflux for 1 hr. After allowing the mixture to cool, saturated aqueous ammonium chloride solution was added to the reaction solution and insoluble materials were filtered off with Celite. The filtrate was extracted with ethyl acetate, and the organic layer was washed with water and saturated brine, and dried over sodium sulfate. After filtration, the filtrate was concentrated under reduced pressure, and the obtained residue was purified by silica gel chromatography (ethyl acetate:hexane=1:1), and then by PTLC (ethyl acetate:chloroform=1:2) to give an object product (562 mg, yield 53%) as a pale-yellow oil.

$^1$H NMR(CDCl$_3$ 300 MHz) (δ), ppm: −0.13(6H,s), 0.79 (9H,s), 1.38(3H,t,J=7.1 Hz), 3.90-4.00(2H,m), 4.23(2H,s), 4.37(2H,q,J=7.1 Hz), 4.40-4.50(2H,m), 7.10-7.50(4H,m), 8.20-8.30(1H,m), 8.39(1H,s)

MS (ESI): M+552

Step 6 Synthesis of ethyl 6-(2,3-dichlorobenzyl)-1,4-dihydro-8-fluoro-1-(2-hydroxyethyl)-4-oxo-3-quinolinecarboxylate

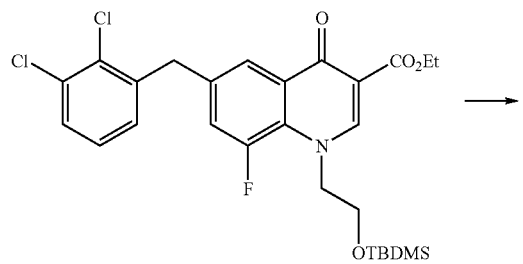

-continued

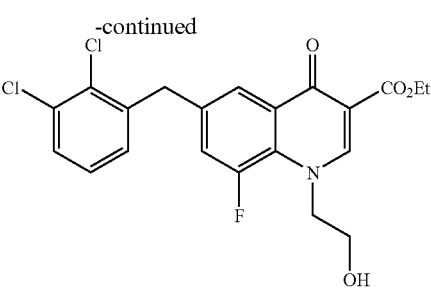

Ethyl 6-(2,3-dichlorobenzyl)-1,4-dihydro-8-fluoro-1-[2-(tert-butyldimethylsilyloxy)ethyl]-4-oxo-3-quinolinecarboxylate (350 mg, 0.63 mmol) obtained in Step 5 was dissolved in THF (25 ml) and tetrabutylammonium fluoride (1M THF solution; 1.9 ml, 1.9 mmol) was added. The mixture was stirred at room temperature for 1 hr. Water was added to the reaction solution and the precipitate was collected by filtration, washed with water and vacuum-dried to give an object product (279 mg, yield quant) as a pale-yellow solid.

$^1$H NMR(DMSO-d$_6$ 300 MHz) (δ) ppm: 1.27(3H,t,J=7.1 Hz), 3.65-3.80(2H,m), 4.21(2H,q,J=7.1 Hz), 4.40-4.50(2H, m), 4.99(1H,m), 7.30-7.90(5H,m), 8.47(1H,s)

MS(ESI): M+438

Step 7 Synthesis of 6-(2,3-dichlorobenzyl)-1,4-dihydro-8-fluoro-1-(2-hydroxyethyl)-4-oxo-3-quinolinecarboxylic acid

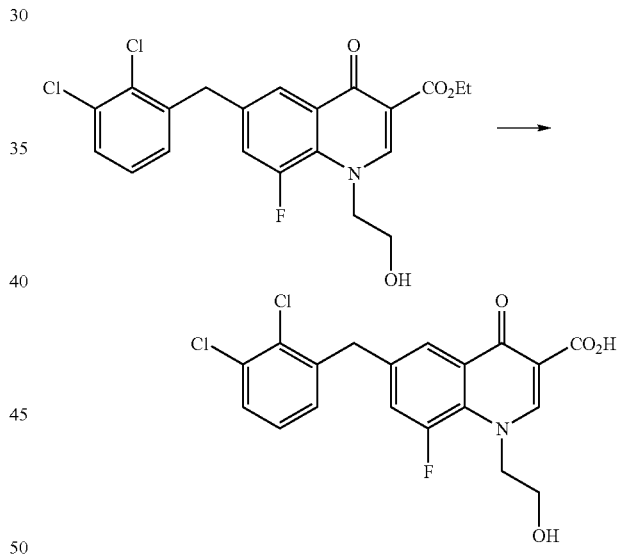

Ethyl 6-(2,3-dichlorobenzyl)-1,4-dihydro-8-fluoro-1-(2-hydroxyethyl)-4-oxo-3-quinolinecarboxylate (80 mg, 0.18 mmol) obtained in Step 6 was dissolved in a mixture of ethanol (2 ml) and THF (1 ml), and 1N aqueous sodium hydroxide solution (1 ml, 1.0 mmol) was added. The mixture was stirred with heating at 60° C. for 1 hr. After allowing the mixture to cool, 10% aqueous citric acid solution was added to the reaction solution. The precipitate was collected by filtration, washed with 30% aqueous ethanol and vacuum-dried to give an object product (70 mg, yield 93%) as a white solid.

$^1$H NMR (DMSO-d$_6$ 300 MHz) (δ) ppm: 3.78 (2H, m), 4.35 (2H, s), 4.64 (2H, m), 5.00 (1H, m), 7.39 (2H, m), 7.47 (1H, m), 7.58 (1H, m), 8.00 (1H, m), 8.81 (1H, s), 14.80 (1H, s).

MS (ESI): M+409

EXAMPLE 3-38

Step 1

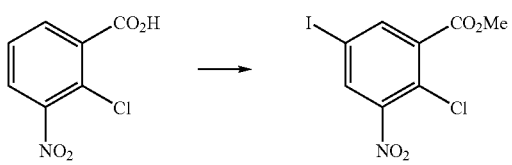

2-Chloro-3-nitrobenzoic acid (6.00 g, 29.77 mmol) was dissolved in trifluoromethanesulfonic acid (40 ml) and N-iodosuccinimide (7.37 g, 32.76 mmol) was added by portions at 0° C. The mixture was stirred at 40° C. for 4 hrs and the reaction solution was added to ice water. After stirring, the precipitate was collected by filtration, washed with water and vacuum-dried. The obtained solid was dissolved in methanol (50 ml), conc. sulfuric acid (catalytic amount) was added, and the mixture was heated under reflux for 5.5 hrs. The reaction solution was concentrated under reduced pressure and the obtained residue was purified by silica gel chromatography (ethyl acetate:hexane=1:4) to give an object product (5.35 g, yield 53%) as a pale-yellow solid.

1H NMR(CDCl$_3$ 300 MHz) ($\delta$) ppm: 3.98(3H, s), 8.11 (1H, d, J=2.1 Hz), 8.24 (1H, d, J=2.1 Hz)

Step 2

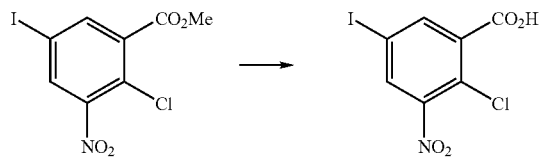

The compound (5.35 g, 15.67 mmol) obtained in Step 1 was dissolved in methanol (25 ml) and 4N aqueous potassium hydroxide solution (10.00 ml, 4.00 mmol) was added. The mixture was heated under reflux for 30 min. After allowing the mixture to cool, 1N hydrochloric acid was added to the reaction solution and the precipitated solid was collected by filtration and vacuum-dried to give an object product (4.99 g, yield 97%) as a white solid.

$^1$H NMR(CDCl$_3$ 300 MHz) ($\delta$) ppm: 8.14 (1H, d, J=2.0 Hz), 8.39 (1H, d, J=2.1 Hz)

Step 3

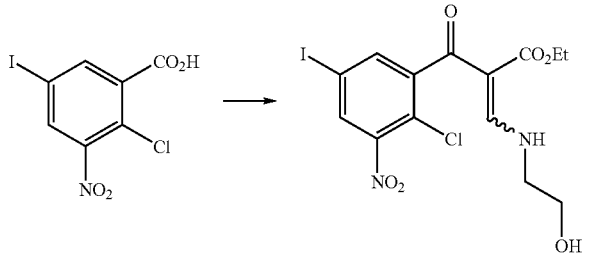

The compound (4.99 g, 15.24 mmol) obtained in Step 2 was dissolved in toluene (50 ml), and thionyl chloride (5.00 ml, 68.54 mmol) and dimethylformamide (catalytic amount) were added. The mixture was heated under reflux for 1 hr. The reaction solution was concentrated under reduced pressure and tetrahydrofuran (80 ml) was added to dissolve the residue. The resulting solution was added dropwise to a solution of ethyl 3,3-dimethylaminoacrylate. (2.29 g, 16.00 mmol) and triethylamine (2.55 ml, 18.30 mmol) in tetrahydrofuran (50 ml) and the mixture was stirred with heating at 50° C. for 10 hrs. After allowing the mixture to cool, aminoethanol (1.10 ml, 18.23 mmol) was added to the reaction mixture and the mixture was stirred with heating at 40° C. for 1.5 hrs. After allowing the mixture to cool, water was added to the reaction mixture and the mixture was extracted with ethyl acetate. The organic layer was washed successively with water and saturated brine, and dried over sodium sulfate. After filtration, the filtrate was concentrated under reduced pressure, and the obtained residue was purified by silica gel chromatography (ethyl acetate:hexane=2:1) to give an object product (5.35 g, yield 75%) of a mixture of E form and Z form as a yellow solid.

$^1$H NMR(CDCl$_3$ 300MHz) ($\delta$) ppm: 0.82-1.01 (3H, m), 3.63 (2H, br), 3.85-4.06 (4H, m), 7.65-7.68 (1H, m), 8.02-8.06 (1H, m), 8.21-8.36 (1H, m), 9.78 (0.16H, br), 11.15 (0.84H, br)

Step 4

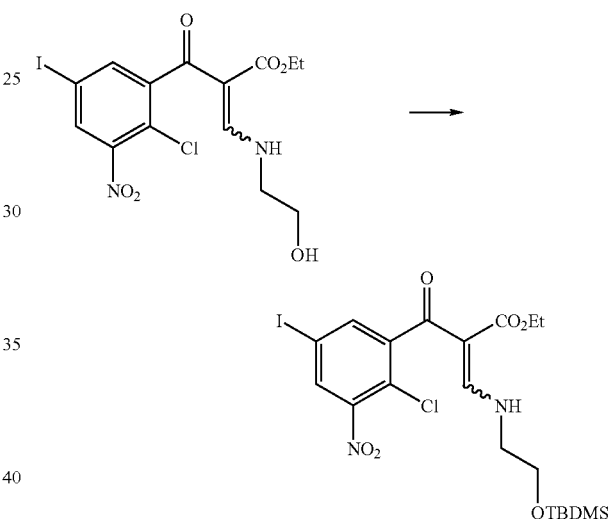

The compound (5.35 g, 11.42 mmol) obtained in Step 3 was dissolved in dimethylformamide (50 ml), and imidazole (1.71 g, 25.12 mmol) and tert-butyldimethylsilyl chloride (3.62 g, 24.02 mmol) were added. The mixture was stirred at room temperature for 30 min. Water was added to the reaction mixture and the mixture was extracted with ethyl acetate. The organic layer was washed successively with water and saturated brine, and dried over sodium sulfate. After filtration, concentration under reduced pressure gave a crude product (7.10 g) as a pale-yellow solid.

Step 5

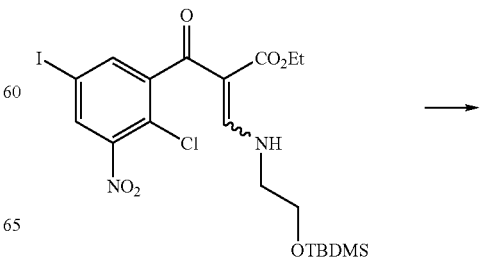

-continued

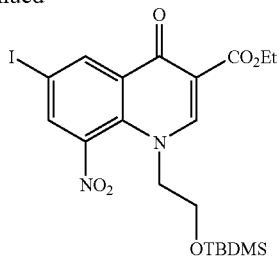

The crude product (7.10 g) obtained in Step 4 was dissolved in tetrahydrofuran (70 ml) and sodium hydride (731 mg, 18.27 mmol) was added with ice-cooling. The mixture was stirred at 0° C. for 45 min. 1N Hydrochloric acid (18.3 ml) and water were added to the reaction solution and stirred, after which the mixture was extracted with ethyl Acetate. The organic layer was washed successively with water and saturated brine, and dried over sodium sulfate. After filtration, the filtrate was concentrated under reduced pressure and purified by silica gel chromatography (ethyl acetate:hexane=1:4 to 1:2) to give an object product (5.58 g, yield 84%) as a yellow solid.

$^1$H NMR(CDCl$_3$ 300 MHz) (δ) ppm: −0.14 (6H, s), 0.73 (9H, s), 1.39 (3H, t, J=7.1 Hz), 3.74 (2H, t, J=4.6 Hz), 4.02 (2H, t, J=4.6 Hz), 4.39 (2H, q, J=7.1 Hz), 8.13 (1H, d, J=2.2 Hz), 8.50 (1H, s), 9.02 (1H, d, J=2.2 Hz)

Step 6

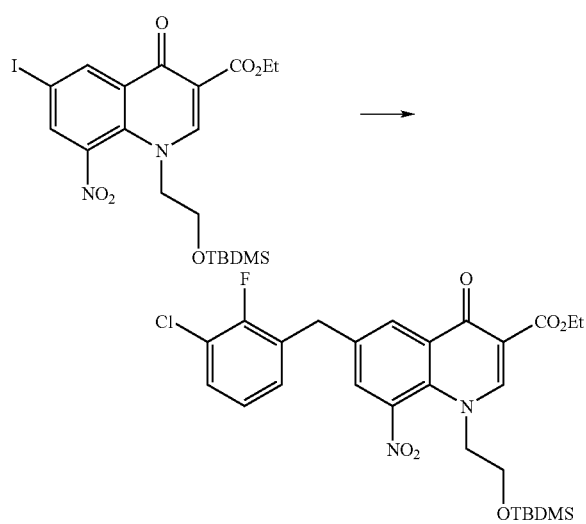

The compound (5.00 g, 9.15 mmol) obtained in Step 5 was dissolved in tetrahydrofuran (100 ml) and bis(dibenzylideneacetone)palladium(0) (105 mg, 0.18 mmol) and tri(2-furyl) phosphine (85 mg, 0.37 mmol) were added under an argon stream. A solution of 3-chloro-2-fluorobenzylzinc bromide (11.90 mmol) in tetrahydrofuran prepared as mentioned in Example 4-32. Step 4 was added dropwise at 60° C. After completion of the addition, the mixture was heated under reflux for 4 hrs. After allowing the mixture to cool, saturated aqueous ammonium chloride solution was added to the reaction solution and insoluble material was filtered off with Celite. The filtrate was extracted with ethyl acetate, and the organic layer was washed successively with water and saturated brine and dried over sodium sulfate. After filtration, the filtrate was concentrated under reduced pressure, and the obtained residue was purified by silica gel chromatography (ethyl acetate:hexane=1:2 to 1:1) to give an object product (2.67 g, yield 52%) as a brown oil.

$^1$H NMR(CDCl$_3$ 300 MHz) (δ) ppm: −0.19 (6H, s), 0.70 (9H, s), 1.39 (3H, t, J=7.1 Hz), 3.73 (2H, t, J=4.6 Hz), 4.03 (2H, t, J=4.6 Hz), 4.14 (2H, s), 4.38 (2H, q, J=7.1 Hz), 7.02-7.14 (2H, m), 7.29-7.35 (1H, m), 7.73 (1H, d, J=2.2 Hz), 8.50 (1H, s), 8.59 (1H, s)

Step 7

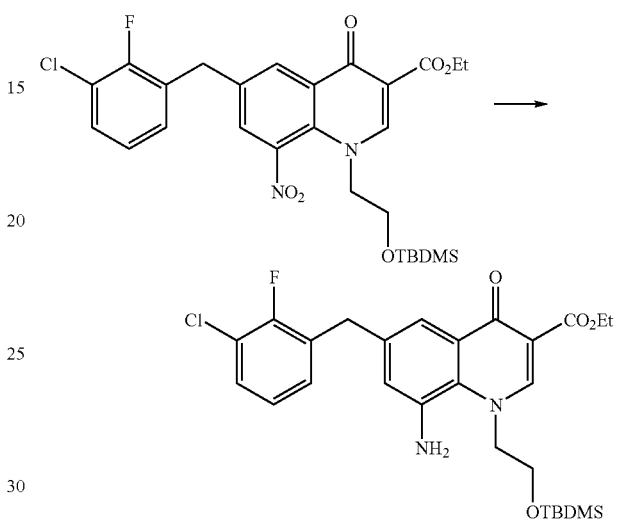

The compound (1.00 g, 1.79 mmol) obtained in Step 6 was dissolved in acetic acid (20 ml) and zinc powder (1.16 g, 17.76 mmol) was added. The mixture was stirred at room temperature for 4 hrs. The reaction mixture was filtered through Celite and saturated aqueous sodium hydrogen carbonate was added to the filtrate. The mixture was extracted with ethyl acetate. The organic layer was washed successively with saturated aqueous sodium hydrogen carbonate, water and saturated brine, and dried over sodium sulfate. After filtration, the filtrate was concentrated under reduced pressure, and the obtained residue was purified by silica gel chromatography (ethyl acetate). To the residue obtained was added ethyl ether and the mixture was sonicated. After filtration, it was vacuum-dried to give an object product (730 mg, yield 77%) as a pale-orange solid.

$^1$H NMR(CDCl$_3$ 300 MHz) (δ) ppm: −0.06 (6H, s), 0.77 (9H, s), 1.41(3H, t, J=7.1 Hz), 4.01 (2H, s), 4.08 (2H, t, J=4.7 Hz), 4.39 (2H, q, J=7.1 Hz), 4.50 (2H, brs), 4.75 (2H, t, J=4.7 Hz), 6.81 (1H, s), 6.94-7.08 (2H, m), 7.20-7.26 (1H, m), 7.91 (1H, s), 8.34 (1H, s)

Step 8

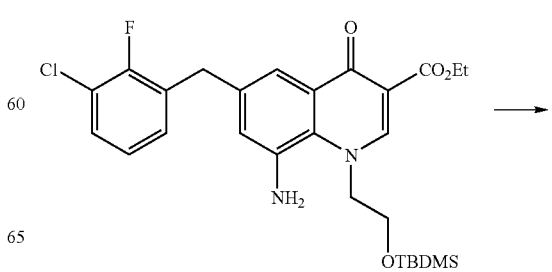

-continued

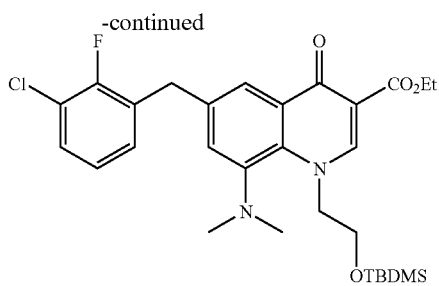

The compound (100 mg, 0.19 mmol) obtained in Step 7 was dissolved in dimethylformamide (2 ml), and methyl iodide (0.029 ml, 0.47 mmol) and sodium hydride (23 mg, 0.56 mmol) were added. The mixture was stirred at room temperature for 2 hrs. A 10% aqueous citric acid solution was added to the reaction mixture, and the mixture was stirred and extracted with ethyl acetate. The organic layer was washed successively with water and saturated brine, and dried over sodium sulfate. After filtration, the filtrate was concentrated under reduced pressure and subjected to silica gel chromatography (ethyl acetate:hexane=2:1) to give a crudely purified product (45 mg) as a pale-red solid.

$^1$H NMR(CDCl$_3$ 300 MHz) (δ) ppm: −0.33−−0.29 (6H, m), 0.64-0.69 (9H, m), 1.23-1.41(3H, m), 2.66-2.70 (6H, m), 3.55-3.59 (2H, m), 4.36-4.4.2 (4H, m), 4.82-4.96 (2H, m), 6.96-7.11 (2H, m), 7.23-7.30(2H, m), 8.16-8.15 (1H, m), 8.40-8.66 (1H, m)

Step 9

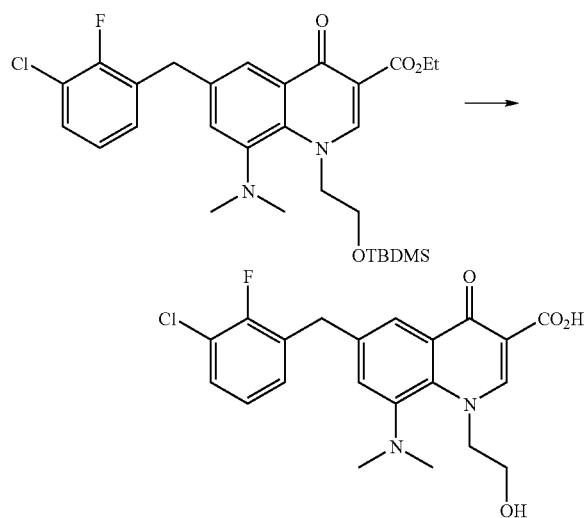

The crudely purified product (45 mg) obtained in Step 8 was dissolved in tetrahydrofuran (1 ml), and 1M solution of tetrabutylammonium fluoride (1.00 ml, 1.00 mmol) in THF was added. The mixture was stirred at room temperature for 5 min. To the reaction solution were added ethanol (1 ml) and 1N aqueous sodium hydroxide solution (1 ml, 1.00 mmol), and the mixture was heated under reflux for 2 hrs. After allowing the mixture to cool, 10% aqueous citric acid solution was added to the reaction solution. The mixture was stirred and extracted twice with chloroform. The organic layer was washed with saturated brine, and dried over sodium sulfate. After filtration, the filtrate was concentrated under reduced pressure and subjected to silica gel chromatography (chloroform:methanol:acetic acid=10:1:0.1) to give a crudely purified product. To the crudely purified product was added aqueous ethanol and the mixture was sonicated. After filtration, the filtrate was vacuum-dried to give an object product (22 mg, yield 27%) as a beige solid.

$^1$H NMR(DMSO-d$_6$ 300 MHz) (δ) ppm: 2.67 (6H, s), 3.39 (2H, m), 4.21 (2H, s), 4.72 (1H, t), 4.97 (2H, t), 7.20-7.22 (1H, m), 7.40-7.50 (2H, m), 7.65 (1H, s), 7.84 (1H, s), 15.10 (1H, s)

MS(ESI): M+419

EXAMPLE 3-62

Step 1

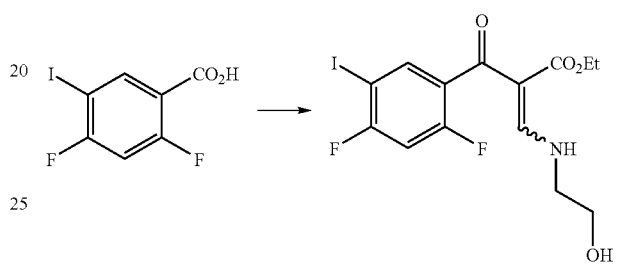

2,4-Difluoro-5-iodobenzoic acid (3.00 g, 10.60 mmol) obtained in Example 4-33. Step 1 was dissolved in toluene (10 ml), and thionyl chloride (3.00 ml, 41.10 mmol) and dimethylformamide (catalytic amount) were added. The mixture was heated under reflux for 1.5 hrs. The reaction solution was concentrated under reduced pressure and tetrahydrofuran (15 ml) was added to dissolve the residue. The resulting solution was added dropwise to a solution of ethyl 3,3-dimethylaminoacrylate (1.66 g, 11.60 mmol) and triethylamine (1.77 ml, 12.70 mmol) in tetrahydrofuran (10 ml), and the mixture was stirred with heating at 50° C. for 2.5 hrs. After, allowing the mixture to cool, the reaction mixture was filtered and washed with tetrahydrofuran (10 ml). To the filtrate was added aminoethanol (0.77 ml, 12.76 mmol) and the mixture was stirred with heating at 40° C. for 1 hr. After allowing the mixture to cool, water was added to the reaction solution and the mixture was extracted with ethyl acetate. The organic layer was washed successively with water and saturated brine, and dried over sodium sulfate. After filtration, the filtrate was concentrated under reduced pressure, and the obtained residue was purified by silica gel chromatography (ethyl acetate:hexane=2:1) to give a crudely purified product (3.00 g, yield 67%) of a mixture of E form and Z form as a yellow solid.

Step 2

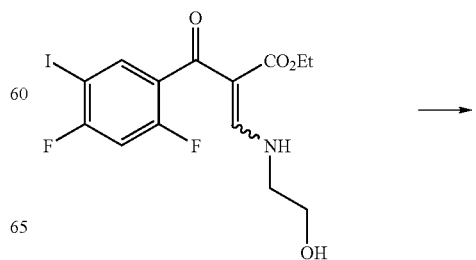

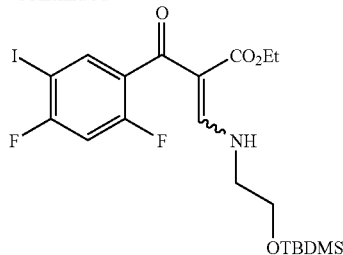

The compound (3.00 g, 7.06 mmol) obtained in Step 1 was dissolved in dimethylformamide (15 ml) and imidazole (1.06 g, 15.52 mmol) and tert-butyldimethylsilyl chloride (2.23 g, 14.82 mmol) were added. The mixture was stirred at room temperature for 14 hrs. Water was added to the reaction mixture and the mixture was extracted with ethyl acetate. The organic layer was washed successively with water and saturated brine, and dried over sodium sulfate. After filtration, the filtrate was concentrated under reduced pressure, and the obtained residue was purified by silica gel chromatography (ethyl acetate:hexane=1.:4) to give an object product (3.22 g, yield 85%) as a white solid.

$^1$H NMR(CDCl$_3$ 300 MHz) (δ) ppm: 0.06 (6H, s), 0.90 (9H, s), 1.08 (3H, t, J=7.1 Hz), 3.51 (2H, br), 3.79(2H, t, J=4.9 Hz), 4.05(2H, q, J=7.1 Hz), 6.78 (1H, dd, J=7.9, 9.4 Hz), 7.71 (1H, dd, J=7.3, 7.3 Hz), 8.11 (1H, d, J=14.0 Hz), 10.91 (1H, br)

Step 3

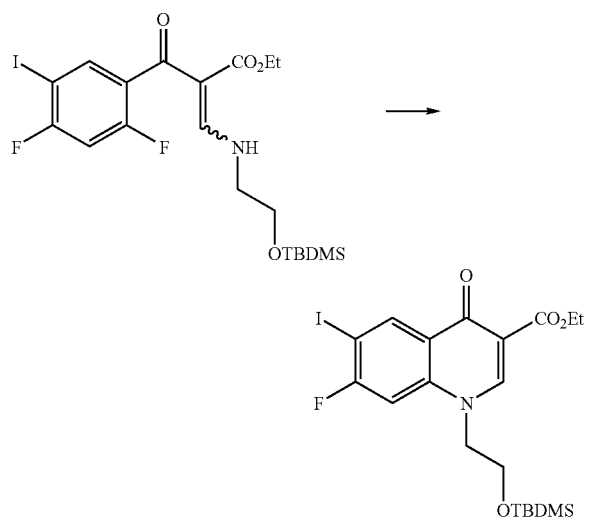

The compound (3.22 g, 5.97 mmol) obtained in Step 2 was dissolved in tetrahydrofuran (35 ml) and sodium hydride (358 mg, 8.95 mmol) was added with ice-cooling. The mixture was stirred at 0° C. for 2.5 hrs. 1N Hydrochloric acid (8.90 ml, 8.90 mmol) and water (35 ml) were added to the reaction mixture and the mixture was stirred. The precipitate was collected by filtration, and purified by silica gel chromatography (ethyl acetate:hexane=1:2 to 2:1) to give an object product (2.52 g, yield 81%) as a pale-yellow solid.

$^1$H NMR(CDCl$_3$ 300 MHz) (δ) ppm: −0.11(6H, s), 0.79 (9H, s), 1.39 (3H, t, J=7.1 Hz), 3.96 (2H, t, J=4.8 Hz), 4.23 (2H, t, J=4.8 Hz), 4.38(2H, q, J=7.1 Hz), 7.14 (1H, d, J=9.3 Hz), 8.47 (1H, s), 8.93 (1H, d, J=7.2 Hz)

Step 4

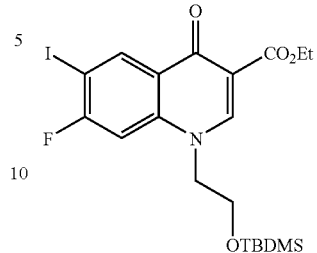

The compound (1.00 g, 1.93 mmol) obtained in Step 3 was dissolved in tetrahydrofuran (20 ml). Under an argon stream, bis(dibenzylideneacetone)palladium(0) (22 mg, 0.039 mmol) and tri(2-furyl)phosphine (18 mg, 0.077 mmol) were added. To this mixture was added a solution of 3-chloro-2-fluorobenzylzinc bromide (2.89 mmol) in tetrahydrofuran prepared as mentioned above dropwise at 60° C. After completion of the addition, the mixture was heated under reflux for 1 hr. After allowing the mixture to cool, saturated aqueous ammonium chloride solution was added to the reaction solution. Insoluble material was filtered off with Celite. The filtrate was extracted with ethyl acetate, and the organic layer was washed successively with water and saturated brine, and dried over sodium sulfate. After filtration, the filtrate was concentrated under reduced pressure, and the obtained residue was purified by silica gel chromatography (ethyl acetate:hexane=2:1) to give an object product (573 mg, yield 55%) as a pale-yellow solid.

$^1$H NMR(CDCl$_3$ 300 MHz) (δ) ppm: −0.12(6H, s), 0.78 (9H, s), 1.38 (3H, t, J=7.1 Hz), 3.99 (2H, t), 4.13(2H, s), 4.23 (2H, t), 4.37 (2H, q, J=7.1 Hz), 6.96-7.13 (3H, m), 7.25-7.31 (1H, m), 8.39 (1H, d), 8.46 (1H, s)

Step 5

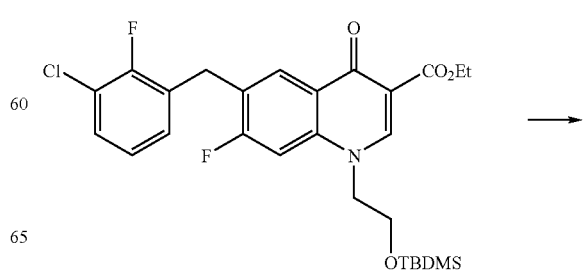

-continued

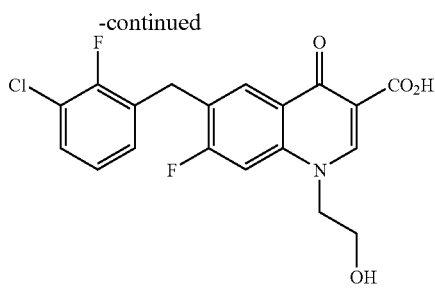

The compound (170 mg, 0.32 mmol) obtained in Step 4 was dissolved in tetrahydrofuran (1 ml) and 2N aqueous sodium hydroxide solution (4.00 ml, 2.00 mmol) was added. The mixture was heated under reflux for 3.5 hrs. After allowing the mixture to cool, 10% aqueous citric acid solution was added to the reaction solution, and the precipitate was collected by filtration, washed with 50% aqueous ethanol and vacuum-dried to give an object product (117 mg, yield 94%) as a white solid.

$^1$H NMR(DMSO-$d_6$ 300 MHz) (δ) ppm: 3.73(2H, br), 4.25 (2H, s), 4.58(2H, br), 4.96(1H, br), 7.19-7.22 (1H, m), 7.30-7.36 (1H, m), 7.49-7.54 (1H, m), 8.03 (1H, d), 8.30 (1H, d), 8.88(1H, s), 15.42 (1H, brs)

Step 6

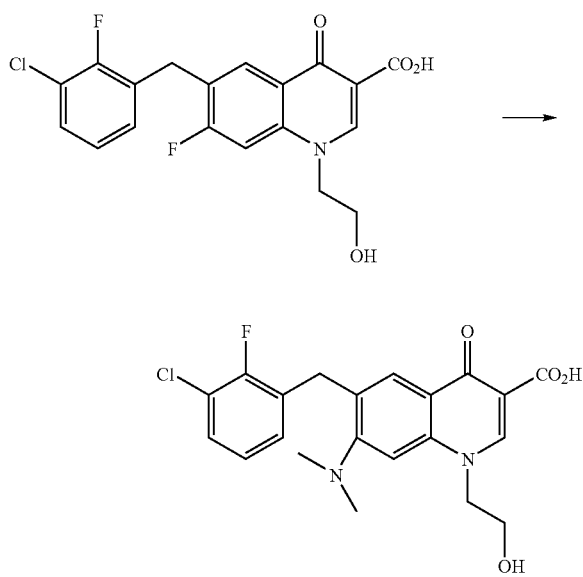

The compound (65 mg, 0.17 mmol) obtained in Step 5 was dissolved in dimethyl sulfoxide (2.5ml) and microwave was irradiated thereon at 50 W and 120° C. or below for 20 min. After allowing the mixture to cool, 10% aqueous citric acid solution was added to the reaction mixture, and the precipitate was collected by filtration, washed with water and vacuum-dried to give an object product (66 mg, yield 96%) as a white solid.

$^1$H NMR(DMSO-$d_6$ 300 MHz) (δ) ppm: 2.88 (6H, s), 3.70-3.80 (2H, m), 4.22(2H, s), 4.60-4.70 (2H, m), 5.05 (1H, t), 7.20-7.31 (3H, m), 7.50-7.60 (1H, m), 7.80 (1H, s), 8.78 (1H, s), 15.30-15.40(1H, brs)

MS(ESI): M+419

EXAMPLE 3-73

Step 1

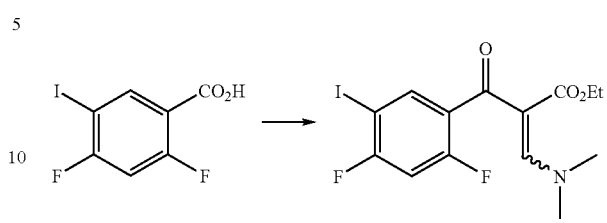

2,4-Difluoro-5-iodobenzoic acid (5.00 g, 17.60 mol) was dissolved in toluene (25 ml), and oxalyl chloride (2.00 ml, 22.93 mmol) and dimethylformamide (catalytic amount) were added. The mixture was stirred at room temperature for 12 hrs. After filtering the reaction solution, the filtrate was concentrated under reduced pressure and toluene (20 ml) was added. Insoluble material was filtered with Celite. The filtrate was concentrated under reduced pressure and tetrahydrofuran (20 ml) was added to dissolve the obtained residue. The resulting solution was added dropwise to a solution of ethyl 3,3-dimethylaminoacrylate (3.28 g, 22.91 mmol) and triethylamine (3.70 ml, 26.55 mmol) in tetrahydrofuran (20 ml). The mixture was heated under reflux for 1 hr. After allowing the mixture to cool, water and ethyl acetate (50 ml) were added to the reaction mixture. The mixture was stirred and partitioned. The organic layer was washed successively with 1N hydrochloric acid (20 ml) and water (200 ml), and dried over sodium sulfate. After filtration, the filtrate was concentrated under reduced pressure to give a crude product (7.24 g) as a brown oil.

Step 2

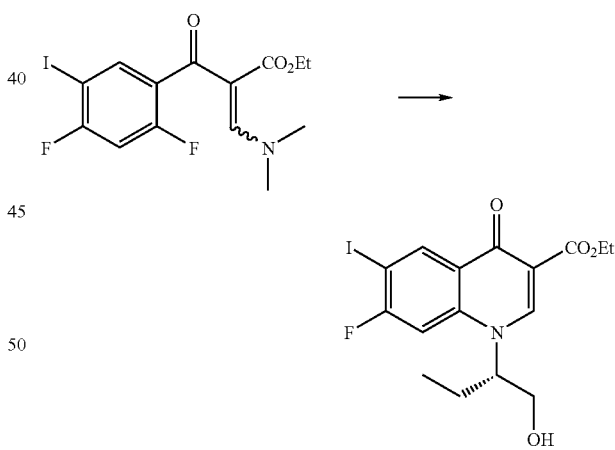

The crude product (7.24 g) obtained in Step 1 was dissolved in tetrahydrofuran (20 ml) and (S)-2-amino-1-butanol (1.89 g, 21.24 mmol) was added. The mixture was stirred with heating at 60° C. for 1.5 hrs. After allowing the mixture to cool, the reaction solution was concentrated under reduced pressure and the obtained residue was dissolved in dimethylformamide (20 ml). Potassium carbonate (7.33 g, 53.02 mmol) was added and the mixture was stirred with heating at 70° C. for 1 hr. After allowing the mixture to cool, the reaction mixture was concentrated under reduced pressure. Water (150 ml) was added to the residue and the mixture was stirred at room temperature for 30 min. The precipitate was collected by filtration. The obtained solid was washed with water (50 ml), and then with a mixture (50 ml) of hexane:diethyl ether=7:3, and vacuum-dried to give an object product (4.69 g, yield 61%) as a white solid.

¹H NMR(CDCl₃ 300 MHz) (δ) ppm: 0.97(3H, t, J=7.4 Hz), 1.40(3H, t, J=7.1 Hz), 1.95-2.05 (1H, m), 2.11-2.21 (1H, m), 4.05 (1H, br), 4.34-4.39 (5H, m), 5.59 (1H, br), 7.30 (1H, d, J=10.0 Hz), 8.04 (1H, d, J=7.1 Hz), 8.58 (1H, s)

Step 3

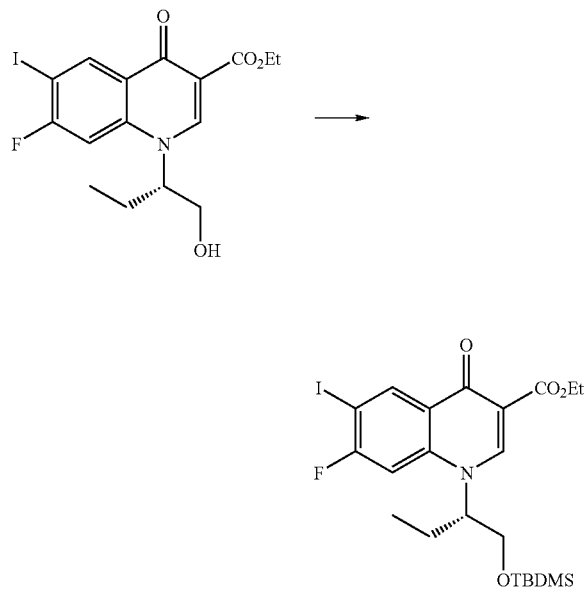

The compound (4.69 g, 10.82 mmol) obtained in Step 2 was dissolved in dimethylformamide (20 ml), and imidazole (950 mg, 13.95 mmol) and tert-butyldimethylsilyl chloride (1.95 g, 12.96 mmol) were added. The mixture was stirred at room temperature for 14.5 hrs. Water was added to the reaction mixture and the mixture was extracted with ethyl acetate (50 ml). The organic layer was washed 3 times with water and then with saturated brine, and dried over sodium sulfate. After filtration, the filtrate was concentrated under reduced pressure, and the obtained residue was purified by silica gel chromatography (ethyl acetate:hexane=3:7) to give an object product (5.06 g, yield 86%) as a yellow oil.

¹H NMR(CDCl₃ 300 MHz) (δ) ppm: −0.08 (3H, s), −0.05 (3H, s), 0.77 (9H, s), 0.98 (3H, t, J=7.5 Hz), 1.40 (3H, t, J=7.2 Hz), 1.94-2.10(2H, m), 3.90 (2H, br), 4.35-4.43(3H, m), 7.26 (1H, d, J=9.9 Hz), 8.59 (1H, s), 8.95 (1H, d, J=7.2 Hz)

Step 4

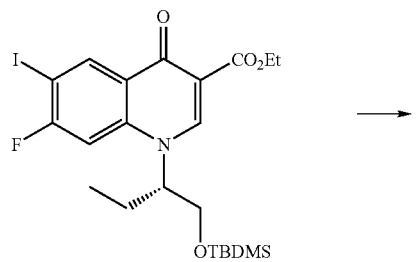

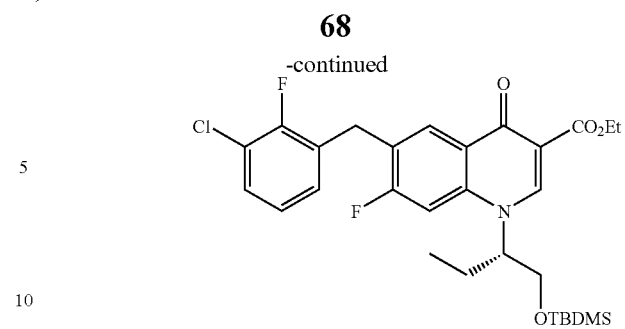

The compound (5.06 g, 9.24 mmol) obtained in Step 3 was dissolved in tetrahydrofuran (20 ml), and bis(dibenzylideneacetone)palladium(0) (266 mg, 0.46 mmol) and tri(2-furyl)phosphine (215 mg, 0.92 mmol) were added under an argon stream. A solution of 3-chloro-2-fluorobenzylzinc bromide (18.50 mmol) in tetrahydrofuran prepared as mentioned above was added dropwise. After completion of the addition, the mixture was stirred with heating at 60° C. for 1 hr. After allowing the mixture to cool, water and ethyl acetate were added to the reaction solution and the mixture was stirred and partitioned. The organic layer was washed successively with 1N hydrochloric acid, water, saturated aqueous sodium hydrogen carbonate and saturated brine, and dried over sodium sulfate. After filtration, the filtrate was concentrated under reduced pressure and the residue was purified by silica gel chromatography (ethyl acetate:hexane=1:1 to 2:1) to give an object product (3.86 g, yield 74%) as a brown oil.

¹H NMR(CDCl₃ 300 MHz) (δ) ppm: −0.10(3H, s), −0.06 (3H, s), 0.752(9H, s), 0.98(3H, t, J=7.4 Hz), 1.403H, t, J=7.1 Hz), 1.90-2.12(2H, m), 3.89 (2H, br), 4.12 (2H, s), 4.35-4.49 (3H, m), 6.97-7.08 (2H, m), 7.22-7.29 (2H, m), 8.40 (1H, d, J=8.7 Hz), 8.58(1H, s)

Step 5

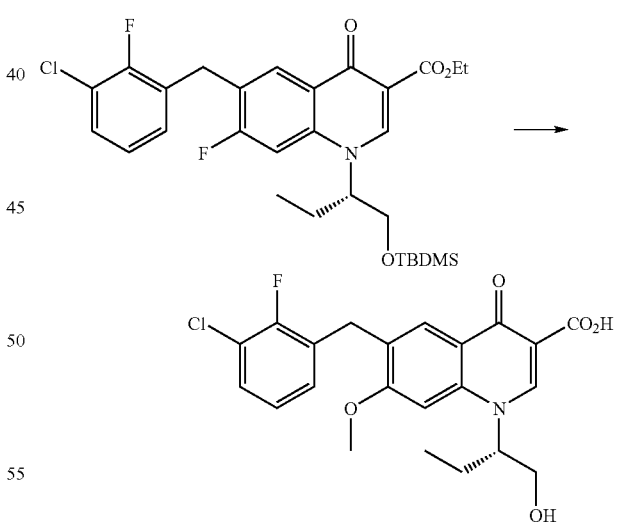

To the compound (3.86 g, 6.85 mmol) obtained in Step 4 were added 28% sodium methoxide in methanol (40.00 ml, 0.20 mol) and water (2.00 ml, 0.11 mol), and the mixture was heated under reflux for 5.5 hrs. After allowing the mixture to cool, the reaction solution was concentrated under reduced pressure and 6N hydrochloric acid was added to the obtained residue. The mixture was stirred, and extracted twice with ethyl acetate. The organic layer was washed successively with water and saturated brine, dried over magnesium sulfate, filtered and concentrated under reduced pressure. The obtained residue was recrystallized from ethanol (200 ml) to give an object product (2.03 g, yield 68%) as a white solid.

$^1$H NMR(DMSO-$d_6$ 300 MHz) (δ) ppm: 0.87 (3H, t, J=7.3 Hz), 1.80-2.10 (2H, m), 3.70-3.90 (2H, m), 4.02 (3H, s), 4.11 (2H, s), 5.00-5.19 (2H, m), 7.16-7.24 (2H, m), 7.44-7.48 (2H, m), 8.04 (1H, s), 8.78 (1H, s), 15.44 (1H, s)

MS(ESI): M+434

EXAMPLE 3-75

Step 1

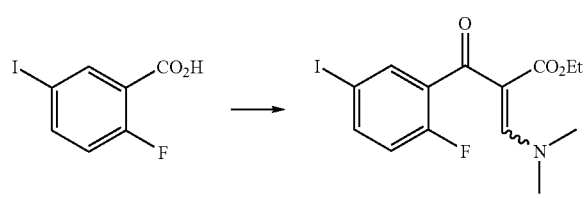

2-Fluoro-5-iodobenzoic acid (6.60 g, 24.81 mmol) was dissolved in chloroform (70 ml) and-oxalyl chloride (4.30 ml, 49.29 mmol) and dimethylformamide (catalytic amount) were added. The mixture was stirred at room temperature for 3 hrs. The reaction solution was concentrated under reduced pressure and chloroform (35 ml), was added to dissolve the residue. The obtained solution was added dropwise to a solution of ethyl 3,3-dimethylaminoacrylate (4.26 g, 29.75 mmol) and triethylamine (5.19 ml, 37.24 mmol) in chloroform (35 ml), and the mixture was stirred-at room temperature for 15 hrs. Water was added to partition the reaction solution, and the organic layer was washed with saturated brine and dried over sodium sulfate. After filtration, the filtrate was concentrated under reduced pressure and the obtained residue was purified by silica gel chromatography (ethyl acetate:hexane=1:2 to 1:1) to give an object product (6.40 g, yield 66%) f a mixture of E form and Z form as an orange solid.

$^1$H NMR(CDCl$_3$ 400 MHz) (δ) ppm: 0.94 (3H, t, J=47.2 Hz), 2.88 (3H, brs), 3.31 (3H, brs), 3.97 (2H, q), 6.78 (1H, dd, J=8.4, 10.0 Hz), 7.65-7.67 (1H, m), 7.78(1H, s), 7.85 (1H, brs)

MS(ESI): M+392

Step 2

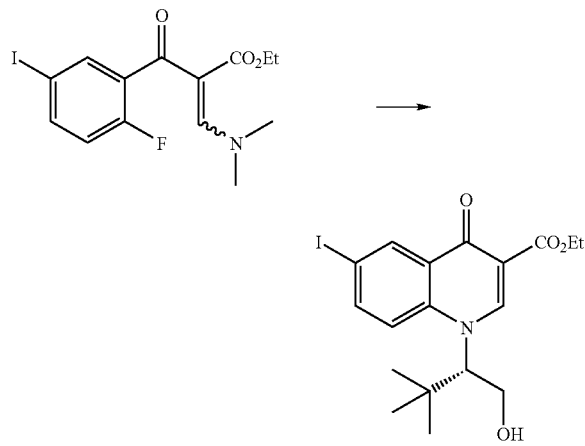

The compound (300 mg, 0.77 mmol) obtained in Step 1 was dissolved in tetrahydrofuran (1.5 ml) and (S)-(+)-tert-leucinol (0.12 ml, 0.92 mmol) was added. The mixture was stirred with heating at 60° C. for 1 hr. The reaction solution was concentrated under reduced pressure and the obtained residue was dissolved in dimethylformamide (1.2 ml). Potassium carbonate (318 mg, 2.30 mmol) was added and the mixture was stirred with heating at 70° C. for 5.5 hrs. After cooling, 1N hydrochloric acid (5 ml) was added to the reaction mixture and the mixture was stirred with ice-cooling for 30 min. The precipitate was collected by filtration and the obtained solid was washed with 30% aqueous ethanol (6 ml), and then with a mixture (5 ml) of hexane:diethyl ether=2:1 and vacuum-dried to give an object product (276 mg, yield 81%) as a pale-yellow solid.

$^1$H NMR(CDCl$_3$ 300 MHz) (δ) ppm: 0.98 (9H, s), 1.41 (3H, t, J=7.0 Hz), 4.25-4.41 (4H, m), 4.64-4.70(1H, m), 5.14 (1H, br), 7.46 (1H, d, J=9.0 Hz), 7.89(1H, dd, J=2.2, 9.1 Hz), 8.06 (1H, d, J=2.1 Hz), 8.69(1H, s)

Step 3

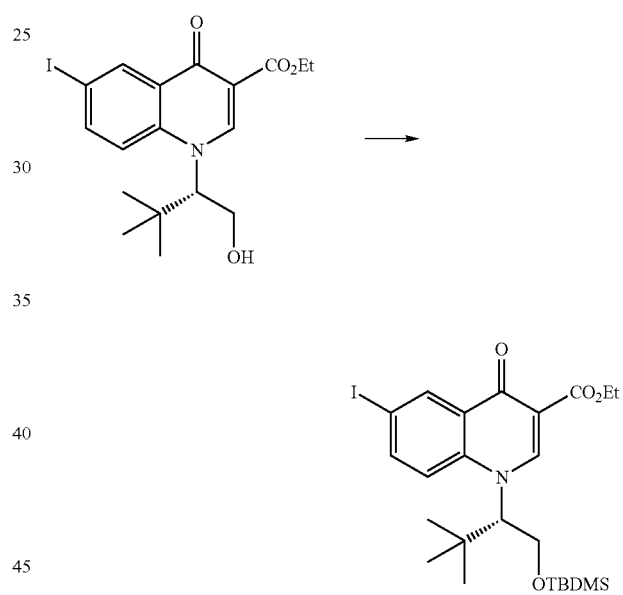

The compound (276 mg, 0.62 mmol) obtained in Step 2 was dissolved in dimethylformamide (1 ml) and imidazole (51 mg, 0.75 mmol) and tert-butyldimethylsilyl chloride (122 mg, 0.81 mmol) were added. The mixture was stirred at room temperature for 30 min. Water was added to the reaction mixture and the mixture was extracted twice with ethyl acetate, and the organic layer was washed twice with water and then with saturated brine, and dried over sodium sulfate. After filtration, the filtrate was concentrated under reduced pressure, and the obtained residue was purified by silica gel chromatography (ethyl acetate:hexane=3:5) to give an object product (314 mg, yield 91%) as a white amorphous form.

$^1$H NMR(CDCl$_3$ 300 MHz) (δ) ppm: −0.09 (3H, s), −0.01 (3H, s), 0.66 (9H, s), 1.04 (9H, s), 1.41 (3H, t, J=7.2 Hz), 4.10-4.14 (2H, m), 4.40 (2H, q, J=7.0 Hz), 4.58-4.63 (1H, m), 7.39(1H, d, J=9.3 Hz), 7.89 (1H, dd, J=2.2, 8.8 Hz), 8.67 (1H, s), 8.87 (1H, d, J=2.1 Hz)

Step 4

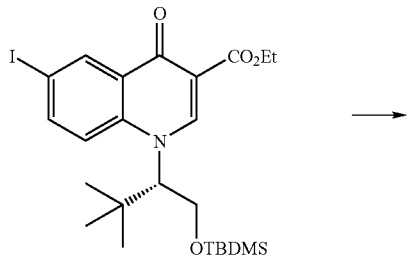

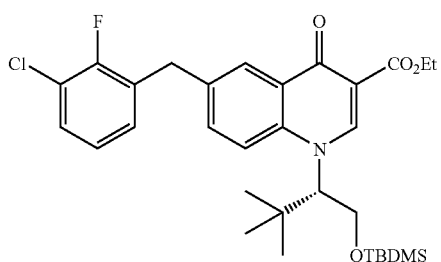

The compound (314 mg, 0.56 mmol) obtained in Step 3 was dissolved in tetrahydrofuran (1.2 ml), and bis(dibenzylideneacetone)palladium(0) (16 mg, 0.028 mmol) and tri(2-furyl)phosphine (13 mg, 0.056 mmol) were added under an argon stream. A solution of 3-chloro-2-fluorobenzylzinc bromide (1.13 mmol) in tetrahydrofuran prepared as mentioned above was added dropwise. After completion of the addition, the mixture was stirred with heating at 50° C. for 1.5 hrs. After allowing the mixture to cool, water and ethyl acetate were added to the reaction solution and the mixture was stirred. Insoluble material was filtered with Celite. The filtrate was partitioned and the organic layer was washed successively with water and saturated brine, and dried over sodium sulfate. After filtration, the filtrate was concentrated under reduced pressure and the obtained residue was purified by silica gel chromatography (ethyl acetate:hexane=1:1) to give an object product (283 mg, yield 87%) as a brown amorphous form.

$^1$H NMR(CDCl$_3$ 400 MHz) (δ) ppm: −0.11 (3H, s), −0.01 (3H, s), 0.63 (9H, s), 1.06 (9H, s), 1.41 (3H, t, J=7.0 Hz), 4.08-4.16 (4H, m), 4.38 (2H, q, J=7.0 Hz), 4.61-4.67 (1H, m), 6.95-7.08(2H, m), 7.23-7.27(1H, m), 7.47-7.49 (1H, m), 7.53-7.55 (1H, m), 8.41 (1H, d, J=2.0 Hz); 8.68 (1H, s)

Step 5

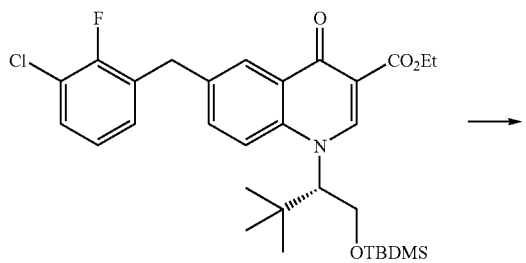

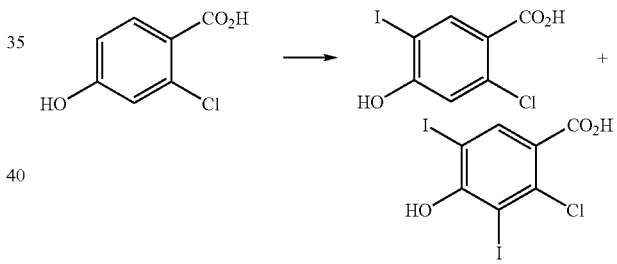

The compound (283 mg, 0.49 mmol) obtained in Step 4 was dissolved in ethanol (2 ml) and 1N aqueous sodium hydroxide solution (1.00 ml, 1.00 mmol) was added. The mixture was heated under reflux for 1 hr. After allowing the mixture to cool, acetic acid (0.35 ml) was added to the reaction solution and the mixture was stirred. The precipitate was collected by filtration and the solid was suspended in diethyl ether (10 ml). After filtration, the mixture was vacuum-dried to give an object product (157 mg, yield 74%) as a white solid.

$^1$H NMR(DMSO-d$_6$ 400 MHz) (δ) ppm: 1.00 (9H, s), 4.07-4.12 (2H, m), 4.30 (2H, ), 5.12-5.14 (2H, m), 7.20-7.25 (1H, m), 7.40-7.45 (1H, m), 7.51-7.53 (1H, m), 7.87 (1H, d), 8.25 (1H, s), 8.41 (1H, d, J=9.2 Hz), 8.85 (1H, s), 15.20-15.21 (1H, br)

MS(ESI): M+432

EXAMPLE 4-20

Step 1

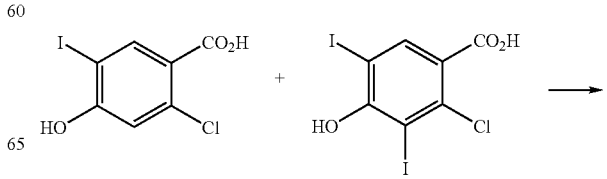

2-Chloro-4-hydroxybenzoic acid (5.18 g, 30.02 mmol) was dissolved in trifluoromethanesulfonic acid. (25 g) and N-iodosuccinimide (6.75 g, 30.00 mmol) was added by portions at 0° C. The mixture was stirred at room temperature for 15 hrs and trifluoromethanesulfonic acid (25 g) was further added. N-Iodosuccinimide (2.02 g, 8.98 mmol) was added by portions at 0° C. The mixture was stirred at room temperature for 13.5 hrs and the reaction mixture was added to ice water (300 ml). The mixture was stirred for 2 hrs. The precipitate was collected by filtration, washed with water and vacuum-dried to give an object product as a mixture of 2-chloro-4-hydroxy-5-iodobenzoic acid and 2-chloro-3,5-diiodo-4-hydroxybenzoic acid (8:2)(5.76 g).

Step 2

-continued

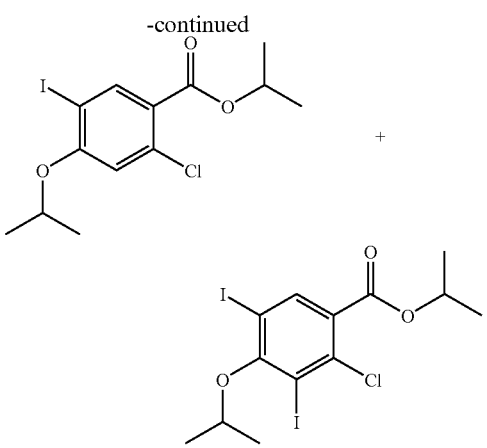

The mixture (3.89 g) obtained in Step 1 was dissolved in dimethylformamide (20 ml) and potassium carbonate (8.97 g, 64.90 mmol) and isopropyl iodide (6.50 ml, 65.15 mmol) were added. The mixture was stirred with heating at 80° C. for 2.5 hrs. The reaction mixture was added to 1N hydrochloric acid (100 ml), and toluene (100 ml) was further added. The mixture was stirred and insoluble material was filtered through Celite. The filtrate was partitioned and the organic layer was washed with water three times, and dried over sodium sulfate. After filtration, the filtrate was concentrated under reduced pressure and the obtained residue was purified by silica gel chromatography (ethyl acetate:hexane=1:9) to give an object product as a mixture (4.08 g).

Step 3

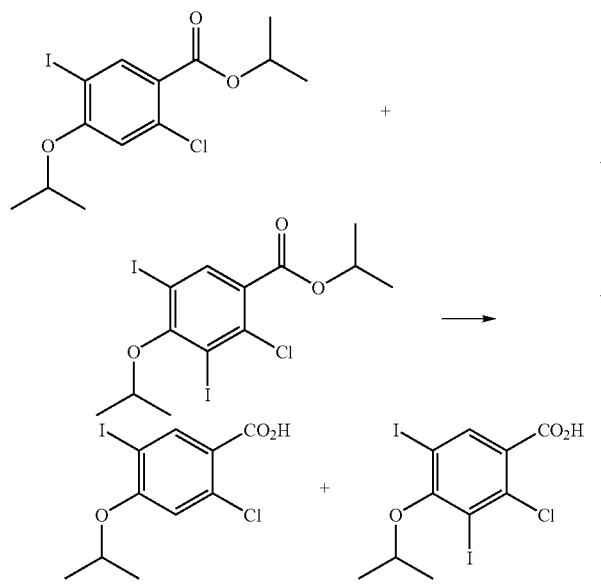

The mixture (4.08 g) obtained in Step 2 was dissolved in ethanol (20 ml) and 1N aqueous sodium hydroxide solution (20.00 ml, 20.00 mmol) was added. The mixture was heated under reflux for 24 hrs. After allowing the mixture to cool, 1N hydrochloric acid (30 ml) was added to the reaction solution and the mixture was stirred. The mixture was extracted with ethyl acetate three times. The organic layer was washed successively with water and saturated brine, and dried over sodium sulfate. After filtration, concentration under reduced pressure gave an object product as a mixture (3.40 g).

Step 4

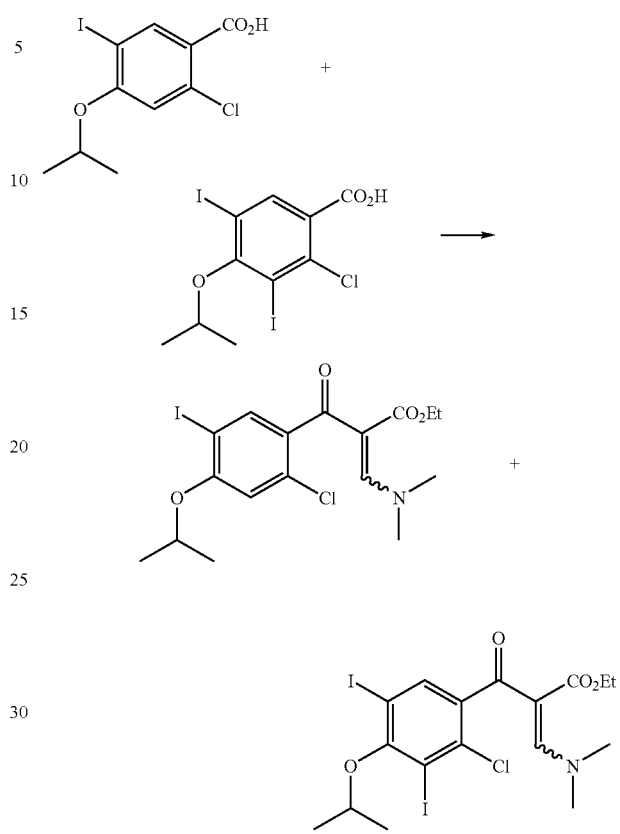

The mixture (3.40 g) obtained in Step 3 was dissolved in toluene (35 ml) and thionyl chloride (3.40 ml, 46.61 mmol) and dimethylformamide (catalytic amount) were added. The mixture was heated under reflux for 1.5 hrs. The reaction solution was concentrated under reduced pressure and tetrahydrofuran (25 ml) was added to dissolve the residue. The obtained solution was added dropwise to a solution of ethyl 3,3-dimethylaminoacrylate (4.29 g, 30.00 mmol) and triethylamine (4.17 ml, 30.00 mmol) in tetrahydrofuran (10 ml) and the mixture was heated under reflux for 14 hrs. After allowing the mixture to cool, water and ethyl acetate were added to the reaction mixture, and the mixture was stirred and partitioned. The organic layer was washed successively with water and saturated brine, and dried over sodium sulfate. After filtration, the filtrate was concentrated under reduced pressure, and the obtained residue was purified by silica gel chromatography (ethyl acetate:hexane=1:1.5 to 1.5:1) to give an object product as a mixture (2.71 g).

Step 5

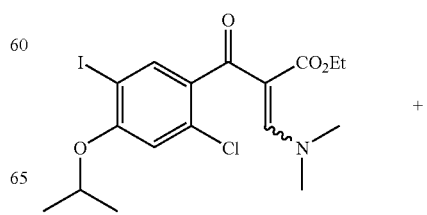

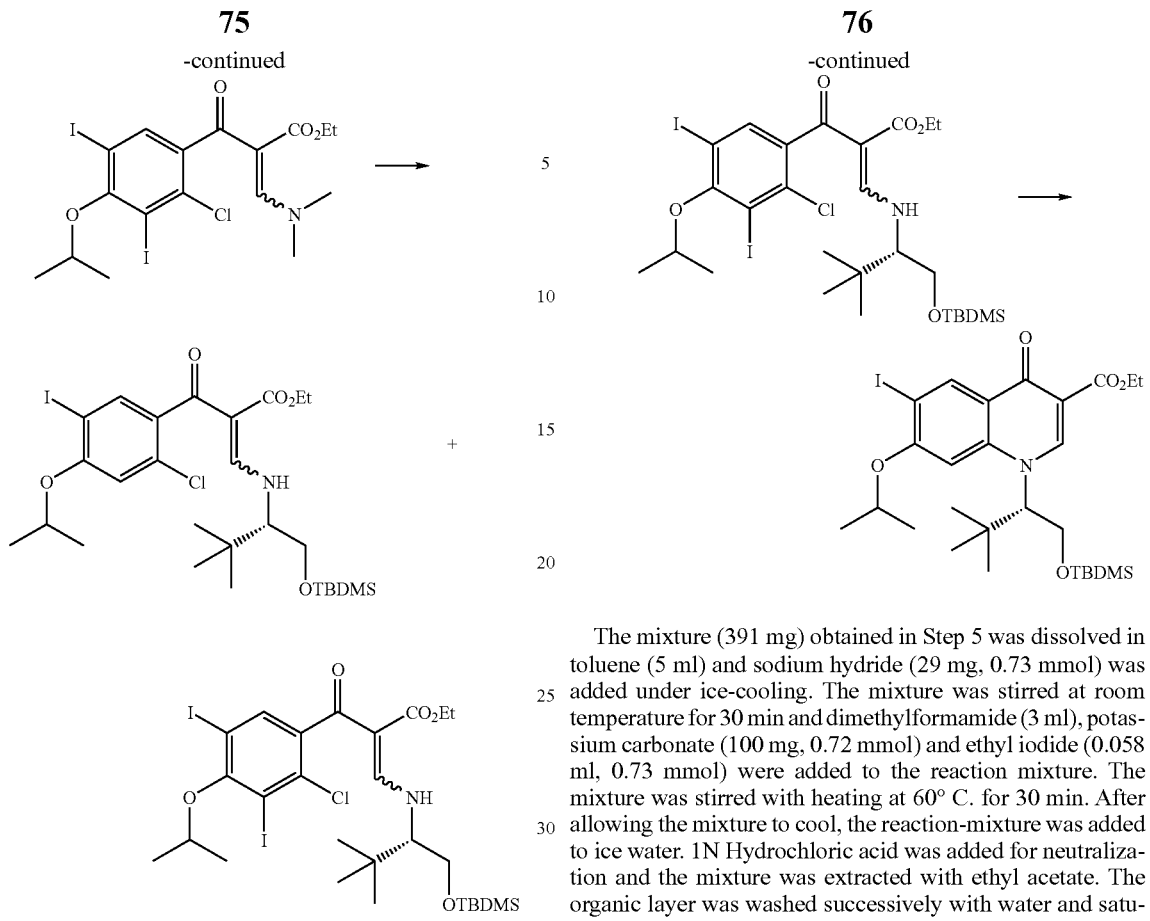

The mixture (300 mg) obtained in Step 4 was dissolved in tetrahydrofuran (2 ml), and (S)-(+)-tert leucinol (0.10 ml, 0.77 mmol) was added. The mixture was heated under reflux for 20 min. After allowing the mixture to cool, the reaction solution was concentrated under reduced pressure and the obtained residue was dissolved in dimethylformamide (4 ml). Imidazole (110 mg, 1.61 mmol) and tert-butyldimethylsilyl chloride (214 mg, 1.42 mmol) were added and the mixture was stirred at room temperature for 20 min. Water was added to the reaction solution and the mixture was extracted with ethyl acetate. The organic layer was washed successively with water and saturated brine, and dried over sodium sulfate. After filtration, the filtrate was concentrated under reduced pressure, and the obtained residue was purified by silica gel chromatography (ethyl acetate:hexane=1:4) to give an object product as a mixture (391 mg).

Step 6

The mixture (391 mg) obtained in Step 5 was dissolved in toluene (5 ml) and sodium hydride (29 mg, 0.73 mmol) was added under ice-cooling. The mixture was stirred at room temperature for 30 min and dimethylformamide (3 ml), potassium carbonate (100 mg, 0.72 mmol) and ethyl iodide (0.058 ml, 0.73 mmol) were added to the reaction mixture. The mixture was stirred with heating at 60° C. for 30 min. After allowing the mixture to cool, the reaction-mixture was added to ice water. 1N Hydrochloric acid was added for neutralization and the mixture was extracted with ethyl acetate. The organic layer was washed successively with water and saturated brine, and dried over sodium sulfate. After filtration, the filtrate was concentrated under reduced pressure and the obtained residue was purified by silica gel chromatography (ethyl acetate:hexane=4:5 to 2:1) to give an object product (258 mg, yield 19%) as a pale-white yellow solid.

$^1$H NMR(CDCl$_3$ 300 MHz) (δ) ppm: −0.09 (3H, s), 0.00 (3H, s), 0.67 (9H, s), 1.05(9H, s), 1.40 (3H, t, J=7.1 Hz), 1.46 (6H, d, J=6.0 Hz), 4.09-4.20(2H, m), 4.39 (2H, q, J=7.1 Hz), 4.43-4.49 (1H, m), 4.61-4.69(1H, m), 6.87 (1H, s), 8.60 (1H, s), 8.94(1H, S)

Step 7

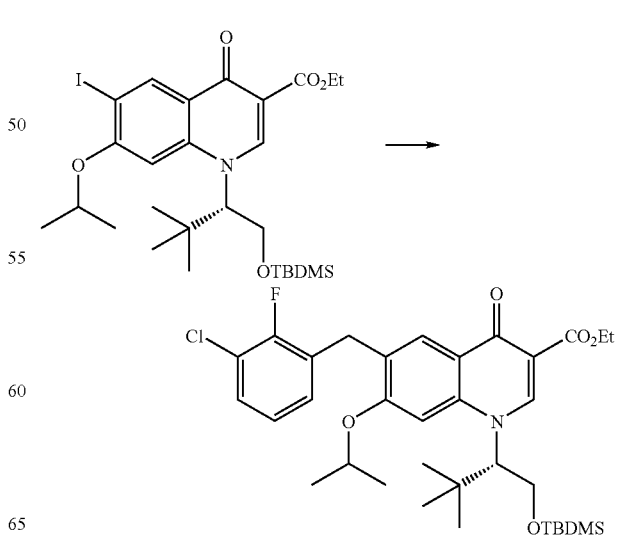

Ethyl 1,4-dihydro-1-{2,2-dimethyl-1-[(tert-butyldimethylsilyloxy)methyl]propyl}-6-iodo-7-isopropyloxy-4-oxo-3-quinolinecarboxylate (258 mg, 0.42 mmol) obtained in Step 6 was dissolved in tetrahydrofuran (5 ml). Under an argon stream, bis(dibenzylideneacetone)palladium(0) (9.7 mg, 0.017 mmol) and tri(2-furyl)phosphine (7.8 mg, 0.034 mmol) were added and a solution of 3-chloro-2-fluorobenzylzinc bromide (0.63 mmol) in tetrahydrofuran prepared as mentioned above was added dropwise at 60° C. After completion of the addition, the mixture was heated under reflux for 1 hr. After allowing the mixture to cool, saturated aqueous ammonium chloride solution was added to the reaction solution and the mixture was stirred and filtered through Celite. Water was added to the filtrate and the mixture was extracted with ethyl acetate. The organic layer was washed successively with water and saturated brine, and dried over sodium sulfate. After filtration, the filtrate was concentrated under reduced pressure and the obtained residue was crudely purified by silica gel chromatography (ethyl acetate:hexane=1:1 to 2:1) to give a crudely purified product (216 mg) as a pale-yellow oil.

Step 8

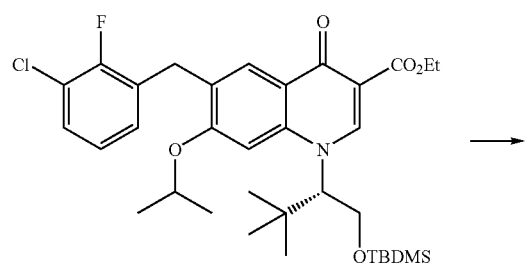

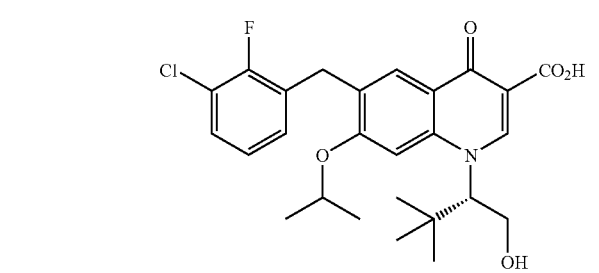

The crudely purified product (216 mg) obtained in Step 7 was dissolved in a mixture of ethanol (2 ml) and tetrahydrofuran (1 ml), and 1N aqueous sodium hydroxide solution (2.00 ml, 2.00 mmol) was added. The mixture was heated under reflux for 1 hr. After allowing the mixture to cool, 10% aqueous citric acid solution was added to the reaction solution and the mixture was stirred. The mixture was extracted with ethyl acetate. The organic layer was washed successively with water and saturated brine, and dried over sodium sulfate. After filtration, the filtrate was concentrated under reduced pressure. The residue was treated with a mixture of diethyl ether and hexane. After filtration, the solid was vacuum-dried to give an object product (140 mg, yield 68%) as a white solid.

$^1$H NMR(DMSO-$d_6$ 300 MHz) (δ) ppm: 0.97 (9H, s), 1.18 (3H, d, J=5.9 Hz), 1.26 (3H, d, J=6.0 Hz), 4.04-4.09 (4H, m), 5.09-5.13 (3H, m), 7.12-7.21 (2H, m), 7.43-7.51 (2H, m), 8.19 (1H, s), 8.78 (1H, s), 15.46 (1H, s) MS(ESI): M+ 490

EXAMPLE 4-32

Step 1

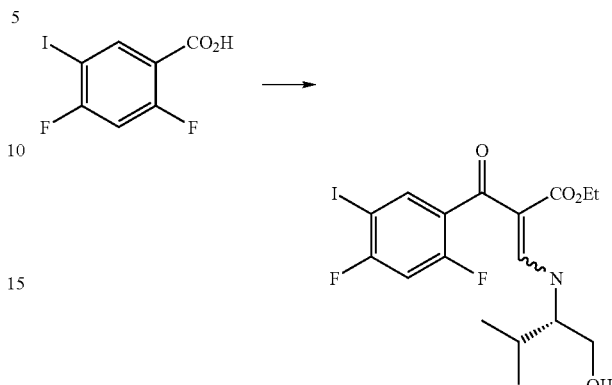

2,4-Difluoro-5-iodobenzoic acid (650.57 g, 2.29 mol) was dissolved in toluene (1300 ml), and thionyl chloride (184 ml, 2.52 mol) and dimethylformamide (catalytic amount) were added The mixture was stirred at 90° C. for 2 hrs. After allowing the mixture to cool, the reaction solution was concentrated under reduced pressure. The residue was dissolved in toluene (330 ml) followed by concentration under reduced pressure, and repeated again. The residue was dissolved in toluene (690 ml) and the obtained solution was added dropwise to a solution of ethyl 3,3-dimethylaminoacrylate (361.52 g, 2.525 mol) and diisopropylethylamine (480 ml, 2.75 mol) in toluene (690 ml) and the mixture was stirred with heating at 90° C. for 3 hrs. After allowing the mixture to cool, (S)-(+)-valinol (260.00 g, 2.52 mol) was added to the reaction mixture and the mixture was stirred at room temperature for 1 hr. Water (2600 ml) was added to the reaction mixture and the mixture was partitioned. The aqueous layer was extracted with toluene (680 ml). The organic layers were combined, washed twice with water (2000 ml), and dried over sodium sulfate. After filtration, concentration under reduced pressure gave a crude product (1180 g) as a brown oil.

Step 2

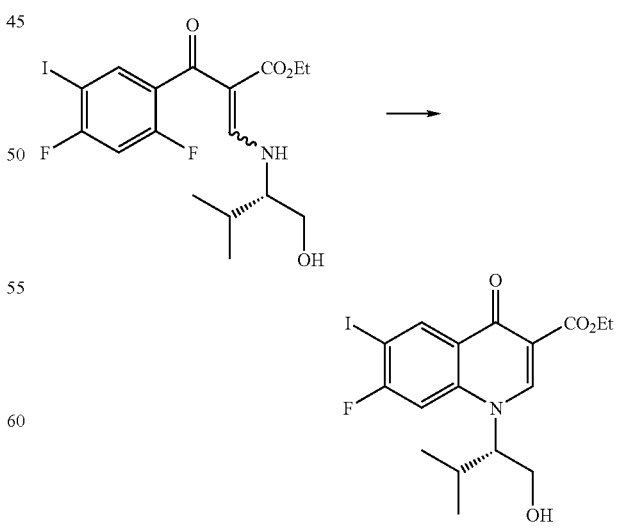

The crude product (1180 g) obtained in Step 1 was dissolved in dimethylformamide (2500 ml) and finely ground potassium carbonate (292.00 g, 1.06 mol) was added. The mixture was stirred at room temperature for 22 hrs. The reaction mixture was added to ice water (ca. 10 L) and the mixture was stirred for 30 min. The precipitate was collected by filtration and washed with water (2000 ml). The obtained solid was vacuum-dried, and suspended in ethyl acetate (5000 ml). Filtration and vacuum-drying gave an object product (774.63 g, yield 82%) as a white yellow solid.

$^1$H NMR(DMSO-d$_6$ 300 MHz) (δ) ppm: 0.72 (3H, d, J=6.6 Hz), 1.10 (3H, d, J=6.6 Hz), 1.28(3H, t, J=7.0 Hz), 2.27 (1H, br), 3.77 (1H, br), 3.86(1H, br), 4.23 (2H, q, J=7.0 Hz), 4.56(1H, br), 5.12 (1H, t, J=4.9 Hz), 8.09(1H, d, J=11.1 Hz), 8.62 (1H, d, J=7.5 Hz), 8.68(1H, s)

MS(ESI): M+ 448

Step 3

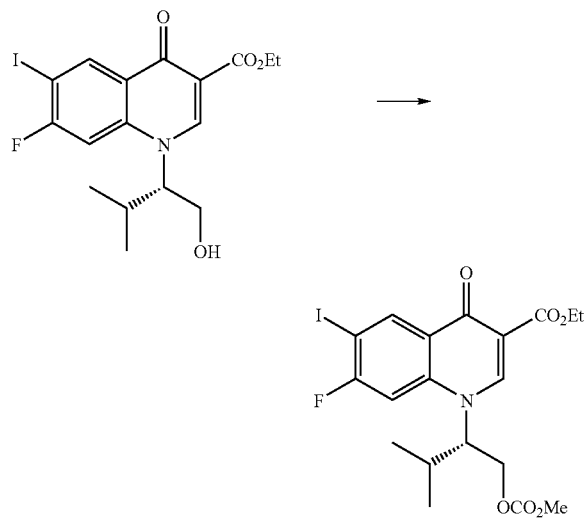

The compound (626.15 g, 1.40 mol) obtained in Step 2 was dissolved in chloroform (1250 ml), and pyridine (433 ml, 5.60 mol) and 4-(dimethylamino)pyridine (17.10 g, 0.14 mol) were added. A solution of methyl chloroformate (529.30 g, 5.60 mol) in chloroform (1250 ml) was added dropwise at 10° C. or below. After completion of the addition, the mixture was stirred at the same temperature for 30 min. The reaction mixture was washed successively with water (1250 ml), 2N hydrochloric acid (1250 ml), water (630 ml) and saturated aqueous sodium hydrogen carbonate (630 ml), and dried over sodium sulfate. After filtration, the residue was concentrated under reduced pressure to give a crude object substance (834.02 g) as a brown oil.

Step 4

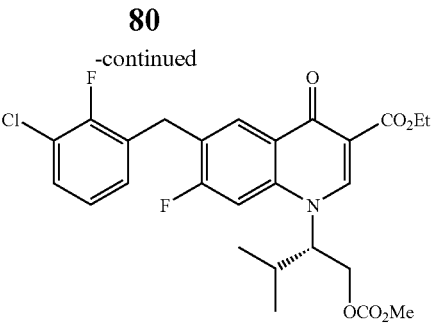

Preparation of 3-chloro-2-fluorobenzylzinc bromide tetrahydrofuran solution

Under an argon stream, zinc powder (113.02 g, 1.73 mol) was suspended in tetrahydrofuran (350 ml), and 1,2-dibromoethane (1.207 ml, 14.00 mmol) and trimethylsilyl chloride (8.88 ml, 70.00 mmol) were added at 60° C. The mixture was stirred with heating at 30 min. A solution of 3-chloro-2-fluorobenzyl bromide (406.73 g, 1.82 mol) in tetrahydrofuran (700 ml) was added dropwise at 60° C. The mixture was stirred with heating for 1 hr to give a solution of 3-chloro-2-fluorobenzylzinc bromide.

(Main Step)

The crude product (834.02 g) obtained in Step 3 was dissolved in tetrahydrofuran (1060 ml), and dichlorobis(triphenylphosphine)palladium(II) (19.65 g, 28.00 mmol) was added under an argon stream and a solution of 3-chloro-2-fluorobenzylzinc bromide (1.82 mol) was added dropwise at 60° C. After completion of the addition, the mixture was heated under reflux for 1.5 hrs. After allowing the mixture to cool, toluene (2120 ml) and 20% aqueous ammonium chloride solution (1410 ml) were added to the reaction solution, and the mixture was stirred and partitioned. The organic layer was washed twice with 20% aqueous ammonium chloride solution (710 ml) and twice with saturated aqueous sodium hydrogen carbonate (710 ml) and dried over magnesium sulfate. After filtration, the filtrate was concentrated under reduced pressure to give a crude product (849.34 g) as a brown oil.

Step 5

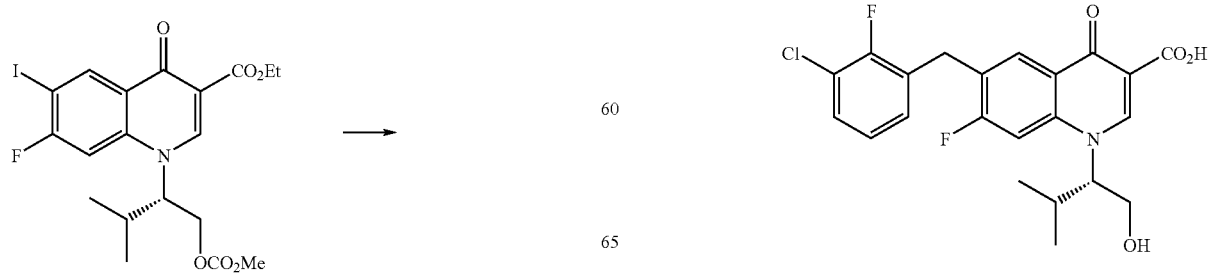

The crude product (849.34 g) obtained in Step 4 was dissolved in isopropanol (1100 ml) and 4N aqueous sodium hydroxide solution (1050 ml, 4.20 mmol) was added. The mixture was stirred with heating at 50° C. for 1.5 hrs. Activated carbon (37 g) was added to the reaction solution and the mixture was stirred at room temperature for 30 min. The mixture was filtered through Celite and 6N hydrochloric acid (740 ml) and ethyl acetate (3650 ml) were added to the filtrate. The mixture was stirred and partitioned. The organic layer was concentrated under reduced pressure and the residue was suspended in isopropanol (1070 ml). The mixture was stirred at 60° C. for 1 hr. After allowing the mixture to cool, the solid was collected by filtration. The obtained solid was washed with isopropanol (740 ml) and vacuum-dried to give an object product (446.51 g, yield 73%) as a pale-yellow solid.

$^1$H NMR(DMSO-d$_6$ 400 MHz) (δ) ppm: 0.71 (3H, d, J=6.5 Hz), 1.13 (3H, d, J=6.5 Hz), 2.36 (1H, br), 3.77(1H, br), 3.94 (1H, br), 4.25 (2H, s), 4.77(1H, br), 5.16 (1H, t, J=2.4 Hz), 7.19-7.23(1H, m), 7.32-7.35 (1H, m), 7.48-7.52 (1H, m), 8.24-8.28 (2H, m), 9.00 (1H, s), 15.00 (1H, s)

MS(ESI): M+ 436

Step 6

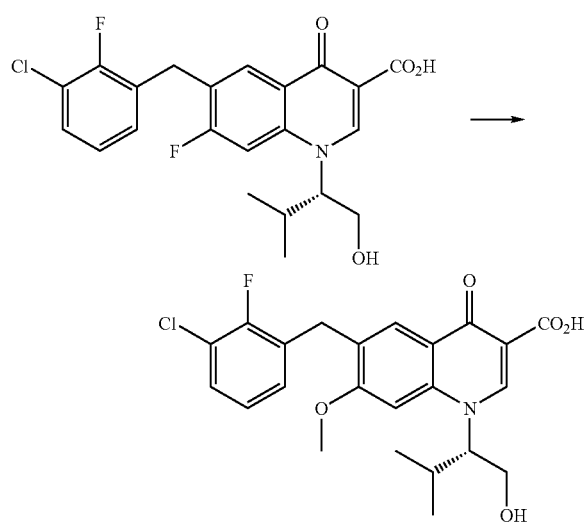

The compound (443.59 g, 1.02 mol) obtained in Step 5 was dissolved in methanol (2400 ml), and a 28% sodium methoxide in methanol (2077 ml, 10.17 mol) and water (44.30 ml, 2.46 mol) were added. The mixture was heated under reflux for 17.5 hrs. Activated carbon (22 g) was added to the reaction solution and the mixture was stirred at room temperature for 1 hr. The mixture was filtered through Celite and the filtrate was concentrated under reduced pressure. Water (1770 ml) was added to the residue and the mixture was stirred with ice-cooling for 1 hr. Then, 6N hydrochloric acid (1790 ml) was further added and the mixture was stirred at room temperature for 2 hrs. Ethyl acetate (1770 ml) was added and the mixture was stirred and partitioned. The organic layer was washed twice with 10% brine (890 ml), and dried over sodium sulfate. After filtration, the filtrate was concentrated under reduced pressure, and a part of the residue was recrystallized several times (final recrystallization solvent was methanol-water) to give an object product (28.60 g, yield 67%) as a white solid.

$^1$H NMR (DMSO-d$_6$ 400 MHz) (δ) ppm: 0.72 (3H, d, J=6.5 Hz), 1.16 (3H, d, J=6.5 Hz), 2.30-2.50 (1H, m), 3.70-3.90 (1H, m), 3.90-4.00 (1H, m), 4.03 (3H, s), 4.12 (2H, s), 4.80-4.90 (1H, m), 5.19 (1H, t, J=5.2 Hz), 7.19-7.25 (2H, m), 7.46-7.51 (2H, m), 8.04 (1H, s), 8.88 (1H, s), 15.44 (1H, s)

MS (ESI): M+ 448

EXAMPLE 4-33

Step 1

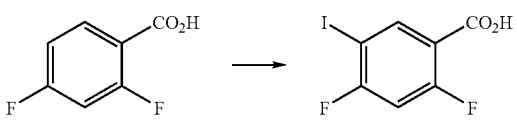

2,4-Difluorobenzoic acid (600.00 g, 3.80 mol) was dissolved in conc. sulfuric acid (2400 ml) and N-iodosuccinimide (854.40 g, 3.60 mol) was added by portions at 5° C. or below. After completion of the addition, the mixture was stirred at the same temperature for 3 hrs. The reaction mixture was poured into ice water (ca. 10 L) and 10% aqueous sodium sulfite solution (40 ml) was added. The mixture was stirred for 30 min. The precipitate was collected by filtration. To be suspended in water (ca. 3 L) and filtration were repeated until the filtrate became not less than pH 3. The obtained wet solid (1677 g) were recrystallized from 50% aqueous ethanol (3000 ml) to give an object product (824.70 g, yield 76%) as a white solid.

$^1$H NMR(CDCl$_3$ 300 MHz) (δ) ppm: 6.94 (1H, dd, J=10.3, 10.3 Hz), 8.46 (1H, d, J=7.5 Hz)

Step 2

The compound (150.00 g, 0.53 mol) obtained in Step 1 was dissolved in ethyl acetate (750 ml), and oxalyl chloride (51.0 ml, 0.581 mol) and dimethylformamide (catalytic amount) were added. The mixture was stirred at room temperature for 3.5 hrs. After filtering the reaction solution, the filtrate was concentrated under reduced pressure. After the residue was dissolved in toluene (150 ml), the mixture was concentrated under reduced pressure, and repeated again. Tetrahydrofuran (300 ml) was added to dissolve the residue, and the obtained solution was added dropwise to a solution of ethyl 3,3-dimethylaminoacrylate (83.2 g, 0.581 mol) and triethylamine (96 ml, 0.686 mol) in tetrahydrofuran (450 ml). The mixture was heated under reflux for 15 hrs. After allowing the mixture to cool, the reaction mixture was filtered, and the filtrate was concentrated under reduced pressure. Ethyl acetate (750 ml) was added-to dissolve the residue. The mixture was washed successively with aqueous ammonium chloride (400 ml), saturated aqueous sodium hydrogen carbonate (200 ml) and saturated brine, and dried over sodium sulfate. After filtration, the filtrate was concentrated under reduced pressure to give a crude object substance (206.50 g) as a brown oil.

Step 3

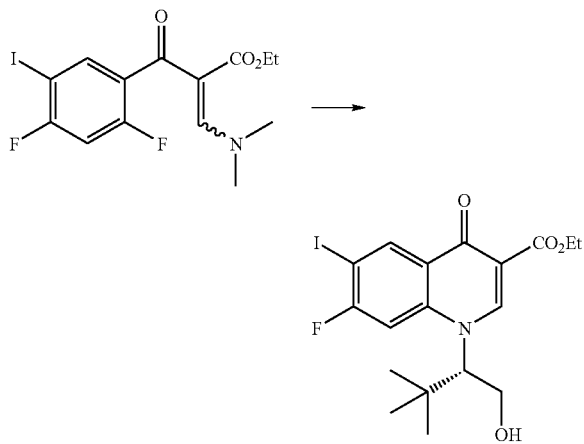

The crude product (206.50 g) obtained in Step 2 was dissolved in tetrahydrofuran (800 ml), and (S)-(+)-tert-leucinol hydrochloride (81.10 g, 0.53 mol) and triethylamine (74 ml, 0. 53 mol) were added. The mixture was stirred at room temperature for 50 min. After filtration of the reaction mixture, the filtrate was concentrated under reduced pressure and the obtained residue was dissolved in dimethylformamide (1000 ml). Potassium carbonate (146.0 g, 1.06 mol) was added and the mixture was stirred with heating at 90° C. for 3 hrs. With ice-cooling, water (700 ml) was added to the reaction mixture and the precipitate was collected by filtration and washed with water. The solid collected by filtration was suspended in 30% aqueous ethanol (1000 ml) and collected by filtration. This operation was repeated with a mixture of hexane:diethyl ether=1:1. After filtration, the filtrate was vacuum-dried to give an object product (184.74 g, yield 76%) as a white solid.

$^1$H NMR(DMSO-d$_6$ 400 MHz) (δ) ppm: 0.968(9H, s), 1.27 (3H, t), 3.96-3.98 (2H, m), 4.18-4.27 (2H, m), 4.80 (1H, t, J=7.0 Hz), 5.05 (1H, br), 8.22(1H, d, J=11.2 Hz), 8.60 (1H, s), 8.61 (1H. d, J=7.2 Hz)

Step 4

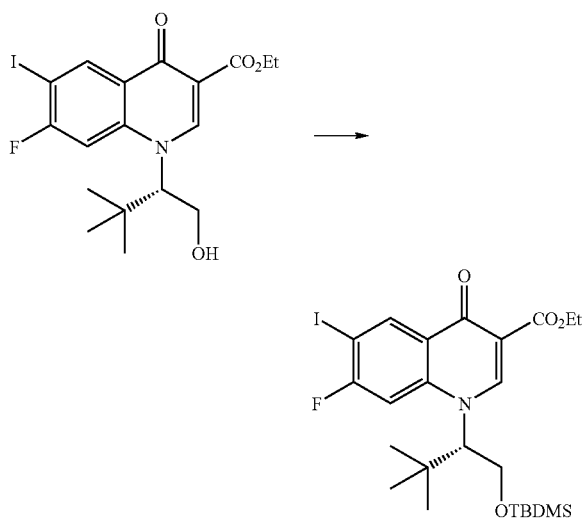

The compound (150.00 g, 0.33 mol) obtained in Step 3 was dissolved in dimethylformamide (600 ml), and imidazole (28.80 g; 0.42 mol) and tert-butyldimethylsilyl chloride (28.80 g, 0.42 mol) were added. The mixture was stirred at room temperature for 6 hrs. Water (1200 ml) was added to the reaction mixture and the mixture was extracted with ethyl acetate (800 ml). The organic layer was washed 3 times with water, and then with saturated brine and dried over sodium sulfate. After filtration, the filtrate was concentrated under reduced pressure and the obtained residue was purified by silica gel chromatography (ethyl acetate:hexane=1:3 to 1:2) to give an object product (164.30 g, yield 88%) as a white amorphous form.

$^1$H NMR(CDCl$_3$ 300 MHz) (δ) ppm: −0.08 (3H, s), 0.00 (3H, s), 0.67(9H, s), 1.06(9H,s), 1.41(3H, t, J=7.1 Hz), 4.05-4.18(2H, m), 4.36-4.43 (3H, m), 7.32(1H, d, J=10.3 Hz), 8.65 (1H, s), 8.95(1H, d, J=7.4 Hz)

Step 5

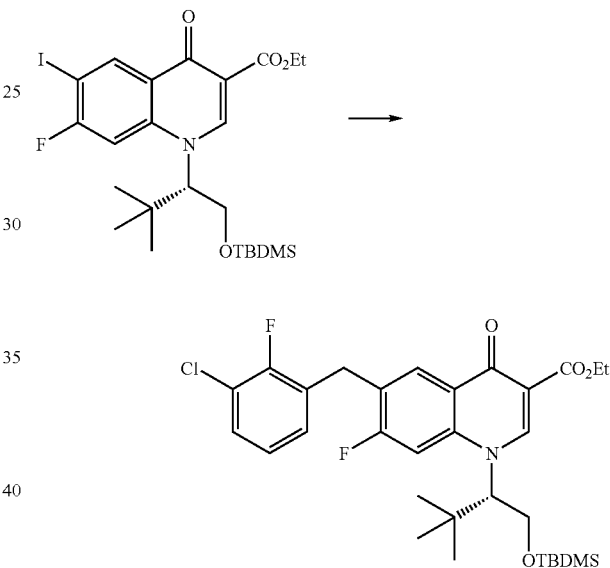

The compound (75.0 g, 0.13 mol) obtained in Step 4 was dissolved in tetrahydrofuran (580 ml). Under an argon stream, bis(dibenzylideneacetone)palladium(0) (2.99 g, 5.20 mmol) and tri(2-furyl)phosphine (2.41 g, 10.38 mmol) were added, and a solution of 3-chloro-2-fluorobenzylzinc bromide (0.1.7 mol) in tetrahydrofuran was added dropwise at 60° C. After completion of the addition, the mixture was heated under reflux for 2 hrs. After allowing the mixture to cool, ethyl acetate (75 ml) and saturated aqueous ammonium chloride solution (38 ml) were added to the reaction solution. The mixture was stirred at room temperature for 30 min. and partitioned. The organic layer was washed twice with water (75 ml) and then with saturated brine (200 ml), and dried over sodium sulfate. After filtration, the filtrate was concentrated under reduced pressure and the obtained residue was purified by silica gel chromatography (ethyl acetate:hexane=1:2 to 11:1) to give an object product (66.80 g, yield 73%) as a brown amorphous form.

$^1$H NMR(CDCl$_3$ 300 MHz) (δ) ppm: −0.10 (3H, s), −0.01 (3H, s), 0.64 (9H, s), 1.06 (9H, s), 1.40 (3H, t, J=7.1 Hz), 4.04-4.15 (4H, m), 4.35-4.46(3H, m), 6.95-7.03(2H, m), 7.24-7.31 (2H, m), 8.38 (1H, d, J=8.8 Hz), 8.66(1H, s)

Step 6

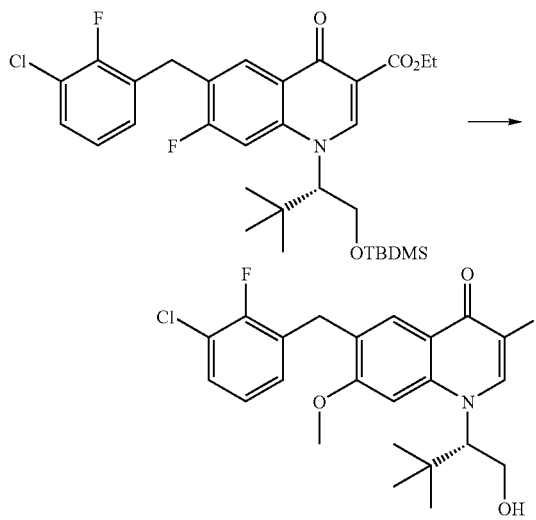

The compound (2.41 g, 4.07 mmol) obtained in Step 5 was dissolved in methanol (20 ml), and 28% sodium methoxide in methanol (8.4 ml, 40.70 mmol). and water (0.15 ml, 8.14 mmol) were added. The mixture was heated under reflux for 18 hrs. Water (1.4 ml) was added to the reaction solution and the mixture was stirred at room temperature for 1.5 hrs and filtered with Celite. The filtrate was concentrated under reduced pressure, and water (2.5 ml) and 2N hydrochloric acid (20 ml) were added to the residue. The mixture was stirred for 5 min and extracted with ethyl acetate. The organic layer was washed with water and saturated brine, and dried over sodium sulfate. After the filtration, the filtrate was concentrated under reduced pressure. The residue was sonicated with hexane (20 ml) and, after standing still, hexane was removed by decantation. This was repeated three times. Diethyl ether (30 ml) was added to the residue and the mixture was sonicated. The solid was collected by filtration and the obtained solid was dissolved by heating in ethyl acetate (15 ml). Hexane (15 ml) was added and recrystallization gave an object product (1.21 g, yield 64%) as a white solid.

$^1$H NMR(DMSO-d$_6$ 300 MHz) (δ) ppm: 0.99 (9H, s), 3.99-4.11 (7H, m), 5.11-5.20 (2H, m), 7.19-7.25 (2H, m), 7.49-7.52 (2H, m), 8.03 (1H, s), 8.78(1H, s), 15.39(1H, s)

MS(ESI): M+ 462

EXAMPLE 4-37

Step 1

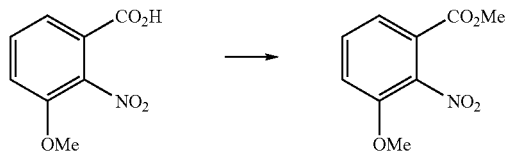

3-Methoxy-2-nitrobenzoic acid (20.00 g, 0.10 mol) was dissolved in dimethylformamide (100 ml), and potassium carbonate (28.10 g, 0.20 mol) and methyl iodide (7.60 ml, 0.12 mol) were added. The mixture was stirred at room temperature for 1 hr. The reaction mixture was added to water (300 ml) and the mixture was stirred. The precipitate was collected by filtration, washed with water (200 ml) and vacuum-dried to give a crude object substance (23.90 g) as a white solid.

Step 2

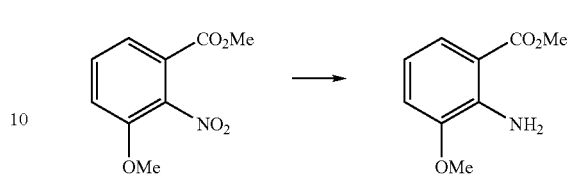

The crude product (23.90 g) obtained in Step 1 was suspended in a mixture of tetrahydrofuran (150 ml) and methanol (50 ml), and 5% palladium-carbon (wet)(2.30 g) was added. The mixture was -stirred under a hydrogen atmosphere at room temperature for 19.5 hrs. Ethyl acetate (200 ml) was added to the reaction mixture and the mixture was filtered with Celite. The filtrate was concentrated under reduced pressure and the water was removed azeotropically with toluene to give a crude product (18.80 g) as a brown oil.

Step 3

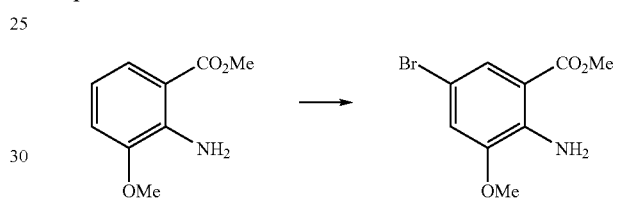

The crude product (18.80 g) obtained in Step 2 was dissolved in dimethylformamide (200 ml), and N-bromosuccinimide (17.98 g, 0.10 mol) was added by portions at 5° C. After completion of the addition, the mixture was stirred at the same temperature for 30 min. The reaction mixture was poured into water (500 ml) and extracted twice with ethyl acetate (300 ml). The organic layer was washed successively with water (300 ml), saturated aqueous sodium hydrogen carbonate and saturated brine, and dried over sodium sulfate. After filtration, the filtrate was concentrated under reduced pressure and the obtained residue was purified by silica gel chromatography (chloroform) to give an object product (25.11 g, yield 95%) as a yellow oil.

$^1$H NMR(CDCl$_3$ 300 MHz) (δ) ppm: 3.86 (6H, s), 6.02 (2H, brs), 6.90 (1H, s), 7.60 (1H, s)

Step 4

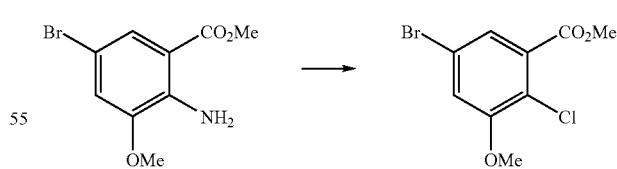

The compound (25.11 g, 96.54 mmol) obtained in Step 3 was suspended in water (50 ml) and conc. hydrochloric acid (25 ml) was added. An aqueous solution (100 ml) of sodium nitrite (7.33 g, 106.22 mmol) was added dropwise at 5° C. After completion of the addition, the mixture was stirred at the s same temperature for 5 min. This reaction solution was added dropwise to a solution of copper (I) chloride (9.55 g, 96.47 mmol) in conc. hydrochloric acid (75 ml) at room temperature. After completion of the addition, the mixture was stirred at room temperature for 13 hrs. Water (200 ml) was added to the reaction solution and the mixture was extracted with ethyl acetate (400 ml). The organic layer was washed successively with water (400 ml) and saturated brine, and dried over sodium sulfate. After filtration, the filtrate was concentrated under reduced pressure to give an object product (15.18 g, yield 56%) as an orange solid.

$^1$H NMR(CDCl$_3$ 300 MHz) (δ) ppm: 3.92 (3H, s), 3.93 (3H, s), 7.16 (1H, d, J=2.1 Hz), 7.49 (1H, d, J=2.2 Hz)

Step 5

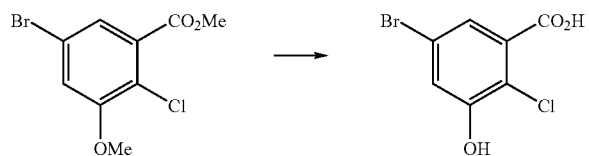

The compound (74.80 g, 0.27 mol) obtained in Step 4 was dissolved in dichloromethane (300 ml) and 1M boran tribromide/dichloromethane solution (700 ml, 0.70 mol) was added dropwise at 10° C. or below. After completion of the addition, the mixture was stirred at room temperature for 1.5 hrs. The reaction mixture was added to ice water (1500 ml) and the precipitated solid was collected by filtration. The filtrate was partitioned, and the aqueous layer was extracted with ethyl acetate (200 ml). The organic layers were combined and concentrated under reduced pressure. The solid collected by filtration and the residue were dissolved in diethyl ether (1000 ml) and 1N aqueous sodium hydroxide solution (1000 ml) was added for extraction. 2N Hydrochloric acid (500 ml) was added to the aqueous layer. The mixture was stirred and extracted with ethyl acetate (800 ml). The mixture was partitioned and the organic layer was washed successively with water and saturated brine, dried over sodium sulfate, filtered, and concentrated under reduced pressure to give an object product (63.83 g, yield 95%) as a beige solid.

$^1$H NMR(DMSO-d$_6$ 300 MHz) (δ) ppm: 7.23(1H, d, J=2.4 Hz), 7.28 (1H, d, J=2.4 Hz), 10.99(1H, s), 13.55 (1H, brs)

Step 6

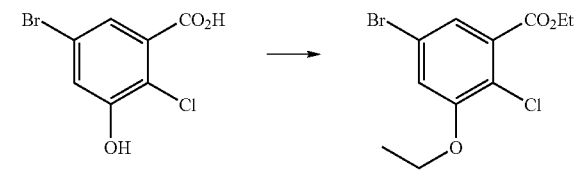

The compound (63.83 g, 0.25 mol) obtained in Step 5 was dissolved in dimethylformamide (400 ml), and potassium carbonate (87.70 g, 0.64 mol) and ethyl iodide (81.20 ml, 1.02 mol) were added. The mixture was stirred with heating at 50° C. for 3 hrs, and saturated aqueous ammonium chloride (600 ml) and ethyl acetate (400 ml) were added to the reaction-mixture. The mixture was partitioned and the aqueous layer was extracted with ethyl acetate (400 ml). The organic layers were. combined and washed successively with brine (3 times) and saturated brine, dried over sodium sulfate, filtered, and concentrated under reduced pressure to give an object product (76.38 g, yield 98%) as a brown solid.

$^1$H NMR(CDCl$_3$ 400 MHz) (δ) ppm: 1.39 (3H, t, J=7.2 Hz), 1.48 (3H, t), 4.11(2H, q), 4.38 (2H, q, J=7.2 Hz), 7.12 (1H, d, J=2.0 Hz), 7.42 (1H, d, J=2.0 Hz)

Step 7

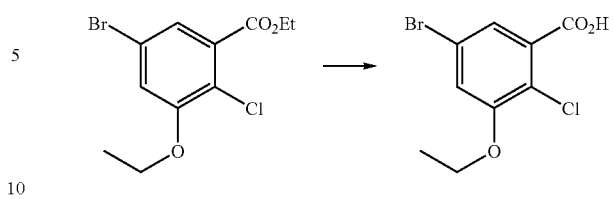

The compound (76.38 g, 0.25 mol) obtained in Step 6 was dissolved in ethanol (250 ml), and 8N aqueous sodium hydroxide-solution (62.00 ml, 0.50 mol) was added. The mixture was stirred with heating at 50° C. for 30 min. 2N Hydrochloric acid (250 ml) was added to the reaction solution with ice-cooling and the mixture was stirred, and extracted twice with ethyl acetate (350 ml). The organic layer was washed successively with water and saturated brine, and dried over sodium sulfate. After filtration, the filtrate was concentrated under reduced pressure to give an object product (68.79 g yield 99%) as a pale-brown solid.

$^1$H NMR(CDCl$_3$ 400 MHz) (δ) ppm: 1.50 (3H, t, J=-6.8 Hz), 4.12 (2H, q, J=6.8 Hz), 7.19 (1H, d, J=2.4 Hz), 7.65(1H, d, J=2.4 Hz)

Step 8

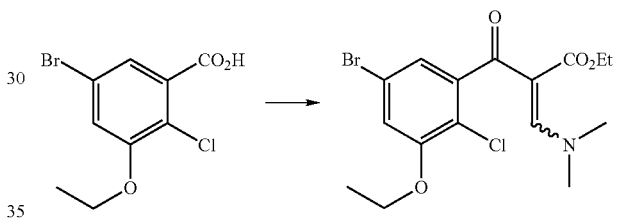

The compound (85.17 g, 0.31 mol) obtained in Step 7 was dissolved in toluene (450 ml), and thionyl chloride(44.40 ml, 0.61 mol) and dimethylformamide (catalytic amount) were added. The mixture was stirred at 90° C. for 1 hr. After allowing the mixture to cool, the reaction solution was concentrated under reduced pressure. After the residue was dissolved in toluene, the mixture was concentrated under reduced pressure. This was repeated two more times. The residue was dissolved in tetrahydrofuran (250 ml) and the obtained solution was added dropwise to a solution of ethyl 3,3-dimethylaminoacrylate (43.60 g, 0.31 mol) and triethylamine (50.90 ml, 0.37 mol) in tetrahydrofuran (200 ml). The mixture was heated under reflux for 15 hrs. After allowing the mixture to cool, water (300 ml) and ethyl acetate (500 ml) were added to the reaction mixture. The mixture was stirred and partitioned. The organic layer was washed successively with water (300 ml) and saturated brine, and dried over sodium sulfate. After filtration, the filtrate was concentrated under reduced pressure to give a crude object substance (124.80 g) as a brown oil.

Step 9

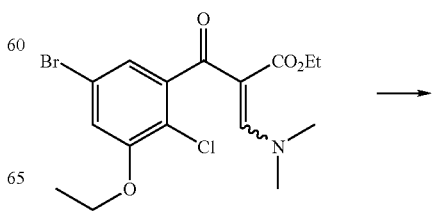

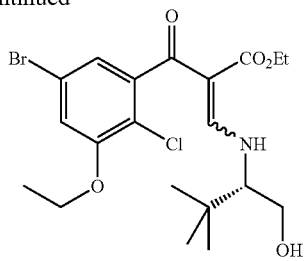

The crude product (124.80 g) obtained in Step 8 was dissolved in tetrahydrofuran (500 ml), and (S)-(+)-tert-leucinol hydrochloride (46.80 g, 0.31 mol) and triethylamine (42.50 ml, 0.31 mol) were added. The mixture was stirred at room temperature for 40 min. After filtration of the reaction mixture, the filtrate was concentrated under reduced pressure. The obtained residue was dissolved in ethyl acetate (800 ml), washed twice with water, and then with saturated brine, and dried over sodium sulfate. After the filtration, the filtrate was concentrated under reduced pressure to give a crude object substance (131.30 g) as a brown oil.

Step 10

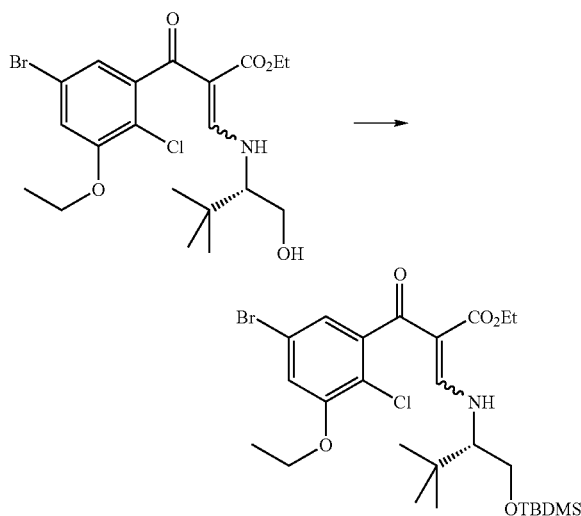

The crude product (131.30 g) obtained in Step 9 was dissolved in dimethylformamide (400 ml), and imidazole (27.00 g, 0.40 mol) and tert-butyldimethylsilyl chloride (41.30 g, 0.27 mol) were added. The mixture was stirred at room temperature for 14 hrs. Water was added to the reaction solution and the mixture was extracted twice with ethyl acetate (500 ml). The organic layer was washed three times with water and then with saturated brine, and dried over sodium sulfate. After filtration, the filtrate was concentrated under reduced pressure to give a crude-object substance.(159.80 g) as a brown oil.

Step 11

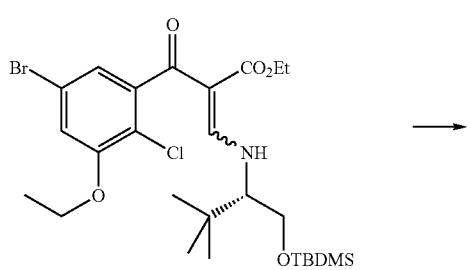

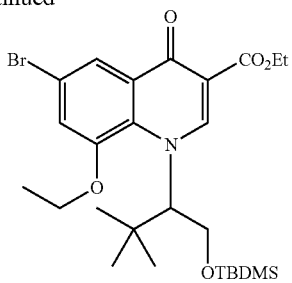

The crude product (159.80 g) obtained in Step 10 was dissolved in toluene (1100 ml), and sodium hydride (15.80 g, 0.40 mol) was added. The mixture was stirred with heating at 100° C. for 14 hrs. In Hydrochloric acid (400 ml) was added to the reaction solution under ice-cooling and the mixture was stirred and partitioned. The organic layer was washed successively with water and saturated brine, and dried over sodium sulfate. After filtration, the filtrate was concentrated under reduced pressure and the obtained residue was dissolved in dimethylformamide (500 ml). Potassium carbonate (42.10 g, 0.31 mol) and ethyl iodide (24.40 ml, 0.31 mol) was added and the mixture was stirred with heating at 50° C. for 1.5 hrs. A saturated aqueous ammonium chloride solution (400 ml) was added to the reaction solution under ice-cooling, and the mixture was stirred and extracted twice with ethyl acetate. The organic layer was washed successively with water, twice with brine and saturated brine, and dried over sodium sulfate. After filtration, the filtrate was concentrated under reduced pressure and the obtained residue was purified by silica gel chromatography (ethyl acetate:hexane=1:3 to 2:3) to give an object product (76.50 g, yield 45%) as a brown oil.

$^1$H NMR(CDCl$_3$ 400 MHz) (δ) ppm: −0.05 (3H, s), 0.01 (3H, s), 0.73 (9H, s), 0.98 (9H, s), 1.40(3H, t), 1.53-1.59 (3H, m), 4.10-4.24 (4H, m), 4.34-4.44(2H,m), 6.10-6.14(1H, m), 7.22 (1H, s), 8.32 (1H, t, J=2.4 Hz), 8.70 (1H, s)

Step 12

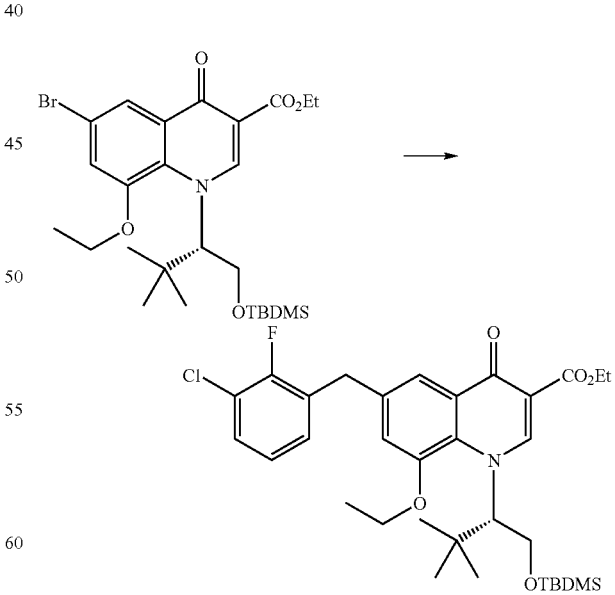

The compound (76.50 g, 0.14 mol) obtained in Step 11 was dissolved in tetrahydrofuran (500 ml), and under an argon stream, bis(dibenzylideneacetone)palladium(0) (3.17 g, 5.51 mmol) and tri(2-furyl)phosphine (2.56 g, 11.03 mmol) were added. A solution of 3-chloro-2-fluorobenzylzinc bromide (0.28 mol) in tetrahydrofuran was added dropwise at 60° C. After completion of the addition, the mixture was cheated under reflux for 2.5 hrs. After allowing the mixture to cool, saturated aqueous ammonium chloride solution (600 ml) was added to the reaction solution. The mixture was stirred at room temperature for 1 hr and filtered with Celite. After the mixture was partitioned, the aqueous layer was extracted with ethyl acetate twice. The organic layer, on the other hand, was concentrated under reduced pressure, and the residue was dissolved in ethyl acetate. All ethyl acetate layers were combined and washed successively with 1N hydrochloric acid and saturated brine, and dried over sodium sulfate. After filtration, the filtrate was concentrated under reduced pressure. The obtained residue was dissolved in dimethylformamide (400 ml) and potassium carbonate (19.00 g, 0.14 mol) and ethyl iodide (11.00 ml, 0.14 mol) were added. The mixture was stirred with heating at 50° C. for 1.5 hrs. A saturated aqueous ammonium chloride solution (400 ml) was added to the reaction mixture with ice-cooling, and the mixture was stirred and extracted with ethyl acetate (500 ml). The organic layer was washed with water, brine (twice) and saturated brine, and dried over sodium sulfate. After filtration, the filtrate was concentrated under reduced pressure and the obtained residue was purified by silica gel chromatography (ethyl acetate:hexane=1:2 to 1:1) to give an object product (72.10 g, yield 85%) as a brown oil.

$^1$H NMR(CDCl$_3$ 400 MHz) (δ) ppm: −0.07 (3H, s), 0.00 (3H, s), 0.70 (9H, s), 1.24 (9H, s), 1.39 (3H, t, J=7.2 Hz), 1.51-1.54 (3H, m), 4.05 (2H, s), 4.07-4.19 (4H, m), 4.33-4.45 (2H, m), 6.12-6.15 (1H, m), 6.99-7.02 (2H, m), 7.04-7.09 (1H, m), 7.19-7.25 (1H, m), 8.06 (1H, d, J=2.4 Hz), 8.69 (1H, s)

Step 13

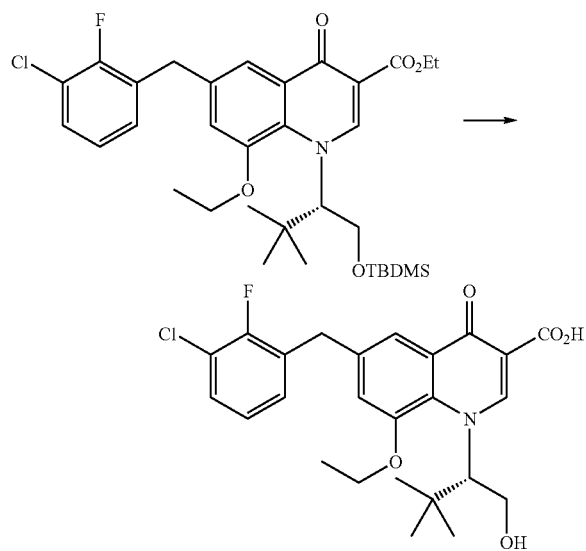

The compound (65.80 g, 0.11 mol) obtained in Step 12 was dissolved in ethanol (200 ml) and 1N aqueous sodium hydroxide solution (640 ml, 0.64 mol) was added. The mixture was heated under reflux for 2 hrs. 2N Hydrochloric acid (350 ml) was added to the reaction solution with ice-cooling and the mixture was stirred and extracted twice with ethyl acetate. The organic layer was washed successively with water and saturated brine, and dried over sodium sulfate. After filtration, the filtrate was concentrated under reduced pressure, and diethyl ether (500 ml) was added the residue. The mixture was sonicated and the obtained solid was collected by filtration. The collected solid was added to ethyl acetate (250 ml) and dissolved with heating. Hexane (50 ml) was added and the precipitated solid was collected by filtration, vacuum-dried to give an object product (41.10 g, yield 81%) as a white solid.

$^1$H NMR (DMSO-d$_6$ 400 MHz) (δ) ppm: 0.93 (9H, s), 1.49 (3H, t, J=6.9 Hz), 4.00 (2H, t, J=6.4 Hz), 4.20 (2H, s), 4.22-4.33 (2H, m), 5.12 (1H, t), 6.36 (1H, t, J=6.8 Hz), 7.21 (1H, m), 7.39-7.48 (,2H, m), 7.54 (1H, s), 7.79 (1H, s), 8.79 (1H, s), 15.04 (1H, s)

MS (ESI): M+ 476

EXAMPLES 1-3-1-102, 2-1-2-8, 3-1-3-86, 4-1-4-54

In the same manner as in Examples 1-1 and 1-2 and the above-mentioned Examples, the compounds of Examples 1-3-1-102, 2-1-2-8, 3-1-3-86 and 4-1-4-54 were obtained. The chemical structures thereof are shown in Tables 1, 2, 3 and 4.

EXPERIMENTAL EXAMPLES

The following explains evaluation methods of the HIV integrase inhibitory activity of the compound of the present invention.

(i) Construction of Recombinant Integrase Gene Expression System

The 185th phenylalanine of HIV integrase full length gene (J. Virol., 67, 425-437 (1993)) was substituted by histidine and inserted into the restriction enzyme NdeI and XhoI sites of plasmid pET21a(+) (Novagen), whereby an integrase expression vector pET21a-IN-F185H was constructed.

(ii) Production and Purification of Integrase Protein

*Escherichia coli* recombinant BL21(DE3) transformed with plasmid pET21a-IN-F185H obtained in (i) was shake cultured at 30° C. in a liquid medium containing ampicillin. When the culture reached the logarithmic growth phase, isopropyl-β-D-thiogalactopyranoside was added to promote expression of integrase gene. The culture was continued for 3 hrs to promote accumulation of the integrase protein. The recombinant *E. coli* was collected in pellets by centrifugal separation and preserved at −80° C.

The *E. coli* was suspended in Lysis buffer (20 mM HEPES (pH 7.5), 5 mM DTT, 10 mM CHAPS, 10% glycerol) containing 1M sodium chloride and subjected to repeat pressurization and depressurization for rupture, and centrifugal separation at 4° C., 40,000×g, 60 min to recover a water-soluble fraction (supernatant). This was diluted 10-fold with Lysis buffer free of sodium chloride, mixed with SP-Sepharose (Pharmacia Corporation) and stirred at 4° C. for 60 min to allow adsorption of integrase protein to the resin. The resin was washed with Lysis buffer containing 100 mM sodium chloride and the integrase protein was eluted with Lysis buffer containing 1M sodium chloride.

The eluted integrase protein solution was applied to a Superdex 75 (Pharmacia Corporation) column for gel filtration. The protein was eluted with Lysis buffer containing 1M sodium chloride.

The obtained fractions of the integrate protein were collected and preserved at −80° C.

(iii) Preparation of DNA Solution

The following DNA synthesized by Greiner was dissolved in TE buffer (10 mM Tris-hydrochloric acid (pH 8.0), 1 mM EDTA) and mixed with donor DNA, target DNA, each complementary strand (+ and − strands) to 1 μM. The mixture was heated at 95° C. for 5 min, 80° C. for 10 min, 70° C. for 10 min, 60° C. for 10 min, 50° C. for 10 min and 40° C. for 10 min and preserved at 25° C. to give a double stranded DNA, which was used for the test. Donor DNA (− strand having biotin attached to the 5' terminal)

```
Donor + strand:
5'-Biotin-ACC CTT TTA GTC AGT GTG      (SEQ ID NO: 1)
GAA AAT CTC TAG CA-3'

Donor − strand:
5'-ACT GCT AGA GAT TTT CCA CAC TGA     (SEQ ID NO: 2)
CTA AAA G-3'

Target DNA (+, − strands both having digoxigenin
added at 3' terminal)
Target + strand:
5'-TGA CCA AGG GCT AAT TCA CT-Dig-3'   (SEQ ID NO: 3)

Target − strand:
5'-AGT GAA TTA GCC CTT GGT CA-Dig-3'   (SEQ ID NO: 4)
```

(iv) Determination of Enzyme (HIV Integrase) Inhibitory activity

The donor DNA was diluted with TE buffer to 10 nM, of which 50 μl was added to each well of streptavidin-coated microtiter plate (Roche) and allowed to adsorb at 37° C. for 60 min. The DNA was washed with phosphate buffer (Dulbecco PBS, Sanko Junyaku Co., Ltd.) containing 0.1% Tween 20 and phosphate buffer. Then, a reaction mixture (70 μl) having the following composition, a test substance (10 μl) diluted with the reaction mixture and 100 μl/ml integrase protein (10 μl) were added to each well and reacted at 37° C. for 60 min.

Then, 50 nM target DNA (1.0 μl) was added, reacted at 37° C. for 10 min and washed with phosphate buffer containing 0.1% Tween 20 to stop the reaction.

Then, 100 mU/ml peroxidase labeled anti-digoxigenin antibody solution (Roche, 100 μl) was added, and the mixture was reacted at 37° C. for 60 min, followed by washing with phosphate buffer containing 0.1% Tween 20.

A peroxidase color solution (Bio Rad, 100 μl) was added and allowed to react at room temperature for 4 min. The color reaction was stopped by adding 1N sulfuric acid (100 μl). The absorbance at 450 nm was measured.

The HIV integrase inhibitory activity ($IC_{50}$) of the compound of the present invention was calculated from the inhibition rate according to the following formula. The results are shown in Tables 5, 6 and 7.

inhibition rate (%)=[1−(Object−Blank)/(Control−Blank)]×100

Object; absorbance of well in the presence of test compound
Control; absorbance of well in the absence of test compound
Blank; absorbance of well in the absence of test compound, in the absence of integrase protein.

Evaluation of Antiviral Activity

The effect of combined use of the compound of the present invention with known anti-HIV agents can be determined as shown below.

For example, the effect of two-drug use of an existing nucleoside reverse transcriptase inhibitor (Zidovudine, Lamivudine, Tenofovir), a non-nucleoside reverse transcriptase inhibitor (Efavirenz) or a protease inhibitor (Indinavir, Nelfinavir) and a test substance A, and the like are evaluated in an acute infection system using HIV-1 IIIB-infected CEM-SS cells by the XTT method.

In addition, the effect of three-drug use of test substance A, Zidovudine and Lamivudine, or test substance A, Tenofovir and Lamivudine and the like is evaluated.

Prior to the combined use test, $IC_{50}$ and $CC_{50}$ of each pharmaceutical agent alone are determined. The effect of two-drug use is evaluated based on the combination of five concentrations of pharmaceutical agent A and nine concentrations of pharmaceutical agent B, which have been determined based on the above results. For three-drug use, high concentrations of pharmaceutical agent B and pharmaceutical agent C are mixed and the obtained concentrations are combined with the concentrations of pharmaceutical agent A for evaluation.

The experimental data of the test substance and pharmaceutical agent to be combined in the case of single use and combined use are analyzed.by the programs of Prichard and Shipman MacSynergy II version 2.01 and Delta graph version 1.5d. A three dimensional plot is created at a 95% (or 68%, 99%) confidence level, from the percent inhibition at the concentration of each combined pharmaceutical agent, which is obtained from triplicate experiments, and the effect of combined use is evaluated based on the numerical values of $\mu M^2\%$ calculated therefrom. The evaluation criteria are shown in the following.

| definition of interaction | $\mu M^2$ % |
|---|---|
| highly synergistic | >100 |
| slightly synergistic | +51 to +100 |
| additive | +50 to −50 |
| slightly antagonistic | −51 to −100 |
| highly antagonistic | <−100 |

TABLE 1

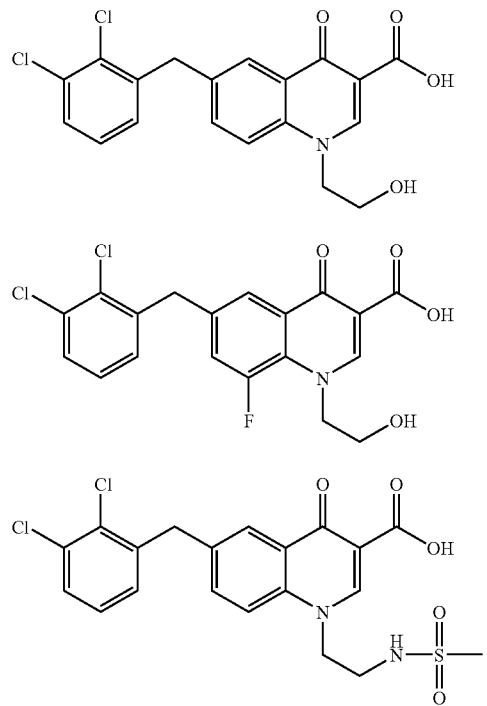

TABLE 1-continued
1-4 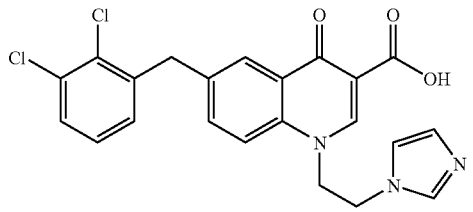
1-5 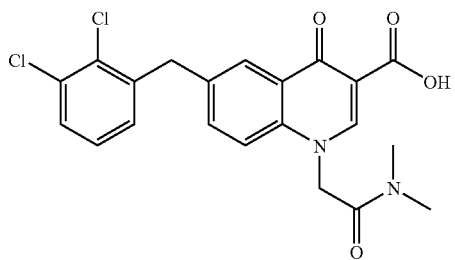
1-6 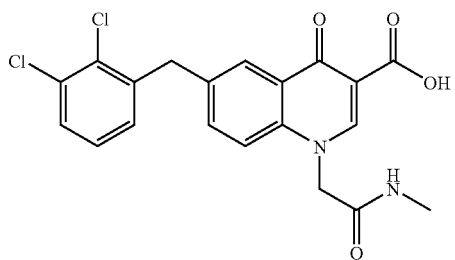
1-7 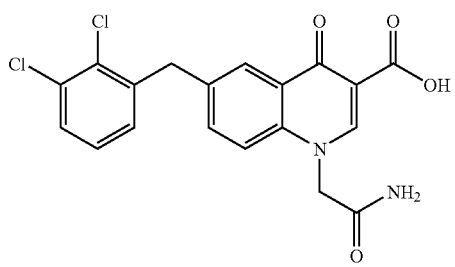
1-8 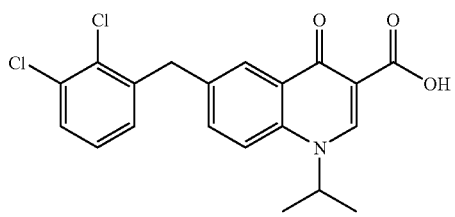
1-9 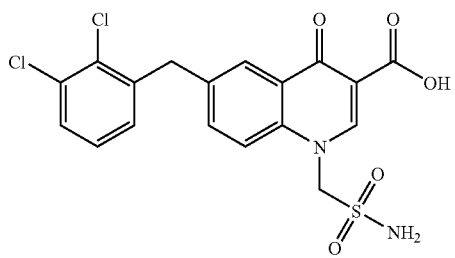
1-10 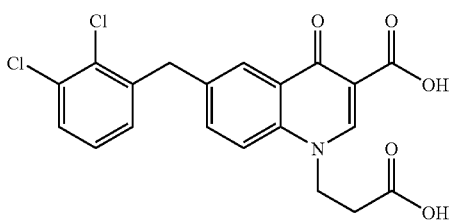
1-11 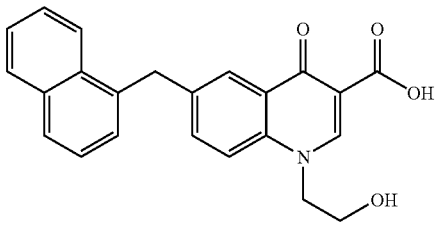
1-12 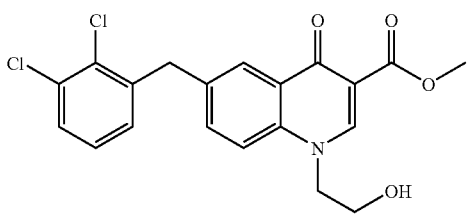
1-13 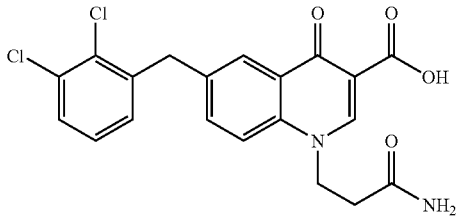
1-14 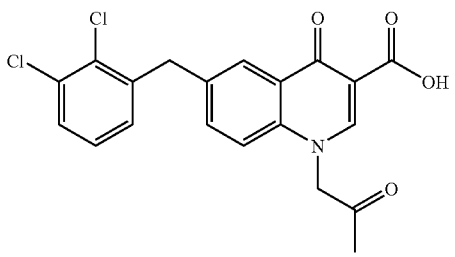
1-15 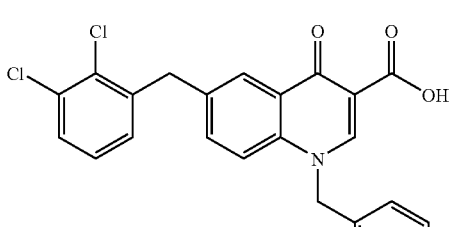

TABLE 1-continued
1-16 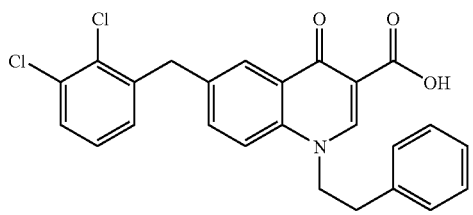
1-17 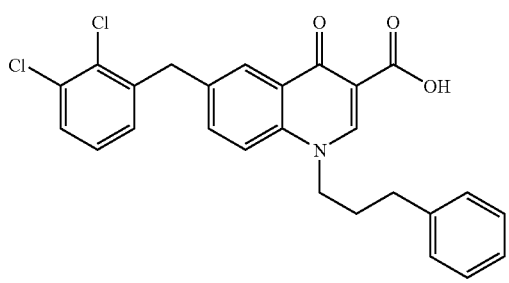
1-18 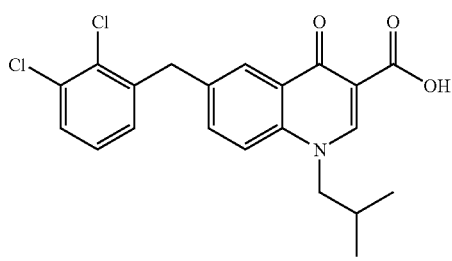
1-19 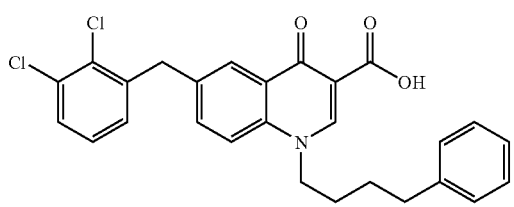
1-20 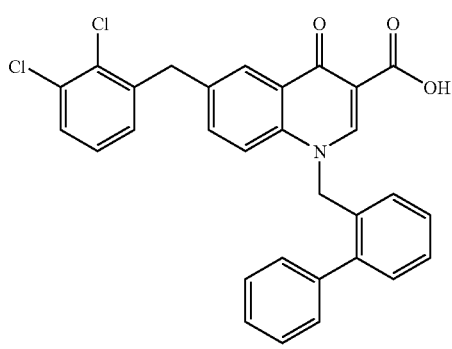
1-21 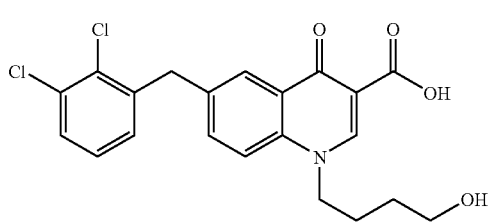
TABLE 1-continued
1-22 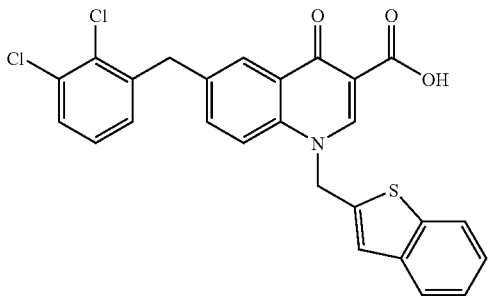
1-23 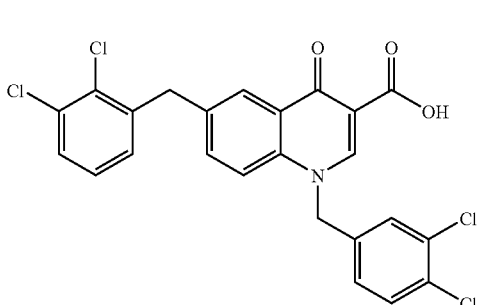
1-24 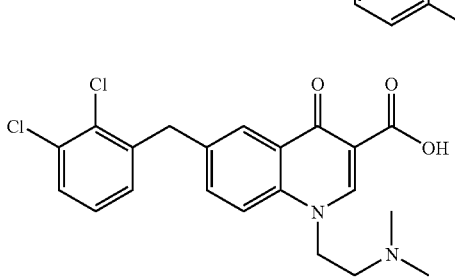
1-25 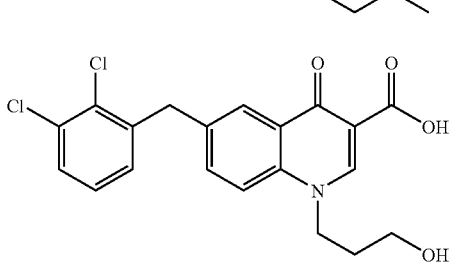
1-26 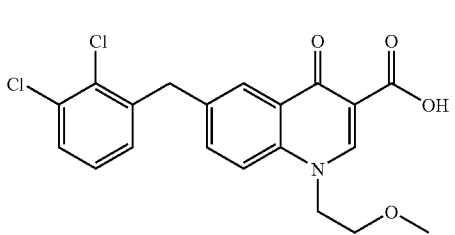
1-27 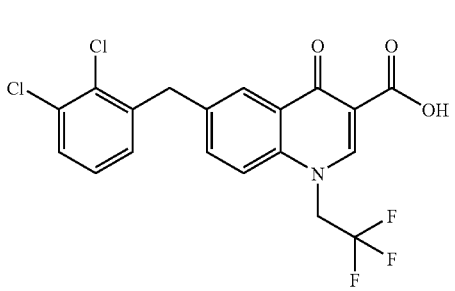

TABLE 1-continued
1-28 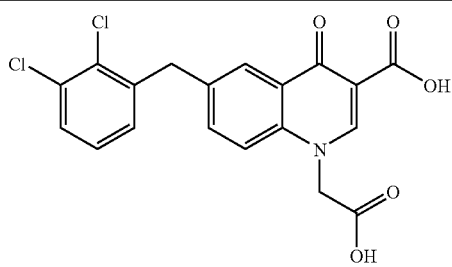
1-29 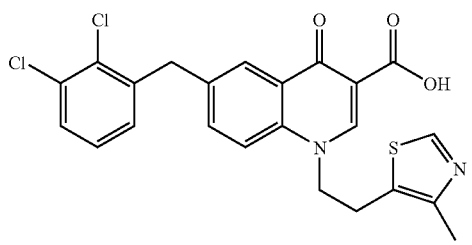
1-30 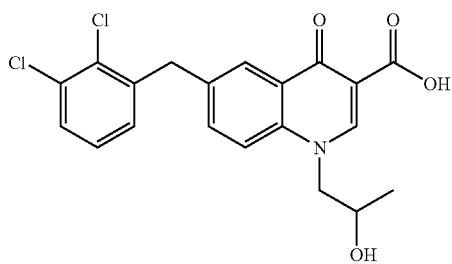
1-31 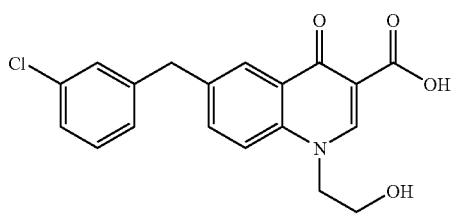
1-32 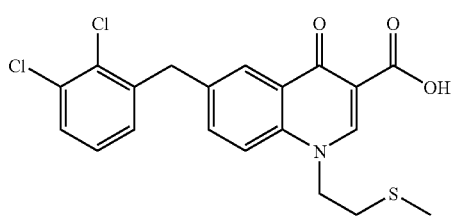
1-33 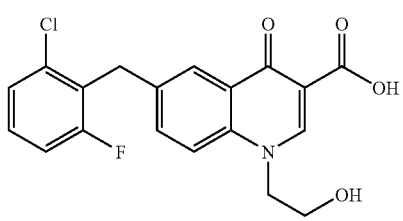
1-34 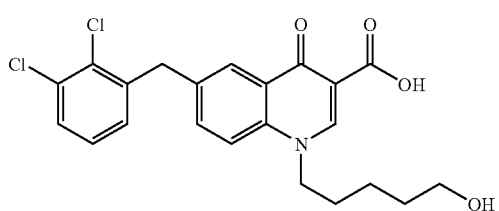
TABLE 1-continued
1-35 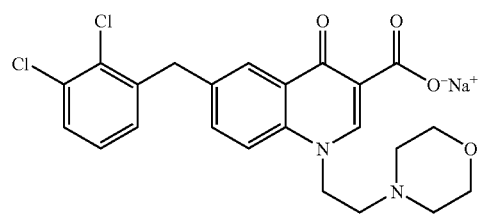
1-36 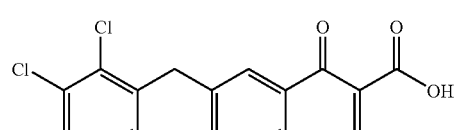
1-37 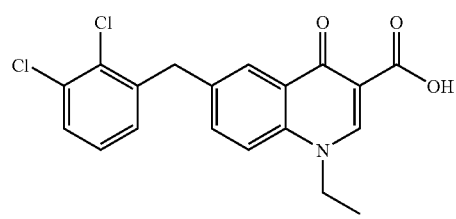
1-38 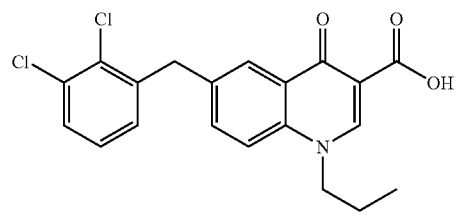
1-39 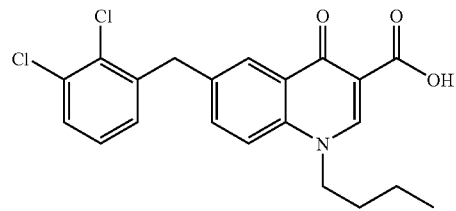
1-40 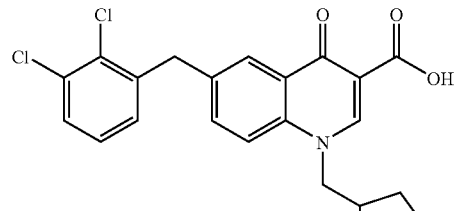
1-41 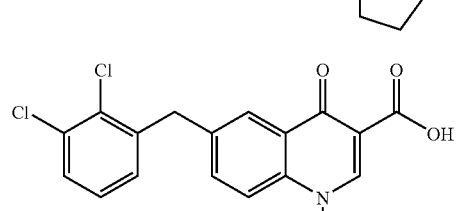

TABLE 1-continued
1-42 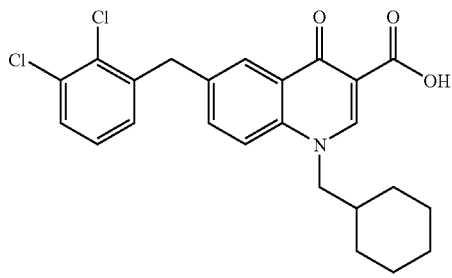
1-43 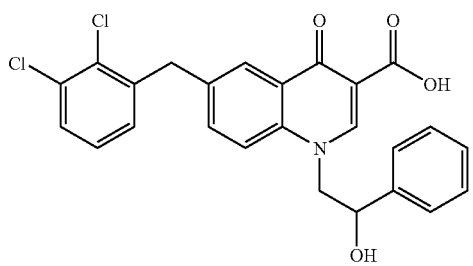
1-44 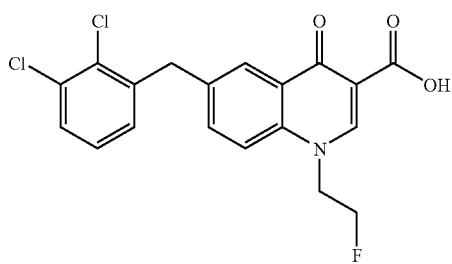
1-45 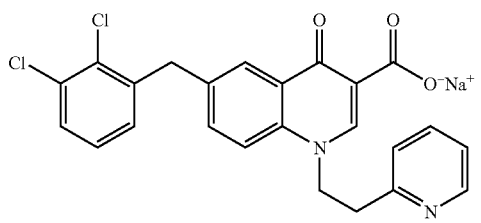
1-46 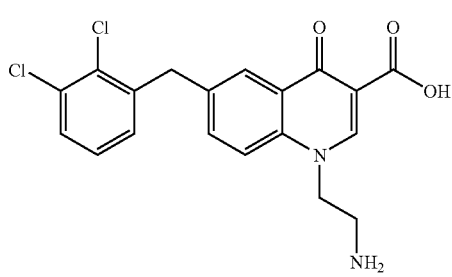
1-47 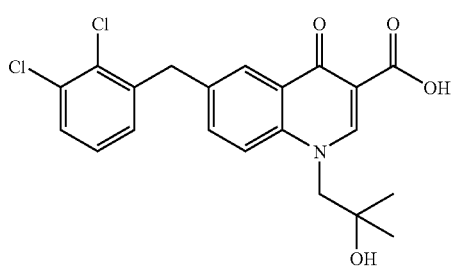
TABLE 1-continued
1-48 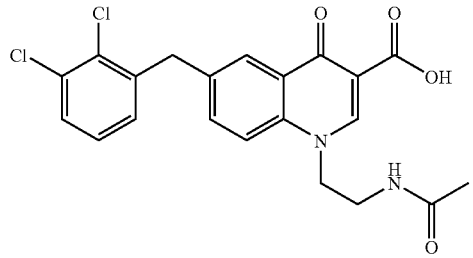
1-49 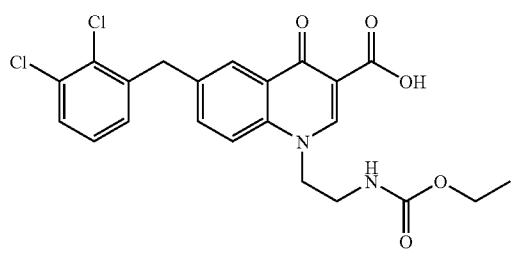
1-50 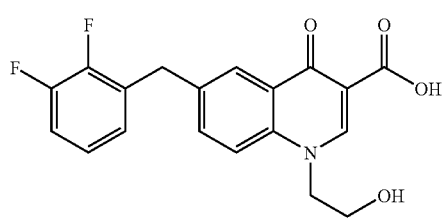
1-51 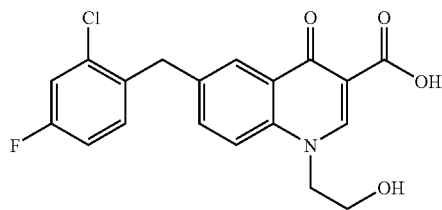
1-52 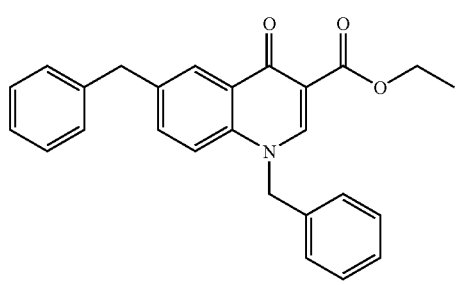
1-53 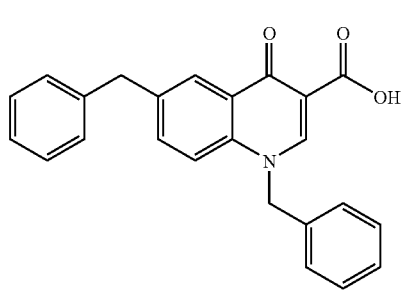

TABLE 1-continued
1-54 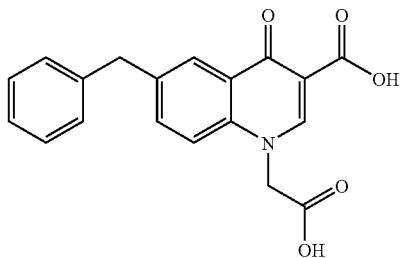
1-55 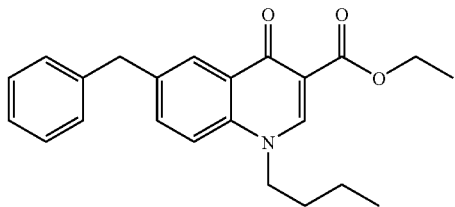
1-56 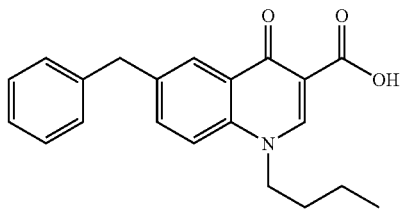
1-57 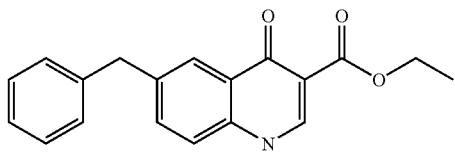
1-58 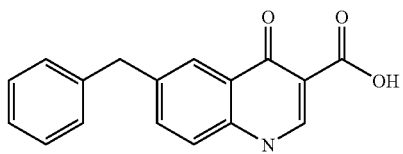
1-59 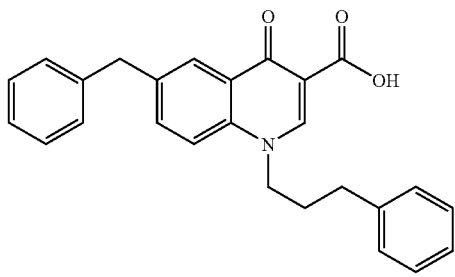
1-60 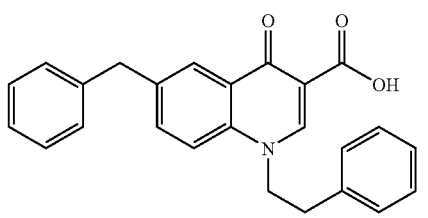
TABLE 1-continued
1-61 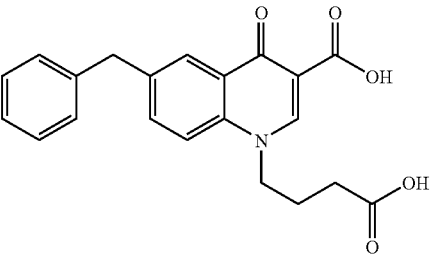
1-62 
1-63 
1-64 
1-65 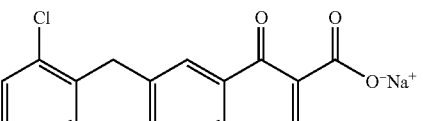
1-66 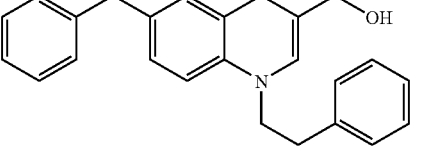
1-67 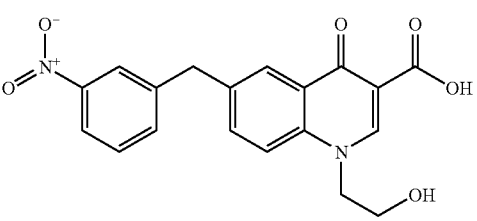

TABLE 1-continued
1-68 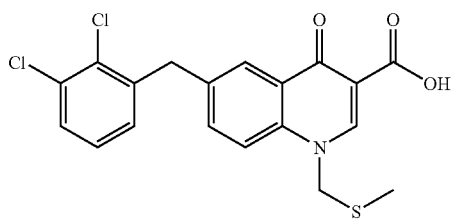
1-69 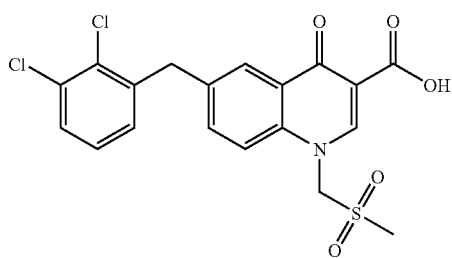
1-70 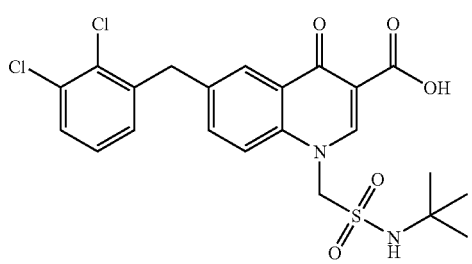
1-71 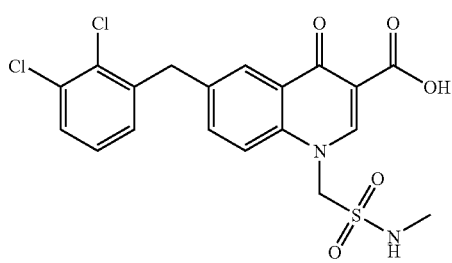
1-72 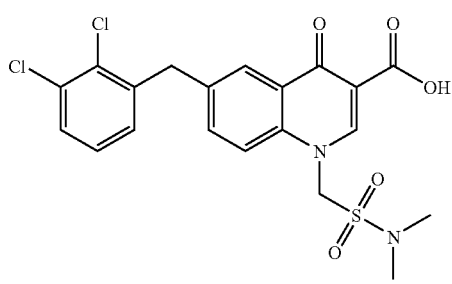
1-73 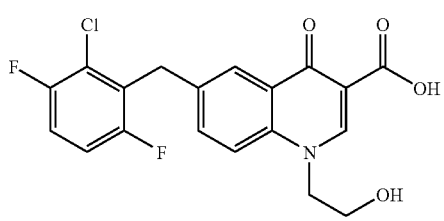
1-74 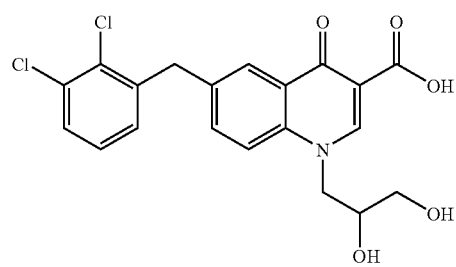
1-75 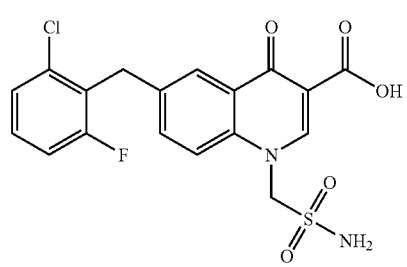
1-76 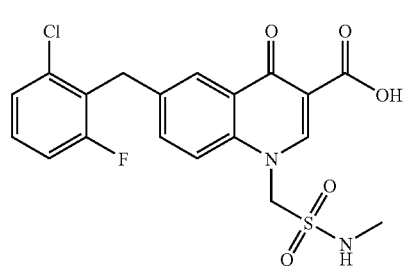
1-77 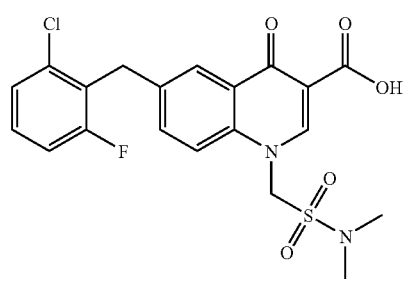
1-78 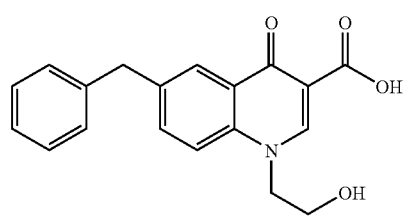
1-79 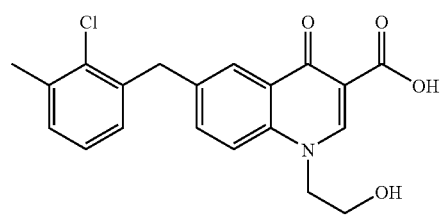

TABLE 1-continued
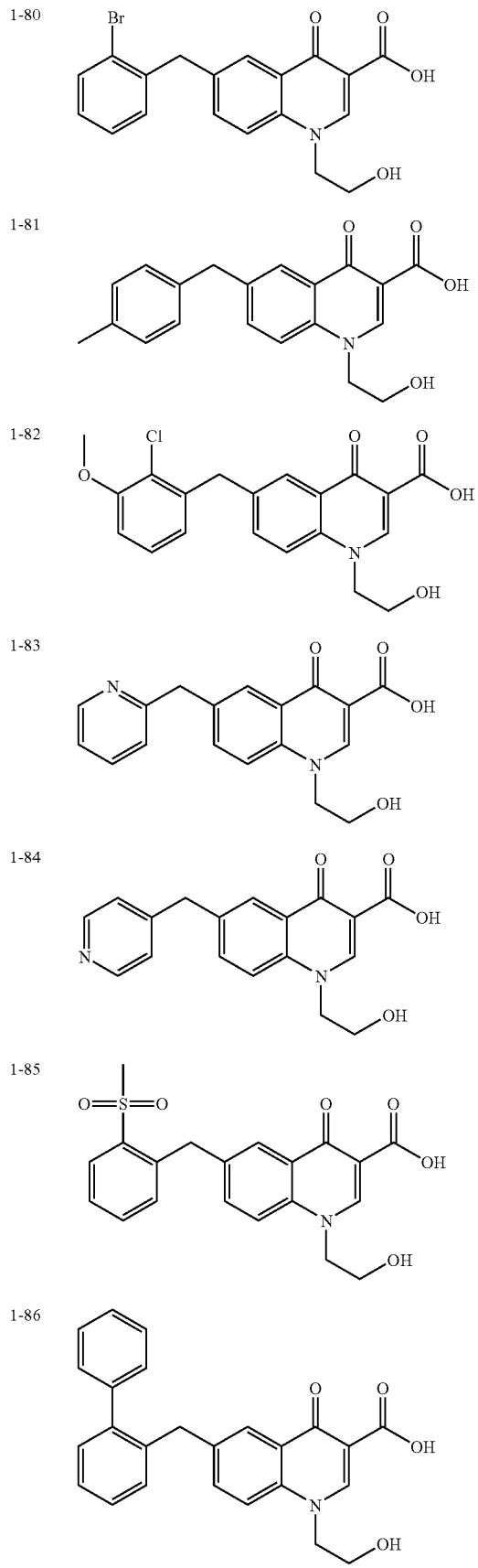
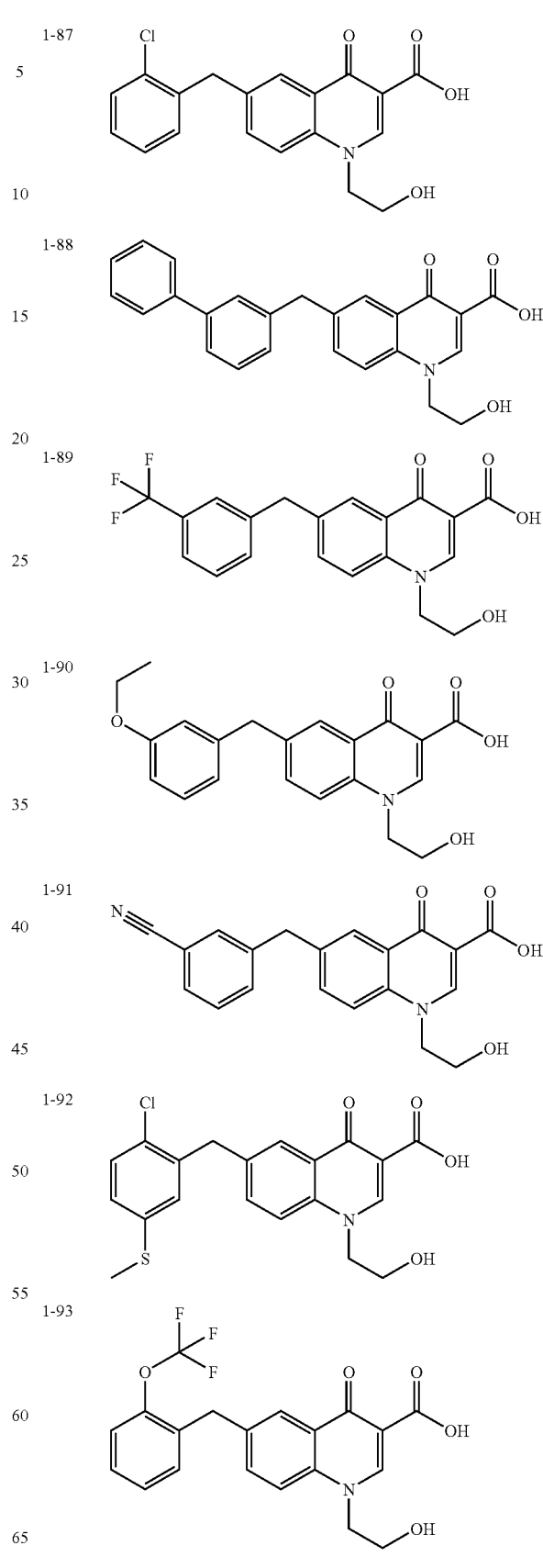

TABLE 1-continued
| | |
|---|---|
| 1-94 |  |
| 1-95 |  |
| 1-96 |  |
| 1-97 |  |
| 1-98 |  |
| 1-99 |  |
| 1-100 |  |
TABLE 1-continued
| | |
|---|---|
| 1-101 | 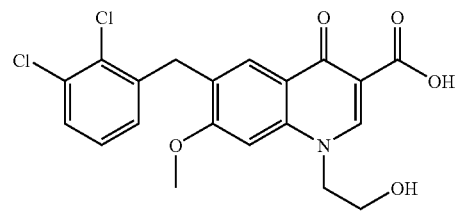 |
| 1-102 | 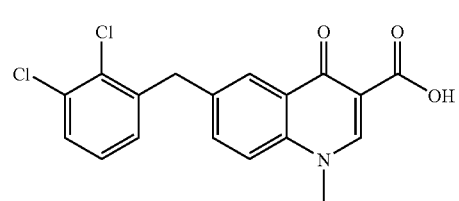 |
TABLE 2
| | |
|---|---|
| 2-1 | 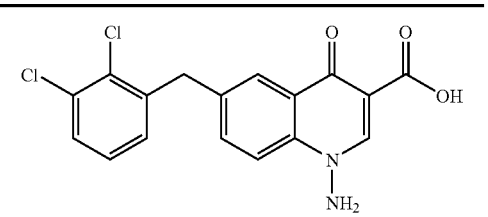 |
| 2-2 | 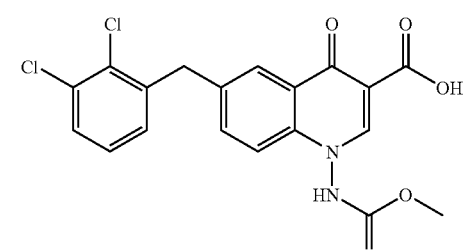 |
| 2-3 | 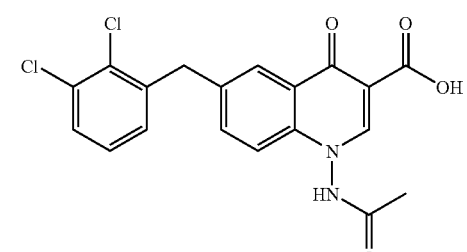 |
| 2-4 | 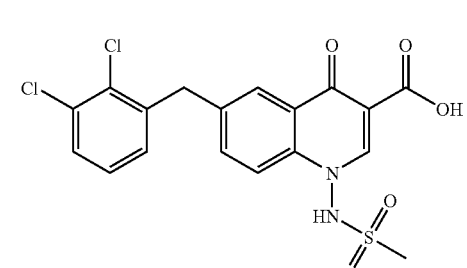 |

TABLE 2-continued
2-5 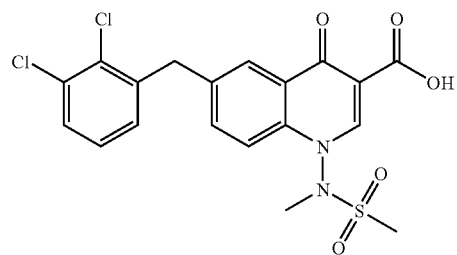
2-6 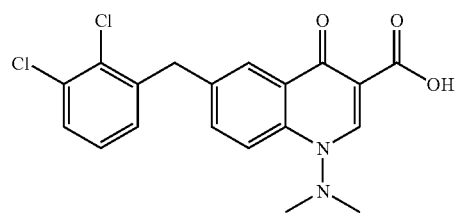
2-7 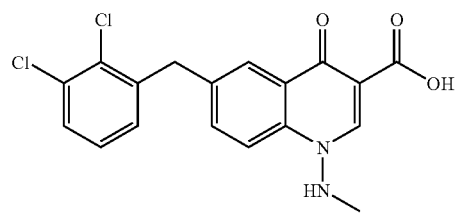
2-8 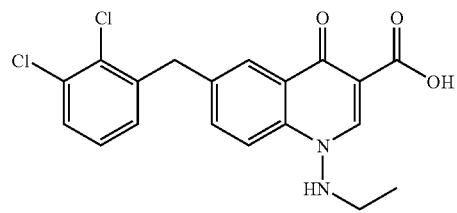
TABLE 3
3-1 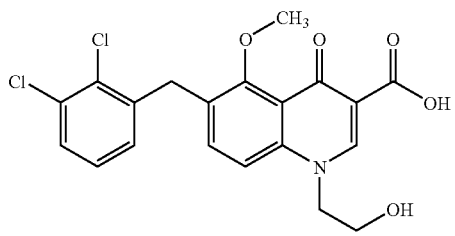
3-2 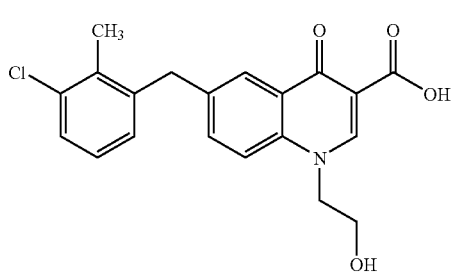
TABLE 3-continued
3-3 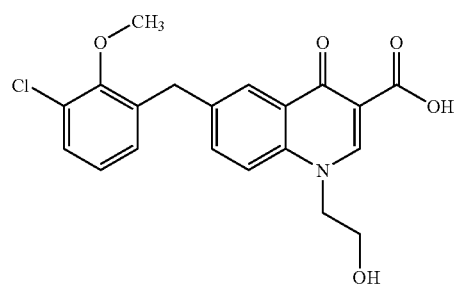
3-4 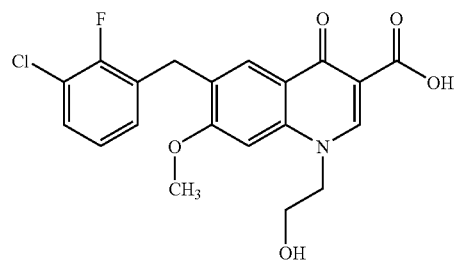
3-5 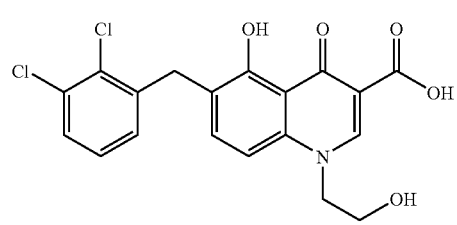
3-6 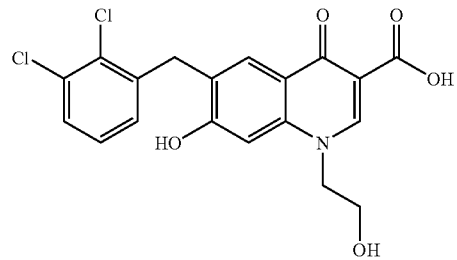
3-7 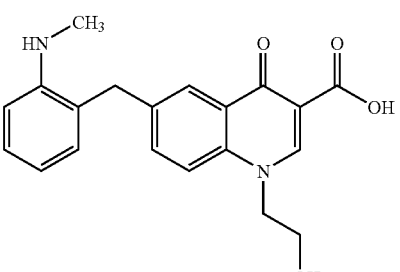
3-8 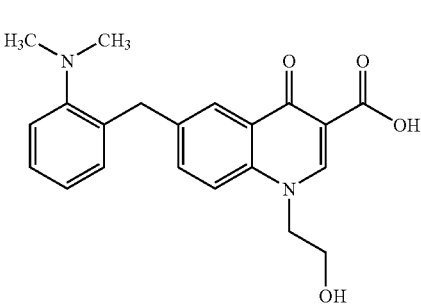

TABLE 3-continued
3-9 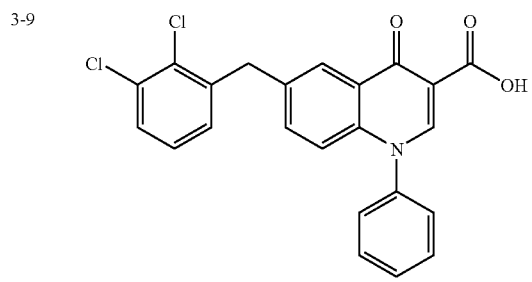
3-10 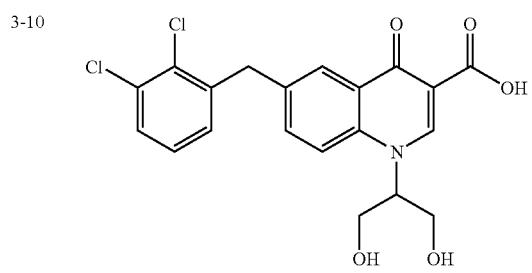
3-11 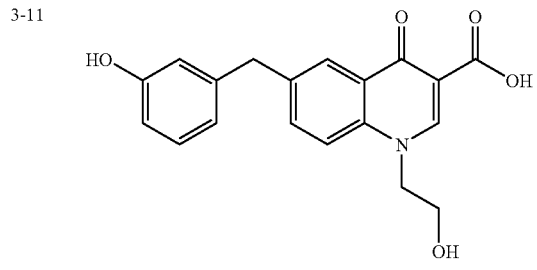
3-12 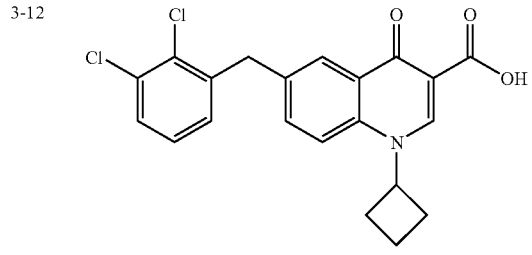
3-13 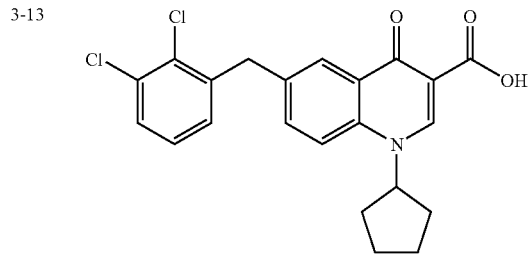
3-14 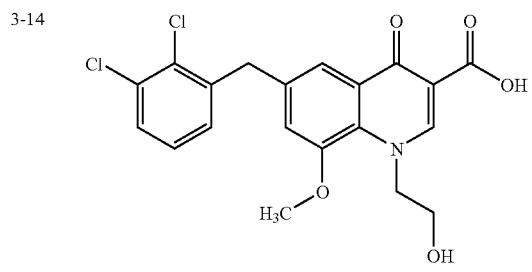
TABLE 3-continued
3-15 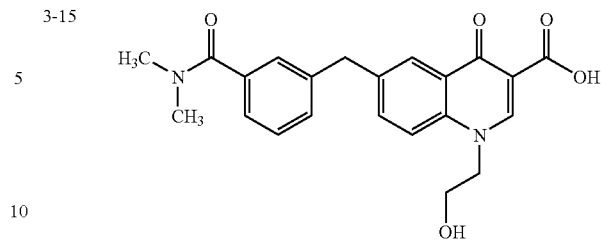
3-16 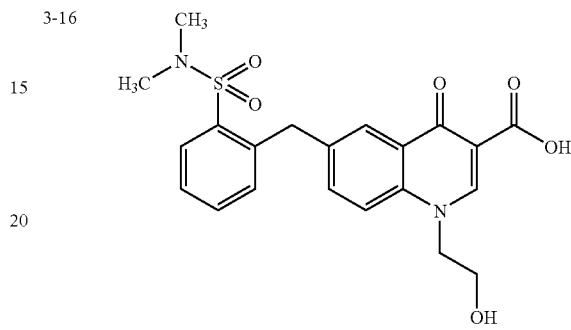
3-17 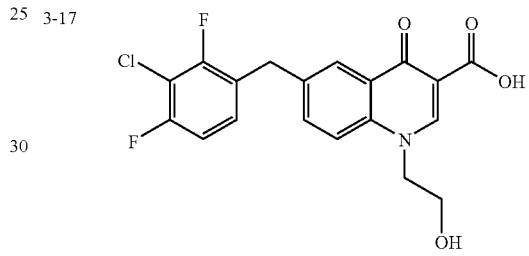
3-18 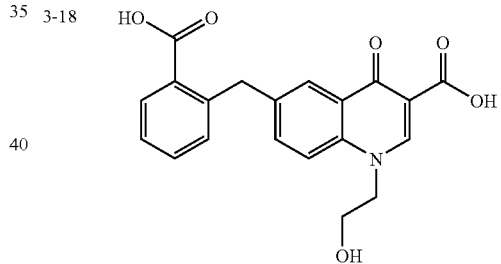
3-19 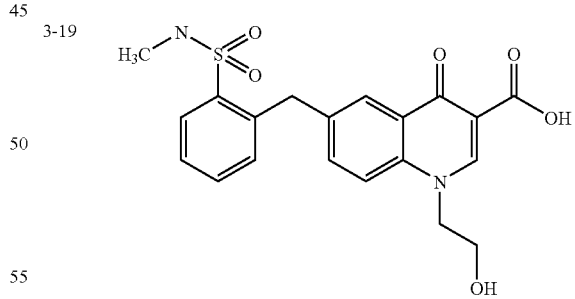
3-20 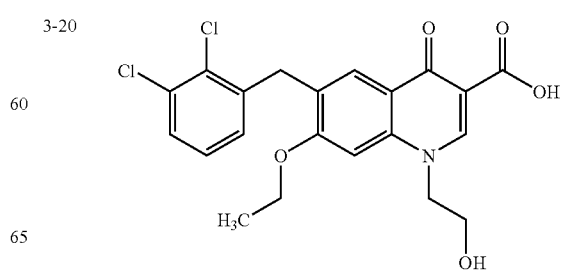

TABLE 3-continued
3-21 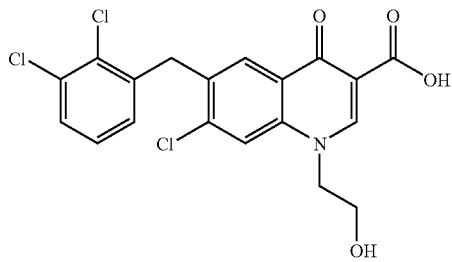
3-22 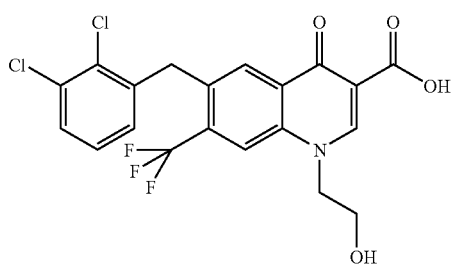
3-23 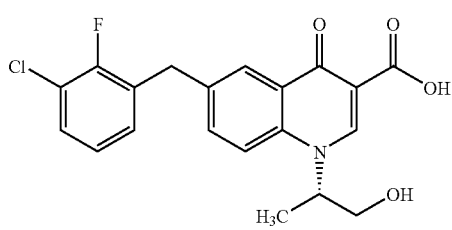
3-24 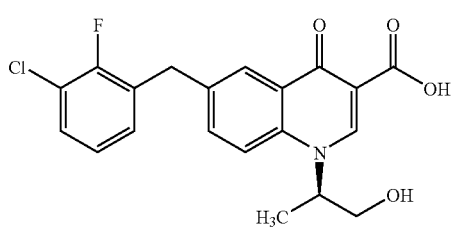
3-25 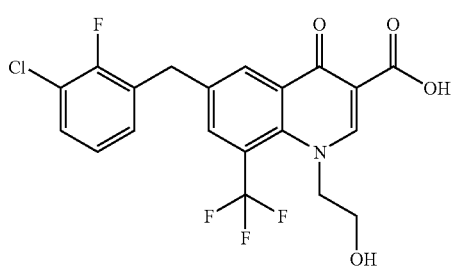
3-26 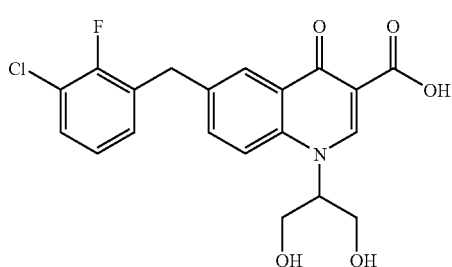
TABLE 3-continued
3-27 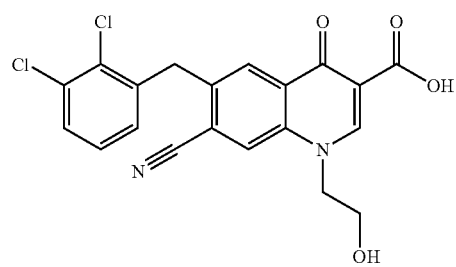
3-28 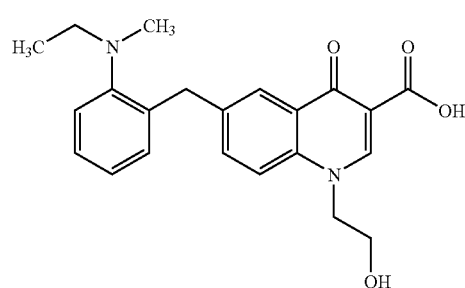
3-29 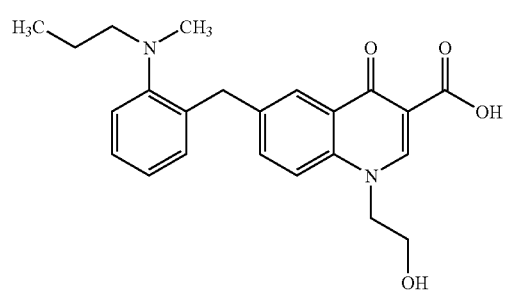
3-30 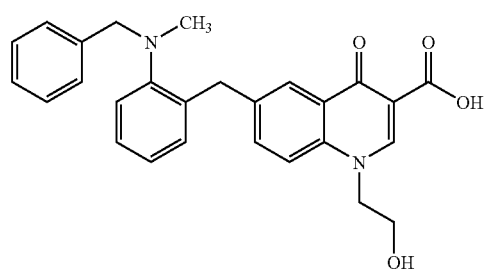
3-31 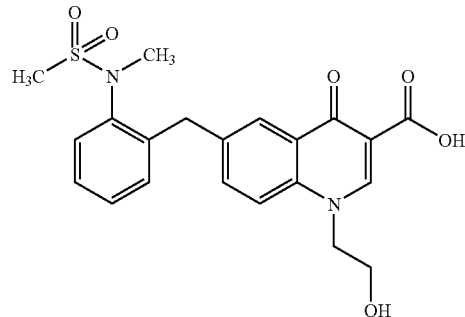

TABLE 3-continued
3-32 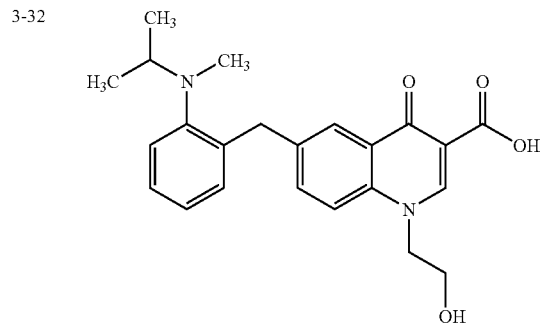
3-33 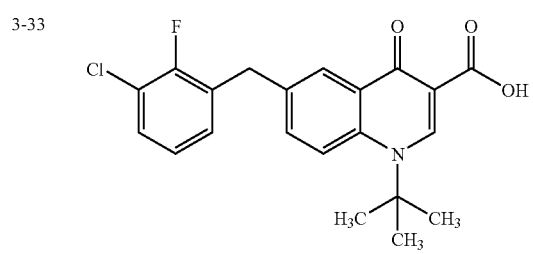
3-34 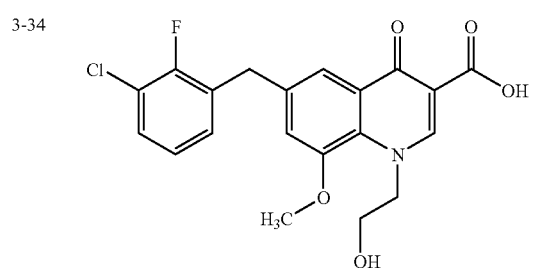
3-35 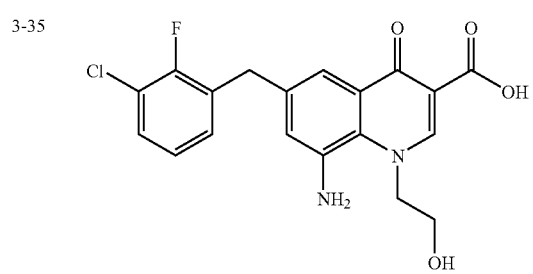
3-36 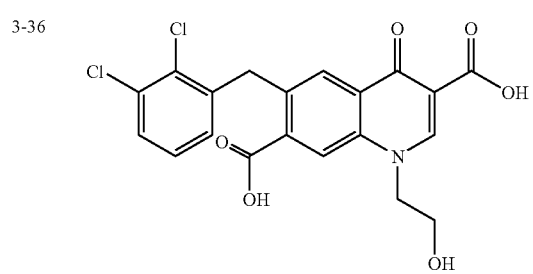
3-37 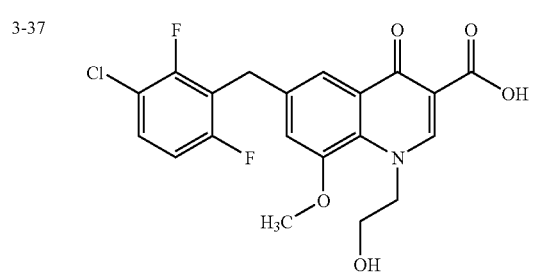
TABLE 3-continued
3-38 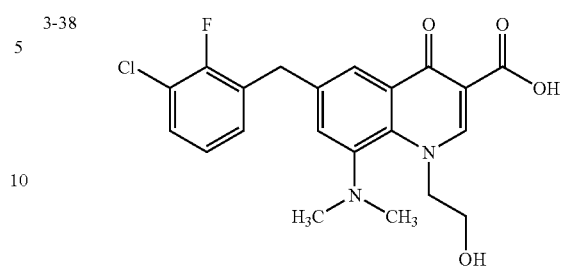
3-39 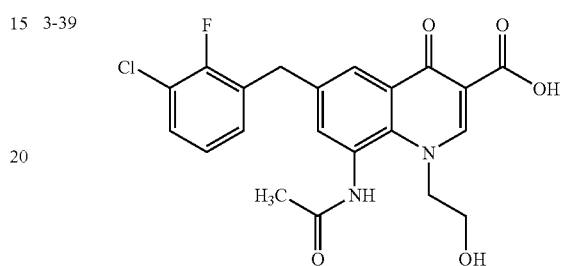
3-40 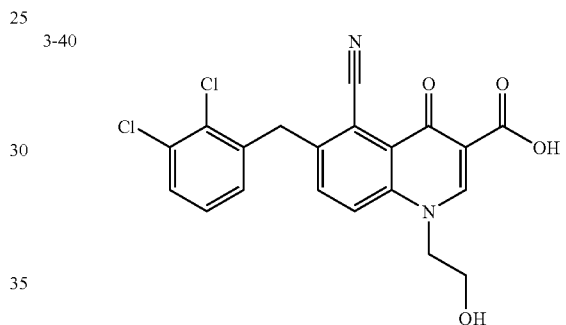
3-41 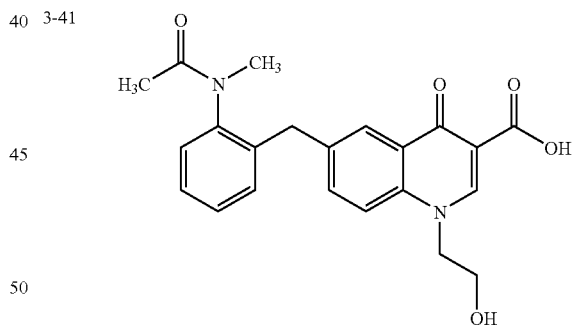
3-42 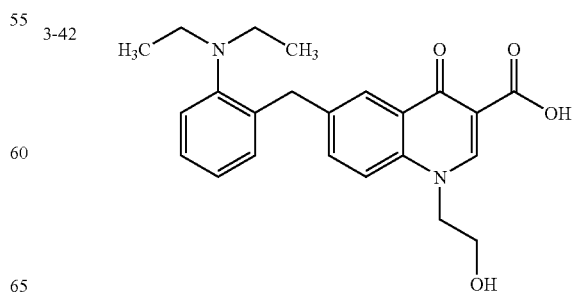

TABLE 3-continued
3-43 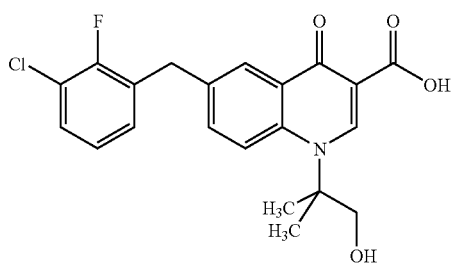
3-44 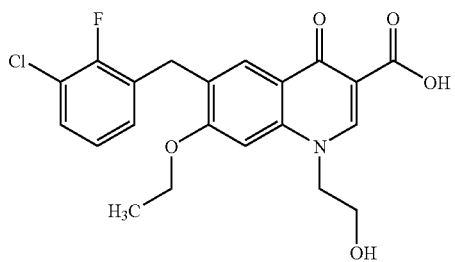
3-45 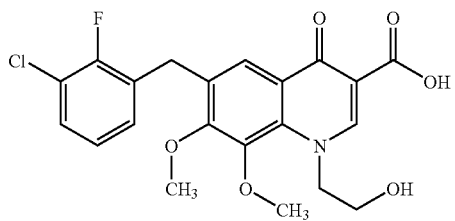
3-46 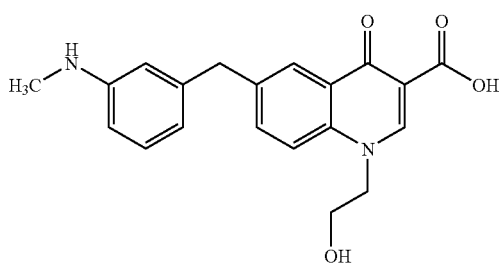
3-47 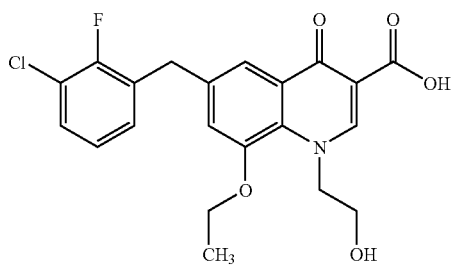
3-48 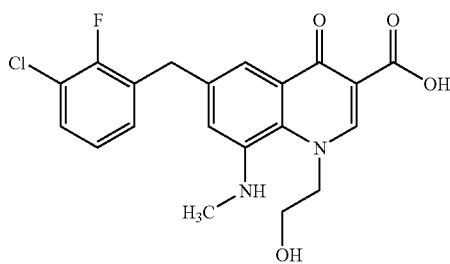
3-49 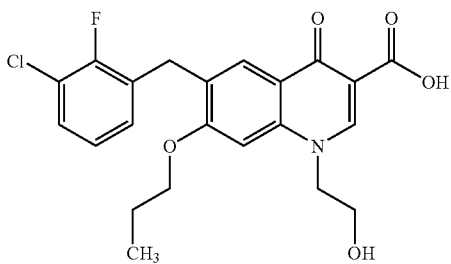
3-50 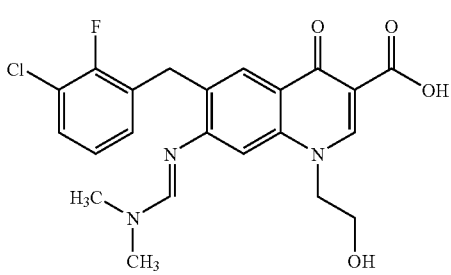
3-51 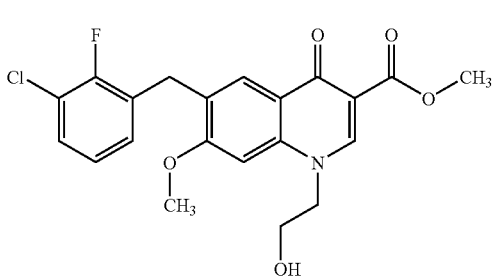
3-52 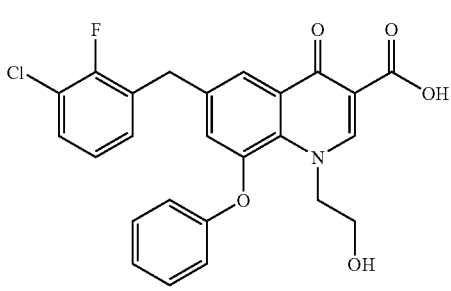
3-53 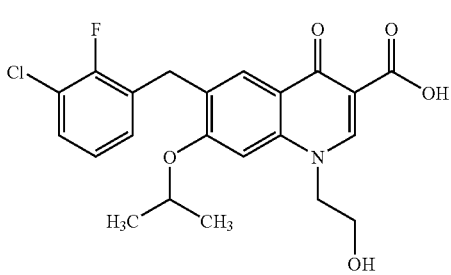
3-54 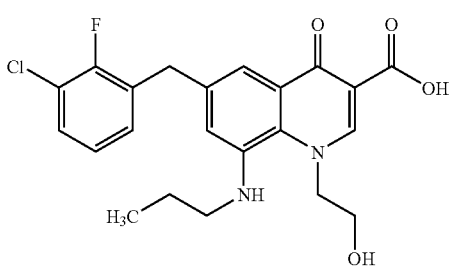

TABLE 3-continued
3-55 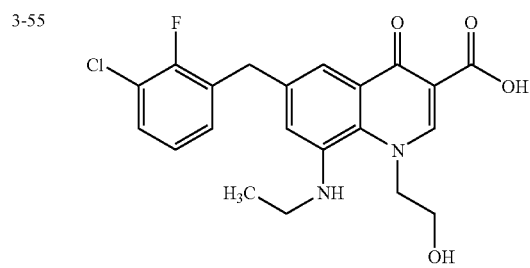
3-56 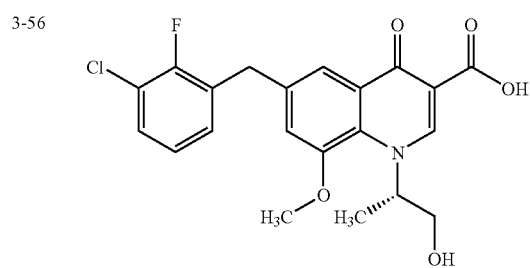
3-57 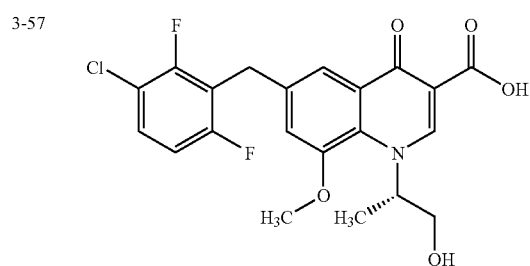
3-58 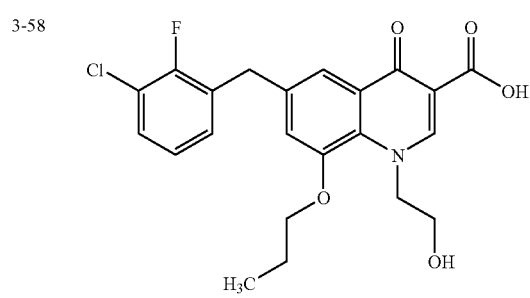
3-59 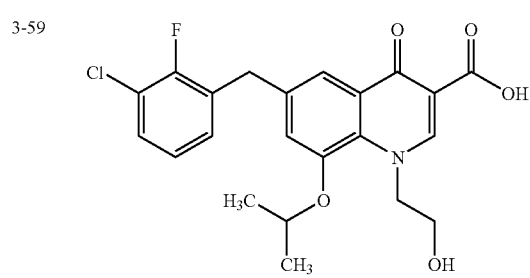
3-60 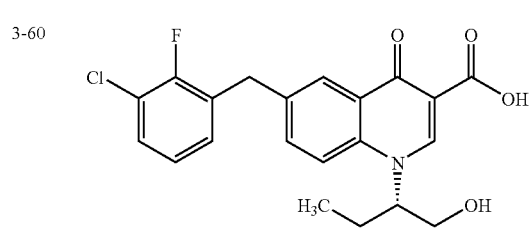
TABLE 3-continued
3-61 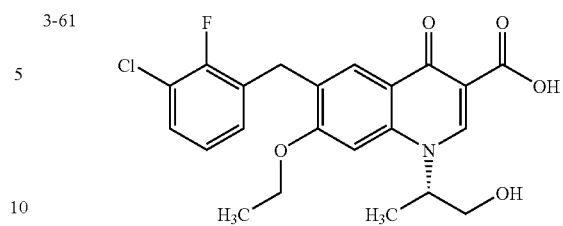
3-62 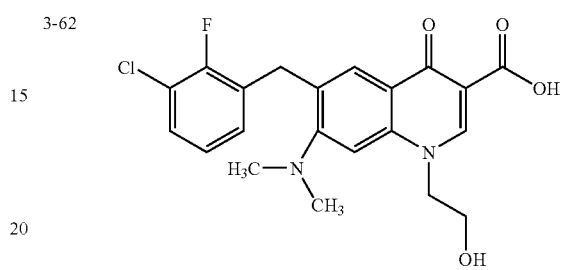
3-63 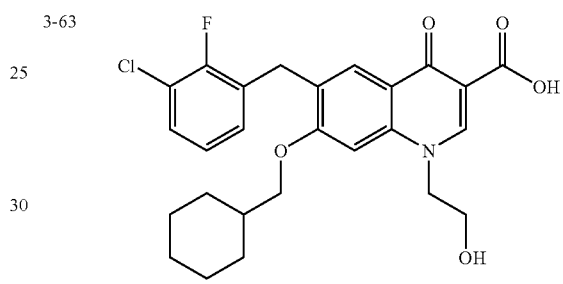
3-64 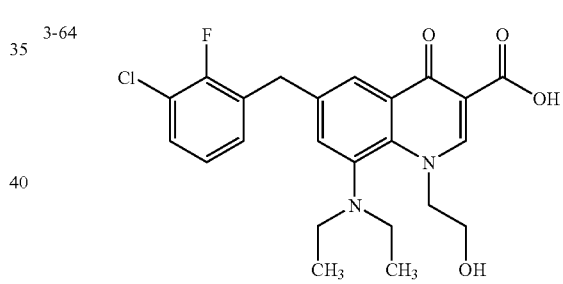
3-65 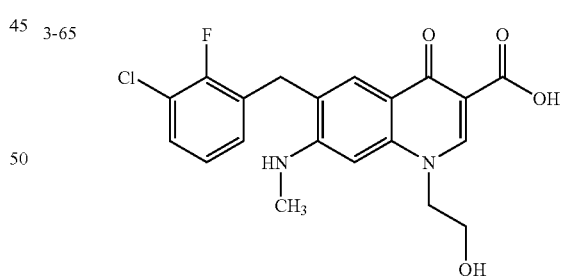
3-66 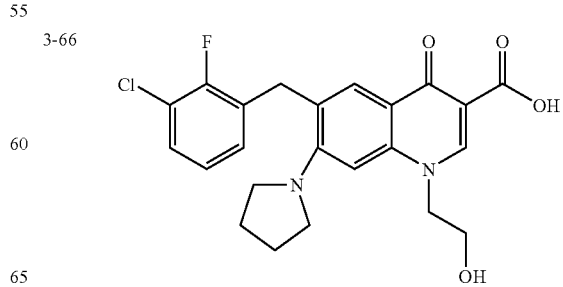

TABLE 3-continued
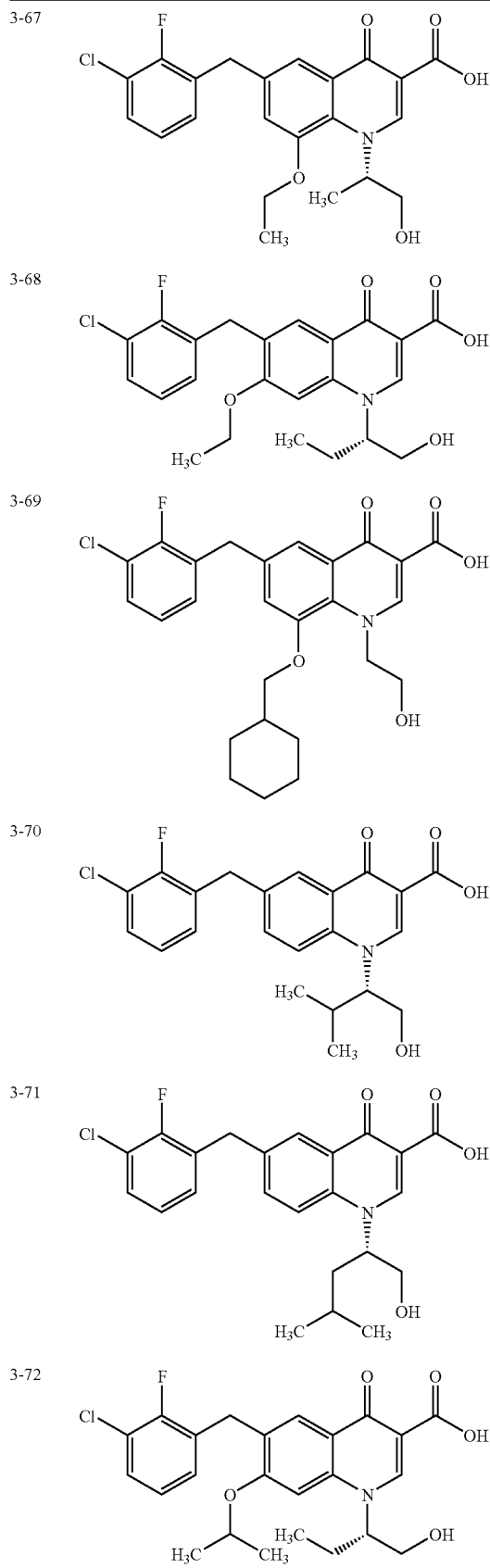
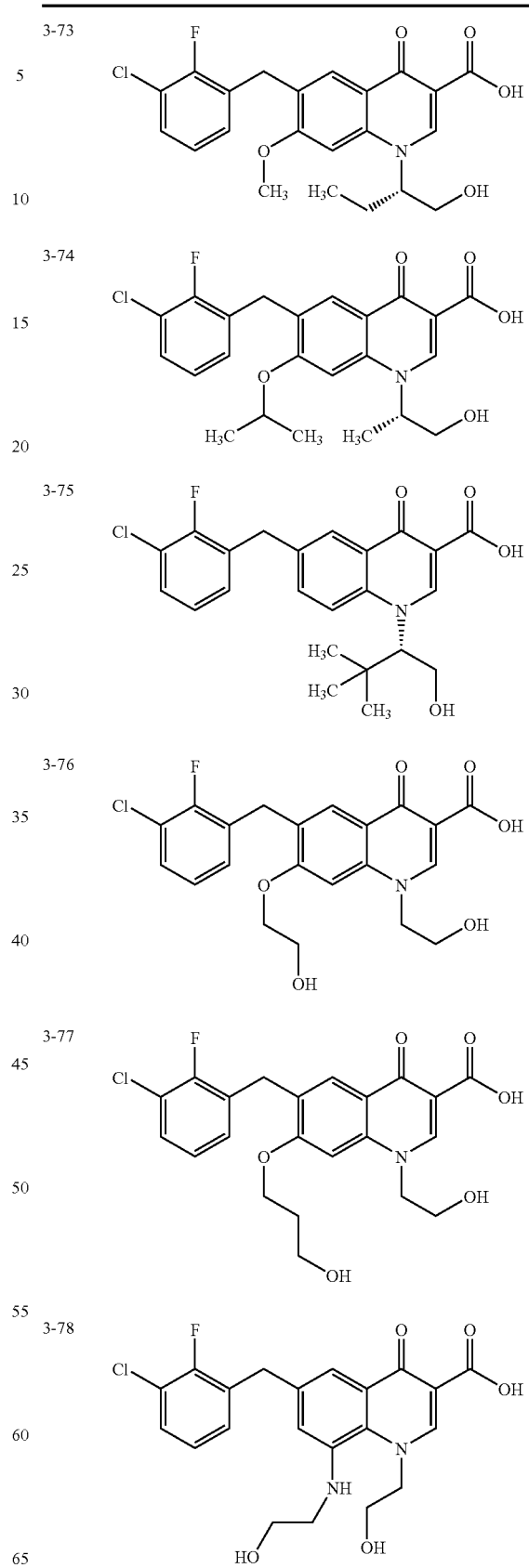

TABLE 3-continued
3-79 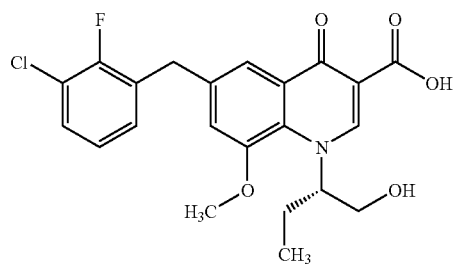
3-80 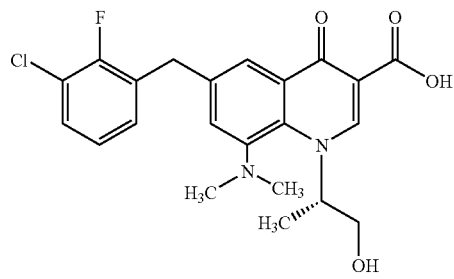
3-81 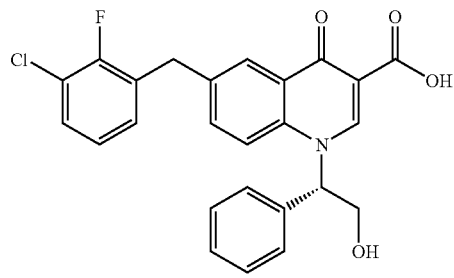
3-82 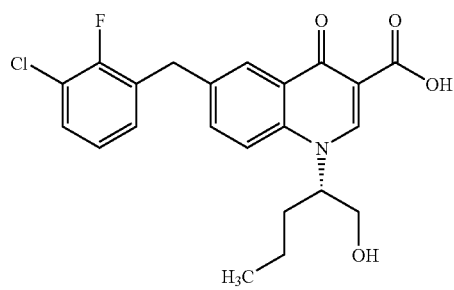
3-83 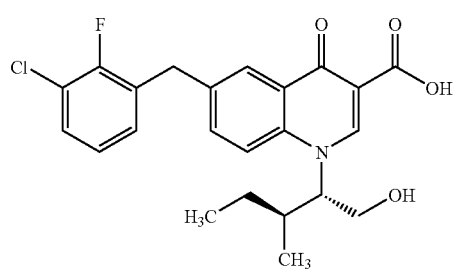
3-84 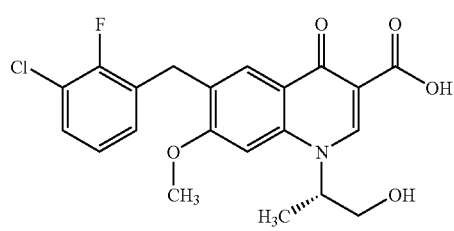
TABLE 3-continued
3-85 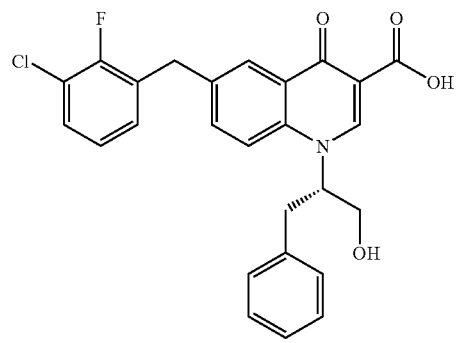
3-86 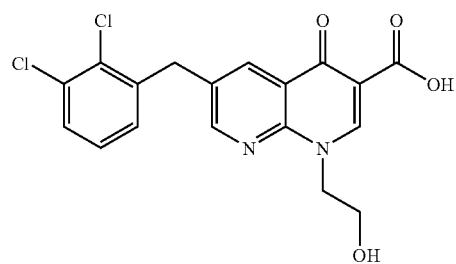
TABLE 4
4-1 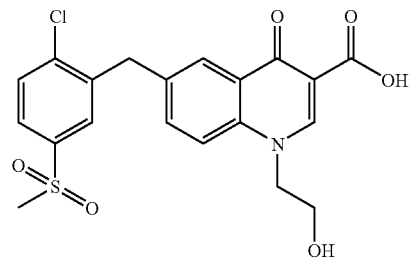
4-2 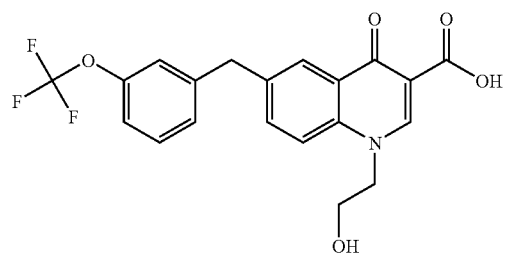
4-3 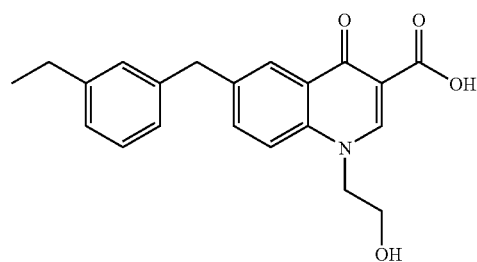

TABLE 4-continued
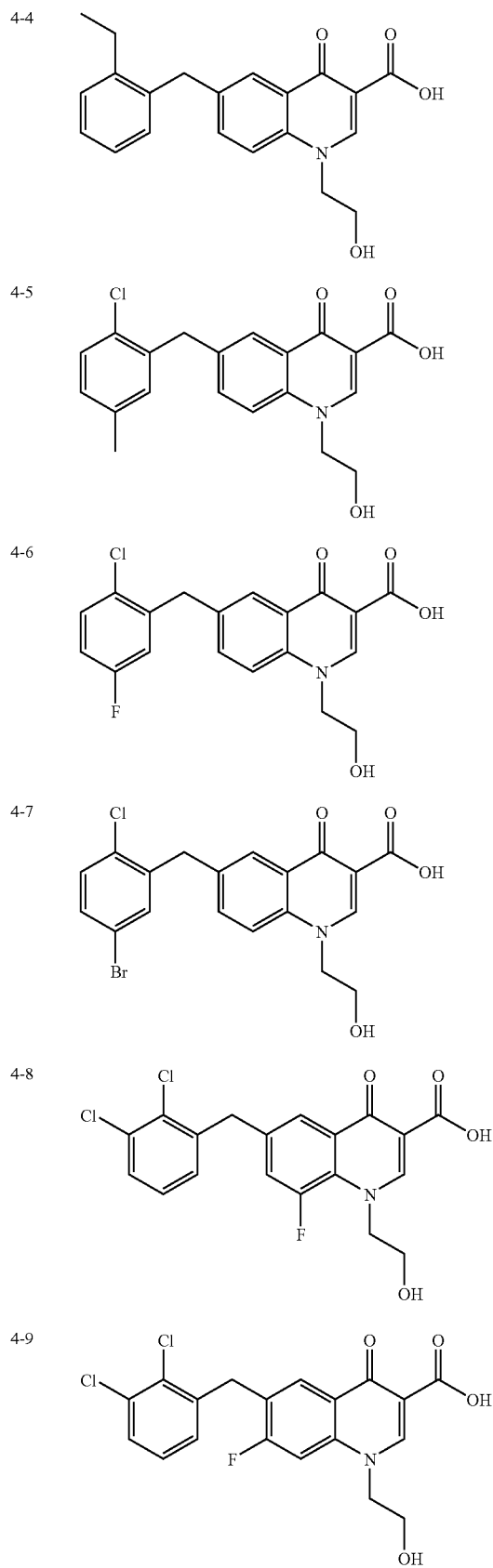
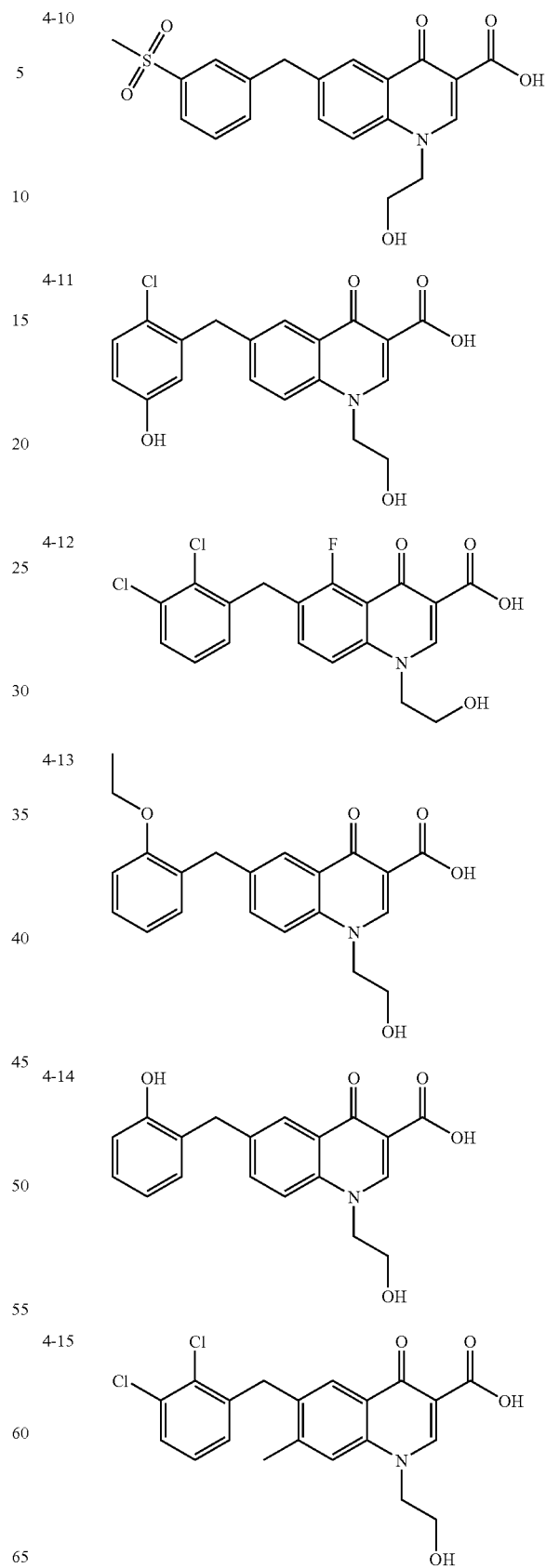

TABLE 4-continued
4-16 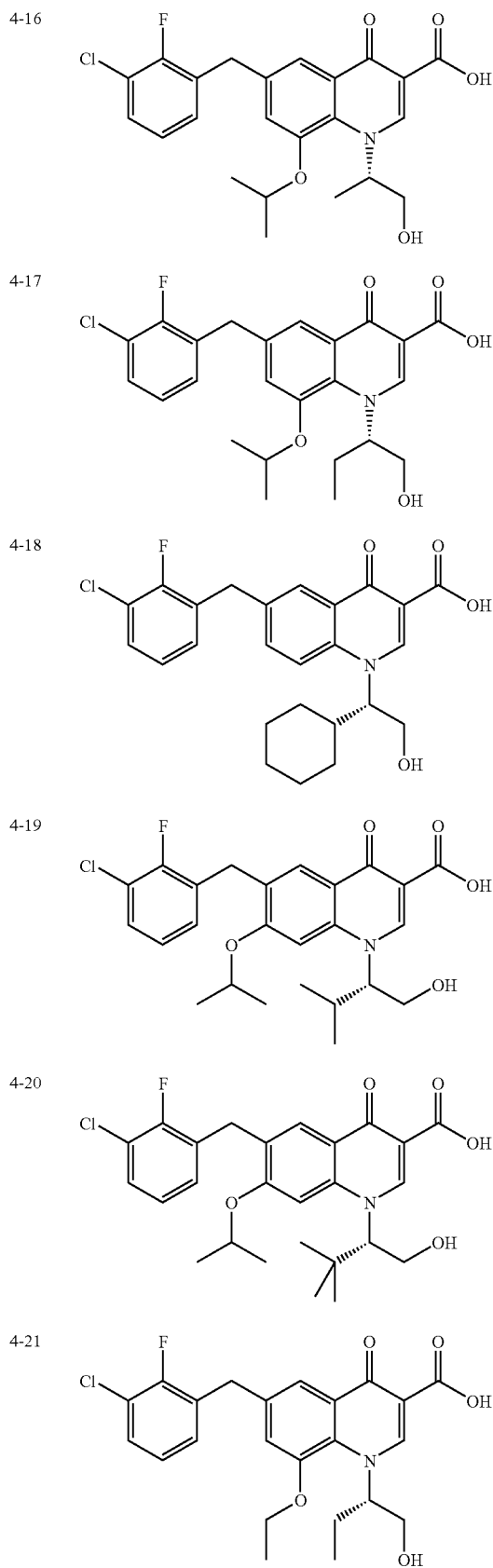
4-17
4-18
4-19
4-20
4-21
TABLE 4-continued
4-22 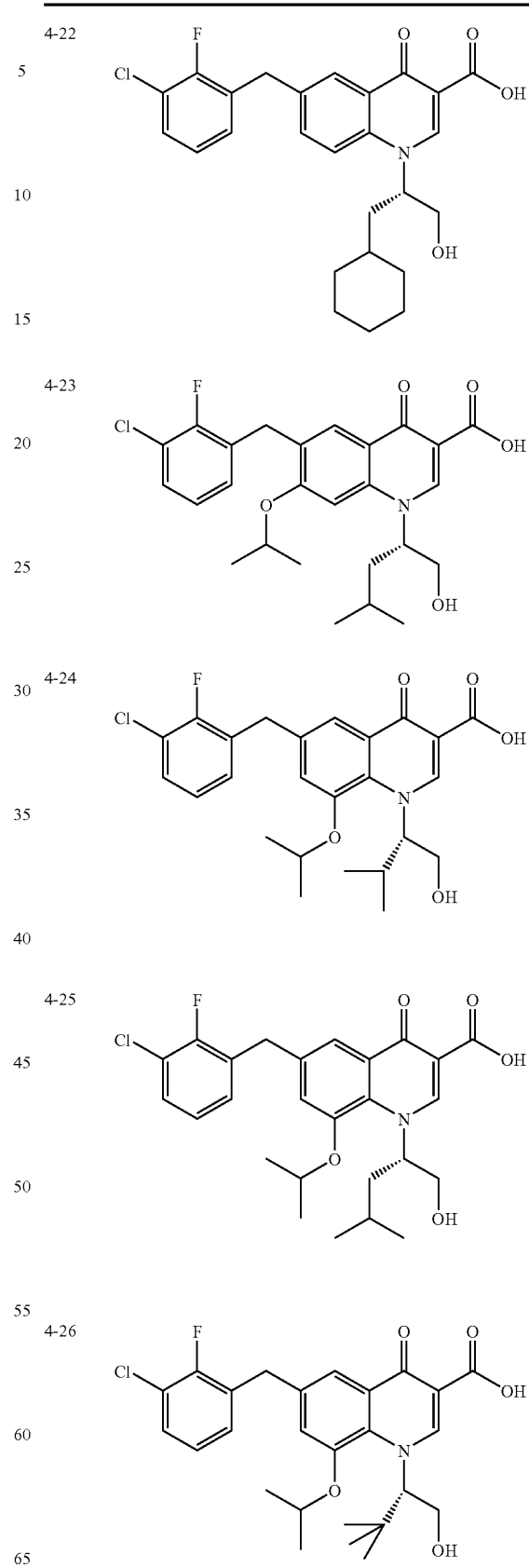
4-23
4-24
4-25
4-26

TABLE 4-continued
4-27 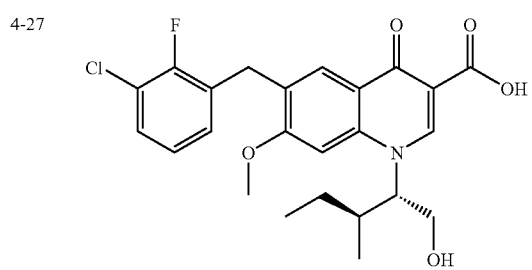
4-28 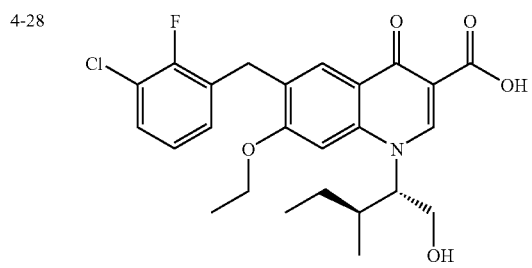
4-29 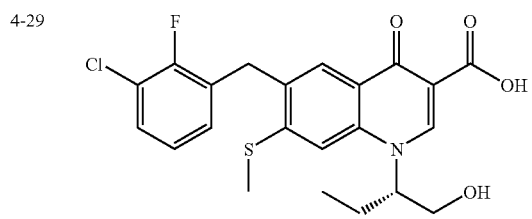
4-30 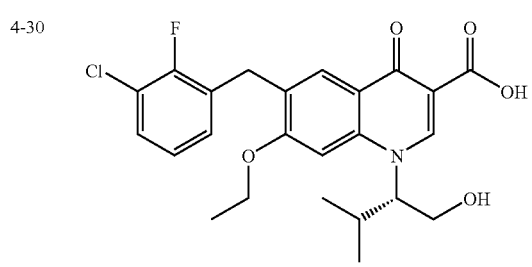
4-31 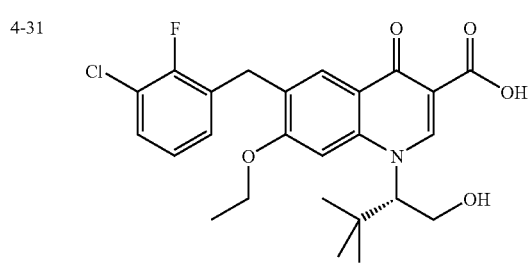
4-32 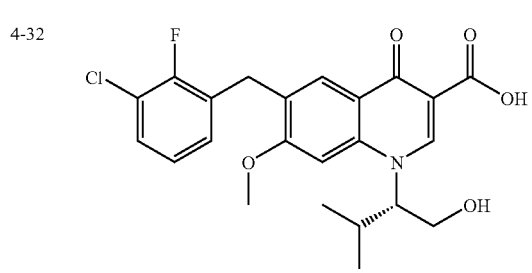
TABLE 4-continued
4-33 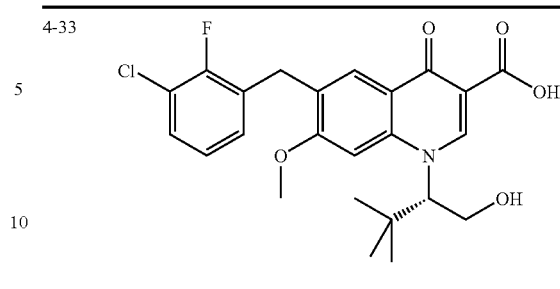
4-34 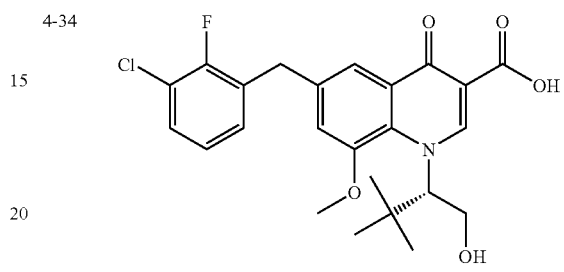
4-35 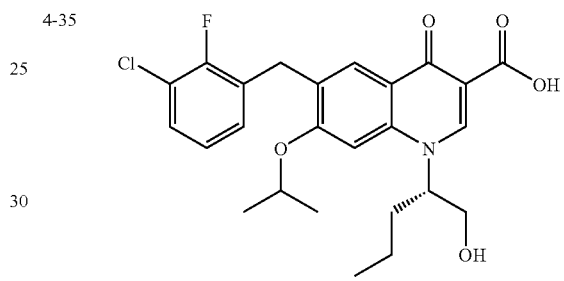
4-36 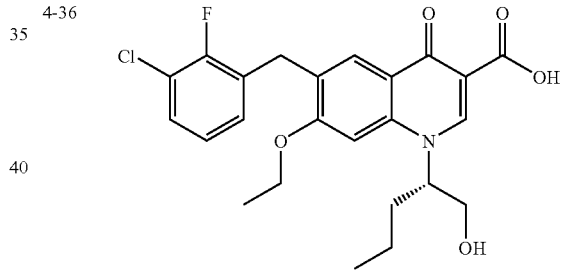
4-37 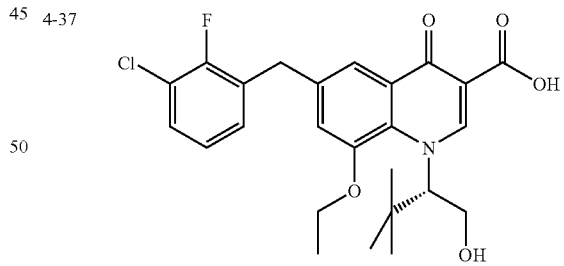
4-38 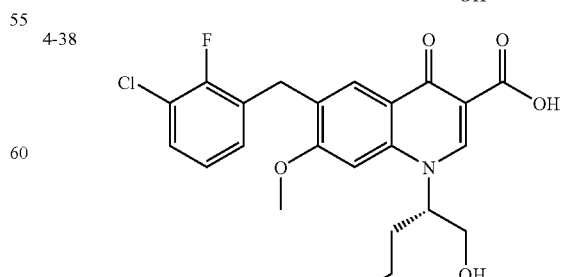

TABLE 4-continued
4-39 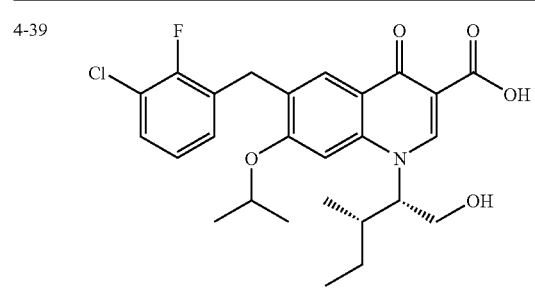
4-40 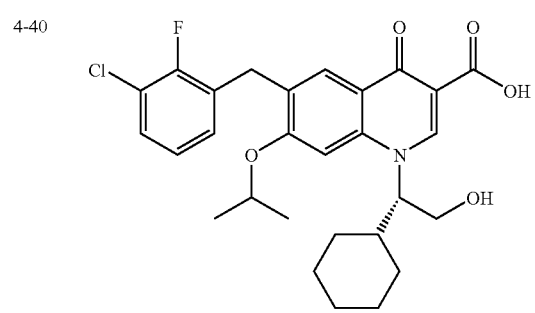
4-41 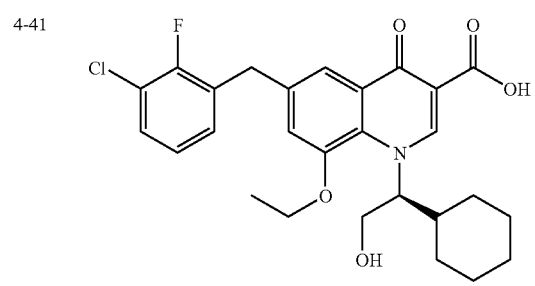
4-42 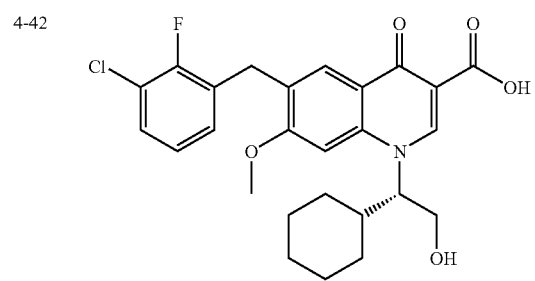
4-43 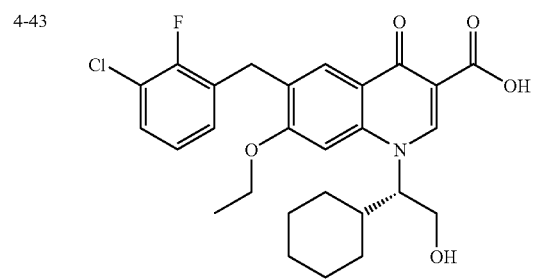
TABLE 4-continued
4-44 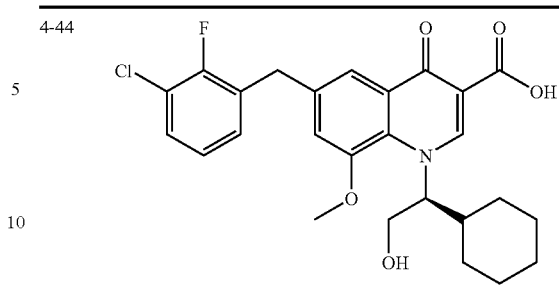
4-45 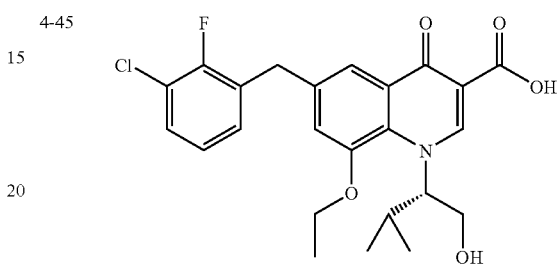
4-46 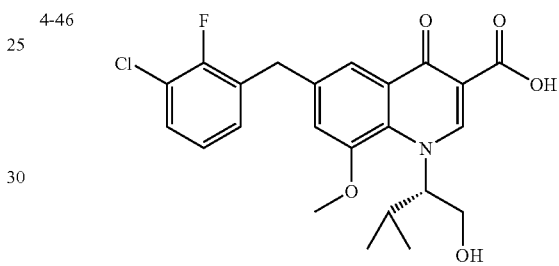
4-47 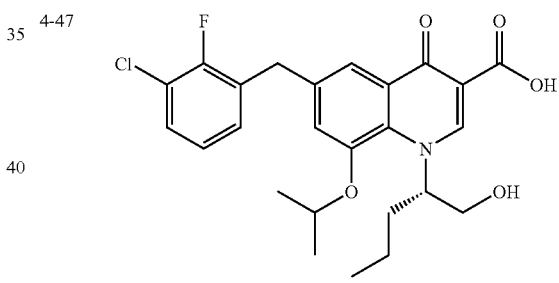
4-48 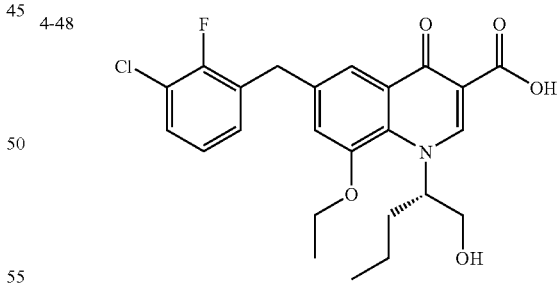
4-49 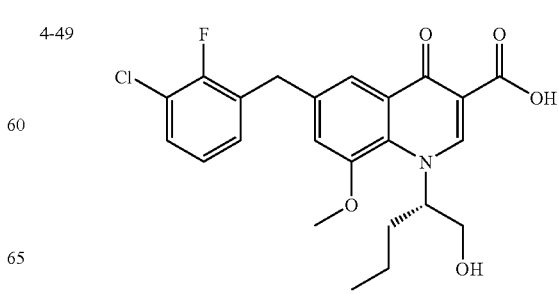

TABLE 4-continued 4-50: [structure: 6-(3-chloro-2-fluorobenzyl)-1-[(1S)-1-cyclohexyl-2-hydroxyethyl]-8-isopropoxy-4-oxo-1,4-dihydroquinoline-3-carboxylic acid]

4-51: [structure: sodium 6-(3-chloro-2-fluorobenzyl)-8-ethoxy-1-[(2S)-1-hydroxy-3-methylbutan-2-yl]-4-oxo-1,4-dihydroquinoline-3-carboxylate]

4-52: [structure: sodium 6-(3-chloro-2-fluorobenzyl)-1-[(2S)-1-hydroxy-3,3-dimethylbutan-2-yl]-4-oxo-1,4-dihydroquinoline-3-carboxylate]

4-53: [structure: sodium 6-(3-chloro-2-fluorobenzyl)-1-[(2S)-1-hydroxy-3-methylbutan-2-yl]-7-methoxy-4-oxo-1,4-dihydroquinoline-3-carboxylate]

4-54: [structure: sodium 6-(3-chloro-2-fluorobenzyl)-1-[(2S)-1-hydroxy-3,3-dimethylbutan-2-yl]-7-methoxy-4-oxo-1,4-dihydroquinoline-3-carboxylate]

TABLE 5

| Ex. No. | Enzyme activity IC$_{50}$ (µM) | Ex. No. | Enzyme activity IC$_{50}$ (µM) |
|---|---|---|---|
| 1-1 | 0.029 | 1-2 | 0.033 |
| 1-3 | 0.36 | 1-4 | 0.24 |
| 1-6 | 0.14 | 1-7 | 0.067 |
| 1-8 | 0.046 | 1-9 | 0.017 |
| 1-10 | 0.072 | 1-11 | 0.18 |
| 1-12 | 0.71 | 1-13 | 0.14 |
| 1-14 | 0.075 | 1-15 | 0.23 |
| 1-16 | 0.032 | 1-17 | 0.084 |
| 1-18 | 0.12 | 1-19 | 0.081 |
| 1-20 | 0.69 | 1-21 | 0.074 |
| 1-22 | 0.11 | 1-23 | 0.19 |
| 1-24 | 0.29 | 1-25 | 0.16 |
| 1-26 | 0.18 | 1-27 | 0.076 |
| 1-28 | 0.059 | 1-29 | 0.24 |
| 1-30 | 0.14 | 1-31 | 0.17 |
| 1-32 | 0.068 | 1-33 | 0.14 |
| 1-34 | 0.35 | 1-36 | 0.18 |
| 1-37 | 0.11 | 1-38 | 0.17 |
| 1-39 | 0.18 | 1-40 | 0.11 |
| 1-41 | 0.21 | 1-42 | 0.13 |
| 1-43 | 0.024 | 1-44 | 0.051 |
| 1-45 | 0.21 | 1-46 | 0.42 |
| 1-47 | 0.098 | 1-48 | 0.38 |
| 1-49 | 0.053 | 1-50 | 0.11 |
| 1-51 | 0.18 | 1-63 | 0.02 |
| 1-64 | 0.056 | 1-65 | 0.12 |
| 1-66 | 0.049 | 1-67 | 0.79 |
| 1-68 | 0.049 | 1-69 | 0.074 |
| 1-70 | 0.082 | 1-71 | 0.013 |
| 1-72 | 0.025 | 1-73 | 0.031 |
| 1-74 | 0.098 | 1-75 | 0.016 |
| 1-76 | 0.028 | 1-77 | 0.063 |
| 1-78 | 0.59 | 1-79 | 0.077 |
| 1-80 | 0.35 | 1-86 | 0.15 |
| 1-87 | 0.14 | 1-88 | 0.45 |
| 1-92 | 0.28 | 1-93 | 0.37 |
| 1-96 | 0.23 | 1-97 | 0.13 |
| 2-1 | 0.17 | 2-2 | 0.18 |
| 2-3 | 0.11 | 2-4 | 0.018 |
| 2-5 | 0.30 | 2-6 | 0.092 |
| 2-7 | 0.079 | 2-8 | 0.085 |

TABLE 6

| Ex. No. | Enzyme activity IC$_{50}$ (µM) | Ex. No. | Enzyme activity IC$_{50}$ (µM) |
|---|---|---|---|
| 3-1 | 0.47 | 3-2 | 0.2 |
| 3-3 | 0.19 | 3-4 | 0.011 |
| 3-5 | 0.024 | 3-6 | 0.011 |
| 3-8 | 0.34 | 3-9 | 0.084 |
| 3-10 | 0.018 | 3-12 | 0.016 |
| 3-13 | 0.029 | 3-14 | 0.014 |
| 3-17 | 0.013 | 3-20 | 0.01 |
| 3-21 | 0.03 | 3-22 | 0.79 |
| 3-23 | 0.0072 | 3-24 | 0.039 |
| 3-25 | 0.069 | 3-26 | 0.011 |
| 3-27 | 0.075 | 3-33 | 0.0087 |
| 3-34 | 0.011 | 3-35 | 0.011 |
| 3-36 | 0.051 | 3-37 | 0.011 |
| 3-38 | 0.015 | 3-39 | 0.049 |
| 3-42 | 0.72 | 3-43 | 0.018 |
| 3-44 | 0.0096 | 3-45 | 0.015 |
| 3-47 | 0.0086 | 3-48 | 0.021 |
| 3-49 | 0.0079 | 3-50 | 0.018 |
| 3-52 | 0.012 | 3-53 | 0.0079 |
| 3-54 | 0.0064 | 3-55 | 0.0087 |
| 3-56 | 0.012 | 3-57 | 0.015 |
| 3-58 | 0.008 | 3-59 | 0.008 |
| 3-60 | 0.0055 | 3-61 | 0.0076 |
| 3-62 | 0.027 | 3-63 | 0.017 |
| 3-64 | 0.018 | 3-65 | 0.015 |
| 3-66 | 0.048 | 3-67 | 0.0064 |
| 3-69 | 0.0043 | 3-72 | 0.0038 |
| 3-73 | 0.0033 | 3-74 | 0.0049 |
| 3-76 | 0.0085 | 3-77 | 0.0089 |
| 3-78 | 0.016 | 3-79 | 0.0067 |
| 3-80 | 0.0088 | 3-86 | 0.14 |

TABLE 7

| Ex. No. | Enzyme activity IC$_{50}$ (μM) | Ex. No. | Enzyme activity IC$_{50}$ (μM) |
|---|---|---|---|
| 4-1 | 0.86 | 4-4 | 0.55 |
| 4-5 | 0.13 | 4-6 | 0.46 |
| 4-7 | 0.13 | 4-8 | 0.033 |
| 4-9 | 0.021 | 4-11 | 0.22 |
| 4-12 | 0.065 | 4-13 | 0.30 |
| 4-15 | 0.031 | 4-16 | 0.0071 |
| 4-17 | 0.0031 | 4-18 | 0.0020 |
| 4-19 | 0.0029 | 4-20 | 0.0017 |
| 4-21 | 0.0045 | 4-22 | 0.0029 |
| 4-23 | 0.0038 | 4-24 | 0.0025 |
| 4-25 | 0.0019 | 4-26 | 0.0015 |
| 4-27 | 0.0029 | 4-28 | 0.0027 |
| 4-29 | 0.0045 | 4-30 | 0.0029 |
| 4-31 | 0.0021 | 4-32 | 0.0029 |
| 4-33 | 0.0020 | 4-34 | 0.0039 |
| 4-35 | 0.0043 | 4-36 | 0.0037 |
| 4-37 | 0.0019 | 4-38 | 0.0033 |
| 4-39 | 0.0041 | 4-40 | 0.0043 |
| 4-41 | 0.0023 | 4-42 | 0.0023 |
| 4-43 | 0.0028 | 4-44 | 0.0024 |
| 4-45 | 0.0034 | 4-46 | 0.0050 |
| 4-47 | 0.0023 | 4-48 | 0.0030 |
| 4-49 | 0.0057 | 4-50 | 0.0031 |

NMR and MS data of the Example compounds shown in the above-mentioned Table 1 to Table 4 are described in the following.

EXAMPLE 1-1

$^1$H NMR (DMSO-d$_6$ 400 MHz) (δ) ppm: 3.75(2H, t, J=4.7 Hz), 4.36(2H, s), 4.60(2H, t, J=4.8 Hz), 4.98(1H, brs), 7.37-7.39(1H, m), 7.45(1H, dd, J=1.4, 7.6 Hz), 7.57(1H, dd, J=1.5, 8.0 Hz), 7.81(1H, dd, J=2.1, 8.9 Hz), 8.02(1H, d, J=8.8 Hz), 8.15(1H, d, J=1.8 Hz),8.86(1H, s), 15.18(1H, brs)
MS (ESI): M+ 392

EXAMPLE 1-2

$^1$H NMR (DMSO-d$_6$ 300 MHz) (δ) ppm: 3.78 (2H, m), 4.35 (2H, s), 4.64 (2H, m), 5.00 (1H, m), 7.39 (2H, m), 7.47 (1H, m), 7.58 (1H, m), 8.00 (1H, m), 8.81 (1H, s), 14.80 (1H, s)
MS (ESI): M+409

EXAMPLE 1-3

$^1$H NMR (DMSO-d$_6$ 400 MHz) (δ) ppm: 2.85(3H, s), 3.41 (2H, m), 4.37(2H, S), 4.63(2H, t, J=5.6 Hz), 7.25-7.29 (1H, m), 7.39(1H, dd, J=7.8, 7.8 Hz), 7.47(1H, dd, J=1.5, 7.7 Hz;), 7.58(1H, dd, J=1.5, 7.8 Hz), 7.84(1H, dd, J=2.0, 8.9 Hz), 8.00(1H, d, J=8.9 Hz), 8.15(1H, d, J=1.8 Hz), 8.91(1H, s)
MS (ESI): M+ 469

EXAMPLE 1-4

$^1$H NMR (DMSO-d$_6$ 300 MHz) (δ) ppm: 4.38 (2H, s), 4.46 (2H, t, J=5.9 Hz), 4.90 (2H, t, J=5.9 Hz), 6.84 (1H, s), 7.14 (1H, S), 7.37-7.47 (3H, m), 7.59 (1H, m), 7.82 (1H, m), 8.01 (1H, m), 8.15 (1H, s), 8.66 (1H, s), 14.99 (1H, s)
MS (ESI): M+441

EXAMPLE 1-5

$^1$H NMR (DMSO-d$_6$ 300 MHz) (δ) ppm: 2.87 (3H, s), 3.12 (3H, s), 4.35 (2H, s), 5.59 (2H, s), 7.38-7.45 (2H, m), 7-7.57 (1H, m), 7.71-7.76 (2H, m), 8.12 (1H, s), 8.94 (1H, s)
MS (ESI): M+432

EXAMPLE 1-6

$^1$H NMR (DMSO-d$_6$ 300 MHz) (δ) ppm: 2.64 (3H, d, J=4.4), 4.35 (2H, s), 5.24 (2H, s), 7.35-7.47 (2H, m), 7.56-7.65 (2H, m), 7.80 (1H, m), 8.13 (1H, s), 8.32 (1H, q, J=4.4 Hz), 9.00 (1H, s)
MS (ESI): M+418

EXAMPLE 1-7

$^1$H NMR (DMSO-d$_6$ 300 MHz) (δ) ppm: 4.36 (2H, s), 5.23 (2H, s), 7.35-7.45 (2H, m), 7.54-7.65 (3H,m), 7.83-7.88 (2H, m), 8.13 (1H, s), 9.01 (1H, s)
MS (ESI): M+404

EXAMPLE 1-8

$^1$H NMR (DMSO-d$_6$ 300 MHz) (δ) ppm: 1.57 (6H, d, J=6.5 Hz), 4.37 (2H, s), 5.24 (1H, m), 7.38 (1H, dd, J=7.7, 7.7 Hz) 7.46 (1H, dd, J=1.6, 7.7 Hz), 7.58 (1H, dd, J=1.6, 7.7 Hz), 7.85 (1H, dd, J=2.1, 8.9 Hz), 8.15-8.18 (2H, m), 8.86 (1H, s)
MS (ESI): M+389

EXAMPLE 1-9

$^1$H NMR (DMSO-d$_6$ 300 MHz) (δ) ppm: 4.35 (2H, s), 5.98 (2H, s), 7.37-7.44 (4H, m), 7.57 (1H, m), 7.83 (1H, m), 8.10-8.12 (2H, m), 8.99 (1H, s)
MS (ESI): M+440

EXAMPLE 1-10

$^1$H NMR (DMSO-d$_6$ 300 MHz) (δ) ppm: 2.85 (2H, Mm), 4.36 (2H, s), 4.74 (2H, m), 7.38-7.46 (2H, m), 7.58 (1H, m), 7.85 (1H, m), 8.00 (1H, m), 8.14 (1H, s), 9.00 (1H, s)
MS (ESI): M+419

EXAMPLE 1-11

$^1$H NMR (DMSO-d$_6$ 300 MHz) (δ) ppm: 3.74 (2H, dt, J=4.8, 5.6 Hz), 4.59 (2H, t, J=4.9 Hz), 4.66 (2H, s), 4.98 (1H, t, J=5.6 Hz), 7.48-7.53 (4H, m), 7.85-8.08 (5H, m), 8.18 (1H, m), 8.83 (1H, s), 15.24 (1H, brs)
MS (ESI): M+373

EXAMPLE 1-12

$^1$H NMR (DMSO-d$_6$ 300 MHz) (δ) ppm: 3.70 (2H, m), 3.72 (3H, s), 4.27 (2H, s), 4.38 (2H, m), 4.96 (1H, br), 7.32-7.41 (2H, m), 7.54 (1H, dd, J=1.8, 7.3 Hz), 7.61 (1H, dd, J=2.2, 8.8 Hz), 7.76 (1H, d, J=8.8 Hz), 8.00 (1H, d, J=2.2 Hz), 8.55 (1H, s)
MS (ESI): M+405

EXAMPLE 1-13

$^1$H NMR (DMSO-d$_6$ 300 MHz) (δ) ppm: 2.67 (2H, m), 4.37 (2H, s), 4.73 (2H, m), 6.97 (1H, br), 7.38-7.48 (3H, m), 7.58 (1H, m), 7.87 (1H, m), 8.01 (1H, -m), 8.15 (1H, s), 8.93 (1H, s)
MS (ESI): M+418

EXAMPLE 1-14

$^1$H NMR (DMSO-d$_6$ 400 MHz) (δ) ppm: 2.30 (3H, s), 4.34 (2H,s), 5.62 (2H, s), 7.37 (1H, m), 7.44 (1H, m), 7.55 (1H, m), 7.72-7.78 (2H, m), 8.10 (1H, s), 8.90 (1H, s)
MS (ESI): M+403

EXAMPLE 1-15

¹H NMR (DMSO-d₆ 300 MHz) (δ) ppm: 4.31 (2H, s), 5.84 (2H, s), 7.26-7.41 (7H, m), 7.55 (1H, m), 7.73 (1H, m), 7.83 (1H, m), 8.13 (1H, m), 9.23 (1H, s), 15.18 (1H, brs)
MS (ESI): M+437

EXAMPLE 1-16

¹H NMR (DMSO-d₆ 300 MHz) (δ) ppm: 3.12 (2H, t, J=7.3 Hz), 4.38 (2H, s), 4.78 (2H, t, J=7.3 Hz), 7.20-7.28 (5H, m), 7.37-7.47 (3H, m), 7.58 (1H, m), 7.85 (1H, m), 8.09 (1H, m), 8.15 (1H, s), 8.79 (1H,s), 15.07 (1H, brs)
MS (ESI): M+451

EXAMPLE 1-17

¹H NMR (DMSO-d₆ 300 MHz) (δ) ppm: 2.13 (2H, tt, J=7.3, 7.6 Hz), 2.70 (1H, t, J=7.6 Hz), 4.36 (2H, s), 4.58 (2H, t, J=7.3 Hz), 7.15-7.24 (5H, m), 7.38-7.44 (3H, m), 7.57 (1H, m), 7.82 (1H, m), 7.96 (1H, m), 8.13 (1H, s), 8.98 (1H, s), 15.14 (1H, brs)
MS (ESI): M+465

EXAMPLE 1-18

¹H NMR (DMSO-d₆ 300 MHz) (δ) ppm: 0.89 (6H, d, J=6.7 Hz), 2.16 (1H, tq, J=6.7, 7.6 Hz), 4.37 (2H, s), 4.39 (2H, d, J=7.6 Hz), 7.38-7.47 (2H, m), 7.58 (1H, m), 7.83 (1H, dd, J=2.0, 8.9 Hz), 8.02 (1H, d, J=8.9 Hz), 8.14 (1H, d, J=2.0 Hz), 8.97 (1H, s), 15.15 (1H, brs)
MS (ESI): M+403

EXAMPLE 1-19

¹H NMR (DMSO-d₆ 400 MHz) (δ) ppm: 1.61-1.64(2H, m), 1.76-1.84(2H, m), 2.60(2H, t, J=7.5 Hz), 4.36(2H, s), 4.56(2H, t, J=7.2 Hz), 7.15-7.17(3H, m), 7.22-7.24(2H, m), 7.38-7.40(1H, m), 7.44(1H, m), 7.56-7.59(1H, m), 7.82(1H, d, J=2 Hz), 7.96(1H, d, J=8.9 Hz), 8.14(1H, d, J=1.8 Hz), 9.01(1H, s), 15.15(1H, brs)
MS (ESI): M+ 514

EXAMPLE 1-20

¹H NMR (DMSO-d₆ 400 MHz) (δ) ppm: 4.28(2H, s), 5.73 (2H, s), 7.02(1H, d, J=7.6 Hz), 7.27-7.43(11H, m), 7.55(1H, d, J=7.6 Hz), 7.60-7.62(1H, m), 8.08(1H, d, J=1.6 Hz), 8.92 (1H, s), 14.97(1H, brs)
MS (ESI): M+ 502

EXAMPLE 1-21

¹H NMR (DMSO-d₆ 400 MHz) (δ) ppm: 1.45-1.49(2H, m), 1.81-1.85(2H, m), 3.42(2H, t, J=6.3 Hz), 4.36(2H, s), 4.56(2H, t, J=7.4 Hz), 7.38(1H, dd, J=7.7, 7.8 Hz), 7.44-7.46 (1H, m), 7.57(1H, dd, J=1.4, 7.8 Hz), 7.83(1H, dd, J=2.0, 8.8 Hz), 8.0(1H, d, J=8.9 Hz), 8.14(1H, d, J=1.8 Hz), 9.01(1H, s), 15.18(1H, brs)
MS (ESI): M+ 420

EXAMPLE 1-22

¹H NMR (DMSO-d₆ 300 MHz) (δ) ppm: 4.32(2H, s), 6.16 (2H, s), 7.32-7.42(4H, m), 7.51-7.55(2H, m), 7.77-7.89(3H, m), 8.06-8.12(2H, m), 9.31(1H, s), 15.02(1H, brs)
MS (ESI): M+ 494

EXAMPLE 1-23

¹H NMR (DMSO-d₆ 300 MHz) (δ) ppm: 4.31(2H, s), 5.83 (2H, s), 7.19-7.21(1H, m), 7.33-7.43(2H, m), 7.54-7.59(2H, m), 7.68-7.79(3H, m), 8.12(1H, s), 9.25(1H, s), 15.05(1H, brs)
MS (ESI): M+ 508

EXAMPLE 1-24

¹H NMR (DMSO-d₆ 400 MHz) (δ) ppm: 2.18(6H, s), 2.64 (2H, br), 4.36(2H, s), 4.63(2H, br), 7.38-7.40(1H, m), 7.45 (1H, d, J=1.3 Hz), 7.56-7.58(1H, m), 7.84(1H, m), 8.00(1H, d, J=8.9 Hz), 8.14(1H, d, J=1.7 Hz), 8.90(1H, s), 15.15(1H, brs)
MS (ESI): M+ 419

EXAMPLE 1-25

¹H NMR (DMSO-d₆ 400 MHz) (δ) ppm: 1.93-1.98(2H, m), 3.45(2H, t, J=5.6 Hz), 4.36(2H, s), 4.59(2H, t, J=7.0 Hz), 4.68(1H, br), 7.37(1H, dd, J=7.7, 7.8 Hz), 7.44-7.468(1H, m), 7.57(1H, d, J=7.8 Hz), 7.83-7.99(1H, m), 8.00(1H, d, J=8.9 Hz), 8.14(1H, s), 8.96(1H, s), 15.16(1H, brs)
MS (ESI): M+ 406

EXAMPLE 1-26

¹H NMR (DMSO-d₆ 300 MHz) (δ) ppm: 3.21(3H, s), 3.70 (2H, t, J=4.8 Hz), 4.36(2H, s), 4.75(2H, t, J=4.8 Hz), 7.38(1H, dd, J=7.7, 7.7 Hz), 7.44-7.47(1H, m), 7.58(1H, dd, J=1.6, 7.8 Hz), 7.83(1H, dd, J=2.1, 8.9 Hz), 8.04(1H, d, J=8.9 Hz), 8.14(1H, d, J=2.0 Hz), 8.89(1H, s), 15.14(1H, brs)
MS (ESI): M+ 406

EXAMPLE 1-27

¹H NMR (DMSO-d₆ 300 MHz) (δ) ppm: 4.36(2H, s), 5.68 (2H, q, J=8.7 Hz), 7.38(1H, dd, J=7.7, 7.7 Hz), 7.46(1H, dd, J=1.7, 7.7 Hz), 7.89(1H, dd, J=2.1, 8.9 Hz), 8.13-8.16(2H, m), 9.11(1H, s), 14.71(1H, brs)
MS (ESI): M+ 430

EXAMPLE 1-28

¹H NMR (DMSO-d₆ 300 MHz) (δ) ppm: 4.34(2H, s), 4.78 (2H, s), 7.34-7.44(2H, m), 7.55-7.57(1H, m), 7.69(1H, d, J=8.7 Hz), 7.76(1H, d, J=9.0 Hz), 8.09(1H, s), 8.85(1H, s), 15.37(1H, brs)
MS (ESI): M+ 406

EXAMPLE 1-29

¹H NMR (DMSO-d₆ 400 MHz) (δ) ppm: 2.04(3H, s), 3.27-3.38(2H, m), 4.37(2H, s), 4.78(2H, t, J=6.8 Hz), 7.37-7.39 (1H, m), 7.45-7.47(1H, m), 7.58-7.61(1H, m), 7.85-7.87(1H, m), 8.03-8.05(1H, m), 8.15(1H, s), 8.73(1H, s), 8.81(1H, s)
MS (ESI): M+ 473

EXAMPLE 1-30

¹H NMR (DMSO-d₆ 300 MHz) (δ) ppm: 1.20(3H, d, J=6.2 Hz), 3.96(1H, br), 4.15-4.23(1H, m), 4.36(2H, s), 4.65-4.69 (1H, m), 5.02(1H, br), 7.37(1H, dd, J=7.7, 8.0 Hz), 7.45(1H, d, J=6,6 Hz), 7.57(1H, d, J=8.1 Hz), 7.81(1H, d, J=8.8 Hz), 8.03(1H, d, J=9.1 Hz), 8.13(1H, s), 8.84(1H, s)
MS (ESI): M+ 406

EXAMPLE 1-31

$^1$H NMR (DMSO-d$_6$ 300 MHz) (δ) ppm: 3.75 (2H, m), 4.19 (2H, s), 4.61 (2H, m), 5.00 (1H, br), 7.27-7.40 (4H, m), 7.86 (1H, m), 8.02 (1H, m), 8.26 (1H, m), 8.86 (1H, s), 15.29 (1H, s)
MS (ESI): M+357

EXAMPLE 1-32

$^1$H NMR (DMSO-d$_6$ 400 MHz) (δ) ppm: 2.10(3H, s), 2.95 (2H, t, J=6.6 Hz), 4.37(2H, s), 4.76(2H, t, J=6.6 Hz), 7.38(1H, dd, J=7.7, 7.8 Hz), 7.45-7.47(1H, m), 7.58(1H, dd, J=1.5, 7.9 Hz), 7.90(1H, dd, J=2.0, 8.9 Hz), 8.00(1H, d, J=8.9 Hz), 8.15(1H, d, J=1.8 Hz), 9.02(1H, s), 15.12(1H, brs)
MS (ESI): M+ 422

EXAMPLE 1-33

$^1$H NMR (DMSO-d$_6$ 400 MHz) (δ) ppm: 3.75(2H, s), 4.33 (2H, s), 4.60(2H, t, J=4.8 Hz), 4.98(1H, br), 7.30-7.33(1H, m), 7.39-7.42(2H, m), 7.80(1H, dd, J=1.7, 8.9 Hz), 8.02(1H, d, J=8.9 Hz), 8.09(1H, s), 8.85(1H, s), 15,14(1H, brs)
MS (ESI): M+ 375

EXAMPLE 1-34

$^1$H NMR (DMSO-d$_6$ 300 MHz) (δ) ppm: 1.33-1.44(4H, m), 1.75-1.81(2H, m), 3.36-3.38(2H, m), 4.54(2H, t, J=7.2 Hz), 7.38(1H, dd, J=7.7, 7.7 Hz), 7.46(1H, d, J=6.1 Hz), 7.57(1H, d, J=7.8 Hz), 7.83(1H, d, J=8.7 Hz), 8.00(1H, d, J=8.9 Hz), 8.14(1H, d), 9.01(1H, s), 15.19(1H, brs)
MS (ESI): M+ 434

EXAMPLE 1-35

$^1$H NMR (DMSO-d$_6$ 400 MHz) (δ) ppm: 2.33-2.45(4H, br), 2.64(2H, t, J=6.2 Hz), 3.52(2H, t, J=4.4 Hz), 4.27(2H, s), 4.40(2H, br), 7.34-7.42(2H, m), 7.55-7.60(2H, m), 7.71(1H, d, J=8.6 Hz), 8.04(1H, s), 8.57(1H, s)
MS (ESI): M+ 461

EXAMPLE 1-36

$^1$H NMR (DMSO-d$_6$ 300 MHz) (δ) ppm: 4.08(3H, s), 4.37 (2H, s), 7.37(1H, dd, J=7.7, 7.7 Hz), 7.44-7.46(1H, m), 7.57 (1H, dd, J=1.7, 7.8 Hz), 7.84-7.87(1H, m), 7.92(1H, d, J=8.8 Hz), 8.12(1H, s), 9.01(1H, s), 15.20(1H, brs)
MS (ESI): M+ 362

EXAMPLE 1-37

$^1$H NMR (DMSO-d$_6$ 400 MHz) (δ) ppm: 1.41(3H, t, J=7.1 Hz), 4.36(2H, s), 4.58(2H, q, J=7.1 Hz), 7.38(1H, dd, J=7.8, 7.7 Hz), 7.44-7.46(1H, m), 7.57(1H, dd, J=1.5, 7.9 Hz), 7.83 (1H, dd, J=2.1, 8.8 Hz), 8.01(1H, d, J=8.8 Hz), 8.14(1H, s), 9.02(1H, s), 15.18(1H, brs)
MS (ESI): M+ 376

EXAMPLE 1-38

$^1$H NMR (DMSO-d$_6$ 300 MHz) (δ) ppm: 0.90(3H, t, J=7.3 Hz), 1.77-1.85(2H, m), 4.36(2H, s), 4.51(2H, t, J=7.3 Hz), 7.38(1H, dd, J=7.8, 7.6 Hz), 7.44-7.46(1H, m), 7.58(1H, dd, J=1.7, 7.8 Hz), 7.83(1H, dd, J=2.1, 8.8 Hz), 8.02(1H, d, J=8.9 Hz), 8.14(1H, d, J=2.0 Hz), 9.02(1H, s), 15.18(1H, brs)
MS (ESI): M+ 390

EXAMPLE 1-39

$^1$H NMR (DMSO-d$_6$ 300 MHz) (δ) ppm: 0.90(3H, t, J=7.3 Hz), 1.30-1.37(2H, m), 1.74-1.79(2H, m), 4.36(2H, s), 4.54 (2H, t, J=7.3 Hz), 7.38(1H, dd, J=7.6, 7.8 Hz), 7.46(1H, dd, J=1.7, 7.6 Hz), 7.58(1H, dd, J=1.7, 7.8 Hz), 7.83(1H, dd, J=2.1, 8.9 Hz), 8.00(1H, d, J=8.9 Hz), 8.14(1H, d, J=2.0 Hz), 9.01(1H, s), 15.18(1H, brs)
MS (ESI): M+ 404

EXAMPLE 1-40

$^1$H NMR (DMSO-d$_6$ 400 MHz) (δ) ppm: 1.27-1.29(2H, m), 1.47-1.50(2H, m), 1.59-1.66(4H, m), 2.31-2.40(1H, m), 4.36(2H, s), 4.51(2H, d, J=7.6 Hz), 7.38-7.47(2H, m), 7.57 (1H, dd, J=1.5, 7.8 Hz), 7.82(1H, dd, J=2.0, 8.8 Hz), 8.05(1H, d, J=8.9 Hz), 8.14(1H, d, J=1.8 Hz), 9.028(1H, s), 15.16(1H, brs)
MS (ESI): M+ 430

EXAMPLE 1-41

$^1$H NMR (DMSO-d$_6$ 300 MHz) (δ) ppm: 3.11(3H, s) 3.77 (2H, t), 4.37(2H, s), 4.99(2H, t), 7.35-7.41(1H, m), 17.47(1H, d), 7.58(1H, d, J=7.8 Hz), 7.83-7.92(2H, m), 8.16(1H, s), 9.05(1H, s)
MS (ESI): M+ 454

EXAMPLE 1-42

$^1$H NMR (DMSO-d$_6$ 300 MHz) (δ) ppm: 1.10(4H, br), 1.54-1.65(4H, br), 1.83(1H, br), 4.36(2H, s), 4.40(2H, d, J=7.4; Hz), 7.38(1H, dd, J=7.7, 7.8 Hz), 7.45-7.48(1H, m), 7.58(1H, dd, J=1.6, 7.8 Hz), 7.81-7.84(1H, m), 8.02(1H, d, J=8.9 Hz), 8.13(1H, s), 8.93(1H, s), 15.17(1H, brs)
MS (ESI): M+ 444

EXAMPLE 1-43

$^1$H NMR (DMSO-d$_6$ 300 MHZ) (δ) ppm: 4.37(2H, s), 4.49-4.56(1H, m), 4.77-4.82(1H, m), 4.91-4.97(1H, m), 5.81 (1H, d, J=4.7 Hz), 7.30-760(8H, m), 7.81(1H, d, J=11.0 Hz), 8.08(1H, d, J=8.9 Hz), 8.17(1H, d), 8.93(1H, s), 15.19(1H, brs)
MS (ESI): M+ 468

EXAMPLE 1-44

$^1$H NMR (DMSO-d$_6$ 300 MHz) (δ) ppm: 4.37(2H, s), 4.72-4.76(1H, m), 4.92(2H, t, J=4.6 Hz), 4.98-5.01(1H, m), 7.38 (1H, dd, J=7.8, 8.1 Hz), 7.44-7.46(1H, m), 7.58(1H, dd, J=1.6, 7.9 Hz), 7.84(1H, dd, J=2.1, 9.0 Hz), 8.03(1H, d, J=9.3 Hz), 8.15(1H, d, J=1.8 Hz), 8.78(1H, s), 8.98(1H, s)
MS (ESI): M+ 394

EXAMPLE 1-45

$^1$H NMR (DMSO-d$_6$ 300 MHz) (δ) ppm: 3.21(2H, br), 4.27(2H, s), 4.65(2H, br), 7.20-7.28(2H, m), 7.33-7.41(2H, m), 7.54-7.70(5H, m), 7.77(1H, d, J=8.7 Hz), 8.05(1H, s), 8.50(1H, s), 8.52(1H, s)
MS (ESI): M+ 453

EXAMPLE 1-46

$^1$H NMR (DMSO-$d_6$ 300 MHz) (δ) ppm: 2.93(2H, t), 4.35 (2H, s), 4.48(2H, s), 7.38(1H, dd, J=7.7, 7.7 Hz), 7.45(1H, d, J=6.2 Hz), 7.57(1H, d, J=7.7 Hz), 7.82(1H, d), 8.02(1H, d, J=9.1 Hz), 8.13(1H, s), 8.92(1H, s)

MS (ESI): M+ 391

EXAMPLE 1-47

$^1$H NMR (DMSO-$d_6$ 300 MHz) (δ) ppm: 1.13(6H, s), 4.35 (2H, s), 4.50(2H, s), 4.90(1H, brs), 7.35-7.46(2H, m), 7.57 (1H, d, J=7.7 Hz), 7.78(1H, d, J=7.1 Hz), 8.10(1H, s), 8.19 (1H, d, J=9.0 Hz), 8.88(1H, s), 15.22(1H, brs)

MS (ESI): M+ 420

EXAMPLE 1-48

$^1$H NMR (DMSO-$d_6$ 300 MHz) (δ) ppm: 1.68(3H, s), 3.46 (2H, br) 4.36(2H, s), 4.56(2H, br), 7.38-7.60(3H, m), 7.81-8.13(4H, m), 8.80(1H, s)

MS (ESI): M+ 433

EXAMPLE 1-49

$^1$H NMR (DMSO-$d_6$ 300 MHz) (δ) ppm: 1.00(3H, t, J=7.0 Hz), 3.41(2H, br), 3.82(2H, q), 4.36(2H, s), 4.57(2H, br), 7.24(1H, m), 7.38(1H, m), 7.46(1H, m), 7.58(1H, m), 7.83 (1H, m), 8.03(1H, m), 8.13(1H, s), 8.82(1H, s)

MS (ESI): M+ 463

EXAMPLE 1-50

$^1$H NMR (DMSO-$d_6$ 300 MHz) (δ) ppm: 3.75(2H, m), 4.26(2H, s), 4.61(2H, t, J=4.8 Hz), 5.00(1H, br), 7.17-7.36 (3H, m), 7.83(1H, dd, J=2.0, 8.8 Hz), 8.03(1H, d, J=8.9 Hz), 8.21(1H, s), 8.87(1H, s), 15.22(1H, brs)

MS (ESI): M+ 360

EXAMPLE 1-51

$^1$H NMR (DMSO-$d_6$ 300 MHz) (δ) ppm: 3.75(2H, m), 4.28(2H, s), 4.61(2H, t, J=4.8 Hz), 5.00(1H, br), 7.24-7.28 (1H, m), 7.44-7.55(2H, m), 7.80(1H, dd, J=2.1, 8.8 Hz), 8.02(1H, d, J=8.9 Hz), 8.13(1H, d, J=1.9 Hz), 8.86(1H, s), 15.22(1H, s)

MS (ESI): M+ 376

EXAMPLE 1-52

$^1$H NMR (CDCl$_3$ 300 MHz) (δ) ppm: 1.42(3H, t, J=7.1 Hz), 4.05(2H, s), 4.40(2H, q, J=7.1 Hz), 5.35(2H, s), 7.13-7.28(8H, m), 7.33-7.35(2H, m), 8.41(1H, d, J=2.0 Hz), 8.58 (1H, s)

MS (ESI): M+ 398

EXAMPLE 1-53

$^1$H NMR (CDCl$_3$ 300 MHz) (δ) ppm: 4.10(2H, s), 5.48(2H, s), 7.13-7.50(12H, m), 8.41(1H, d, J=1.9 Hz), 8.87(1H, s), 14.96(1H, brs)

MS (ESI): M+ 370

EXAMPLE 1-54

$^1$H NMR (DMSO-$d_6$ 300 MHz) (δ) ppm: 4.16(2H, s), 5.44 (2H, s), 7.19-7.34(5H, m), 7.74(1H, d, J=8.8 Hz), 7.83(1H, dd, J=2.0, 8.9 Hz), 8.22(1H, d, J=1.9 Hz), 9.08(1H, s), 13.58 (1H, brs), 15.13(1H, brs)

MS (ESI): M+ 338

EXAMPLE 1-55

$^1$H NMR (DMSO-$d_6$ 300 MHz) (δ) ppm: 0.89(3H, t, J=7.3 Hz), 1.25-1.35(5H, m), 1.66-1.76(2H, m), 4.09(2H, s), 4.21 (2H, q, J=7.1 Hz), 4.34(2H, t, J=7.2 Hz), 7.20-7.33(5H, m), 7.66(1H, dd, J=2.1, 8.7 Hz), 7.74(1H, d, J=8.7 Hz), 8.06(1H, d, J=1.9 Hz), 8.64(1H, s)

MS (ESI): M+ 364

EXAMPLE 1-56

$^1$H NMR (CDCl$_3$ 300 MHz) (δ) ppm: 0.99(3H, t, J=7.3 Hz), 1.43(2H, m), 1.84-1.94(2H, m), 4.15(2H, s), 4.28(2H, t, J=7.4 Hz), 7.20-7.34(5H, m), 7.52(1H, d, J=8.8 Hz), 7.65(1H, dd, J=2.1, 8.8 Hz), 8.42(1H, d, J=1.9 Hz), 8.72(1H, s), 15.04 (1H, brs)

MS (ESI): M+ 336

EXAMPLE 1-57

$^1$H NMR (CDCl$_3$ 300 MHz) (δ) ppm: 1.41(3H, t, J=7.2 Hz), 3.85(3H, s), 4.11(2H, s), 4.39(2H, q, J=7.2 Hz), 7.17-7.35(6H, m), 7.51(1H, dd, J=2.4, 8.4 Hz), 8.42(1H, d, J=1.8 Hz), 8.45(1H, s)

MS (ESI): M+ 322

EXAMPLE 1-58

$^1$H NMR (CDCl$_3$ 300 MHz) (δ) ppm: 3.99(3H, s), 4.16(2H, s), 7.19-7.33(5H, m), 7.52(1H, d, J=8.7 Hz), 7.68(1H, dd, J=2.0, 8.7 Hz), 8.41(1H, s), 8.72(1H, s)

MS (ESI): M+ 294

EXAMPLE 1-59

$^1$H NMR (DMSO-$d_6$ 400 MHz) (δ) ppm: 2.08-2.15(2H, m), 2.69(2H, t, J=7.8 Hz), 4.16(2H, s), 4.57(2H, t, J=7.3 Hz), 7.15-7.31(10H, m), 7.81(1H, dd, J=2.0, 8.8 Hz), 7.92(1H, d, J=8.8 Hz), 8.20(1H, d, J=1.9 Hz), 8.96(1H, s), 15.21(1H, brs)

MS (ESI): M+ 398

EXAMPLE 1-60

$^1$H NMR (DMSO-$d_6$ 400 MHz) (δ) ppm: 3.11(2H, t, J=7.3 Hz), 4.18(2H, s), 4.77(2H, t, J=7.4 Hz), 7.19-7.35(10H, m), 7.86(1H, d, J=8.7 Hz), 8.06(1H, d, J=8.8 Hz), 8.22(1H, s), 8.76(1H, s), 15.14(1H, brs)

MS (ESI): M+ 384

EXAMPLE 1-61

$^1$H NMR (DMSO-$d_6$ 300 MHz) (δ) ppm: 1.99-2.03(2H, m), 2.37(2H, t, J=7.1 Hz), 4.17(2H, s), 4.54(2H, t, J=7.3 Hz), 7.21-7.34(5H, m), 7.87(1H, dd, J=2.0, 8.8 Hz), 8.05(1H, d, J=8.8 Hz), 8.21(1H, d, J=1.9 Hz), 8.98(1H, s), 12.01(1H, brs), 15.28(1H, brs)

MS (ESI): M+ 366

EXAMPLE 1-62

$^1$H NMR (DMSO-$d_6$ 300 MHz) (δ) ppm: 4.15(2H, s), 5.48 (2H, s), 7.06-7.10(1H, m), 7.20-7.22(1H, m), 7.28-7.34(6H, m), 7.56-7.58(2H, m), 7.74(1H, d, J=8.8 Hz), 7.848.9 Hz), 8.23(1H, s), 9.10(1H, s), 10.63(1H, brs), 15.18(1H, brs)

MS (ESI): M+ 413

EXAMPLE 1-63

¹H NMR (DMSO-d₆ 300 MHz) (δ) ppm: 3.72 (2H, m), 4.26 (2H, s), 4.35 (2H, m), 5.23 (1H, br), 7.32-7.41 (2H, m), 7.53-7.58 (2H, m), 7.72 (1H, m), 8.05 (1H, s), 8.63 (1H, s)
MS (ESI): M+391

EXAMPLE 1-64

¹H NMR (DMSO-d₆ 300 MHz) (δ) ppm: 3.72 (2H, m), 4.23 (2H, s), 4.35 (2H, m), 5.24 (1H, br), 7.25-7.40 (3H, m), 7.57 (1H, m), 7.72 (1H, m), 8.03 (1H, s), 8.63 (1H, s)
MS (ESI): M+375

EXAMPLE 1-65

¹H NMR (DMSO-d₆ 400 MHz) (δ) ppm: 3.12 (2H, t, J=7.3 Hz), 4.31 (2H, s), 4.78 (2H, t, J=7.3 Hz), 7.20-7.36 (7H, m), 7.46-7.48 (2H, m), 7.86 (1H, m), 8.09 (1H, m), 8.15 (1H, s), 8.78 (1H, s), 15.08 (1H, brs)
MS (ESI): M+417

EXAMPLE 1-66

¹H NMR (DMSO-d₆ 300 MHz) (δ) ppm: 3.79 (2H, m), 4.39 (2H, s), 4.65 (2H, m), 5.04 (1H, m), 7.31-7.47 (3H, m), 7.88 (1H, m), 8.07 (1H, m), 8.19 (1H, m), 8.90 (1H, s), 15.25 (1H, s)
MS (ESI): M+375

EXAMPLE 1-67

¹H NMR (DMSO-d₆ 300 MHz) (δ) ppm: 3.74 (2H, m), 4.35 (2H, s), 4.62 (2H, m), 5.00 (1H, br), 7.62 (1H, m), 7.81 (1H, m), 7.90 (1H, m), 8.02-8.13 (2H, m), 8.23 (1H, m), 8.32 (1H, m), 8.87 (1H, s)
MS (ESI): M+368

EXAMPLE 1-68

¹H NMR (DMSO-d₆ 300 MHz) (δ) ppm: 2.09 (3H, s), 4.35 (2H, s), 5.75 (2H, s), 7.37 (1H, m), 7.44 (1H, m), 7.55 (1H, m), 7.83 (1H, m), 8.01 (1H, m), 8.12 (1H, m), 9.10 (1H, s)
MS (ESI): M+407

EXAMPLE 1-69

¹H NMR (DMSO-d₆ 300 MHz) (δ) ppm: 3.20 (3H, s) 4.36 (2H, s), 6.22 (2H, s), 7.36-7.47 (2H, m), 7.58 (1H, m), 7.86 (1H, m), 8.12-8.15 (2H, m), 9.04 (1H, s)
MS (ESI): M+439

EXAMPLE 1-70

¹H NMR (DMSO-d₆ 300 MHz) (δ) ppm: 1.22 (9H, s), 4.36 (2H, s), 5.99 (2H, s), 7.35-7.46 (3H, m), 7.58 (1H, m), 7.84 (1H, m), 8.08-8.11 (2H, m), 8.95 (1H, s), 14.75 (1H, br)
MS (ESI): M+496

EXAMPLE 1-71

¹H NMR (DMSO-d₆ 300 MHz) (δ) ppm: 2.62 (3H, d, J=4.7 Hz), 4.36 (2H, s), 6.11 (2H, s), 7.36-7.47 (2H, m), 7.54-7.60 (2H, m), 7.84 (1H, m), 8.10-8.13 (2H, m), 8.98 (1H, s), 14.79 (1H, br)
MS (ESI): M+454

EXAMPLE 1-72

¹H NMR (DMSO-d₆ 300 MHz) (δ) ppm: 2.77 (6H, s), 4.37 (2H, s), 6.20 (2H, s), 7.39 (1H, dd, J=7.8, 7.8 Hz), 7.47 (1H, dd, J=1.7, 7.8 Hz), 7.59 (1H, dd, J=1.7, 7.8 Hz), 7.89 (1H, m), 8.11-8.14 (2H, m), 9.04 (1H, s), 14.69 (1H, br)
MS (ESI): M+468

EXAMPLE 1-73

¹H NMR (DMSO-d₆ 300 MHz) (δ) ppm: 3.75 (2H, br), 4.36 (2H, s), 4.60 (2H, m), 5.00 (1H, br), 7.39-7.49 (2H, m), 7.82 (1H, m), 8.04 (1H, m), 8.11 (1H, s), 8.87 (1H, s), 15.14 (1H, brs)
MS (ESI): M+393

EXAMPLE 1-74

¹H NMR (DMSO-d₆ 300 MHz) (δ) ppm: 3.41 (1H, m), 3.51 (1H, m) 3.82 (1H, m), 4.26 (1H, m), 4.36-(2H, s), 4.79 (1H, m), 4.93 (1H, m), 5.19 (1H, m), 7.38 (1H, m), 7.46 (1H, m), 7.58 (1H, m), 7.84 (1H, m), 7.97 (1H, m), 8.15 (1H, m), 8.84 (1H, s)
MS (ESI): M+421

EXAMPLE 1-75

¹H NMR (DMSO-d₆ 300 MHz) (δ) ppm: 4.32 (2H, s), 5.98 (2H, s), 7.31-7.43 (5H, m), 7.80 (1H, m), 8.06 (1H, m), 8.12 (1H, m), 8.99 (1H, m), 14.81 (1H, brs)
MS (ESI): M+424

EXAMPLE 1-76

¹H NMR (DMSO-d₆ 300 MHz) (δ) ppm: 2.62 (3H, d, J=4.4 Hz), 4.32 (2H, s), 6.11 (2H, s), 7.30-7.43 (3H, m), 7.53 (1H, q, J=4.4 Hz), 7.84 (1H, m), 8.06 (1H, s), 8.12 (1H, m), 8.98 (1H, m), 14.74 (1H, s)
MS (ESI): M+438

EXAMPLE 1-77

¹H NMR (DMSO-d₆ 300 MHz) (δ) ppm: 2.77 (6H, s), 4.33 (2H, s), 6.19 (2H, s), 7.27-7.44 (3H, m), 7.89 (1H, m), 8.06-8.14 (2H, m), 9.03 (1H, s), 14.64 (1H, s)
MS (ESI): M+452

EXAMPLE 1-78

¹H NMR (DMSO-d₆ 400 MHz) (δ) ppm: 3.74 (2H, dt, J=4.8, 5.6 Hz), 4.17 (2H, s), 4.60 (2H, t, J=4.8 Hz), 4.99 (1H, t, J=5.6 Hz), 7.20-7.32 (5H, m), 7.82 (1H, m), 7.99 (1H, m), 8.21 (1H, m), 8.84 (1H, s), 15.27 (1H, s)
MS (ESI): M+323

EXAMPLE 1-79

¹H NMR (DMSO-d₆ 300 MHz) (δ) ppm: 2.34 (3H, s), 3.75 (2H, br), 4.30 (2H, s), 4.61 (2H, t, J=4.7 Hz), 5.00 (1H, br), 7.21-7.31 (3H, m), 7.81 (1H, dd, J=2.0, 8.9 Hz), 8.01 (1H, d, J=8.9 Hz), 8.15 (1H, d, J=2.0 Hz), 8.86 (1H, s), 15.23 (1H, s)
MS (ESI): M+371

EXAMPLE 1-80

$^1$H NMR (DMSO-d$_6$ 300 MHz) (δ) ppm: 3.76 (2H, m), 4.31 (2H, s), 4.61 (2H, m), 5.01 (1H, m), 7.23 (1H, m), 7.36-7.47 (2H, m), 7.65 (1H, m), 7.81 (1H, m), 8.02 (1H, m), 8.14 (1H, m), 8.86 (1H, s)
MS (ESI): M+401

EXAMPLE 1-81

$^1$H NMR (DMSO-d$_6$ 300 MHz) (δ) ppm: 2.26 (3H, s), 3.75 (2H, m), 4.12 (2H, s), 4.60 (2H, m), 4.99 (1H, m), 7.10-7.18 (4H, m), 7.80 (1H, m), 7.99 (1H, m), 8.20 (1H, m), 8.85 (1H, s), 15.29 (1H, s)
MS (ESI): M+337

EXAMPLE 1-82

$^1$H NMR (DMSO-d$_6$ 400 MHz) (δ) ppm: 3.73 (2H, dt, J=4.8, 5.2 Hz), 3.84 (3H, s), 4.28 (2H, s), 4.60 (2H, t, J=4.8 Hz), 5.00 (1H, t, J=5.2 Hz), 7.04-7.07 (2H, m), 7.30 (1H, m), 7.79 (1H, m), 8.00 (1H, m), 8.11 (1H, m), 8.84 (1H, s), 15.22 (1H, s)
MS (ESI): M+387

EXAMPLE 1-83

$^1$H NMR (DMSO-d$_6$ 400 MHz) (δ) ppm: 3.75 (2H, m), 4.50 (2H, s), 4.62 (2H, m), 7.60-8.15 (5H, m), 8.35 (1H, s), 8.68 (1H, m), 8.87 (1H, s), 15.25 (1H, br)
MS (ESI): M+324

EXAMPLE. 1-84

$^1$H NMR (DMSO-d$_6$ 300 MHz) (δ) ppm: 3.75 (2H, m), 4.33 (2H, s), 4.62- (2H, m), 7.57 (2H, d, J=6.3 Hz), 7.89 (1H, dd, J=2.1, 8.7 Hz), 8.07 (1H, d, J=8.7 Hz), 8.32 (1H, d, J=2.1 Hz), 8.62 (1H, d, J=6.3 Hz), 8.88 (2H, s)
MS (ESI): M+324

EXAMPLE 1-85

$^1$H NMR (DMSO-d$_6$ 300 MHz) (δ) ppm: 3.21 (3H, s), 3.77 (2H, m), 4.61 (2H, m), 4.66 (2H, s), 5.02 (1H, m), 7.38 (1H, m), 7.55 (1H, m), 7.68 (1H, m), 7.81 (1H, m), 8.00-8.05 (2H, m), 8.19 (1H, m), 8.87 (1H, s)
MS (ESI): M+401

EXAMPLE 1-86

$^1$H NMR (DMSO-d$_6$ 300 MHz) (δ) ppm: 3.73 (2H, m), 4.15 (2H, s), 4.58 (2H, m), 5.00 (1H, m), 7.23-7.50 (10 H, m), 7.88-7.92 (2H, m), 8.83 (1H, s)
MS (ESI): M+399

EXAMPLE 1-87

$^1$H NMR (DMSO-d$_6$ 300 MHz) (δ) ppm: 3.75 (2H, m), 4.30 (2H, s), 4.61 (2H, m), 5.00 (1H, br), 7.26-7.38 (2H, m), 7.43-7.49 (2H, m), 7.82 (1H, m), 8.02 (1H, m), 8.14 (1H, m), 8.86 (1H, s), 15.32 (1H, s)
MS (ESI): M+357

EXAMPLE 1-88

$^1$H NMR (DMSO-d$_6$ 300 MHz) (δ) ppm: 3.74 (2H, m), 4.25 (2H, s), 4.60 (2H, m), 4.98 (1H, br), 7.25-7.53 (6H, m), 7.59-7.66 (3H, m), 7.87 (1H, m), 8.10 (1H, m), 8.29 (1H, m), 8.85 (1H, s), 15.30 (1H, s)
MS (ESI): M+399

EXAMPLE 1-89

$^1$H NMR (DMSO-d$_6$ 300 MHz) (δ) ppm: 3.79 (2H, m), 4.33 (2H, s), 4.64 (2H, m), 5.03 (1H, m), 7.57-7.65 (3H, m), 7.76 (1H, m), 7.91 (1H, m), 8.06 (1H, m), 8.32 (1H, m), 8.90 (1H, s), 15.31 (1H, s)
MS (ESI): M+391

EXAMPLE 1-90

$^1$H NMR (DMSO-d$_6$ 400 MHz) (δ) ppm: 1.30 (3H, t, J=6.8 Hz), 3.74 (2H, m), 3.98 (2H, q, J=6.8 Hz), 4.12 (2H, s), 4.60 (2H, m), 5.01 (1H, m), 6.76 (1H, m), 6.82-6.84 (2H, m), 7.20 (1H, m), 7.82 (1H, m), 7.99 (1H, m), 8.22 (1H, m), 8.85 (1H, s) MS (ESI): M+367

EXAMPLE 1-91

$^1$H NMR (DMSO-d$_6$ 300 MHz) (δ) ppm: 3.75 (2H, m), 4.25 (2H, s), 4.61 (2H, m), 7.53 (1H, m), 7.66-7.71 (2H, m), 7.83-7.89 (2H, m), 8.02 (1H, m), 8.28 (1H, m), 8.87 (1H, s)
MS (ESI): M+348

EXAMPLE 1-92

$^1$H NMR (DMSO-d$_6$ 400 MHz) (δ) ppm: 2.48 (3H, m), 3.74 (2H, m), 4.26 (2H, s), 4.61 (2H, m), 5.09 (1H, br), 7.19 (1H, m), 7.39 (2H, m), 7.82 (1H, m), 8.04 (1H, m), 8.13 (1H, s), 8.85 (1H, s), 15.22 (1H, s)
MS (ESI): M+403

EXAMPLE 1-93

$^1$H NMR (DMSO-d$_6$ 300 MHz) (δ) ppm: 3.75 (2H, m), 4.24 (2H, s), 4.61 (2H, m), 5.02 (1H, br), 7.38-7.47 (4H, m), 7.80 (1H, m), 8.03 (1H, m), 8.16 (1H, m), 8.86 (1H, s), 15.23 (1H, s)
MS (ESI): M+407

EXAMPLE 1-94

$^1$H NMR (DMSO-d$_6$ 300 MHz) (δ) ppm: 3.76 (2H, m), 3.99 (2H, s) 4.61 (2H, m), 5.01 (3H, m), 6.41 (3H, m), 6.93 (1H, m), 7.78 (1H, m), 8.00 (1H, m), 8.20 (1H, m), 8.86 (1H, s)
MS (ESI): M+338

EXAMPLE 1-95

$^1$H NMR (DMSO-d$_6$ 300 MHz) (δ) ppm: 1.00 (3H, s), 3.76 (2H, m), 4.13 (2H, s), 4.61 (2H, m), 5.01 (1H, m), 6.98 (1H, m), 7.23 (1H, m), 7.43 (2H, m), 7.81 (1H, m), 8.01 (1H, m), 8.21 (1H, m), 8.86 (1H, s), 9.87 (1H, s)
MS (ESI): M+380

EXAMPLE 1-96

$^1$H NMR (DMSO-d$_6$ 300 MHz) (δ) ppm: 3.73 (2H, m), 4.18 (2H, s), 4.59 (2H, m), 4.98 (1H, br), 7.26 (1H, s), 7.29 (1H, m), 7.39 (1H, m), 7.53 (1H, m), 7.99 (1H, m), 8.24 (1H, m), 8.85 (1H, s), 15.25 (1H, s)
MS (ESI): M+401

EXAMPLE 1-97

¹H NMR (DMSO-d₆ 300 MHz) (δ) ppm: 2.28 (3H, s), 3.75 (2H, m), 4.25 (2H, s), 4.61 (2H, m), 5.04 (1H, br), 7.13 (1H, s), 7.29-7.36 (2H, m), 7.81 (1H, m), 8.03 (1H, m), 8.13 (1H, s), 8.86 (1H, s), 15.24 (1H, s)
MS (ESI): M+371

EXAMPLE 1-98

¹H NMR (DMSO-d₆ 400 MHz) (δ) ppm: 2.59 (6H, s), 3.75 (2H, m), 4.33 (2H, s), 4.61 (2H, m), 5.00 (1H, m), 7.59-7.64 (3H, m), 7.73 (1H, m), 7.87 (1H, m), 8.03 (1H, m), 8.27 (1H, s), 8.86 (1H, s), 15.27 (1H, s)
MS (ESI): M+430

EXAMPLE 1-99

¹H NMR (DMSO-d₆ 300 MHz) (δ) ppm: 3.75 (2H, m), 4.26 (2H, s), 4.61 (2H, m), 5.00 (1H, br), 7.21 (1H, m), 7.38-7.51 (2H, m), 7.83 (1H, m), 8.03 (1H, m), 8.22 (1H, s), 8.87 (1H, s)
MS (ESI): M+375

EXAMPLE 1-100

¹H NMR (DMSO-d₆ 300 MHz) (δ) ppm: 3.76 (2H, m), 4.26 (2H, s), 4.61 (2H, m), 4.99 (1H, m), 7.25 (1H, m), 7.61 (1H, m), 7.81 (1H, m), 8.04 (1H, m), 8.16 (1H, m), 8.87 (1H, s), 15.16 (1H, s)
MS (ESI): M+393

EXAMPLE 1-101

¹H NMR (DMSO-d₆ 400 MHz) (δ) ppm: 3.79(2H, m), 4.01(3H, s), 4.19(2H, s), 4.64-4.65(2H, m), 5.02(1H, t, J=5.5 Hz), 7.25(1H, d, J=1.6 Hz), 7.31-7.35(2H, m), 7.56-7.58(1H, m), 7.82(1H, s), 8.78(1H, s), 15.38(1H, brs)
MS (ESI): M+ 422

EXAMPLE 1-102

¹H NMR (DMSO-d₆ 400 MHz) (δ) ppm: 1.19 (2H, m), 1.30 (2H, m), 3.83 (1H, m), 4.37 (2H, s), 7.38 (1H, m), 7.46 (1H, m), 7.57 (1H, m), 7.89 (1H, m), 8.12 (1H, m), 8.24 (1H, m), 8.73 (1H, s), 15.05 (1H, s)
MS (ESI): M+387

EXAMPLE 2-1

¹H NMR (DMSO-d₆ 300 MHz) (δ) ppm: 4.37 (2H, s), 6.88 (2H, brs), 7.35-7.47 (2H, m), 7.58 (1H, m), 7.87 (1H, dd, J=2.1, 8.9 Hz), 8.08 (1H, d, J=2.1 Hz), 8.16 (1H, d, J=8.9 Hz), 8.86 (1H, s), 15.24 (1H, brs)
MS (ESI): M+362

EXAMPLE 2-2

¹H NMR (DMSO-d₆ 400 MHz) (δ) ppm: 3.75 (3H, brs), 4.36 (2H, s), 7.35 (1H, m), 7.42 (1H, m), 7.54 (1H, m), 7.72 (1H, m), 7.85 (1H, m), 8.10 (1H, m), 9.03 (1H, s), 11.61 (1H, brs)
MS (ESI): M+420

EXAMPLE 2-3

¹H NMR (DMSO-d₆ 300 MHz) (δ) ppm: 2.16(3H, s), 4.36 (2H, s), 7.35-7.45(2H, m), 7.58(1H, dd, J=1.8, 7.8 Hz), 7.76-7.85(2H, m), 8.10(1H, s), 8.96(1H, s), 12.02(1H, brs), 14.77 (1H, brs)
MS (ESI): M+ 405

EXAMPLE 2-4

¹H NMR (DMSO-d₆ 300 MHz) (δ) ppm: 3.32 (3H, s), 4.37 (2H, s), 7.38 (1H, m), 7.46 (1H, m), 7.58 (1H, m), 7.86 (1H, m), 8.06-8.10 (2H, m), 8.82 (1H, s), 14.60 (1H, br)
MS (ESI): M+440

EXAMPLE 2-5

¹H NMR (DMSO-d₆ 300 MHz) (δ) ppm: 3.46 (3H, s), 3.53 (3H, s), 4.37 (2H, s), 7.38 (1H, dd, J=7.8, 7.8 Hz), 7.47 (1H, dd, J=2.1, 7.8 Hz), 7.58 (1H, dd, J=2.1, 7.8 Hz), 7.88 (1H, dd, J=1.8, 8.7 Hz), 7.97 (1H, d, J=8.7 Hz), 8.12 (1H, d, J=1.8 Hz), 9.11 (1H, s), 15.54 (1H, brs)
MS (ESI): M+454

EXAMPLE 2-6

¹H NMR (DMSO-d₆ 300 MHz) (δ) ppm: 2.96 (6H, s), 4.36 (2H, s), 7.38 (1H, dd, J=7.8, 7.8 Hz), 7.46 (1H, dd, J=2.0, 7.8 Hz), 7.57 (1H, dd, J=2.0, 7.8 Hz), 7.86 (1H, dd, J=2.2, 8.8 Hz), 8.12 (1H, d, J=2.2 Hz), 8.25 (1H, d, J=8.8 Hz), 9.25 (1H, s), 15.14 (1H, brs)
MS (ESI): M+390

EXAMPLE 2-7

¹H NMR (DMSO-d₆ 400 MHz) (δ) ppm: 2.84 (3H, d), 4.35(2H, s), 7.19 (1H, q), 7.38 (1H, m), 7.45 (1H, m), 7.55 (1H, m), 7.85 (1H, m), 8.09-8.11 (2H, m), 8.99 (1H, m)
MS (ESI): M+376

EXAMPLE 2-8

¹H NMR (DMSO-d₆ 300 MHz) (δ)ppm: 1.09 (3H, t, J=7.1 Hz), 3.13 (2H, dq, J=6.1, 7.1 Hz), 4.36 (2H, s), 7.19 (1H, t, J=6.1 Hz), 7.38 (1H, dd, J=7.7, 7.7 Hz), 7.46 (1H, dd, J=1.7, 7.7 Hz), 7.58 (1H, dd, J=1.7, 7.8 Hz), 7.85 (1H, dd, J=2.1, 8.8 Hz), 8.10 (1H, d, J=2.1 Hz), 8.15 (1H, d, J=8.8 Hz), 8.99 (1H, s), 15.14 (1H, brs)
MS (ESI): M+390

EXAMPLE 3-1

¹H NMR (DMSO-d₆ 300 MHz) (δ)ppm: 3.75 (2H, m), 3.79 (3H, s), 4.28 (2H, s), 4.57 (2H, m), 5.02 (1H, m), 7.17 (1H, m), 7.32 (1H, m), 7.57 (2H, m), 7.76 (1H, m), 8.83 (1H, m), 15.75(1H, s)
MS (ESI): M+421

EXAMPLE 3-2

¹H NMR (DMSO-d₆ 400 MHz) (δ) ppm: 2.24 (3H, s), 3.77 (2H, dd, J=5.2, 5.6 Hz), 4.27 (2H, s), 4.61 (2H, t, J=5.2 Hz), 5.05 (1H, t, J=5.6 Hz), 7.23 (2H, m), 7.34 (1H, m), 7.76 (1H, m), 8.03 (1H, m), 8.08 (1H, m), 8.86 (1H, s), 15.23(1H, s)
MS (ESI): M+371

EXAMPLE 3-3

¹H NMR (DMSO-d₆ 400 MHz) (δ) ppm: 3.73 (5H, s), 4.21 (2H, s), 4.61 (2H, t, J=4.8 Hz), 5.01 (1H, t, J=5.2 Hz), 5.02

(1H, m), 7.12 (1H, m), 7.25 (1H, m), 7.37 (1H, m), 7.81 (1H, m), 8.01 (1H m), 8.19 (1H, m), 8.86 (1H, s), 15.26 (1H, s)
MS (ESI): M+387

EXAMPLE 3-4

¹H NMR (DMSO-d₆ 300 MHz) (δ) ppm: 3.80 (2H, m), 4.01 (3H, s), 4.12 (2H, s), 4.65 (2H, m), 5.02 (1H, m), 7.17-7.50 (4H, m), 8.03 (1H, s), 8.81 (1H, s), 15.45 (1H, s).
MS (ESI): M+405

EXAMPLE 3-5

¹H NMR (DMSO-d₆ 300 MHz) (δ) ppm: 3.74 (2H, t), 4.17 (2H, s), 4.56 (2H, t), 5.02 (1H, br), 7.20(1H, m), 7.31 (1H, m), 7.38 (1H, m), 7.52-7.56 (2H, m), 8.86 (1H, s), 13.63 (1H, s)
MS (ESI): M+407

EXAMPLE 3-6

¹H NMR (DMSO-d₆ 400 MHz) (δ) ppm: 3.78 (2H, t), 4.18 (2H, s), 4.44-4.49 (2H, m), 5.08 (1H, t), 7.20-7.25 (2H, m), 7.34-7.40 (1H, m), 7.56 (1H, d), 7.82 (1H, s), 8.77 (1H, s), 11.10-11.30 (1H, br), 15.49 (1H, s)
MS (ESI): M+ 408

EXAMPLE 3-7

¹H NMR (DMSO-d₆ 400 MHz) (δ) ppm: 2.68 (3H, d, J=4.4 Hz), 3.74 (2H, t, J=4.8 Hz), 4.04 (2H, s), 4.60 (2H, t, J=4.8 Hz), 5.01 (1H, t), 5.27 (1H, q, J=5.2 Hz), 6.51-6.56 (2H, m), 6.95 (1H, d), 7.07-7.09 (1H, m), 7.78 (1H, d, J=9.2 Hz), 7.98 (1H, d, J=8.8 Hz), 8.21 (1H, s), 8.84 (1H, s), 15.33 (1H, s)
MS (ESI): M+ 353

EXAMPLE 3-8

¹H NMR (DMSO-d₆ 400 MHz) (δ) ppm: 2.62 (6H, s), 3.74 (2H, t), 4.24 (2H, s), 4.60 (2H, t, J=4.8 Hz), 5.01 (1H, t), 6.97-7.05 (2H, m), 7.21 (2H, m), 7.77 (1H, d, J=11.2 Hz), 7.97 (1H, d), 8.16 (1H, s), 8.85 (1H, s), 15.29 (1H, s)
MS (ESI): M+ 367

EXAMPLE 3-9

¹H NMR (DMSO-₆ 400 MHz) (δ) ppm: 4.35 (2H, s), 7.11 (1H, d, J=8.8HZ), 7.37-7.40 (1H, m), 7.44 (1H, d), 7.56 (1H, d), 7.69-7.74 (6H, m), 8.19 (1H, s), 8.68 (1H, s), 14.99 (1H, s)
MS (ESI): M+ 424

EXAMPLE 3-10

¹H NMR (DMSO-d₆ 400 MHz) (δ) ppm: 3.84-3.95 (4H, m), 4.36 (2H, s), 5.11-5.19 (3H, m), 7.38 (1H, m), 7.45 (1H, d), 7.57 (1H, d), 7.82 (1H, d, J=9.2 Hz), 8.15 (1H, d, J=8.8 Hz), 8.90 (1H, s), 15.21 (1H, s)
MS (ESI): M+ 422

EXAMPLE 3-11

¹H NMR (DMSO-d₆ 400 MHz) (δ) ppm: 3.76 (2H, t), 4.05 (2H, s), 4.59 (2H, t), 5.00 (1H, t), 6.61 (1H, d), 6.64 (1H, s), 6.70 (1H, d, J=8.0 Hz), 7.09-7.11 (1H, m), 7.81 (1H, d, J=8.8 Hz), 8.00 (1H, d, J=8.8 Hz), 8.21 (1H, s), 8.86 (1H, s), 9.30 (1H, s), 15.30 (1H, s)
MS (ESI): M+ 340

EXAMPLE 3-12

¹H NMR (DMSO-d₆ 400 MHz) (δ) ppm: 1.80-1.90 (2H, m), 2.45-2.50 (2H, m), 2.60-2.70 (2H, m), 4.36 (2H, s), 5.11-5.16 (1H, m), 7.38-7.40 (1H, m), 7.45 (1H, d), 7.57 (1H, d), 7.81 (1H, d, J=8.8 Hz), 7.93 (1H, d), 8.14 (1H, s), 8.68 (1H, s), 15.16 (1H, s)
MS (ESI): M+ 402

EXAMPLE 3-13

¹H NMR (DMSO-d₆ 400 MHz) (δ) ppm: 1.70-1.90 (4H, m), 1.91-2.00 (2H, m), 2.20-2.30 (2H, m), 4.37 (2H, s), 5.20-5.30 (1H, m), 7.38-7.40 (1H, m), 7.45 (1H, d), 7.57 (1H, d), 7.86 (1H, d), 8.16 (1H, d), 8.19 (1H, s), 8.75 (1H, s), 15.16 (1H, s)
MS (ESI): M+ 416

EXAMPLE 3-14

¹H NMR (DMSO-d₆ 300 MHz) (δ) ppm: 3.70-3.80 (2H, m), 3.96 (3H, s), 4.32 (2H, s), 4.81 (2H, t), 4.90 (1H, t), 7.35-7.43 (2H, m), 7.54-7.59 (2H, m), 7.69 (1H, s), 8.69 (1H, s),15.16 (1H, s)
MS (ESI): M+ 422

EXAMPLE 3-15

¹H NMR (DMSO-d₆ 300 MHz) (δ) ppm: 2.88 (3H, s), 2.95 (3H, s), 3.70-3.80 (2H, m), 4.21 (2H, s), 4.61 (2H, t), 4.99 (1H, t), 7.20-7.23 (1H, m), 7.33 (1H, s), 7.37-7.38 (2H, dx2), 7.86 (1H, d), 8.02 (1H, d, J=8.8Hz), 8.26 (1H, s), 8.86 (1H, s), 15.30 (1H, s)
MS (ESI): M+ 395

EXAMPLE 3-16

¹H NMR (DMSO-d₆ 400 MHz) (δ) ppm: 2.71 (6H, s), 3.70-3.76 (2H, m) 4.58 (2H, s), 4.60 (2H, t, J=5.2 Hz), 5.02 (1H, t), 7.42 (1H, d), 7.51 (1H, m), 7.64 (1H, m), 7.80 (1H, d)I, 7.84 (1H, d), 8.01 (1H, d, J=8.8 Hz), 8.11 (1H, s), 8.86 (1H, s), 15.25 (1H, s)
MS (ESI): M+ 431

EXAMPLE 3-17

¹H NMR (DMSO-d₆ 400 MHz) (δ) ppm: 3.73-3.75 (2H, m), 4.24 (2H, s), 4.61 (2H, t), 5.00 (1H, t, J=5.6 Hz), 7.31 (1H, m), 7.48-7.51 (1H, m), 7.84 (1H, d), 8.02 (1H, d), 8.21 (1H, s), 8.87 (1H, s), 15.22 (1H, s)
MS (ESI): M+ 394

EXAMPLE 3-18

¹H NMR (DMSO-d₆ 300 MHz) (δ) ppm: 3.70-3.80 (2H, m), 4.56 (2H, s), 4.60 (2H, t), 5.00 (1H, t), 7.38-7.43 (2H, m), 7.52-7.54 (1H, m), 7.78 (1H, d), 7.87 (1H, d, J=7.8 Hz), 7.98 (1H, d, J=8.9 Hz), 8.11 (1H, s), 8.84 (1H, s), 12.60-13.00 (1H, br), 15.29 (1H, s)
MS (ESI): M+ 368

EXAMPLE 3-19

¹H NMR (DMSO-d₆ 400 MHz) (δ) ppm: 3.74-3.77 (2H, m), 4.58 (2H, s), 4.61 (2H, t), 5.02 (1H, t, J=5.6 Hz), 7.29 (1H, d), 7.46 (1H, m), 7.56 (1H, m), 7.70 (1H, m), 7.81 (1H, d), 7.87 (1H, d), 8.01 (1H, s), 8.18 (1H, s), 8.86 (1H, s), 15.27 (1H, s)

MS (ESI): M+ 417

EXAMPLE 3-20

$^1$H NMR (DMSO-$d_6$ 300 MHz) (δ) ppm: 1.37 (3H, t, J=6.9 Hz), 3.70-3.80 (2H, m), 4.22 (2H, s), 4.28 (2H, q, J=6.9 Hz), 4.65 (2H, t), 5.00 (1H, t), 7.30-7.34 (3H, m), 7.60 (1H, d), 7.92 (1H, s), 8.80 (1H, s), 15.44 (1H, s)

MS (ESI): M+ 436

EXAMPLE. 3-21

$^1$H NMR (DMSO-$d_6$ 400 MHz) (δ) ppm: 3.76 (2H, m), 4.40 (2H, s), 4.63 (2H, t, J=5.1 Hz), 5.02 (1H, t, J=5.6 Hz) 7.20 (1H, d, J=6.3 Hz), 7.35-7.39 (1H, m), 7.62 (1H, d, J=6.3 Hz), 8.00 (1H, s), 8.32 (1H, s), 8.89 (1H, s), 15.87 (1H, s)

MS (ESI): M+ 426

EXAMPLE 3-22

$^1$H NMR (DMSO-$d_6$ 400 MHz) (δ) ppm: 3.80 (2H, t, J=5.3 Hz), 4.48 (2H, s), 4.75 (2H, t, J=4.6 Hz), 5.06 (1H, t, J=5.6 Hz), 7.24 (1H, d, J=6.3 Hz), 7.39-7.42 (1H, m), 7.65 (1H, d, J=6.7 Hz), 7.95 (1H, s), 8.40 (1H, s), 9.00 (1H, s), 14.62 (1H, s)

MS (ESI): M+ 460

EXAMPLE 3-23

$^1$H NMR (DMSO-$d_6$ 400 MHz) (δ) ppm: 1.53 (3H, d, J=6.4 Hz), 3.76-3.83 (2H, m), 4.26 (2H, s), 5.19-5.23 (2H, m), 7.20-7.22 (1H, m), 7.41-7.49 (2H, m), 7.86 (1H, d), 8.17 (1H, d, J=8.8 Hz), 8.24 (1H, s), 8.88 (1H, s)

MS (ESI): M+ 390

EXAMPLE 3-24

$^1$H NMR (DMSO-$d_6$ 400 MHz) (δ) ppm: 1.53 (3H, d, J=6.8 Hz), 3.76-3.82 (2H, m), 4.26 (2H, s), 5.19-5.23 (2H, m), 7.22-7.24 (1H, m), 7.41-7.49 (2H, m), 7.86 (1H, d), 8.17 (1H, d, J=9.2 Hz), 8.24 (1H, s), 8.88 (1H, s)

MS (ESI): M+ 390

EXAMPLE 3-25

$^1$H NMR (DMSO-$d_6$ 400 MHz) (δ) ppm: 3.40-3.50 (2H, m), 4.34 (2H, s), 4.57 (2H, t), 4.89 (1H, t), 7.24-7.27 (1H, m), 7.45-7.51 (2H, m), 8.35 (1H, s), 8.45 (1H, s), 9.00 (1H, s), 14.30-14.40 (1H, br)

MS (ESI): M+ 444

EXAMPLE 3-26

$^1$H NMR (DMSO-$d_6$ 400 MHz) (δ) ppm: 3.84-3.96 (4H, m), 4.26 (2H, s), 5.13-5.18 (3H, m), 7.19-7.21 (1H, m), 7.40-7.48 (2H, m), 7.84 (1H, d, J=9.2 Hz), 8.15 (1H, d, J=8.8 Hz), 8.23 (1H, s), 8.90 (1H, s), 15.24 (1H, s)

MS (ESI): M+ 406

EXAMPLE 3-27

$^1$H NMR (DMSO-$d_6$ 400 MHz) (δ) ppm: 3.77 (2H, t, J=5.2 Hz), 4.53 (2H, s), 4.68 (2H, t, J=4.8 Hz), 5.01 (1H, t, J=5.16 Hz), 7.32 (1H, d, J=6.0 Hz), 7.39-7.43 (1H, m), 7.64 (1H, d, J=6.4 Hz), 8.07 (1H, s), 8.79 (1H, s), 8.96 (1H, s), 14.61 (1H, s)

MS (ESI): M+ 417

EXAMPLE 3-28

$^1$H NMR (DMSO-$d_6$ 400 MHz) (δ) ppm: 0.97 (3H, t, J=7.2 Hz), 2.58 (3H, s), 2.84 (2H, q, J=7.2 Hz), 3.77 (2H, t), 4.21 (2H, s), 4.60 (2H, t), 5.00 (1H, t), 7.00-7.02 (1H, m), 7.12 (1H, d), 7.20-7.24 (2H, m), 7.78 (1H, d, J=8.8 Hz), 7.98 (1H, d, J=8.8 Hz), 8.17 (1H, s), 8.84 (1H, s), 15.31 (1H, s)

MS (ESI): M+381

EXAMPLE 3-29

$^1$H NMR (DMSO-$d_6$ 400 MHz) (δ) ppm: 0.78 (3H, t, J=7.2 Hz), 1.42 (2H, m), 2.56 (3H, s), 2.76 (2H, t, J=6.8 Hz), 3.74 (2H, t), 4.23 (2H, s), 4.60 (2H, t, J=4.8 Hz), 5.02 (1H, t, J=5.6 Hz), 7.00-7.03 (1H, m), 7.09 (1H, d), 7.20-7.21 (2H, m), 7.77 (1H, d, J=9.2 Hz), 7.99 (1H, d, J=8.8 Hz), 8.15 (1H, s), 8.85 (1H, s), 15.30 (1H, s)

MS (ESI): M+395

EXAMPLE 3-30

$^1$H NMR (DMSO-$d_6$ 400 MHz) (δ) ppm: 2.52 (3H, s), 3.77 (2H, t, J=4.8 Hz), 4.01 (2H, s), 4.30 (2H, s), 4.61 (2H, t), 4.90-5.10 (1H, br), 7.03-7.09 (2H, m), 7.20-7.26 (7H, m), 7.76 (1H, d), 7.98 (1H, d), 8.17 (1H, s), 8.85 (1H, s), 15.30 (1H, s)

MS (ESI): M+443

EXAMPLE 3-31

$^1$H NMR (DMSO-$d_6$ 400 MHz) (δ) ppm: 2.94 (3H, s), 3.09 (3H, s), 3.75 (2H, m), 4.13-4.18 (1H, m), 4.44-4.48 (1H, m), 4.61 (2H, t), 5.02 (1H, t, J=5.6 Hz), 7.33-7.37 (3H, m), 7.52 (1H, d, J=9.2 Hz), 7.81 (1H, d), 8.01 (1H, d, J=8.8 Hz), 8.15 (1H, s), 8.86 (1H, s), 15.27 (1H, s)

MS (ESI): M+431

EXAMPLE 3-32

$^1$H NMR (DMSO-$d_6$ 400 MHz) (δ) ppm: 1.01 (6H, d), 2.52 (3H, s), 3.12-3.19 (1H, m), 3.73-3.75 (2H, m), 4.20 (2H, s), 4.60 (2H, t), 5.02 (1H, t), 7.00-7.02 (1H, m), 7.11 (1H, d), 7.19-7.22 (2H, m), 7.77 (1H, d, J=8.8 Hz), 7.98 (1H, d, J=9.2 Hz), 8.18 (1H, s), 8.84 (1H, s), 15.31 (1H, s)

MS (ESI): M+395

EXAMPLE 3-33

$^1$H NMR (DMSO-$d_6$ 400 MHz) (δ) ppm: 1.86 (9H, s), 4.26 (2H, s), 7.22-7.24 (1H, m), 7.42-7.49 (2H, m), 7.79 (1H, d, J=9.2 Hz), 8.28 (1H, s), 8.39 (1H, d, J=8.8 Hz), 8.98 (1H, s), 15.16 (1H, s)

MS (ESI): M+388

EXAMPLE 3-34

$^1$H NMR (DMSO-$d_6$ 300 MHz) (δ) ppm: 3.71 (2H, m), 3.96 (3H, s), 4.21 (2H, s), 4.81 (2H, t), 4.89 (1H, t), 7.19-7.24 (1H, m), 7.40-7.52 (3H, m), 7.77 (1H, s), 8.68 (1H, s), 15.17 (1H, s)

MS (ESI): M+406

EXAMPLE 3-35

$^1$H NMR (DMSO-d$_6$ 300 MHz) (δ) ppm: 3.75 (2H, m), 4.09 (2H, s), 4.83 (2H, t), 5.33 (1H, t), 5.81 (2H, s), 7.15 (1H, s), 7.15-7.24 (1H, m)r, 7.36 (1H, m), 7.48 (1H, m), 7.57 (1H, s), 8.77 (1H, s), 15.37 (1H, s)
MS (ESI): M+391

EXAMPLE 3-36

$^1$H NMR (DMSO-d$_6$ 400 MHz) (δ) ppm: 3.79 (2H, t), 4.60 (2H, s), 4.68 (2H, t), 5.05 (1H, t), 7.11 (1H, d, J=6.0 Hz), 7.30-7.34 (1H, m), 7.57 (1H, d, J=6.8 Hz), 8.02 (1H, s), 8.38 (1H, s), 8.95 (1H, s), 13.60-14.00 (1H, br), 14.88 (1H, s)
MS (ESI): M+436

EXAMPLE 3-37

$^1$H NMR (DMSO-d$_6$ 300 MHz) (δ) ppm: 3.70-3.72 m), 4.98 (3H, s), 4.23 (2H, s), 4.81 (2H, t), 4.89 (1H, t), 7.20-7.26 (1H, m), 7.50 (1H, s), 7.62-7.67 (2H, m), 8.68 (1H, s), 15.10 (1H, s)
MS (ESI): M+424

EXAMPLE 3-38

$^1$H NMR (DMSO-d$_6$ 300 MHz) (δ) ppm: 2.67 (6H, s), 3.39 (2H, m), 4.21 (2H, s), 4.72 (1H, t), 4.97 (2H, t), 7.20-7.22 (1H, m), 7.40-7.50 (2H, m), 7.65 (1H, s), 7.84 (1H, s), 15.10 (1H, s)
MS (ESI): M+419

EXAMPLE 3-39

$^1$H NMR (DMSO-d$_6$ 300 MHz) (δ) ppm: 2.10 (3H, s), 4.50-4.60 (2H, m), 4.23 (2H, s), 4.65 (2H, t), 5.00 (1H, t), 7.20-7.30 (1H, m), 7.40-7.50 (2H, m), 7.65 (1H, s), 8.20 (1H, s), 8.83 (1H, s), 10.20 (1H, s), 15.00 (1H, s)
MS (ESI): M+433

EXAMPLE 3-40

$^1$H NMR (DMSO-d$_6$ 300 MHz) (δ) ppm: 3.74-3.75 (2H, m), 4.55 (2H, s), 4.65 (2H, t), 5.00 (1H, t), 7.17 (1H, d, J=6.3 Hz), 7.34-7.39 (1H, m), 7.62 (1H, d, J=6.6 Hz), 7.73 (1H, d, J=9.3 Hz), 8.34 (1H, d, J=9.3 Hz), 8.97 (1H, S), 14.62 (1H, s)
MS (ESI): M+417

EXAMPLE 3-41

$^1$H NMR (DMSO-d$_6$ 400 MHz) (δ) ppm: 1.45 (3H, s), 2.97 (3H, s), 3.74-3.76 (2H, m), 4.12 (2H, s), 4.61 (2H, m), 5.03 (1H, t, J=5.6 Hz), 7.24-7.30 (1H, m), 7.30-7.39 (3H, m), 7.76 (1H, d), 8.01 (1H, d, J=8.8 Hz), 8.13 (1H, s), 8.87 (1H, s), 15.23 (1H, s)
MS (ESI): M+ 395

EXAMPLE 3-42

$^1$H NMR (DMSO-d$_6$ 400 MHz) (δ) ppm: 0.88 (6H, t, J=7.2 Hz), 2.91 (4H, q, J=6.8 Hz), 3.75 (2H, m), 4.23 (2H, s), 4.60 (2H, t), 5.02 (1H, t, J=5.6 Hz), 7.00-7.06 (1H, m), 7.14-7.25 (3H, m), 7.77 (1H, d), 7.98 (1H, d, J=8.8 Hz), 8.16 (1H, s), 8.84 (1H, s), 15.32 (1H, s)
MS (ESI): M+ 395

EXAMPLE 3-43

$^1$H NMR (DMSO-d$_6$ 400 MHz) (δ) ppm: 1.78 (6H, s), 3.99 (2H, s), 4.25 (2H, s), 4.23 (2H, s), 5.52 (1H, br), 7.20-7.22 (1H, m), 7.42-7.49 (2H, m), 7.76 (1H, d, J=9.2 Hz), 8.27 (1H, s), 8.34 (1H, d, J=9.2 Hz), 9.05 (1H, s)
MS (ESI): M+ 404

EXAMPLE 3-44

$^1$H NMR (DMSO-d$_6$ 300 MHz) (δ) ppm: 1.36 (3H, t, J=6.9 Hz), 3.70-3.80 (2H, m), 4.12 (2H, s), 4.24 (2H, q, J=7.0 Hz), 4.62 (2H, t), 5.00 (1H, t), 7.16-7.27 (3H, m), 7.40-7.50 (1H, m), 8.12 (1H, s), 8.80 (1H, s), 15.50 (1H, s)
MS (ESI): M+ 420

EXAMPLE 3-45

$^1$H NMR (DMSO-d$_6$ 300 MHz) (δ) ppm: 3.70-3.80 (2H, m), 3.84 (3H, s), 3.85 (3H,s), 4.19 (2H, s), 4.75 (2H, t), 4.92 (1H, t, J=5.6 Hz), 7.21-7.28 (2H, m), 7.45-7.50 (1H, m), 7.95 (1H, s), 8.75 (1H, s), 15.09 (1H, s)
MS (ESI): M+ 436

EXAMPLE 3-46

$^1$H NMR (DMSO-d$_6$ 300 MHz) (δ) ppm: 2.62 (3H, s), 3.74 (2H, m), 4.02 (2H, s), 4.61 (2H, t), 5.01-(1H, t), 5.50-5.60 (1H, m), 6.30-6.43 (3H, m), 6.95-7.01 (1H, m), 7.82 (1H, d), 7.99 (1H, d, J=8.8 Hz), 8.21 (1H, s), 8.85 (1H, s), 15.33 (1H, s)
MS (ESI): M+ 353

EXAMPLE 3-47

$^1$H NMR (DMSO-d$_6$ 300 MHz) (δ) ppm: 1.42 (3H, t, J=6.8 Hz), 3.70-3.80 (2H, m), 4.20-4.23 (4H, m), 4.84-5.00 (3H, m), 7.20-7.30 (1H, m), 7.40-7.49 (3H, m), 7.77 (1H, s), 8.67 (1H, s)
MS (ESI): M+ 420

EXAMPLE. 3-48

$^1$H NMR (DMSO-d$_6$ 300 MHz) (δ) ppm: 2.78 (3H, s), 3.60-3.70 (2H, m), 4.16 (2H, s), 4.75-4.79 (2H, m), 5.38 (1H, t), 6.20-6.27 (1H, m), 7.07 (1H, s), 7.20-7.23 (1H, m), 7.39-7.49 (3H, m), 8.80 (1H, s), 15.32 (1H, s)
MS (ESI): M+ 405

EXAMPLE 3-49

$^1$H NMR (DMSO-d$_6$ 400 MHz) (δ) ppm: 0.94 (3H, t, J=7.2 Hz), 1.72-1.78 (2H, m), 3.77 (2H, m), 4.13-4.14 (4H, m), 4.62 (2H, t), 5.00 (1H, br), 7.12-7.18 (2H, m), 7.26 (1H, s), 7.44-7.46 (1H, m), 8.13 (1H, s), 8.79 (1H, s), 15.49 (1H, s)
MS (ESI): M+ 434

EXAMPLE 3-50

$^1$H NMR (DMSO-d$_6$ 400 MHz) (δ) ppm: 3.00 (3H, s), 3.08 (3H, s), 3.75-3.77 (2H, m), 4.16 (2H, s), 4.57 (2H, t), 5.00 (1H, t, J=5.6 Hz), 7.09-7.18 (2H, m), 7.24 (1H, s), 7.40-7.41 (1H, m), 7.85 (1H, s), 8.01 (1H, s), 8.72 (1H, s), 15.67 (1H, s)
MS (ESI): M+ 446

EXAMPLE 3-51

$^1$H NMR (DMSO-d$_6$ 300 MHz) (δ) ppm: 3.72 (3H, s), 3.72-3.80 (2H, m), 3.95 (3H, s), 4.06 (2H, s), 4.40-4.50 (2H, m), 5.00 (1H, t), 7.12 (1H, s), 7.15-7.19 (2H, m), 7.40-7.45 (1H, m), 7.88 (1H, s), 8.51 (1H, s)
MS (ESI): M+ 420

EXAMPLE 3-52

$^1$H NMR (DMSO-d$_6$ 400 MHz) (δ) ppm: 3.77 (2H, m), 4.17 (2H, s), 4.72 (2H, t, J=4.8 Hz), 4.97 (1H, t, J=5.6 Hz), 7.08 (2H, d, J=7.6 Hz), 7.09-7.2.5 (2H, m), 7.31-7.36 (2H, m), 7.43-7.49 (3H, m), 8.04 (1H, s), 7.76 (1H, s), 15.02 (1H, s)
MS (ESI): M+ 468

EXAMPLE 3-53

$^1$H NMR (DMSO-d$_6$ 400 MHz) (δ) ppm: 1.24 (6H, d, J=7.2 Hz), 3.75 (2H, t), 4.08 (2H, s), 4.61 (2H, t), 4.99-5.04 (2H, m), 7.11-7.20 (2H, m), 7.28 (1H, s), 7.43-7.45 (1H, m), 8.17 (1H, s), 8.79 (1H, s), 15.52 (1H, s)
MS (ESI): M+ 434

EXAMPLE 3-54

$^1$H NMR (DMSO-d$_6$ 300 MHz) (δ) ppm: 0.99 (3H, t, J=7.3 Hz), 1.60-1.70 (2H, m), 3.00-3.10 (2H, m), 3.70-3.80 (12H, m), 4.15 (2H, s), 4.82 (2H, t), 5.50 (1H, t), 6.20 (1H, t), 7.08 (1H, s), 7.10-7.20 (1H, m), 7.40-7.51 (3H, m), 8.78 (1H, s), 15.30-15.40 (1H, br)
MS (ESI): M+ 433

EXAMPLE 3-55

$^1$H NMR (DMSO-d$_6$ 300 MHz) (δ) ppm: 1.24 (3H, t, J=6.9 Hz), 3.08 (2H, m), 3.71-3.80 (2H, m), 4.15 (2H, s), 4.83 (2H, t), 5.43 (1H, t), 6.21 (1H, t),+7.10 (1H, s), 7.17-7.23 (1H, m), 7.36-7.52 (3H, m), 8.78 (1H, s)
MS (ESI): M+ 419

EXAMPLE 3-56

$^1$H NMR (DMSO-d$_6$ 300 MHz) (δ) ppm: 1.53 (3H, d, J=6.8 Hz), 3.72 (2H, m), 3.99 (3H, s), 4.21 (2H, s), 5.12 (1H, t), 5.70-5.90 (1H, m), 7.20-7.21 (1H, m), 7.40-7.55 (3H, m), 7.76 (1H, s), 8.85 (1H, s), 15.00-15.20 (1H, br)
MS (ESI): M+ 420

EXAMPLE 3-57

$^1$H NMR (DMSO-d$_6$ 300 MHz) (δ) ppm: 1.52 (3H, d, J=6.8 Hz), 3.71 (2H, t), 4.00 (3H, s), 4.23 (2H, s), 5.10 (1H, t), 5.80-5.90 (1H, m), 7.20-7.30 (1H, m), 7.51 (1H, s), 7.60-7.67 (2H, m), 8.85 (1H, s), 14.90-15.10 (1H, br)
MS (ESI): M+ 438

EXAMPLE 3-58

$^1$H NMR (DMSO-d$_6$ 400 MHz) (δ) ppm: 1.03 (3H, d, J=8.4 Hz), 1.78-1.87 (2H, m), 3.73-3.75 (2H, m), 4.12 (2H, t), 4.20 (2H, s), 4.85 (2H, t), 4.92 (1H, t), 7.20 (1H, m), 7.39-7.51 (3H, m), 7.76 (1H, s), 8.68 (1H, s), 15.17 (1H, s)
MS (ESI): M+ 434

EXAMPLE 3-59

$^1$H NMR (DMSO-d$_6$ 400 MHz) (δ) ppm: 1.35 (6H, s), 3.72-3.75 (2H, m), 4.20 (2H, s), 4.83-4.91 (4H, m), 7.20 (1H, m), 7.39-7.49 (3H, m), 7.74 (1H, s), 8.66 (1H, s), 15.18 (1H, s)
MS (ESI): M+ 434

EXAMPLE 3-60

$^1$H NMR (DMSO-d$_6$ 300 MHz) (δ) ppm: 0.86 (3H, t, J=7.3 Hz), 1.80-2.10 (2H, m), 3.70-3.90: (2H, m), 4.26 (2H, s), 5.00-5.10 (1H, m), 5.17 (1H, t, J=5.4 Hz), 7.19-7.24 (1H, m), 7.39-7.51 (2H, m), 7.84 (1H, d, J=8.8 Hz), 8.20 (1H, d, J=8.8 Hz), 8.23 (1H, s), 8.86 (1H, s), 15.24 (1H, s)
MS (ESI): M+ 404

EXAMPLE 3-61

$^1$H NMR (DMSO-d$_6$ 300 MHz) (δ) ppm: 1.36 (3H, t, J=6.9 Hz), 1.52 (3H, d, J=6.6 Hz), 3.78-3.80 (2H, m), 4.12 (2H, s), 4.26 (2H, q, J=7.0 Hz), 5.21-5.30 (2H, m), 7.16-7.24 (2H, m), 7.40-7.46 (2H, m), 8.14 (1H, s), 8.81 (1H, s), 15.40-15.60 (1H, br)
MS (ESI): M+ 434

EXAMPLE 3-62

$^1$H NMR (DMSO-d$_6$ 300 MHz) (δ) ppm: 2.88 (6H, s), 3.70-3.80 (2H, m), 4.22 (2H, s), 4.60-4.70 (2H, m), 5.05 (1H, t), 7.20-7.31 (3H, m), 7.50-7.60 (1H, m), 7.80 (1H, s), 8.78 (1H, s), 15.30-15.40 (1H, br)
MS (ESI): M+ 419

EXAMPLE 3-63

$^1$H NMR (DMSO-d$_6$ 400 MHz) (δ) ppm: 0.90-1.29 (5H, m), 1.62-1.80 (6H, m), 3.75-3.78 (2H, m), 3.96 (2H, d, J=10.8 Hz), 4.13 (2H, s), 4.60-4.62 (2H, m), 5.02 (1H, t), 7.06-7.24 (2H, m), 7.14 (1H, s), 7.42-7.44 (1H, m), 8.16 (1H, s), 8.79 (1H, s)
MS (ESI): M+ 488

EXAMPLE 3-64

$^1$H NMR (DMSO-d$_6$ 400 MHz) (δ) ppm: 0.85-0.89 (6H, m), 2.96-3.00 (2H, m), 3.10-3.20 (2H, m), 3.33-3.40 (2H, m), 4.22 (2H, s), 4.74 (1H, t), 5.09-5.10 (2H, m), 7.20 (1H, m), 7.38-7.47 (2H, m), 7.59 (1H, s), 7.89 (1H, s), 8.72 (1H, s), 15.08 (1H, s)
MS (ESI): M+ 447

EXAMPLE 3-65

$^1$H NMR (DMSO-d$_6$ 300 MHz) (δ) ppm: 2.91 (3H, d, J=4.7 Hz), 3.75-3.81 (2H, m), 4.01 (2H, s), 4.50-4.55 (2H, m), 5.04 (1H, t, J=5.5 Hz), 6.59 (1H, s), 6.60-6.68 (1H, m), 7.15-7.24 (2H, m), 7.51-7.55 (1H, m), 7.63 (1H, s), 8.65 (1H, s), 15.90 (1H, s)
MS (ESI): M+ 405

EXAMPLE 3-66

$^1$H NMR (DMSO-d$_6$ 300 MHz) (δ) ppm: 1.91-2.00 (4H, m), 3.40-3.50 (4H, m), 3.70-3.81, (2H, m), 4.30 (2H, s), 4.50-4.55 (2 H, m), 5.05(1H, t), 6.87 (1H, s), 7.10-7.12 (1H, m), 7.18-7.21 (1H, m), 7.49-7.52 (1H, m), 7.72 (1H, s), 8.69 (1H, s), 15.65 (1H, s)
MS (ESI): M+ 445

EXAMPLE 3-67

$^1$H NMR (DMSO-d$_6$ 400 MHz) (δ) ppm: 1.44 (3H, t), 1.55 (3H, d), 3.70-3.77, (2H, m), 4.19 (2H, s), 4.28 (2H, q, J=8.8 Hz), 5.14(1H, t), 5.83-5.90 (1H, m), 7.20 (1H, m), 7.39-7.40 (1H, m), 7.48-7.50 (2H, m), 7.75 (1H, s), 8.86 (1H, s), 15.13 (1H, s)
MS (ESI): M+ 434

EXAMPLE 3-68

$^1$H NMR (DMSO-$_6$ 300 MHz) (δ) ppm: 0.86 (3H, t, J=7.3 Hz), 1.37 (3H, t, J=6.9 Hz), 1.80-2.00, (2H, m), 3.70-3.90 (2H, m), 4.12 (2H, s), 4.20-4.28 (2H, m), 5.00-5.17(2H, m), 7.14-7.30 (2H, m), 7.42-7.49 (2H, m), 8.14 (1H, s), 8.78 (1H, s),15.50 (1H, s)
MS (ESI): M+ 448

EXAMPLE 3-69

$^1$H NMR (DMSO-$_6$ 400 MHz) (δ) ppm: 1.09-1.27 (5H, m), 1.68-1.82 (6H, m), 3.71-3.73 (2H, m), 3.99 (2H, d, J=5.6 Hz), 4.20 (2H, s), 4.80-4.85 (2H, m), 4.92(1H, t, J=5.6 Hz), 7.20 (1H, m), 7.38-7.40 (1H, m), 7.40-7.53 (2H, m), 7.75 (1H, s), 8.68 (1H, s), 15.16 (1H, s)
MS (ESI): M+ 488

EXAMPLE 3-70

$^1$H NMR (DMSO-d$_6$ 400 MHz) (δ) ppm: 0.70 (3H, d, J=6.4 Hz), 1.12 (3H, d, J=6.4 Hz), 2.30-2.40 (1H, m), 3.75-3.78 (1H, m), 3.95-4.00 (1H, m), 4.25 (2H, s), 4.80-4.85 (1H, m), 5.18(1H, t), 7.20-7.21 (1H, m), 7.41-7.48 (2H, m), 7.84 (1H, d), 8.21 (1H, s), 8.25 (1H, d, J=9.2 Hz), 8.92 (1H, s),15.21 (1H, s)
MS (ESI): M+ 418

EXAMPLE 3-71

$^1$H NMR (DMSO-$_6$ 400 MHz) (δ) ppm: 0.85 (3H, d), 0.90 (3H, d), 1.40-1.50 (1H, m), 1.80-1.91 (2H, m), 3.71-3.80 (2H, m), 4.25 (2H, s), 5.15-5.20 (2H, m), 7.20-7.21 (1H, m), 7.41-7.48 (2H, m), 7.84 (1H, d, J=8.8 Hz), 8.22 (1H, s), 8.24 (1H, d, J=8.8 Hz), 8.83 (1H, s),15.20 (1H, s)
MS (ESI): M+ 432

EXAMPLE 3-72

$^1$H NMR (DMSO-d$_6$ 300 MHz) (δ) ppm: 0.86 (3H, t, J=7.3 Hz), 1.23 (6H, m), 1.80-2.00 (2H, m), 3.70-3.90 (2H, m), 4.09 (2H, s), 5.00-5.18 (3H, m), 7.12-7.21 (2H, m), 7.44-7.47 (2H, m), 8.20 (1H, s), 8.79 (1H, s),15.54 (1H, s)
MS (ESI): M+ 462

EXAMPLE 3-73

$^1$H NMR (DMSO-d$_6$ 300 MHz) (δ) ppm: 0.87 (3H, t, J=7.3 Hz), 1.80-2.10 (2H, m), 3.70-3.90 (2H, m), 4.02 (3H, s), 4.11 (2H, s), 5.00-5.19 (2H, m), 7.16-7.24 (2H, m), 7.44-7.48 (2H, m), 8.04 (1H, s), 8.78 (1H, s),15.44 (1H, s)
MS (ESI): M+ 434

EXAMPLE 3-74

$^1$H NMR (DMSO-d$_6$ 300 MHz) (δ) ppm: 1.23 (6H, d×2), 1.51 (3H, d, J=6.6 Hz), 3.77 (2H, t), 4.09 (2H, t), 4.90-5.10 (1H, m), 5.19-5.30 (2H, m), 7.12-7.21 (2H, m), 7.41-7.47 (2H, m), 8.20 (1H, s), 8.81 (1H, s), 15.55 (1H, s)
MS (ESI): M+ 448

EXAMPLE 3-75

$^1$H NMR (DMSO-d$_6$ 400 MHz) (δ) ppm: 1.00 (9H, s), 4.07-4.12 (2H, m), 4.30 (2H, s), 5.12-5.14 (2H, m), 7.20-7.25 (1H, m), 7.40-7.45 (1H, m), 7.51-7.53 (1H, m), 7.87 (1H, d), 8.25 (1H, s), 8.41 (1H, d, J=9.2 Hz), 8.85 (1H, s), 15.20-15.21 (1H, br)
MS (ESI): M+ 432

EXAMPLE 3-76

$^1$H NMR (DMSO-d$_6$ 300 MHz) (δ) ppm: 3.70-3.81 (4H, m), 4.15 (2H, s), 4.24 (2H, t, J=5.0 Hz), 4.60-4.62 (2H, m), 5.00-5.02 (2H, m), 7.15-7.20 (1H, m), 7.32-7.34 (2H, m), 7.44-7.49 (1H, m), 8.06 (1H, s), 8.79(1H, s), 15.48 (1H, s)
MS (ESI): M+ 436

EXAMPLE 3-77

$^1$H NMR (DMSO-d$_6$ 300 MHz) (δ) ppm: 1.90-1.92 (2H, m), 3.53-3.54 (2H, m), 3.70-3.80 (2H, m), 4.12 (2H, s), 4.20-4.30 (2H, m), 4.60-4.70 (3H, m), 5.02 (1H, t), 7.16-7.22 (2H, m), 7.30 (1H, s), 7.40-7.50 (1H, m), 8.11 (1H, s), 8.80 (1H, s)
MS (ESI): M+ 450

EXAMPLE 3-78

$^1$H NMR (DMSO-d$_6$ 300 MHz) (δ) ppm: 3.10-3.20 (2H, m), 3.60-3.80 (4H, m), 4.15 (2H, s), 4.78-4.85 (3H, m), 5.30-5.40 (1H, m), 6.10-6.20 (1H, m), 7.15-7.20 (2H, m), 7.30-7.52 (3H, m), 8.77 (1H, s), 15.33 (1H, s)
MS (ESI): M+ 435

EXAMPLE 3-79

$^1$H NMR (DMSO-d$_6$ 300 MHz) (δ) ppm: 0.89 (3H, t, J=7.4 Hz), 1.90-2.06 (2H, m), 3.70-3.80 (2H, m), 3.99 (3H, s), 4.22 (2H, s), 5.15 (1H, t, J=5.4 Hz), 5.70-5.80 (1H, m), 7.19-7.24 (1H, m), 7.38-7.52 (2H, m), 7.55 (1H, s), 7.77 (1H, s), 8.86 (1H, s), 15.12 (1H, s)
MS (ESI): M+ 434

EXAMPLE 3-80

$^1$H NMR (DMSO-d$_6$ 400 MHz) (δ) ppm: 1.59 (3H, d, J=7.2 Hz), 2.61 (3H, s), 2.80 (3H, s), 4.20 (2H, s), 4.96 (1H, t, J=5.6 Hz), 6.50-6.60 (1H, m), 7.19-7.23 (1H, m), 7.40-7.49 (2H, m), 7.60 (1H, s), 7.80 (1H, s), 8.81 (1H, s), 15.06 (1H, s)
MS (ESI): M+ 433

EXAMPLE 3-81

$^1$H NMR (DMSO-d$_6$ 300 MHz) (δ) ppm: 4.10-4.40 (4H, m), 5.50-5.60 (1H, m), 6.20-6.30 (1H, m), 7.19-7.22 (1H, m), 7.30-7.40 (6H, m), 7.40-7.50 (1H, m), 7.77 (1H, d), 8.00 (1H, d), 8.21 (1H, s), 9.03 (1H, s), 15.11 (1H, s)
MS (ESI): M+ 452

EXAMPLE 3-82

$^1$H NMR (DMSO-$d_6$ 400 MHz) (δ) ppm: 0.86 (3H, t), 1.18-1.34 (2H, m), 1.8.7-1.98 (2H, m), 3.73-3.84 (2H, m), 4.25 (2H, s), 5.13-5.17 (2H, m), 7.21 (1H, m), 7.41-7.48 (2H, m), 7.83 (1H, d, J=8.0 Hz), 8.19 (1H, d), 8.22 (1H, s), 8.85 (1H, s), 15.22 (1H, s)

MS (ESI): M+ 418

EXAMPLE 3-83

$^1$H NMR (DMSO-$d_6$ 300 MHz) (δ) ppm: 0.72 (3H, t, J=7.3 Hz), 0.90-1.20 (5H, m), 2.10-2.30 (1H, m), 3.70-3.80 (1H, m), 3.90-4.10 (1H, m), 4.26 (2H, s), 4.90-5.00 (1H, m), 5.10-5.20 (1H, m) 7.20-7.25 (1H, m), 7.40-7.52 (2H, m), 7.84 (1H, d, J=7.8 Hz), 8.23 (1H, s), 8.26(1H, d), 8.92 (1H, s), 15.22 (1H, s)

MS (ESI): M+ 432

EXAMPLE 3-84

$^1$H NMR (DMSO-$d_6$ 300 MHz) (δ) ppm: 1.54 (3H, d, J=6.6 Hz), 3.81-3.82 (2H, m), 4.02 (3H, s), 4.12 (2H, s), 5.22 (1H, t, J=5.4 Hz), 5.23-5.40 (1H, m), 7.15-7.26 (2H, m), 7.44-7.50 (2H, m), 8.05 (1H, s), 8.82 (1H, s), 15.46 (1H, s)

MS (ESI): M− 418

EXAMPLE 3-85

$^1$H NMR (DMSO-$d_6$ 400 MHz) (δ) ppm: 3.25-3.38 (2H, m), 3.82-3.89 (2H, m), 4.21 (2H, s), 5.27 (1H, t), 5.40-5.50 (1H, m), 7.10-7.21 (6H, m), 7.30-7.40 (1H, m), 7.40-7.50 (1H, m), 7.77 (1H, d), 8.14 (1H, d), 8.14 (1H, s), 8.96 (1H, s), 15.15 (1H, s)

MS (ESI): M+ 466

EXAMPLE 3-86

$^1$H NMR (DMSO-$d_6$ 300 MHz) (δ) ppm: 3.70-3.80 (2H, m), 4.42 (2H, s) 4.69 (2H, t), 4.95 (1H, t), 7.37-7.42 (1H, m), 7.51 (1H, d, J=6.2 Hz), 7.59 (1H, d, J=7.9 Hz), 8.48 (1H, s), 8.99 (1H, s), 9.04 (1H, s), 14.68 (1H, s)

MS (ESI): M+ 393

EXAMPLE 4-1

$^1$H NMR (DMSO-$d_6$ 400 MHz) (δ) ppm: 3.26 (3H, s), 3.74 (2H, m), 4.42 (2H, s), 4.61 (2H, m), 5.09 (1H, br), 7.78 (1H, m), 7.84 (2H, m), 8.04-8.07 (2H, m), 8.18 (1H, m), 8.86 (1H, s), 15.19 (1H, s)

MS (ESI): M+435

EXAMPLE 4-2

$^1$H NMR (DMSO-$d_6$ 300 MHz) (δ) ppm: 3.73 (2H, m), 4.23 (2H, s), 4.59 (2H, m), 4.99 (1H, br), 7.20 (1H, m), 7.31-7.34 (2H, m), 7.44 (1H, m), 7.85 (1H, m), 8.01 (1H, s), 8.26 (1H, m), 8.85 (1H, s), 15.27 (1H, s)

MS (ESI): M+407

EXAMPLE 4-3

$^1$H NMR (DMSO-$d_6$ 400 MHZ) (δ) ppm: 1.15 (3H, t, J=7.6 Hz), 2.57 (2H, q, J=7.6 Hz), 3.73 (2H, m), 4.13 (2H, s), 4.59 (2H, m), 4.99 (1H, m), 7.05 (2H, m), 7.13 (1H, m), 7.20 (1H, m), 7.81 (1H, m), 7.98 (1H, m), 8.21 (1H, s), 8.84 (1H, s), 15.28 (1H, s)

MS (ESI): M+351

EXAMPLE 4-4

$^1$H NMR (DMSO-$d_6$ 300 MHz) (δ) ppm: 1.07 (3H, t, J=7.53 Hz), 2.58 (2H, q, J=7.53 Hz), 3.76 (2H, m), 4.22 (2H, s), 4.61 (2H, m), 5.02 (1H, m), 7.19-7.23 (4H, m), 7.76 (1H, m), 8.01 (1H, m), 8.09 (1H, s), 8.86 (1H, s), 15.26 (1H, s)

MS (ESI): M+351

EXAMPLE 4-5

$^1$H NMR (DMSO-$d_6$ 300 MHz) (δ) ppm: 2.28(3H, s), 3.75 (2H, m), 4.24(2H, s), 4.61(2H, m), 5.04(1H, br), 7.13(1H, d, J=8.1 Hz), 7.28-7.36(2H, m), 7.81(1H, d, J=6.7 Hz), 8.03(1H, d, J=8.9 Hz), 8.13(1H, s), 8.86(1H, s), 15.24(1H, brs)

MS (ESI): M+ 372

EXAMPLE 4-6

$^1$H NMR (DMSO-$d_6$ 300 MHz) (δ) ppm: 3.75 (2H, m), 4.29 (2H, s), 4.62 (2H, m), 5.07 (1H, m), 7.19 (1H, m), 7.40 (1H, m), 7.52 (1H, m), 7.84 (1H, m), 8.05 (1H, m), 8.19 (1H, s), 8.87 (1H, s), 15.20 (1H, s)

MS (ESI): M+375

EXAMPLE 4-7

$^1$H NMR (DMSO-$d_6$ 400 MHz) (δ) ppm: 3.75(2H, m), 4.29(2H, s), 4.61(2H, t, J=5.0 Hz), 5.01(2H, t, J=5.4 Hz), 7.45(1H, d), 7.51(1H, d, J=11.2 Hz), 7.74(1H, d), 7.84(1H, dd), 8.01(1H, d), 8.15(1H, s), 8.86(1H, s), 15.21(1H, brs)

MS (ESI): M+ 436

EXAMPLE 4-8

EXAMPLE 4-9

$^1$H NMR (DMSO-$d_6$ 300 MHz) (δ) ppm: 3.76 (2H, m), 4.34 (2H, s), 4.59 (2H, m), 5.01 (1H, m), 7.37 (2H, m), 7.62 (1H, m), 8.07 (2H, m), 8.88 (1H, s), 14.99 (1H, s)

MS (ESI): M+409

EXAMPLE 4-10

$^1$H NMR (DMSO-$d_6$ 300 MHz) (δ) ppm: 3.20(3H, s), 3.74 (2H, m), 4.31(2H, s), 4.61(2H, t), 5.00(1H, t), 7.55-7.66(2H, m), 7.78(1H, d), 7.84-7.89(2H, m), 8.03(1H, d, J=8.9 Hz), 8.30(1H, s), 8.86(1H, s), 15.27(1H, brs)

MS (ESI): M+ 402

EXAMPLE 4-11

$^1$H NMR (DMSO-$d_6$ 400 MHz) (δ) ppm: 3.75 (2H, m), 4.18 (2H, s), 4.61 (2H, m), 5.02 (1H, m), 6.69 (1H, m), 6.77 (1H, m)), 7.23 (1H, m), 7.80 (1H, m), 8.02 (1H, m), 8.15 (1H, s), 8.86 (1H, s), 9.66 (1H, s), 15.24 (1H, s)

MS (ESI): M+373

EXAMPLE 4-12

$^1$H NMR (DMSO-$d_6$ 300 MHz) (δ) ppm: 3.75 (2H, m), 4.29 (2H, s), 4.58 (2H, m), 5.00 (1H, s), 7.31 (1H, m), 7.35 (1H, m), 7.58 (1H, m), 7.71 (1H, m), 7.82 (1H, m), 8.86 (1H, s)

MS (ESI): M+409

EXAMPLE 4-13

$^1$H NMR (DMSO-d$_6$ 400 MHz) (δ) ppm: 1.34 (3H, t, J=6.8 Hz), 3.73 (2H, m), 4.00 (2H, q, J=6.8 Hz), 4.09 (2H, s), 4.59 (2H, m), 5.00 (1H, m), 6.89 (1H, m), 6.95 (1H, m), 7.19 (1H, m), 7.27 (1H, m), 7.83 (1H, m), 7.97,(1H, m), 8.24 (1H, s), 8.84 (1H, s), 15.33 (1H, s)
MS (ESI): M+367

EXAMPLE 4-14

$^1$H NMR (DMSO-d$_6$ 400 MHz) (δ) ppm: 3.73 (2H, m), 4.06 (2H, s), 4.60 (2H, m), 5.05 (1H, m), 6.74 (1H, m), 6.85 (1H, m), 7.05 (1H, m), 7.14 (1H, m), 7.82 (1H, m), 7.99 (1H, m), 8.19 (1H, s), 8.84 (1H, s), 9.55 (1H, s), 15.34 (1H, s)
MS (ESI): M+339

EXAMPLE 4-15

$^1$H NMR (DMSO-d$_6$ 400 MHz) (δ) ppm: 2.49 (3H, s), 3.77 (2H, m), 4.27 (2H, s), 4.60 (2H, m), 5.01 (1H, s), 7.17 (1H, m), 7.35 (1H, m), 7.59 (1H, m), 7.78 (1H, s), 7.95 (1H, s), 8.81 (1H, s), 15.22 (1H, s)
MS (ESI): M+406

EXAMPLE 4-16

$^1$H NMR (DMSO-d$_6$ 400 MHz) (δ) ppm: 1.35 (3H, d), 1.40 (3H, d), 1.54 (3H, d, J=6.8 Hz), 3.72 (2H, m), 4.20 (2H, s), 4.86-4.92 (1H, m), 5.12 (1H, t, J=5.2 Hz), 5.80-5.90 (1H, m), 7.20 (1H, m), 7.39-7.52 (3H, m), 7.74 (1H, s), 8.84 (1H, s), 15.13 (1H, s)
MS (ESI): M+ 448

EXAMPLE 4-17

$^1$H NMR (DMSO-d$_6$ 400 MHz) (δ) ppm: 0.89 (3H, t, J=7.2 Hz), 1.35-1.37 (6H, d), 1.88-2.06 (2H, m), 3.73-3.79 (2H, m), 4.20 (2H, s), 4.80-5.00 (1H, m), 5.16 (1H, t), 5.81-5.84 (1H, m), 7.20 (1H, m), 7.40-7.53 (3H, m), 7.75 (1H, s), 8.83 (1H, s), 15.09 (1H, s)
MS (ESI): M+ 462

EXAMPLE 4-18

$^1$H NMR (DMSO-d$_6$ 300 MHz) (δ) ppm: 0.80-1.40 (6H, m), 1.40-1.60 (2H, m), 1.70-1.80 (1H, m), 1.80-2.10 (2H, m), 3.70-3.80 (1H, m), 3.90-4.00 (1H, m), 4.26 (2H, s), 4.80-5.00 (1H, m), 5.19 (1H, t), 7.22-7.25 (1H, m), 7.42-7.49 (2H, m), 7.85 (1H, d), 8.22 (1H, s), 8.26 (1H, d, J=9.1 Hz), 8.95 (1H, s)
MS (ESI): M+ 458

EXAMPLE 4-19

$^1$H NMR (DMSO-d$_6$ 300 MHz) (δ) ppm: 0.70 (3H, d, J=6.6 Hz), 1.14 (3H, d, J=6.4 Hz), 1.21-1.24 (6H, m), 2.20-2.40 (1H, m), 3.70-3.80 (1H, m), 3.90-4.00 (1H, m), 4.09 (2H, s), 4.80-4.90 (1H, m), 5.00-5.20 (2H, m), 7.12-7.22 (2H, m), 7.43-7.47 (2H, m), 8.19 (1H, s), 8.87 (1H, s), 15.51 (1H, s)
MS (ESI): M+ 476

EXAMPLE 4-20

$^1$H NMR (DMSO-d$_6$ 300 MHZ) (δ) ppm: 0.97 (9H, s), 1.18 (3H, d, J=5.9 Hz), 1.26 (3H, d, J=6.0 Hz), 4.04-4.09 (4H, m), 5.09-5.13 (3H, m), 7.12-7.21 (2H, m), 7.43-7.51 (2H, m), 8.19 (1H, s), 8.78 (1H, s), 15.46 (1H, s)
MS (ESI): M+ 490

EXAMPLE 4-21

$^1$H NMR (DMSO-d$_6$ 400 MHz) (δ) ppm: 0.89 (3H, t, J=7.6 Hz), 1.44 (3H, t), 1.92-2.06 (2H, m), 3.78 (2H, m), 4.19 (2H, s), 4.25 (2H, q), 5.17 (1H, t, 5.6 Hz), 5.78-5.83 (1H, m), 7.20 (1H, m), 7.39-7.51 (3H, m), 7.76 (1H, s), 8.85 (1H, s), 15.11 (1H, s)
MS (ESI): M+ 448

EXAMPLE 4-22

$^1$H NMR (DMSO-d$_6$ 300 MHz) (δ) ppm: 0.80-1.30 (6H, m), 1.50-1.80 (5H, m), 1.80-1.90 (2H, m), 3.60-3.80 (2H, m), 4.26 (2H, s), 5.10-5.20 (2H, m), 7.22 (1H, m), 7.30-7.50 (2H, m), 7.85 (1H,d), 8.23 (1H, d), 8.23 (1H, s), 8.84 (1H, s), 15.20 (1H, s)
MS (ESI): M+ 472

EXAMPLE 4-23

$^1$H NMR (DMSO-d$_6$ 400 MHz) (δ) ppm: 0.85 (3H, d), 0.91 (3H, d), 1.24-1.27 (6H, m), 1.35-1.43 (1H, m), 1.70-1.80 (1H, m), 1.91-1.95 (1H, m), 3.75-3.80 (2H, m), 4.08 (2H, s), 5.00-5.10 (1H, m), 5.16-5.19 (2H, m), 7.14-7.21 (2H, m), 7.43-7.44 (2H, m), 8.18 (1H, s), 8.79 (1H, s)
MS (ESI): M+ 490

EXAMPLE 4-24

$^1$H NMR (DMSO-d$_6$ 400 MHz) (δ) ppm: 0.72 (3H, d), 1.09 (3H, d), 1.37-1.40 (6H, m), 2.35-2.38 (1H, m), 3.77-3.79 (1H, m), 3.91-3.94 (1H, m), 4.20 (2H, s), 4.92-4.96 (1H, m), 5.23 (1H, t), 5.74-5.76 (1H, m), 7.21 (1H, m), 7.40-7.53 (3H, m), 7.75 (1H,s), 8.88 (1H, s), 15.08 (1H, s)
MS (ESI): M+ 476

EXAMPLE 4-25

$^1$H NMR (DMSO-d$_6$ 400 MHz) (4) ppm: 0.84 (3H, d, J=6.8 Hz), 0.87 (3H, d, J=6.4 Hz), 1.37 (3H, d, J=11.2 Hz), 1.42 (3H, d, J=10.8 Hz), 1.83-1.87 (2H, m), 3.79-3.80 (2H, m), 4.20 (2H, s), 4.90-4.96 (1H, m), 5.20 (1H, t) 6.08-6.10 (1H, m), 7.21 (1H, m), 7.39-7.55 (3H, m), 7.75 (1H,s), 8.78 (1H, s), 15.08 (1H, s)
MS (ESI): M+ 490

EXAMPLE 4-26

$^1$H NMR (DMSO-d$_6$ 400 MHz) (δ) ppm: 0.91 (9H, s), 1.35 (3H, d), 1.44 (3H, d), 4.02-4.03 (2H, m), 4.20 (2H, s), 4.92-4.95 (1H, m), 5.15 (1H, t), 6.43 (1H, t), 7.19-7.21 (1H, m), 7.39-7.48 (2H, m), 7.55 (1H, s), 7.79 (1H,s), 8.80 (1H, s), 15.05 (1H, s)
MS (ESI): M+ 490

EXAMPLE 4-27

$^1$H NMR (DMSO-d$_6$ 400 MHz) (δ) ppm: 0.76 (3H, t), 0.97-1.03 (2H, m), 1.12 (3H, d), 2.10-2.20 (1H, m), 3.75-3.80 (1H, m), 3.98-4.02 (1H, m), 4.02 (3H, s), 4.11 (2H, s), 4.92-4.95 (1H, m), 5.19 (1H, t), 7.16-7.25 (2H, m), 7.44-7.50 (2H, m), 8.02 (1H, s), 8.87 (1H, s), 15.40 (1H, s)
MS (ESI): M+ 462

EXAMPLE 4-28

$^1$H NMR (DMSO-$d_6$ 400 MHz) (δ) ppm: 0.74 (3H, t, J=7.6 Hz), 0.99-1.03 (2H, m), 1.11 (3H, d), 1.37 (3H, t, J=6.8 Hz), 2.10-2.20 (1H, m), 3.70-3.80 (1H, m), 3.96-4.00 (1H, m), 4.11 (2H, s), 4.26 (2H, q, J=7.2 Hz), 4.92-5.00 (1H, m), 5.18 (1H, t), 7.14-7.18 (1H, m), 7.24-7.25 (1H, m), 7.40 (1H, s), 7.44-7.46 (1H, m), 8.12 (1H, s), 8.86 (1H, s), 15.46 (1H, s)

MS (ESI): M+ 476

EXAMPLE 4-29

$^1$H NMR (DMSO-$d_6$ 300 MHz) (δ) ppm: 0.89 (3H, t, J=7.3 Hz), 1.98-2.01 (2H, m), 2.70 (3H, s), 3.80-3.90 (2H, m), 4.21 (2H, s), 5.10-5.21 (2H, m), 7.15-7.22 (2H, m), 7.49-7.51 (1H, m), 7.65 (1H, s), 8.04 (1H, S), 8.84 (1H, s), 15.25 (1H, s)

MS (ESI): M+ 450

EXAMPLE 4-30

$^1$H NMR (DMSO-$d_6$ 300 MHz) (δ) ppm: 0.70 (3H, d, J=6.5 Hz), 1.15 (3H, d, J=6.5 Hz), 1.37 (3H, t, J=6.9 Hz), 2.30-2.40 (1H, m), 3.70-3.80(1H, m), 3.90-4.00 (1H, m), 4.11 (2H, s), 4.20-4.30 (2H, m), 4.80-4.90 (1H, m), 5.18 (1H, t), 7.14-7.20 (1H, m), 7.24-7.26 (1H, m), 7.43-7.49 (2H, m), 8.13 (1H, s), 8.87 (1H, s), 15.49 (1H, s)

MS (ESI): M+ 462

EXAMPLE 4-31

$^1$H NMR (DMSO-$d_6$ 300 MHz) (δ) ppm: 0.97 (9H, s), 1.37 (3H, t, J=6.9 Hz), 4.02-4.11 (4H, m), 4.25-4.31 (2H, m), 5.10-5.20 (2H, m), 7.14-7.26 (2H, m), 7.44-7.49 (2H, m), 8.12 (1H, s), 8.78 (1H, s), 15.43 (1H, s)

MS (ESI): M+ 476

EXAMPLE 4-32

$^1$H NMR (DMSO-$d_6$ 300 MHz) (δ) ppm: 0.72 (3H, d, J=6.5 Hz), 1.16 (3H, d, J=6.5 Hz), 2.30-2.50 (1H, m), 3.70-3.90 (1H, m),3.90-4.00 (1H, m), 4.03 (3H, s), 4.12 (2H, s), 4.80-4.90 (1H, m), 5.19 (1H, t), 7.19-7.25 (2H, m), 7.46-7.51 (2H, m), 8.04 (1H, s), 8.88 (1H, s), 15.44 (1H, s)

MS (ESI): M+ 448

EXAMPLE 4-33

$^1$H NMR (DMSO-$d_6$ 300 MHz) (δ) ppm: 0.99 (9H, s), 3.99-4.11(7H, m), 5.11-5.20 (2H, m), 7.19-7.25 (2H, m), 7.49-7.52 (2H, m), 8.03 (1H, s), 8.78 (1H, s), 15.39 (1H, s)

MS (ESI): M+ 462

EXAMPLE 4-34

$^1$H NMR (DMSO-$d_6$ 300 MHz) (δ) ppm: 0.93 (9H, s), 3.90-4.03(5H, m), 4.22 (2H, s), 5.10 (1H, t), 6.20 (1H, t), 7.20-7.30 (1H, m), 7.40-7.57 (2H, m), 7.60 (1H, s), 7.79 (1H, s), 8.78 (1H, s), 15.05 (1H, s)

MS (ESI): M+ 462

EXAMPLE 4-35

$^1$H NMR (DMSO-$d_6$ 400 MHz) (δ) ppm: 0.86 (3H, t, J=7.2 Hz), 1.19-1.29 (8H, m), 1.90-1.93 (2H, m), 3.72-3.80 (2H, m), 4.08 (2H, s), 5.02-5.04 (1H, m), 5.10-5.20 (2H, m), 7.11-7.22 (2H, m), 7.43-7.46 (2H, m), 8.18 (1H, s), 8.78 (1H, s), 15.51 (1H, s)

MS (ESI): M+ 476

EXAMPLE 4-36

$^1$H NMR (DMSO-$d_6$ 400 MHz) (δ) ppm: 0.88 (3H, t, J=7.2 Hz), 1.20-1.35 (2H, m), 1.36 (3H, t, J=6.8 Hz), 1.80-2.00 (2H, m), 3.70-3.80 (2H, m), 4.11 (2H, s), 4.25 (2H, q, J=7.2 Hz), 5.17-(1H, t, J=5.6 Hz), 7.14-7.18 (1H, m), 7.24-7.26 (1H, m), 7.41 (1H, s), 7.41-7.45 (1H, m), 8.13 (1H, s), 8.78 (1H, s), 15.48 (1H, s)

MS (ESI): M+ 462

EXAMPLE 4-37

$^1$H NMR (DMSO-$d_6$ 400 MHz) (δ) ppm: 0.93 (9H, s), 1.49 (3H, t), 4.00 (2H, t, J=6.4 Hz), 4.20 (2H, s), 4.22-4.33 (2H, m), 5.12 (1H, t), 6.36 (1H, t, J=6.8 Hz), 7.21 (1H, m), 7.39-7.48 (2H, m), 7.54 (1H, s), 7.79 (1H, s), 8.79 (1H, s), 15.04 (1H, s)

MS (ESI): M+ 476

EXAMPLE 4-38

$^1$H NMR (DMSO-$d_6$ 400 MHz) (δ) ppm: 0.89 (3H, t, J=8.0 Hz), 1.23-1.40 (2H, m), 1.80-2.00 (2H, m), 3.75-3.90 (2H, m), 4.02 (3H, s), 4.11 (2H, s), 5.10-5.21 (2H, m), 7.16-7.24 (2H, m), 7.44-7.49 (2H, m), 8.03 (1H, s), 8.80 (1H, s), 15.44 (1H, br)

MS (ESI): M+ 448

EXAMPLE 4-39

$^1$H NMR (DMSO-$d_6$ 300 MHz) (δ) ppm: 0.74 (3H, t, J=7.1 Hz), 0.84-1.24 (11H, m), 2.10-2.30 (1H, m), 3.70-3.80 (1H, m), 3.90-4.00 (1H, m), 4.09 (2H, s), 4.80-5.17 (3H, m), 7.15-7.22 (2H, m), 7.40-7.50 (2H, m), 8.19 (1H, s), 8.87 (1H, s), 15.51 (1H, s)

MS (ESI): M+ 490

EXAMPLE 4-40

$^1$H NMR (DMSO-$d_6$ 400 MHz) (δ) ppm: 0.80-0.89 (1H, m), 1.04-1.30 (11H, m), 1.50-1.60 (2H, m), 1.70-1.80 (1H, m), 1.93-2.01 (2H, m), 3.73-3.76 (1H, m), 3.96-4.00 (1H, m), 4.07 (2H, s), 4.80-4.89 (1H, m), 5.00-5.17 (2H, m), 7.12-7.21 (2H, m), 7.40-7.42 (2H, m), 8.17 (1H, s), 8.87 (1H, s)

MS (ESI): M+ 516

EXAMPLE 4-41

$^1$H NMR. (DMSO-$d_6$ 300 MHz) (δ) ppm: 0.80-1.30 (6H, m), 1.46 (3H, t, J=6.9 Hz), 1.50-1.70 (2H, m), 1.70-1.80 (1H, m),1.90-2.10 (2H, m), 3.70-3.81 (1H, m), 3.92-4.00 (1H, m), 4.20 (3H, s), 4.23 (2H, q, J=6.6 Hz), 5.20 (1H, t, J=4.8 Hz), 5.70-5.81 (1H, m), 7.19-7.24 (1H, m), 7.38-7.51 (3H, m), 7.77 (1H, s), 8.91 (1H, s), 15.11 (1H, s)

MS (ESI): M+ 502

EXAMPLE 4-42

$^1$H NMR (DMSO-$d_6$ 300 MHz) (δ) ppm: 0.84-1.30 (6H, m), 1.50-1.70 (2H, m), 1.70-1.90 (1H, m), 1.94-2.10 (2H, m), 3.70-3.79 (1H, m), 3.90-4.00 (1H, m), 4.03 (3H, s), 4.10 (2H, s), 4.80-5.00 (1H, m), 5.19 (1H, m), 7.19-7.30 (2H, m), 7.43-7.48-(2H, m), 8.02 (1H, s), 8.87 (1H, s), 15.45 (1H, s)

MS (ESI): M+ 488

EXAMPLE 4-43

$^1$H NMR (DMSO-$d_6$ 300 MHz) ($\delta$) ppm: 0.80-1.00 (1H, m), 1.14-1.28 (5H, m), 1.37 (3H, t, J=6.9 Hz), 1.50-1.70 (2H, m), 1.70-1.80 (1H, m), 1.90-2.10 (2H, m), 3.70-3.80 (1H, m), 3.90-4.00 (1H, m), 4.11 (2H, s), 4.25(2H, q), 4.80-5.00 (1H, m), 5.18 (1H, m), 7.17-7.26 (2H, m), 7.41-7.47 (2H, m), 8.13 (1H, s), 8.89 (1H, s)

MS (ESI): M+ 502

EXAMPLE 4-44

$^1$H NMR (DMSO-$d_6$ 300 MHz) ($\delta$) ppm: 0.80-1.00 (1H, m), 1.00-1.40 (5H, m), 1.50-1.70 (2H, m), 1.70-1.80 (1H, m), 1.90-2.10 (2H, m), 3.70-3.80 (1H, m), 3.90-4.00 (1H, m), 3.98 (3H, s), 4.21(2H, s), 5.20 (1H, m), 5.60-5.70 (1H, m), 7.19-7.25 (1H, m), 7.39-7.54 (3H, m), 7.77 (1H, s), 8.92 (1H, s)

MS (ESI): M+ 488

EXAMPLE 4-45

$^1$H NMR (DMSO-$d_6$ 400 MHz) ($\delta$) ppm: 0.74 (3H, d, J=4.0 Hz), 1.08 (3H, d, J=8.0 Hz), 1.45 (3H, t, J=8.0 Hz), 2.36-2.40 (2H, m), 3.70-3.80 (1H, m), 3.89-3.93 (1H, m), 4.19 (2H, s), 4.26(2H, q, J=8.0 Hz), 5.20 (1H, t, J=8.0 Hz), 5.69-5.73(1H, m), 7.17-7.20 (1H, m), 7.39 (1H, m), 7.48-7.51 (2H, m), 7.76 (1H, s), 8.89 (1H, s)

MS (ESI): M+ 462

EXAMPLE 4-46

$^1$H NMR (DMSO-$d_6$ 400 MHz) ($\delta$) ppm: 0.73 (3H, d, J=6.8 Hz), 1.08 (3H, d, J=6.8 Hz), 2.20-2.40 (2H, m), 3.81-3.91 (1H, m), 3.91-3.99 (1H, m), 3.99 (3H, s), 4.22 (2H, s), 5.20 (1H, m), 5.55-5.58(1H, m), 7.10-7.22 (1H, m), 7.41-7.55 (3H, m), 7.77 (1H, s), 8.91 (1H, s), 15.09 (1H, s)

MS (ESI): M+ 448

EXAMPLE 4-47

$^1$H NMR (DMSO-$d_6$ 300 MHz) ($\delta$) ppm: 0.85 (3H, d, J=7.3 Hz), 1.10-1.34 (2H, m), 1.33 (6H, d, J=6.0 Hz), 1.70-2.00 (2H, m), 3.75 (2H, m), 4.17(2H, s), 4.80-4.90(1H, m), 5.14 (1H, m), 5.80-6.00(1H,, m), 7.10-7.20 (1H, m), 7.30-7.50 (3H, m), 7.72 (1H, s), 8.80 (1H, s)

MS (ESI): M+ 476

EXAMPLE 4-48

$^1$H NMR (DMSO-$d_6$ 400 MHz) ($\delta$) ppm: 0.89 (3H, t), 1.20-1.40 (2H, m), 1.44 (3H, t), 1.80-2.00 (2H, m), 3.78 (2H, m), 4.20 (2H, s), 4.23 (2H, q, J=6.8 Hz), 5.16 (1H, t, J=5.6 Hz), 5.90-5.92(1H, m), 7.15-7.21 (1H, m), 7.39-7.52 (3H, m), 7.76 (1H, s), 8.84 (1H, s), 15.10 (1H, s)

MS (ESI): M+ 462

EXAMPLE 4-49

$^1$H NMR (DMSO-$d_6$ 400 MHz) ($\delta$) ppm: 0.89 (3H, t), 1.23-1.35 (2H, m) 1.87-1.96 (2H, m), 3.72-3.79 (2H, m), 3.98 (3H, s), 4.21 (2H, s), 5.15 (1H, t, J=5.2 Hz), 5.85-5.88(1H, m), 7.15-7.21 (1H, m), 7.39-7.48 (2H, m), 7.54 (1H, s), 7.76 (1H, s), 8.85 (1H, s), 15.10 (1H, s).

MS (ESI): M+ 448

EXAMPLE 4-50

$^1$H NMR (DMSO-$d_6$ 400 MHz) ($\delta$) ppm: 0.80-1.00 (1H, m), 1.11-1.20 (4H, m), 1.20-1.30 (1H, m), 1.35 (3H,d), 1.40-(3H, d), 1.55-1.70 (2H, m), 1.72-1.80 (1H, m), 1.95-2.10 (2H, m), 3.77-3.79 (1H, m), 3.95-3.98 (1H, m), 4.20 (2H, s), 4.91-4.94 (1H, m), 5.24 (1H, t), 5.81-5.83(1H, m), 7.15-7.21 (1H, m), 7.39-7.50 (2H, m), 7.53 (1H, s), 7.74 (1H, s), 8.89 (1H, s), 15.09 (1H, s)

MS (ESI): M+ 516

EXAMPLE 4-51

$^1$H NMR (DMSO-$d_6$ 300 MHz) ($\delta$) ppm: 0.91 (9H, s), 1.48 (3H, t, J=6.9 Hz), 3.90-4.00 (2H, m), 4.13 (2H, s), 4.22(2H, q, J=7.0 Hz), 4.90-5.00 (1H, m), 6.10-6.20 (1H, m), 7.17-7.22 (1H, m), 7.34-7.36 (2H, m), 7.45-7.50 (1H, m), 7.77 (1H, s), 8.75 (1H, s)

MS (ESI): M+ 476

EXAMPLE 4-52

$^1$H NMR (DMSO-$d_6$ 400 MHz) ($\delta$) ppm: 0.93 (9H, s), 3.90-4.02 (2H, m), 4.15 (2H, s), 4.80-4.81 (1H, m), 5.05 (1H, m), 7.19-7.21 (1H, m), 7.35-7.40 (1H, m), 7.43-7.45 (1H, m), 7.57 (1H, d), 8.01-8.03 (1H, d, J=8.8 Hz), 8.12 (1H, s), 8.76 (1H, s)

MS (ESI): M+ 432

EXAMPLE 4-53

$^1$H NMR (DMSO-$d_6$ 400 MHz) ($\delta$) ppm: 0.81 (3H, d), 1.20 (3H, d), 2.28-2.41 (1H, m), 3.98 (3H, s), 4.00-4.05 (2H, m), 4.08 (2H, 5)1 4.51-4.60 (1H, m), 7.02-7.08 (2H, m), 7.19 (1H, s), 7.28-7.30 (1H, m), 8.15 (1H, s), 8.60 (1H, s)

MS (ESI): M+ 448

EXAMPLE 4-54

$^1$H NMR (DMSO-$d_6$ 300 MHz) ($\delta$) ppm: 0.95 (9H, s), 3.96 (3H, s), 3.96-4.03 (4H, m), 4.83 (1H, m), 5.17 (1H, m), 7.13-7.23 (2H, m), 7.28 (1H, s), 7.42-7.47 (1H, m), 7.80 (1H, s), 8.73 (1H, s)

MS (ESI): M+ 462

Sequence Listing Free Text

SEQ ID NO:1: Donor+chain for HIV integrase activity determination

SEQ ID NO:2: Donor–chain for HIV integrase activity determination

SEQ ID NO:3: Target+chain for HIV integrase activity determination

SEQ ID NO:4: Target–chain for HIV integrase activity determination

Industrial Field of Utilization

As is clear from the above results, the compounds of the present invention has high HIV integrase inhibitory activity.

Therefore, the compounds can be useful pharmaceutical agents for the prophylaxis or therapy of AIDS, as anti-HIV agents having HIV integrase inhibitory activity. Moreover, by a combined use with other anti-HIV agents such as protease inhibitors, reverse transcriptase inhibitors and the like, the compounds can become more effective anti-HIV agents. Since the compounds have high inhibitory activity specific for integrases, they can provide safe pharmaceutical agents for human with a fewer side effects.

This application is based on patent application Nos. 2002-336843, 2003-65807 and 2003-139616 filed in Japan, the contents of which are all hereby incorporated by reference.

The invention claimed is:

1. A compound selected from the group of formulas (a)-(d):

-continued (c)
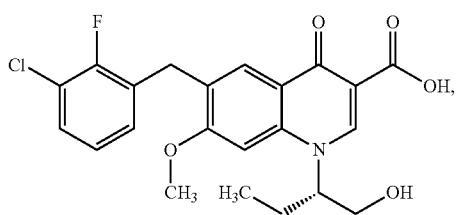

(d)
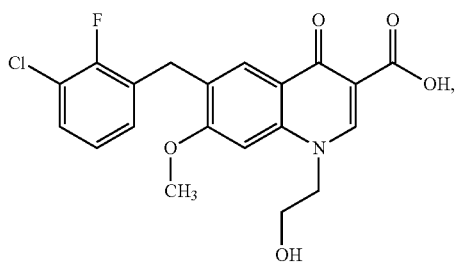

or a stereoisomer thereof, or a tautomer thereof, or a pharmaceutically acceptable salt thereof.

2. A pharmaceutical composition comprising a compound according to claim 1, or a stereoisomer thereof, or a tautomer thereof, or a pharmaceutically acceptable salt thereof, and a pharmaceutically acceptable carrier.

3. A method for the treatment of an HIV infectious disease comprising administering to a mammal the compound of claim 1, or a stereoisomer thereof, or a tautomer thereof, or a pharmaceutically acceptable salt thereof.

4. A compound of the formula:

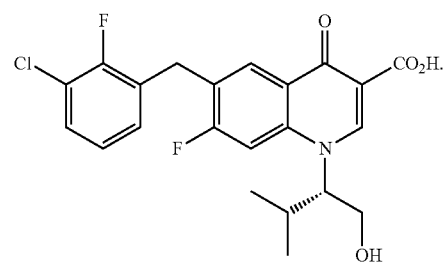

* * * * *